US010413183B2

(12) United States Patent
Antonio et al.

(10) Patent No.: US 10,413,183 B2
(45) Date of Patent: Sep. 17, 2019

(54) INSERTION DEVICE

(71) Applicant: Medtronic MiniMed, Inc., Northridge, CA (US)

(72) Inventors: David C. Antonio, Pasadena, CA (US); Eric Allan Larson, Simi Valley, CA (US); Jose J. Ruelas, San Fernando, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 335 days.

(21) Appl. No.: 15/357,952

(22) Filed: Nov. 21, 2016

(65) Prior Publication Data

US 2017/0290533 A1    Oct. 12, 2017

Related U.S. Application Data

(60) Provisional application No. 62/320,290, filed on Apr. 8, 2016, provisional application No. 62/344,847, filed
(Continued)

(51) Int. Cl.
*A61B 5/145* (2006.01)
*A61B 5/00* (2006.01)
(Continued)

(52) U.S. Cl.
CPC .......... *A61B 5/0022* (2013.01); *A61B 5/1486* (2013.01); *A61B 5/14503* (2013.01);
(Continued)

(58) Field of Classification Search
CPC ............ A61B 5/14503; A61B 5/14865; A61B 5/1473; A61B 5/150236
See application file for complete search history.

(56) References Cited

U.S. PATENT DOCUMENTS

| 4,755,173 A | 7/1988 | Konopka et al. |
| 5,391,250 A | 2/1995 | Cheney, II et al. |

(Continued)

FOREIGN PATENT DOCUMENTS

| EP | 2701600 | 3/2014 |
| EP | 2701600 B1 | 6/2016 |

(Continued)

OTHER PUBLICATIONS

"Invitation to Pay Additional Fees And, Where Applicable, Protest Fee" for International Application No. PCT/US2017/025996 dated Jun. 23, 2017.
(Continued)

*Primary Examiner* — Puya Agahi
(74) *Attorney, Agent, or Firm* — Medtronic MiniMed, Inc.

(57) ABSTRACT

Embodiments relate to an insertion device that includes: a plunger coupled with a lock collar. The insertion device houses contents including: a striker including self-locking striker snap arm(s) where the striker is kept from firing by a striker spring captured between the plunger and the striker when the insertion device is in a cocked position; a sensor assembly; and a needle carrier that holds a piercing member, the needle carrier captured between the striker and a needle carrier spring where a self-releasing snap(s) keeps the needle carrier cocked, where the plunger prevents the self-releasing snap(s) from repositioning and releasing the needle carrier. The striker fires the needle carrier such that the self-locking striker snap arm(s) are positioned to allow the striker to snap down. The needle carrier is then retracted when the user releases the plunger and the piercing member is encapsulated within the insertion device.

8 Claims, 107 Drawing Sheets

Related U.S. Application Data on Jun. 2, 2016, provisional application No. 62/344,852, filed on Jun. 2, 2016, provisional application No. 62/402,676, filed on Sep. 30, 2016.

(51) Int. Cl.
| | |
|---|---|
| *A61B 5/1486* | (2006.01) |
| *A61B 5/15* | (2006.01) |
| *A61M 5/172* | (2006.01) |
| *A61M 5/158* | (2006.01) |
| *A61B 5/1473* | (2006.01) |

(52) U.S. Cl.
CPC .... *A61B 5/14532* (2013.01); *A61B 5/150236* (2013.01); *A61B 5/150633* (2013.01); *A61B 5/150732* (2013.01); *A61B 5/6832* (2013.01); *A61B 5/6833* (2013.01); *A61M 5/158* (2013.01); *A61M 5/1723* (2013.01); *A61B 5/1473* (2013.01); *A61B 5/14865* (2013.01); *A61B 2560/0214* (2013.01); *A61B 2560/045* (2013.01); *A61B 2562/04* (2013.01); *A61B 2562/16* (2013.01); *A61B 2562/227* (2013.01); *A61M 2005/1585* (2013.01); *A61M 2005/1586* (2013.01); *A61M 2005/1726* (2013.01); *A61M 2205/3569* (2013.01)

(56) References Cited

U.S. PATENT DOCUMENTS

| | | | |
|---|---|---|---|
| 5,485,408 | A | 1/1996 | Blomquist |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |
| 6,355,021 | B1 | 3/2002 | Nielsen et al. |
| 6,379,301 | B1 | 4/2002 | Worthington et al. |
| 6,544,212 | B2 | 4/2003 | Galley et al. |
| 6,558,351 | B1 | 5/2003 | Steil et al. |
| 6,591,876 | B2 | 7/2003 | Safabash |
| 6,641,533 | B2 | 11/2003 | Causey, III et al. |
| 6,736,797 | B1 | 5/2004 | Larsen et al. |
| 6,749,587 | B2 | 6/2004 | Flaherty |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,399,277 | B2 | 7/2008 | Saidara et al. |
| 7,442,186 | B2 | 10/2008 | Blomquist |
| 7,602,310 | B2 | 10/2009 | Mann et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,181,849 | B2 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 * | 9/2012 | Brauker .............. A61B 5/0031 600/345 |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 2007/0123819 | A1 | 5/2007 | Mernoe et al. |
| 2010/0160861 | A1 | 6/2010 | Causey, III et al. |
| 2010/0198034 | A1 | 8/2010 | Thomas et al. |
| 2013/0150691 | A1 | 6/2013 | Pace et al. |
| 2013/0313130 | A1 | 11/2013 | Little et al. |
| 2016/0015303 | A1 | 1/2016 | Bernstein et al. |
| 2016/0058380 | A1 | 3/2016 | Lee et al. |

FOREIGN PATENT DOCUMENTS

| | | |
|---|---|---|
| WO | 9610442 A1 | 4/1996 |
| WO | 2006094513 A2 | 9/2006 |
| WO | 2006094513 A3 | 9/2006 |
| WO | 2011041531 A1 | 4/2011 |
| WO | 2012149143 A1 | 11/2012 |

OTHER PUBLICATIONS

"Invitation to Pay Additional Fees And, Where Applicable, Protest Fee" for International Application No. PCT/US2017/026007 dated Jul. 17, 2017.

"Notification of Transmittal of the International Search Report and the Written Opinion of the International Searching Authority, or the Declaration" for International Application No. PCT/US2017/025996 dated Aug. 17, 2017.

"Notification of Transmittal of the International Search Report and the Written Opinion of the International Searching Authority, or the Declaration" for International Application No. PCT/US2017/026007 dated Sep. 18, 2017.

\* cited by examiner

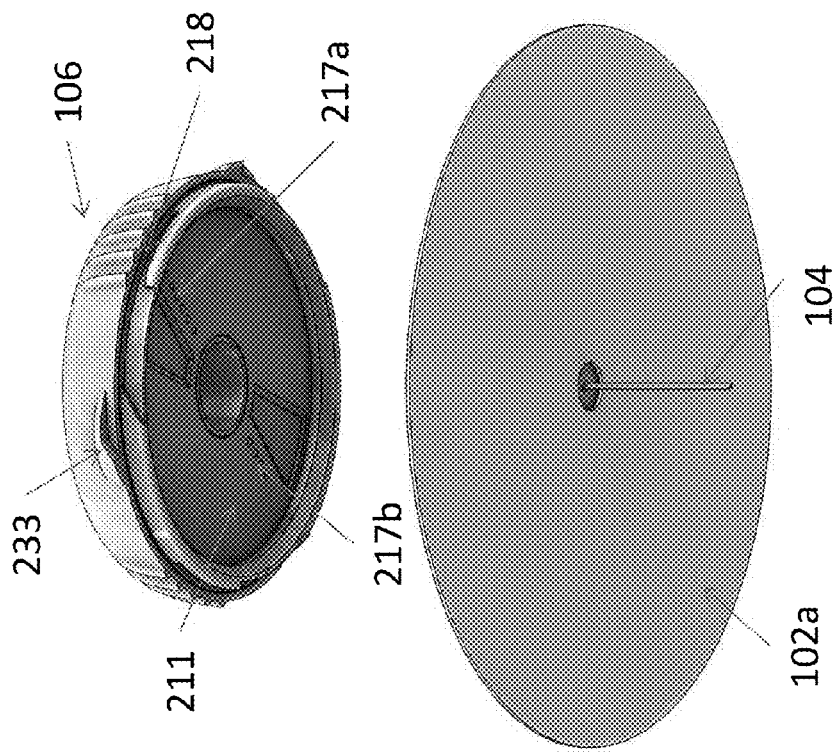
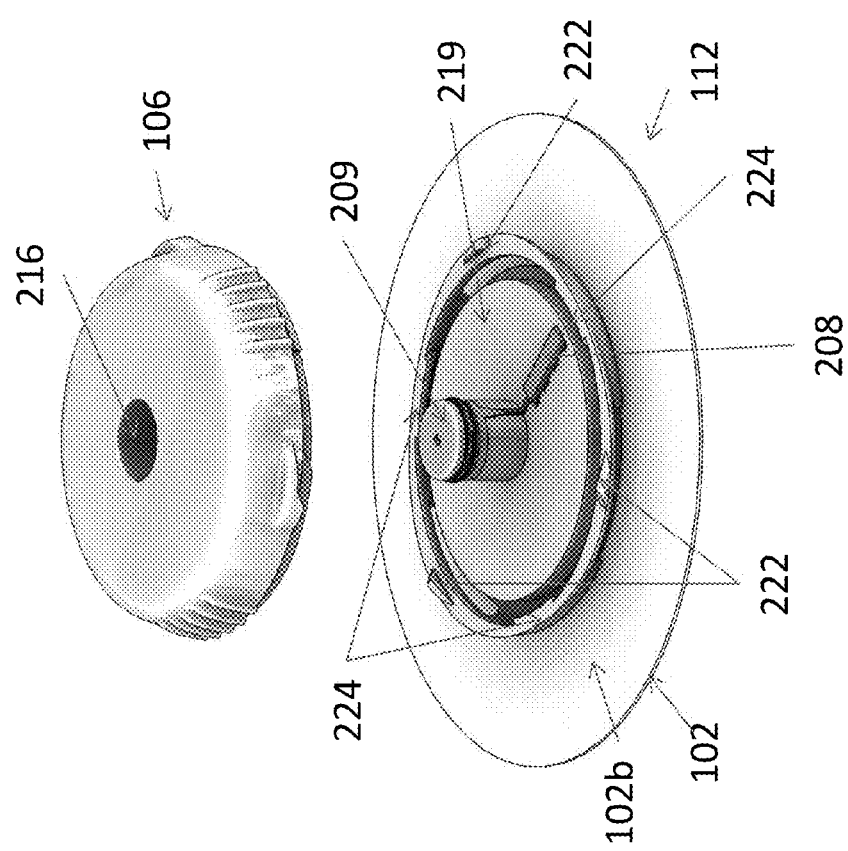

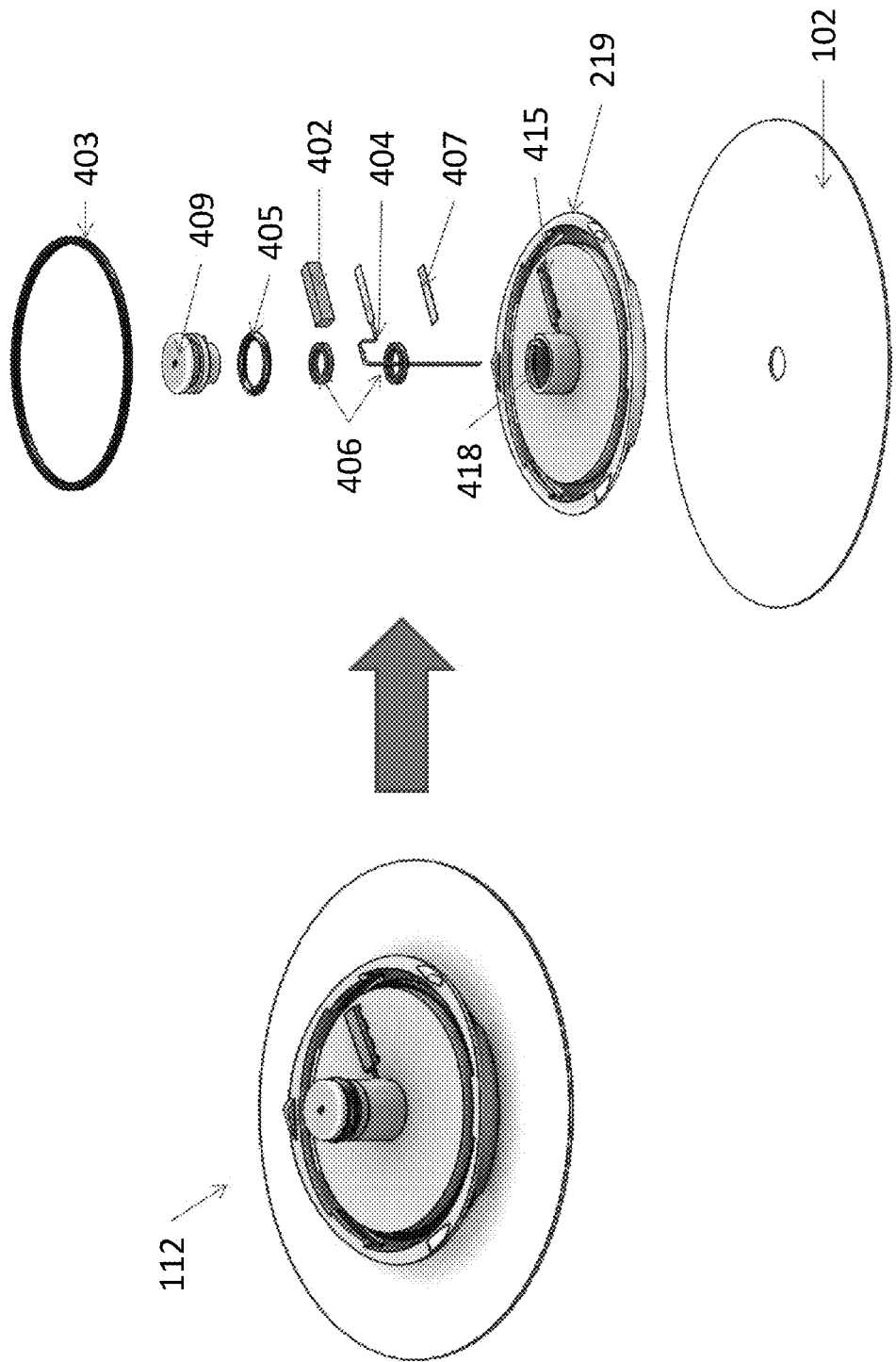

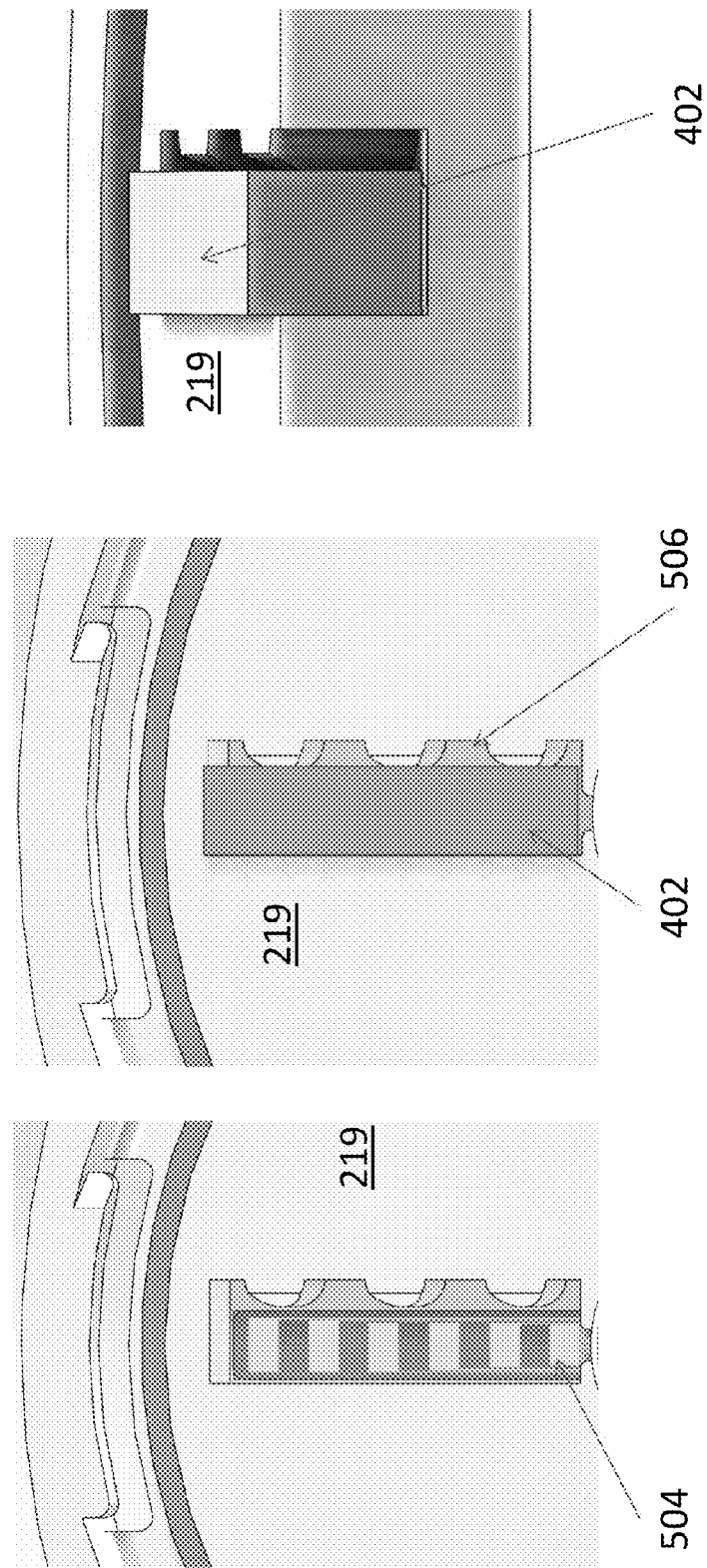

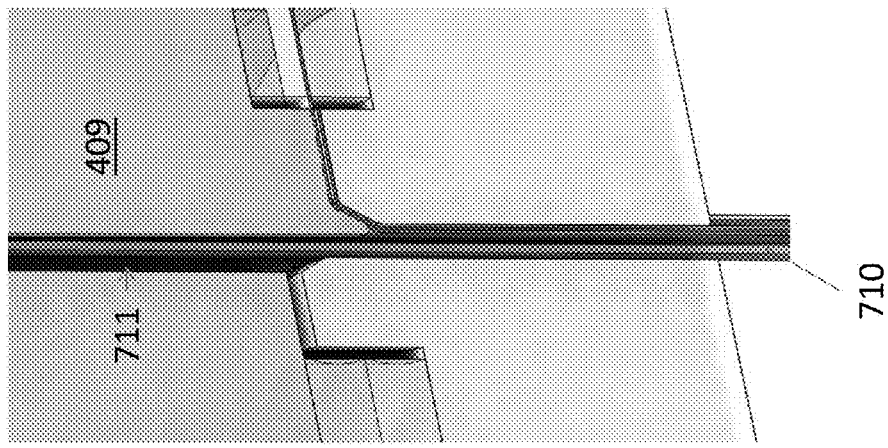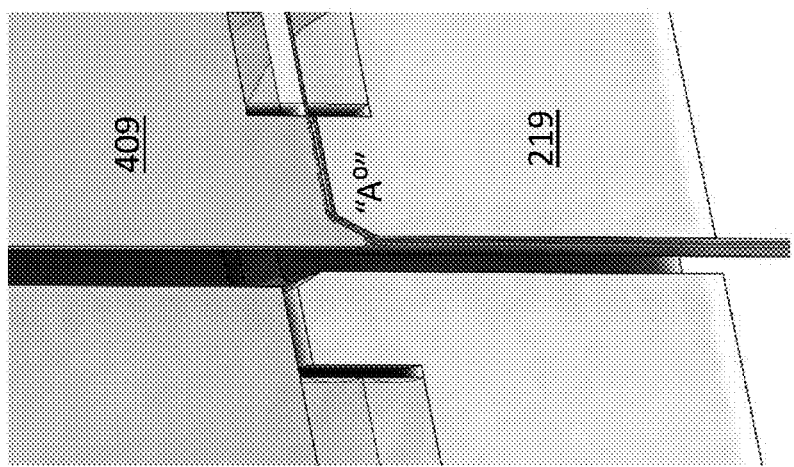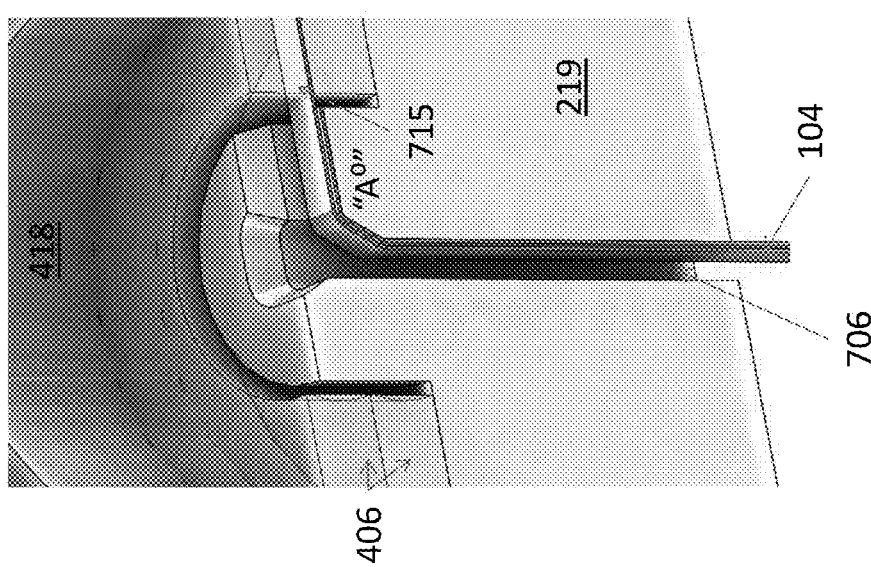

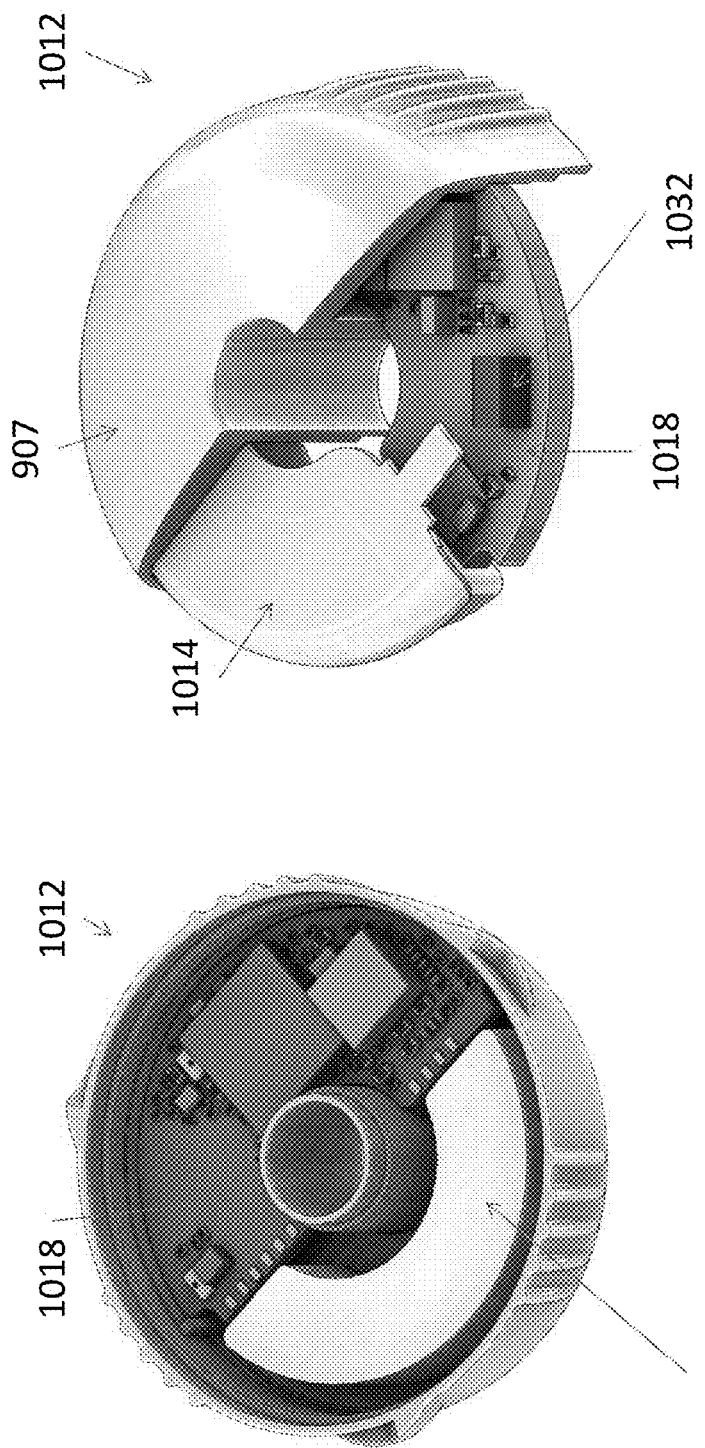

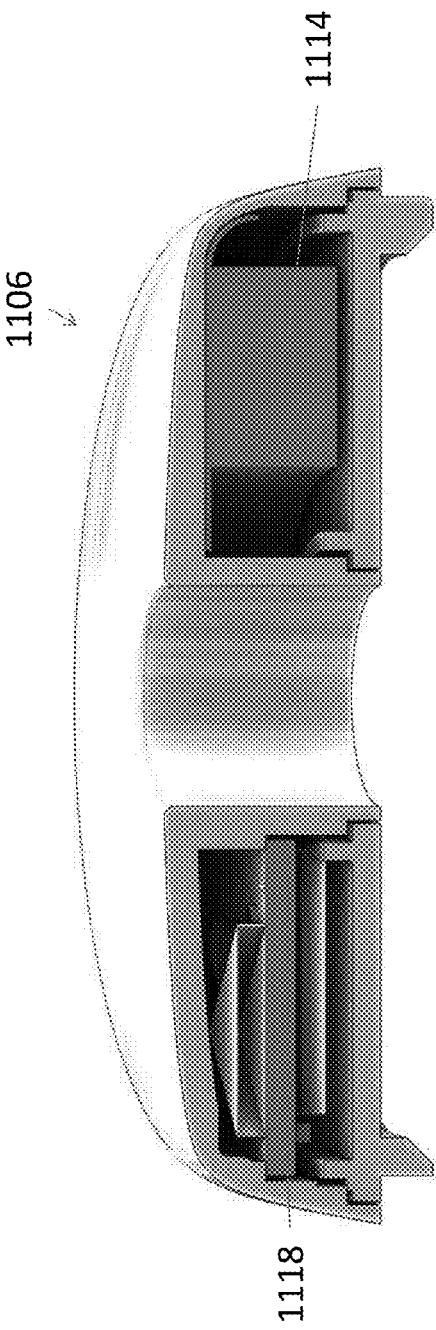
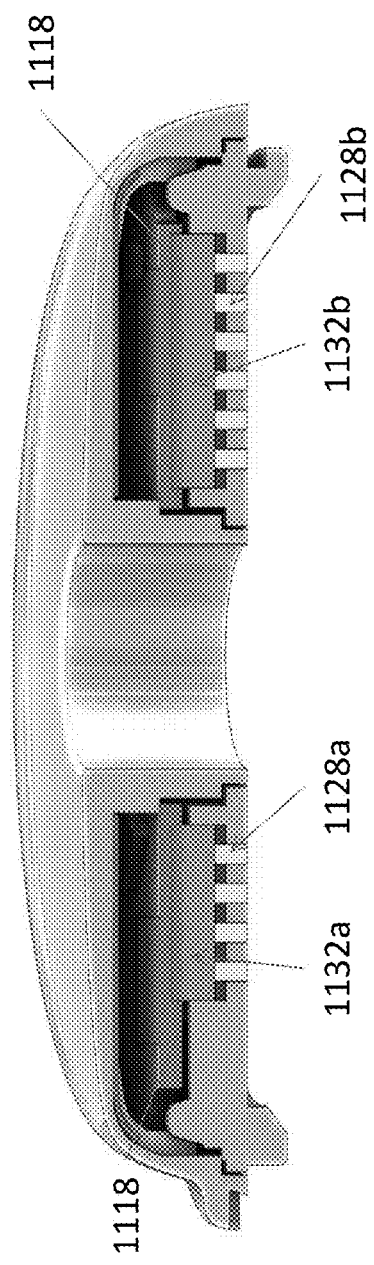
FIG. 11A
FIG. 11B

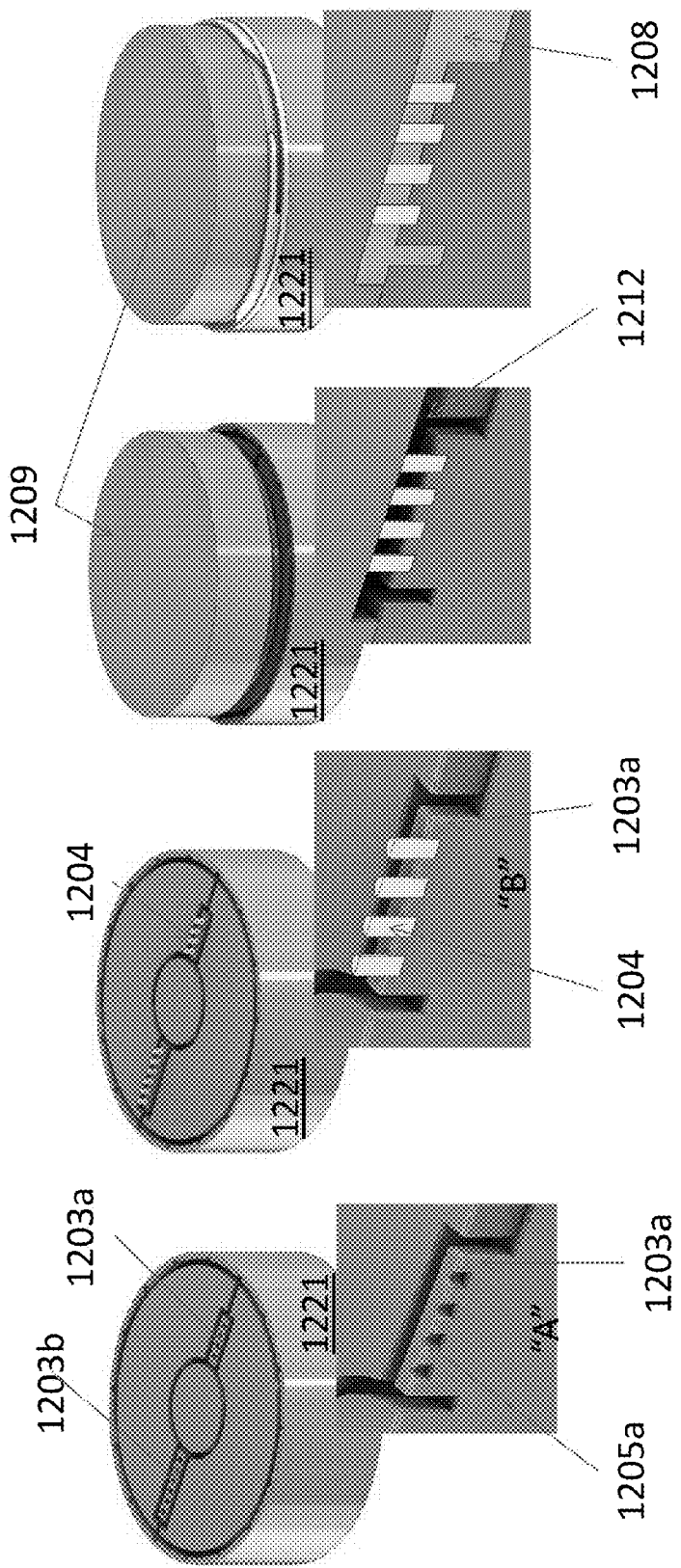

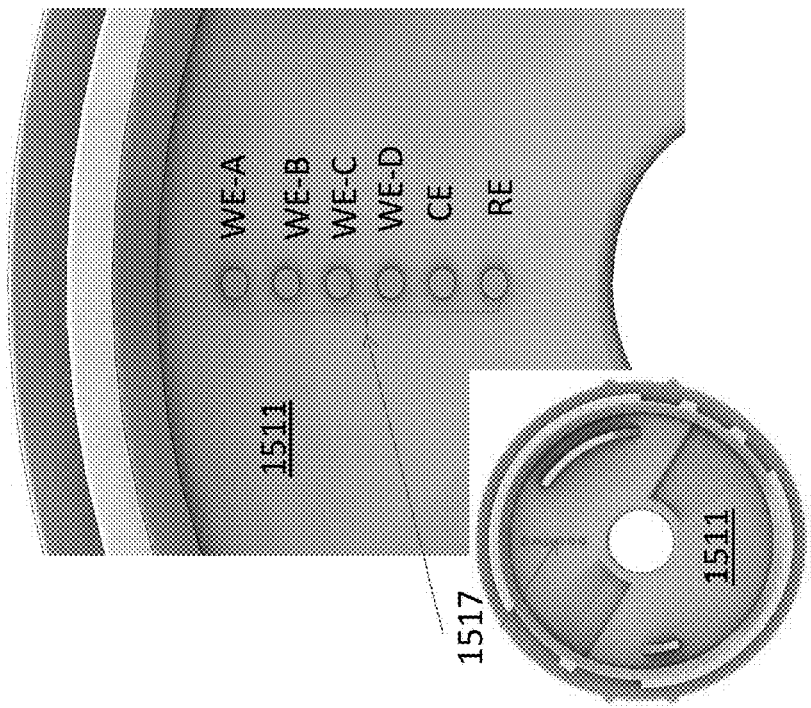
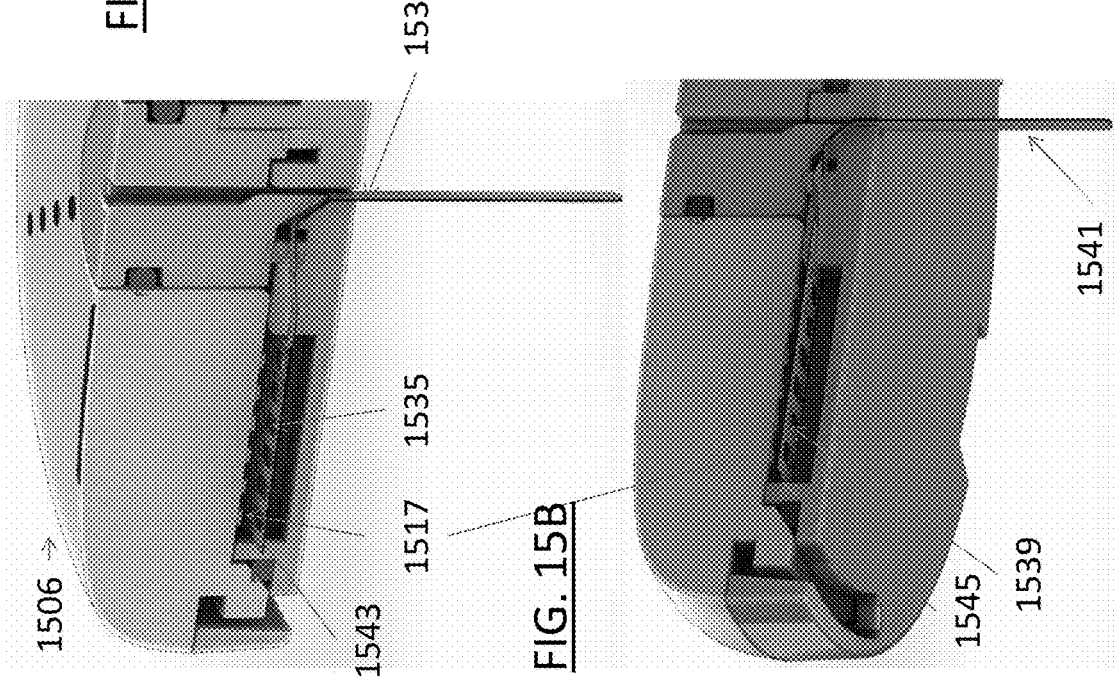

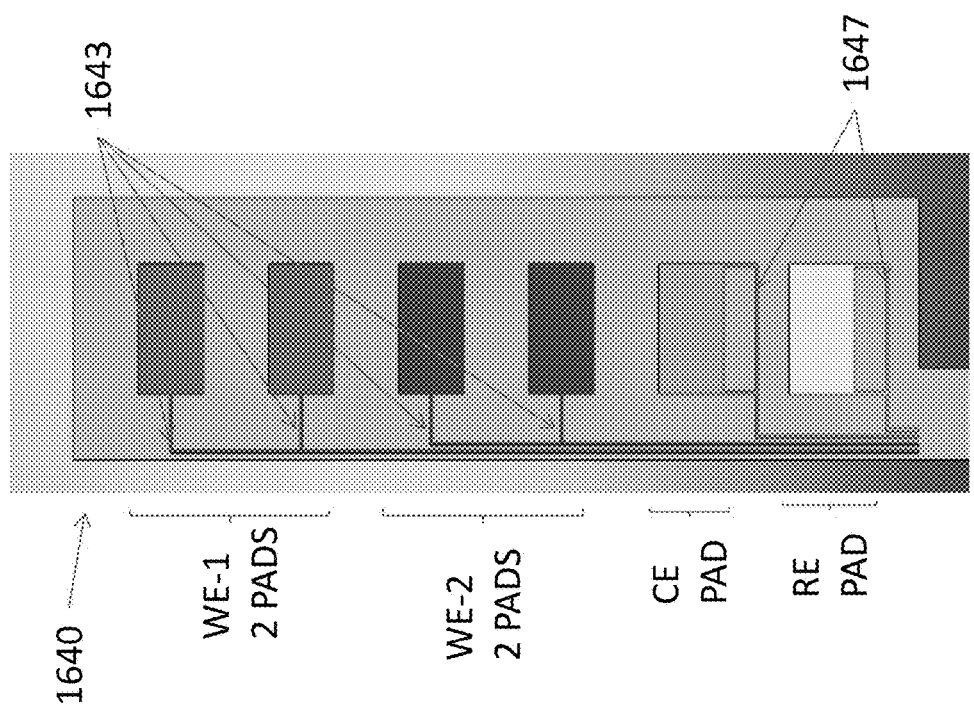

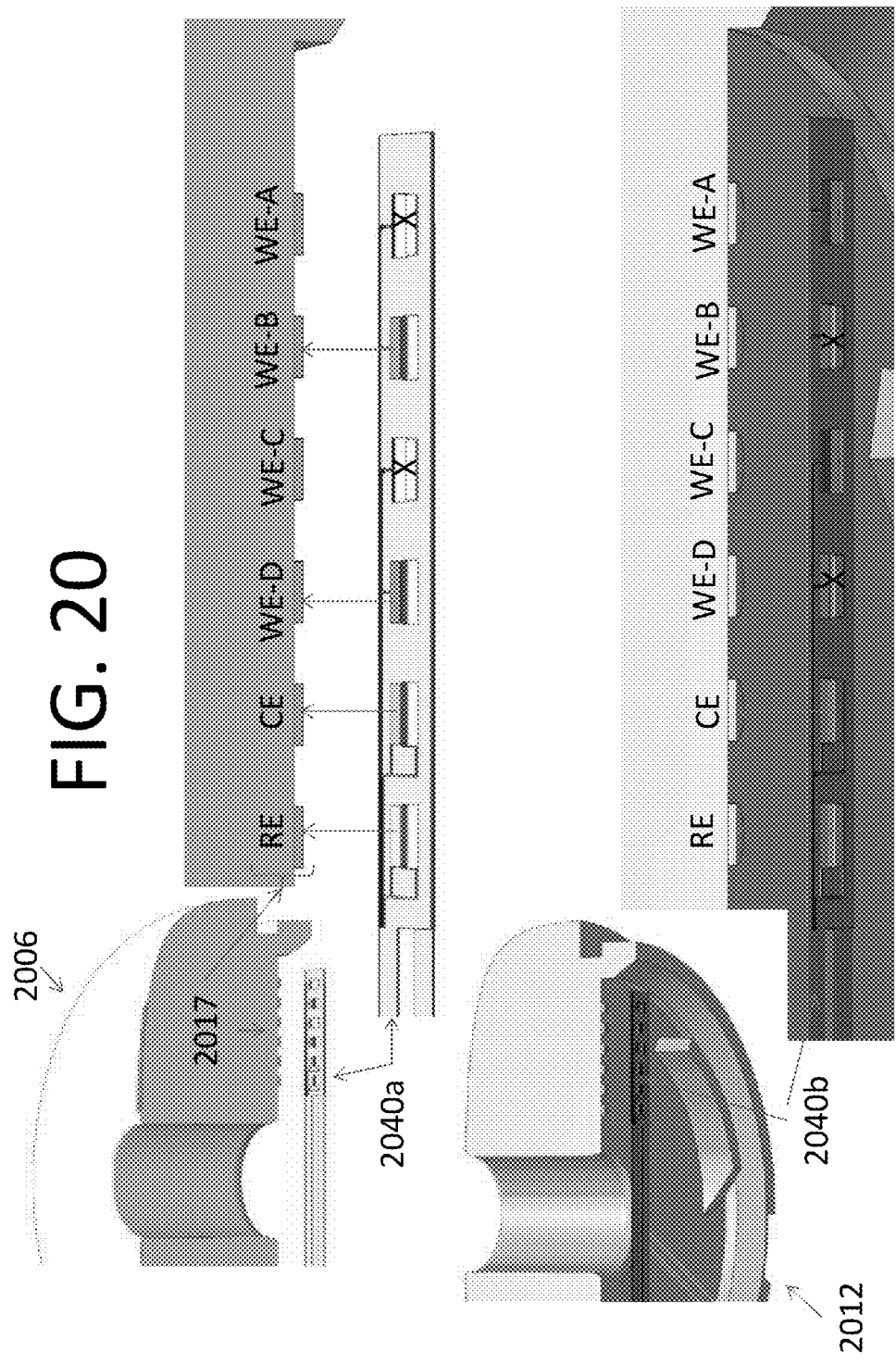

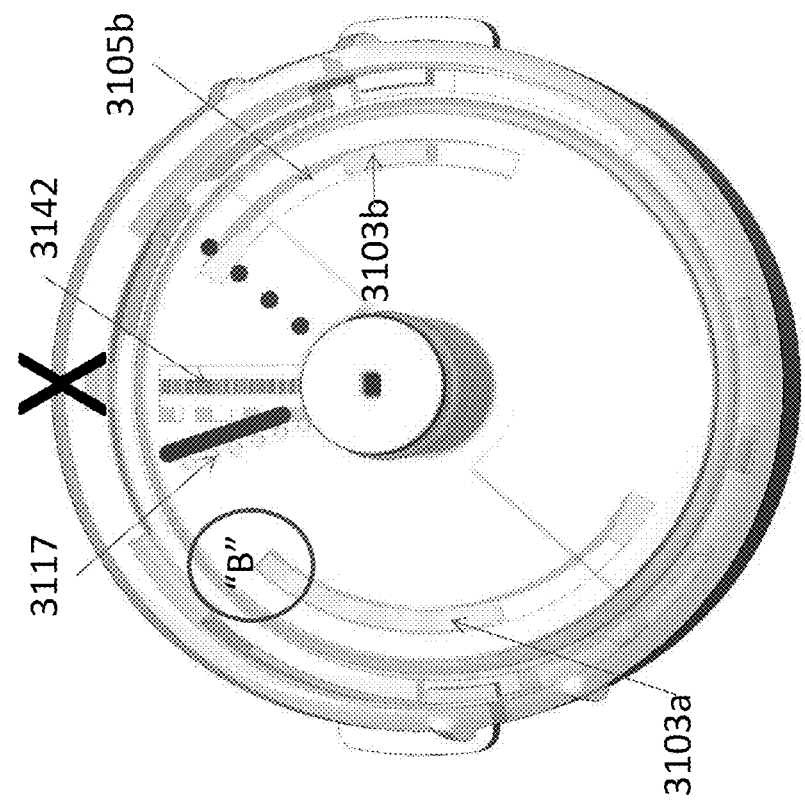
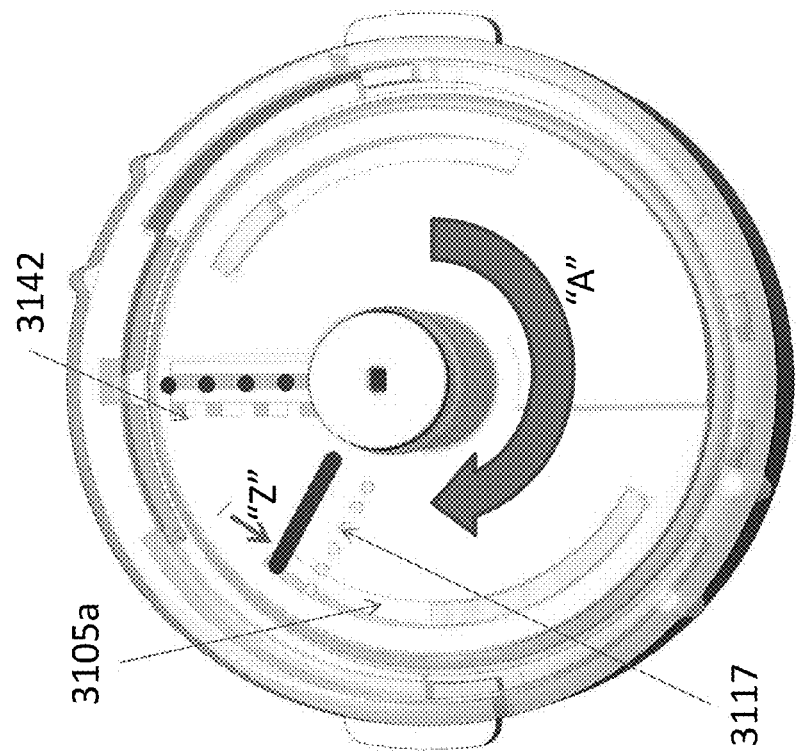

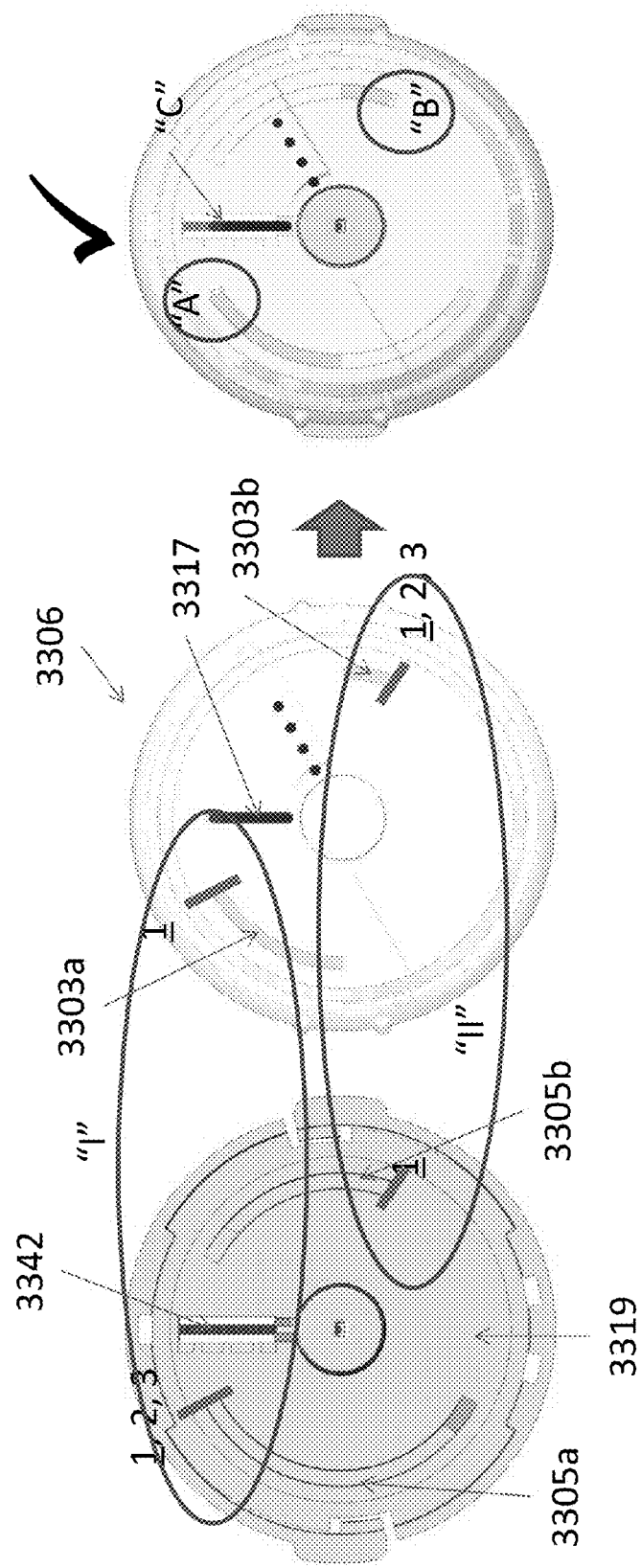

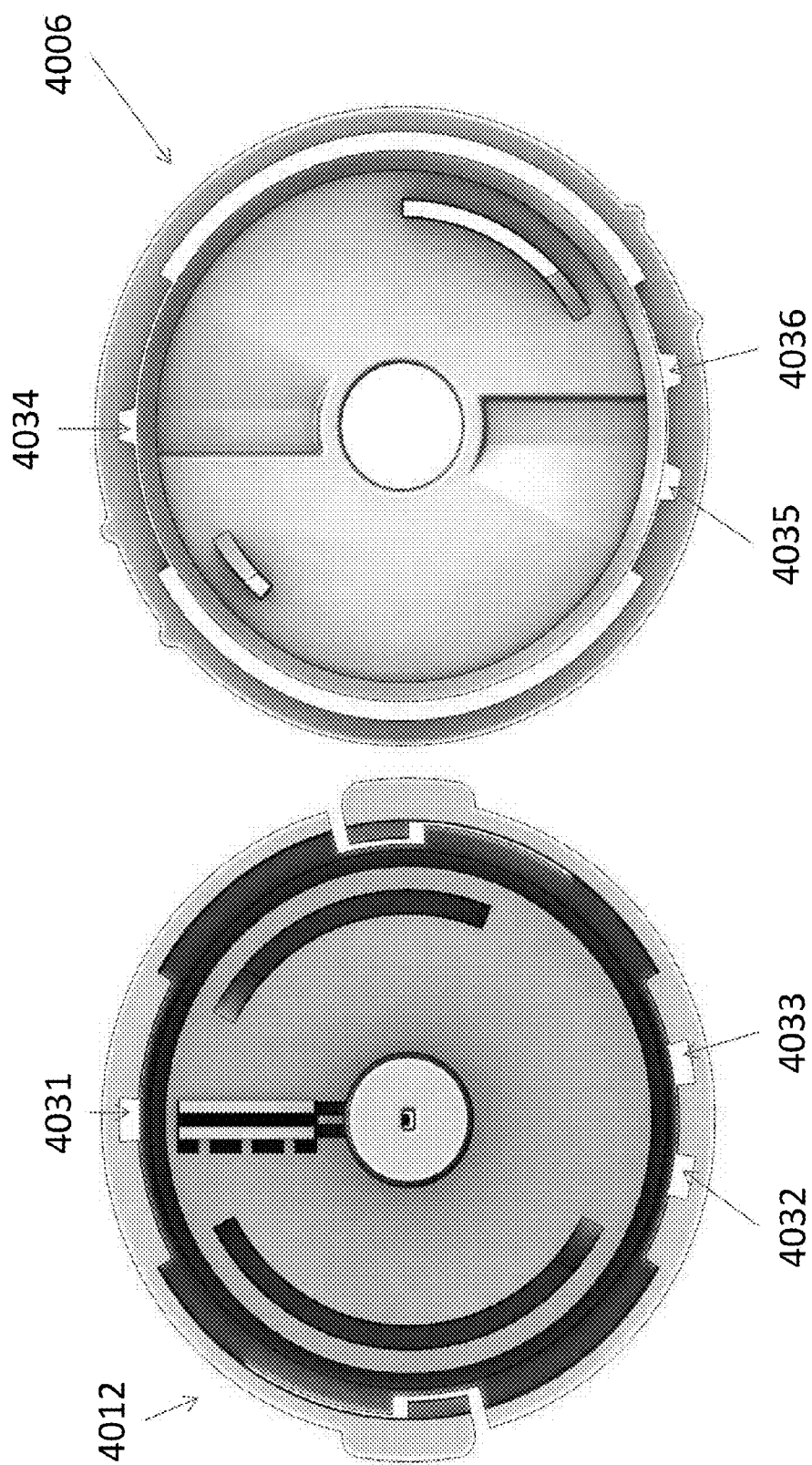

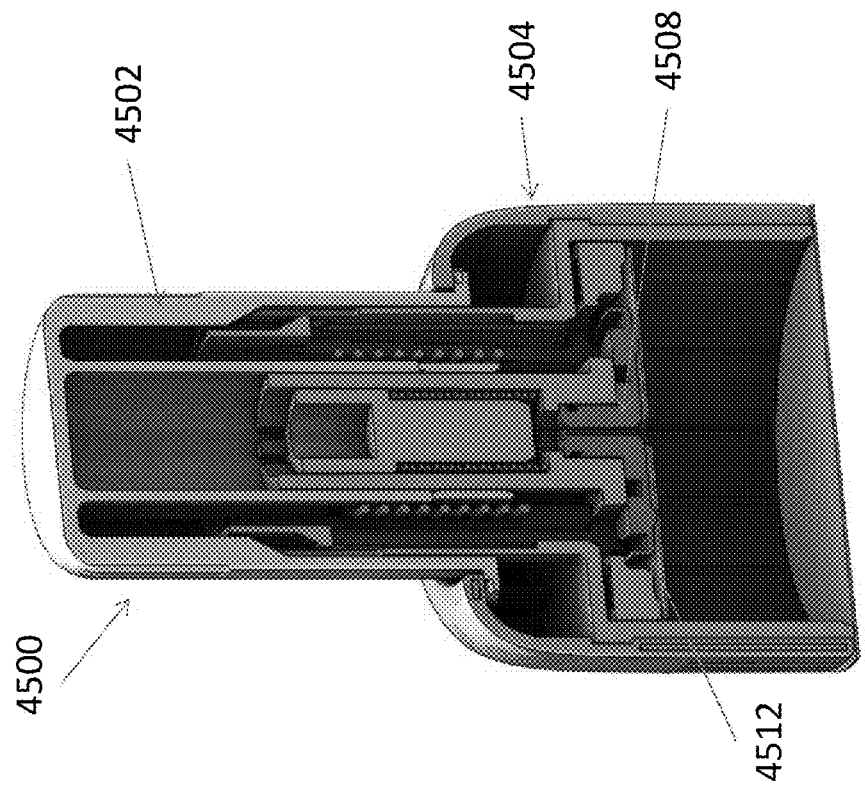
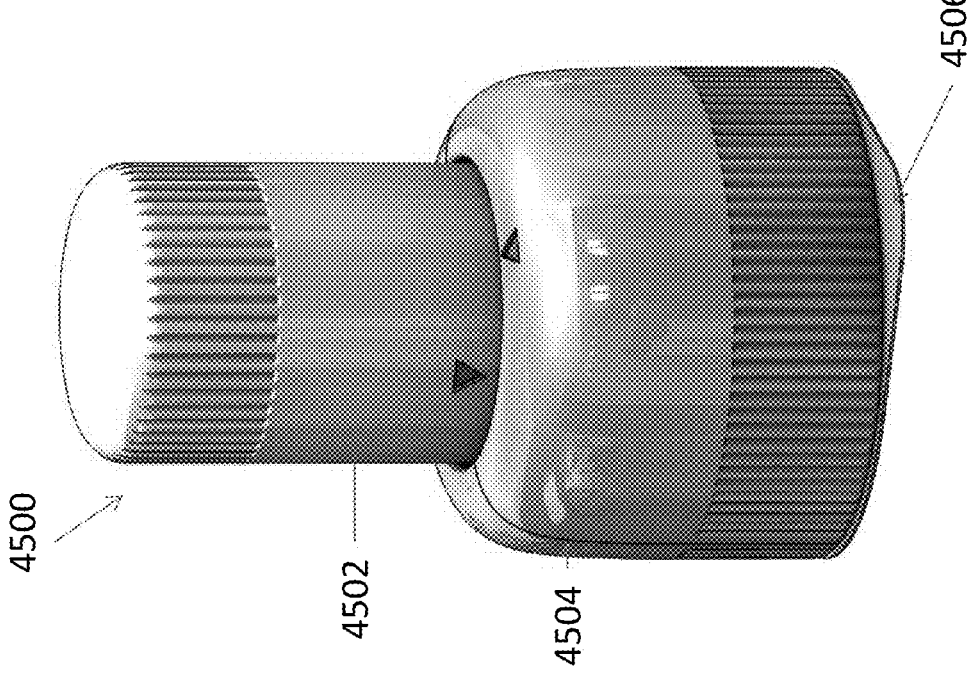

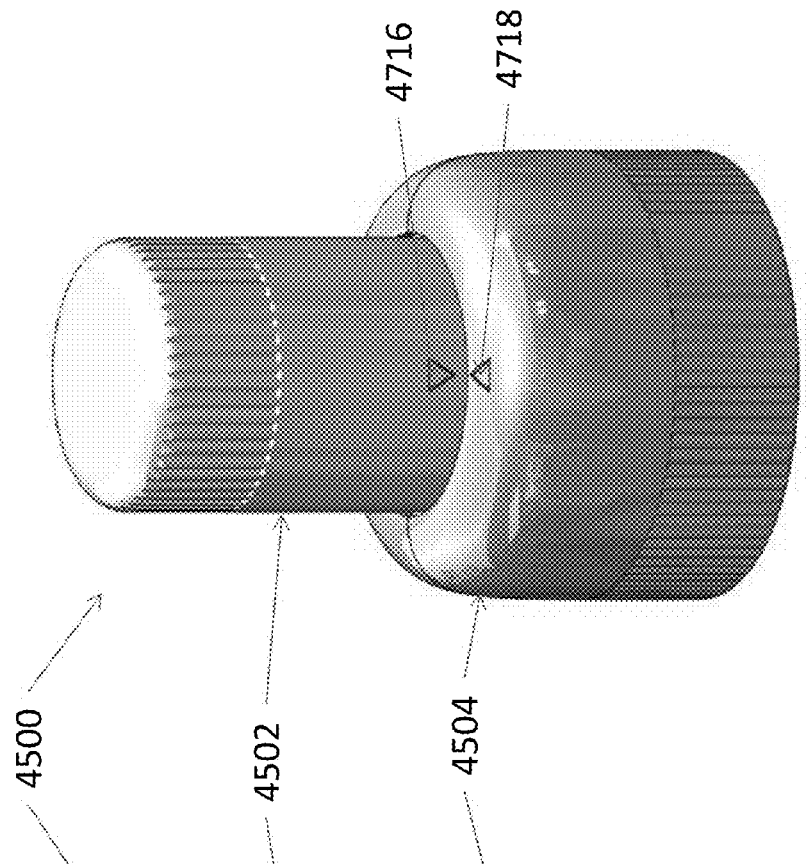
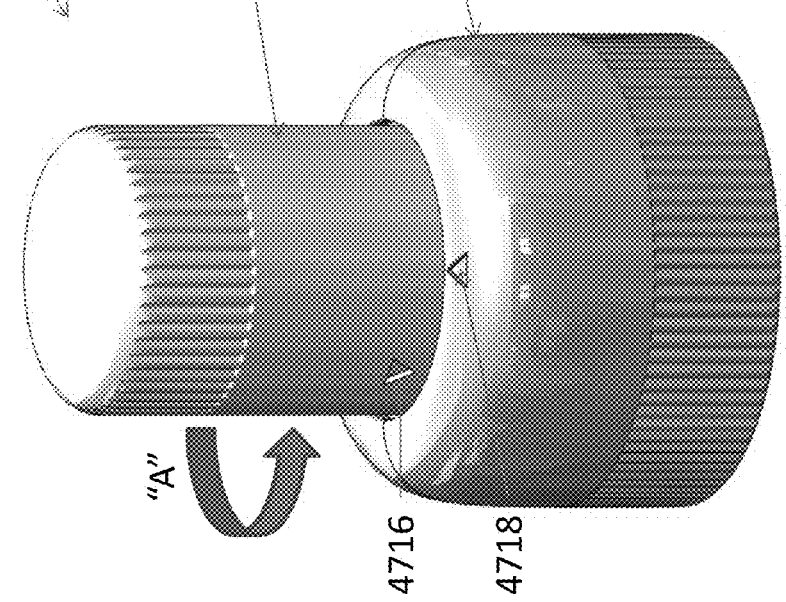

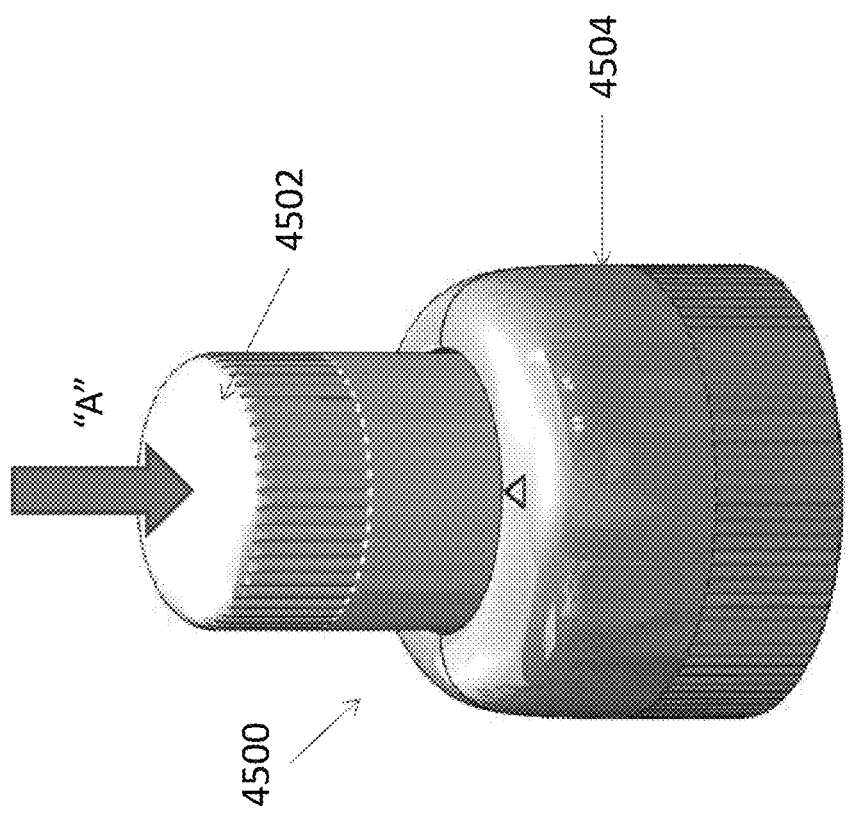

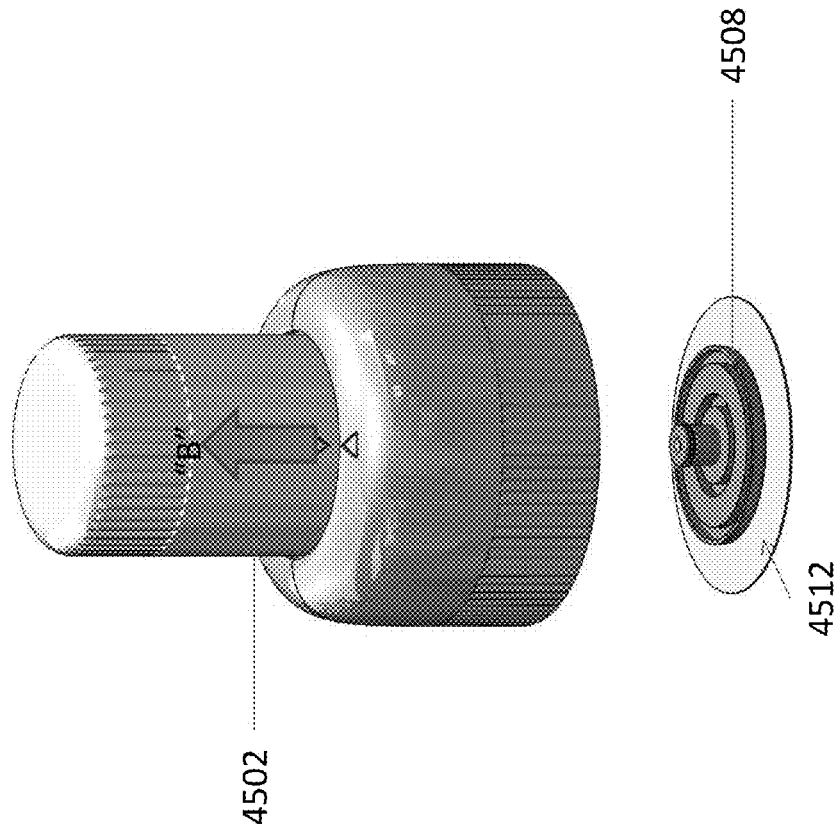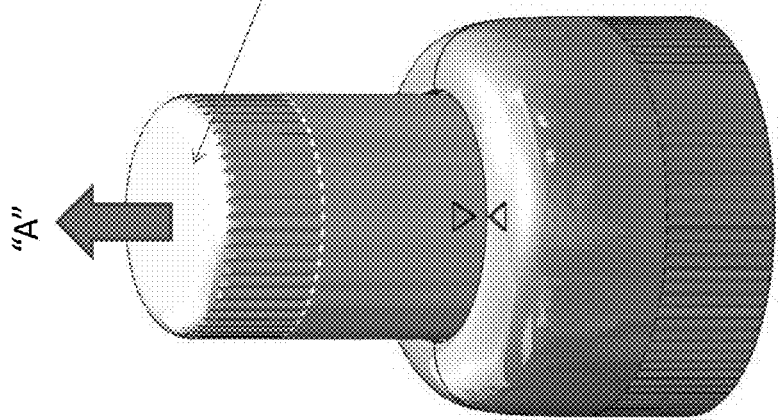

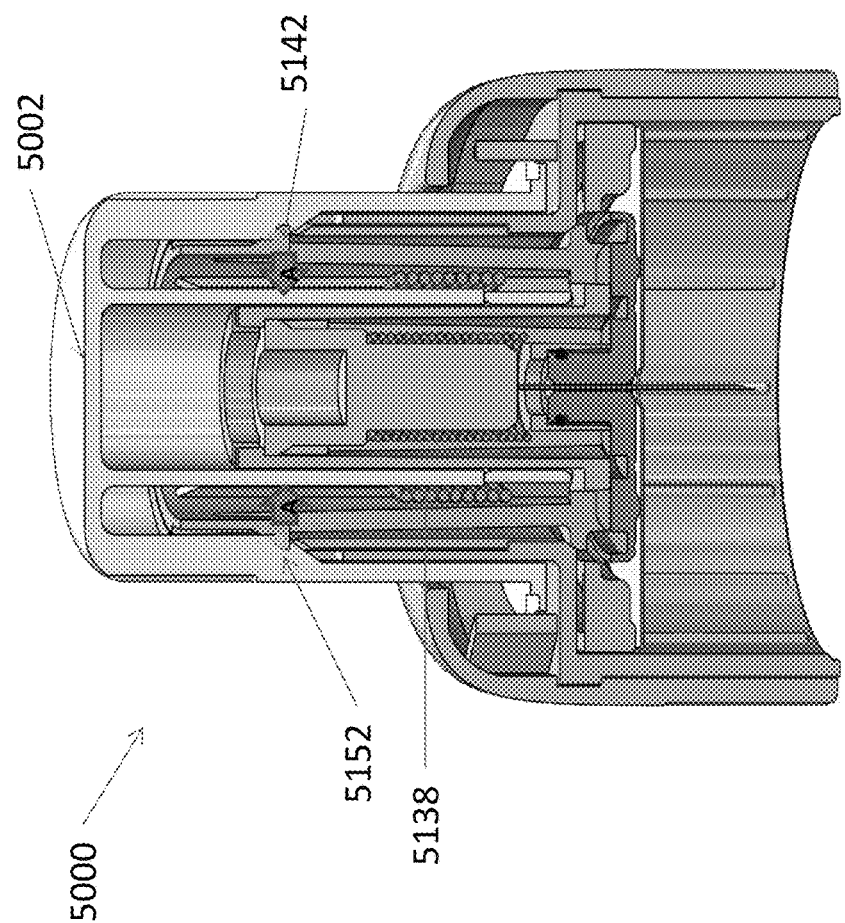

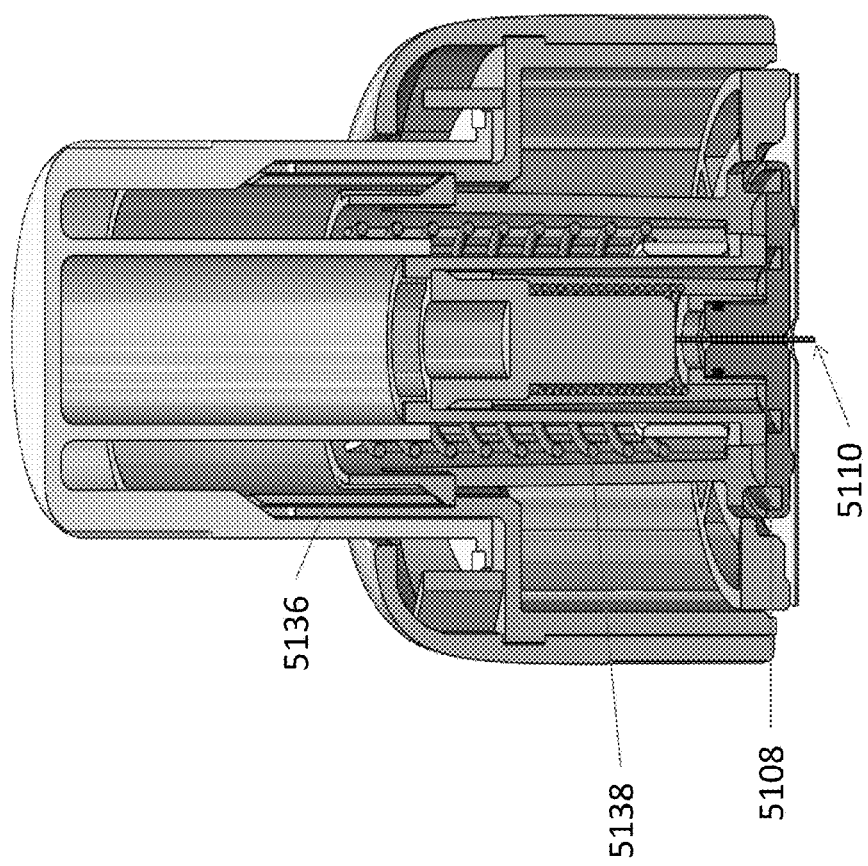

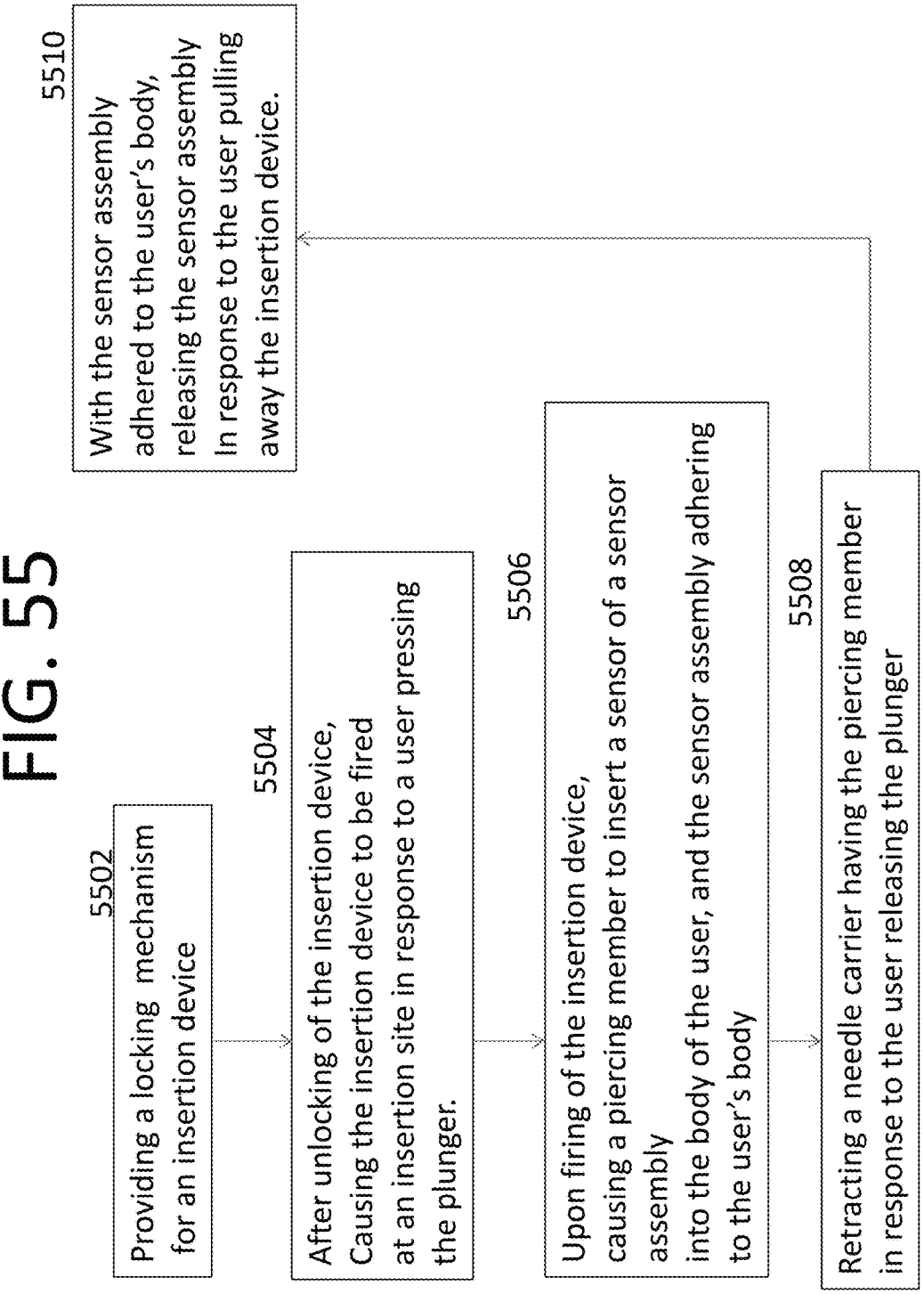

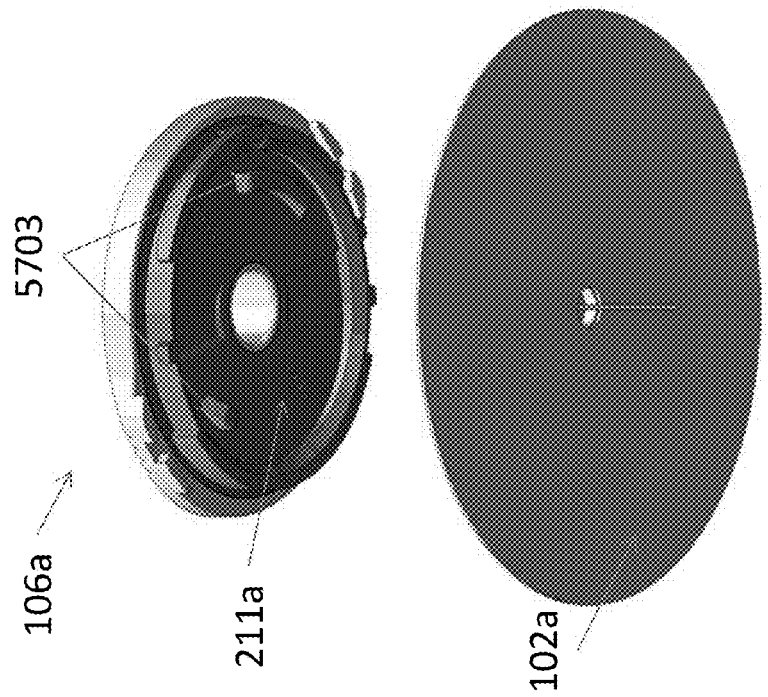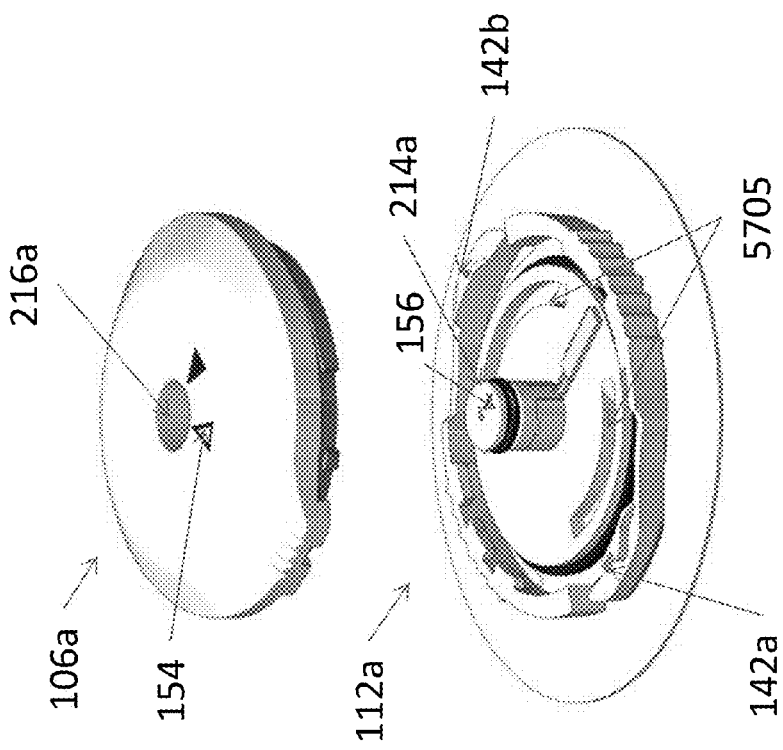

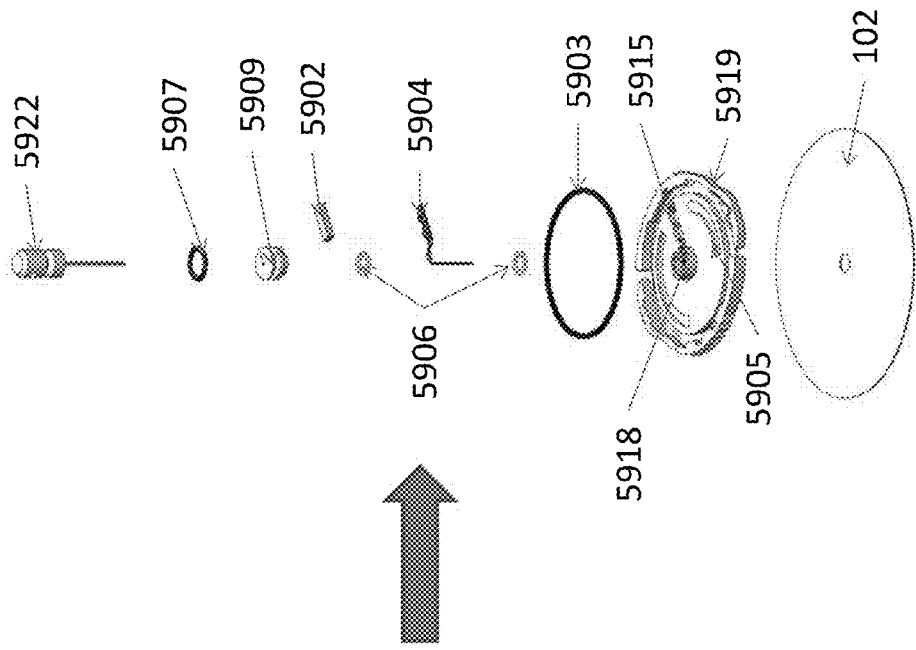
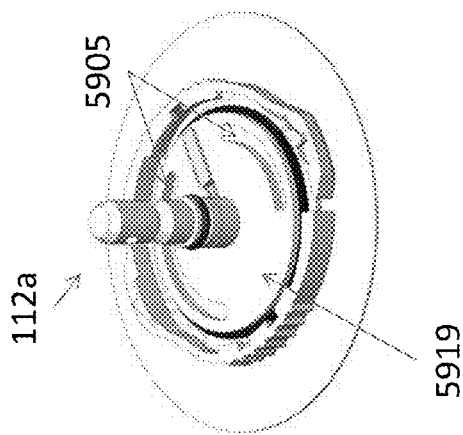
FIG. 59

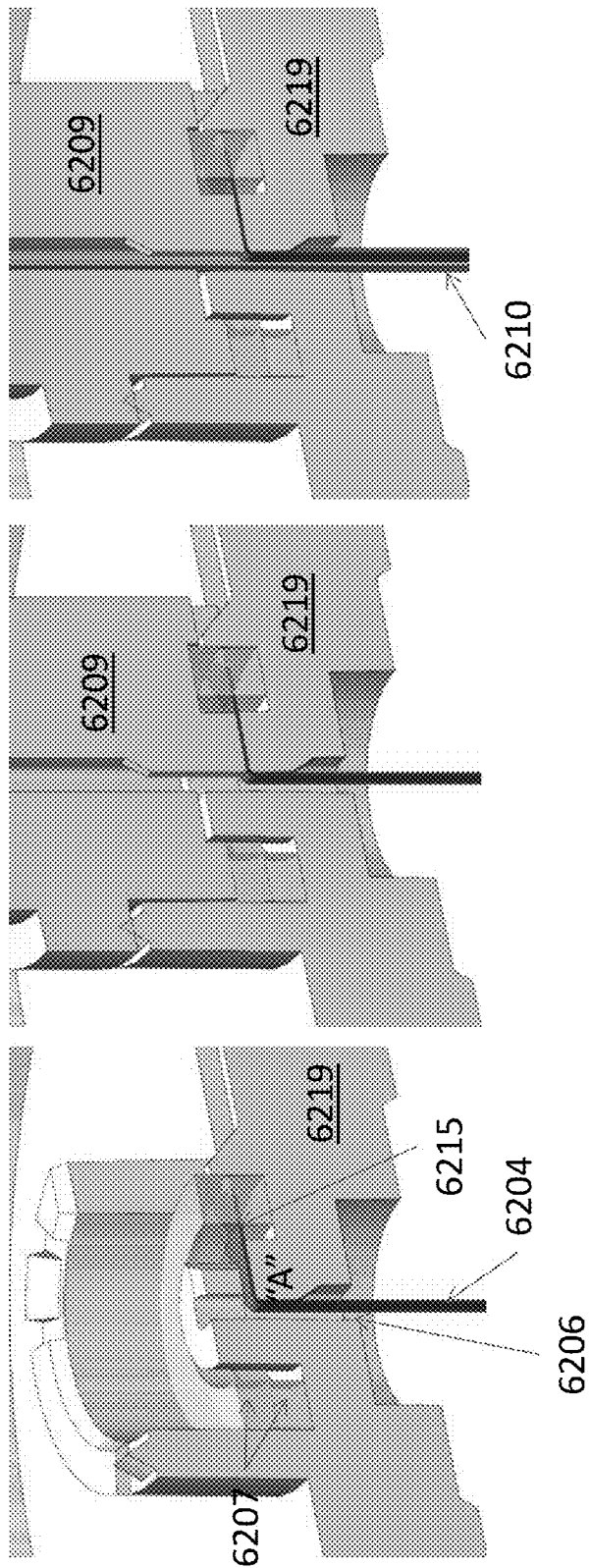

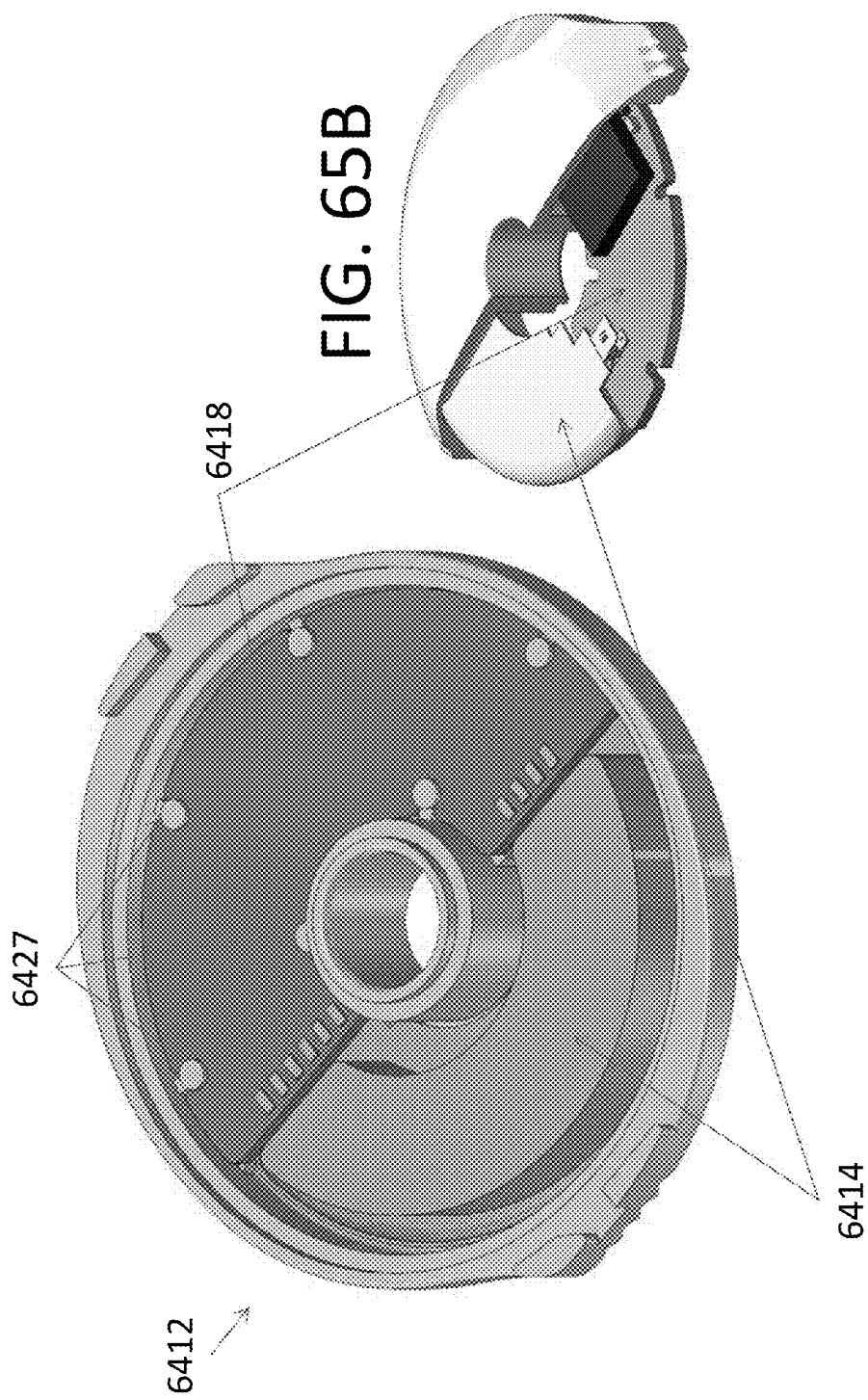

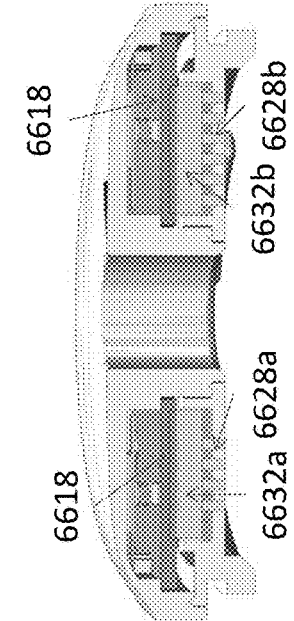
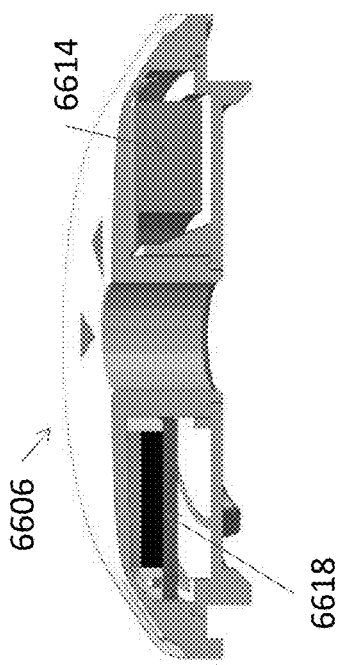
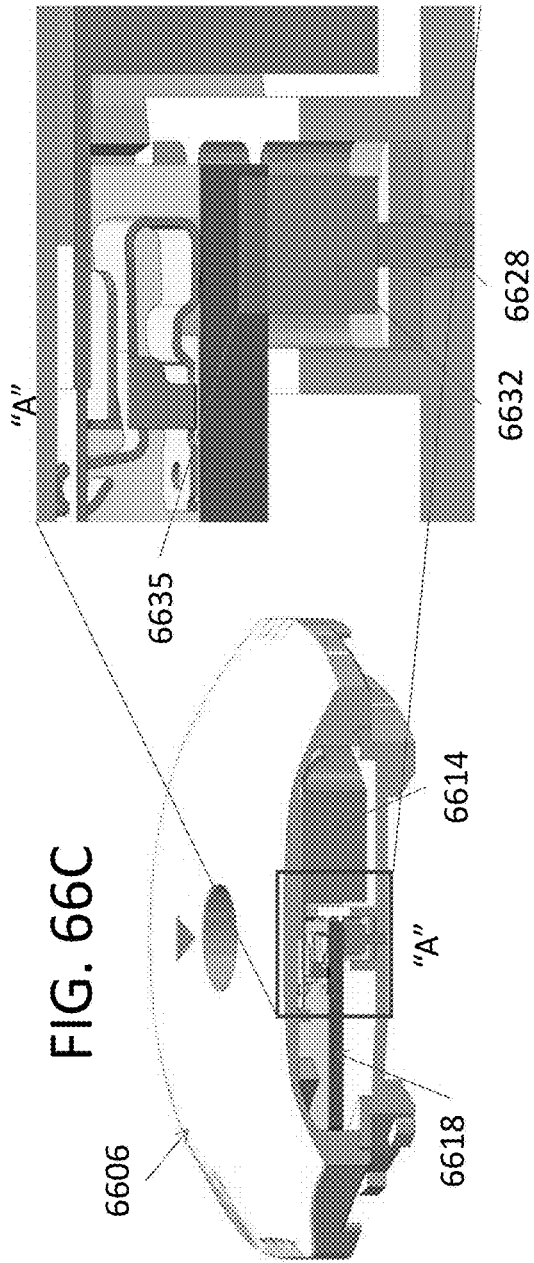

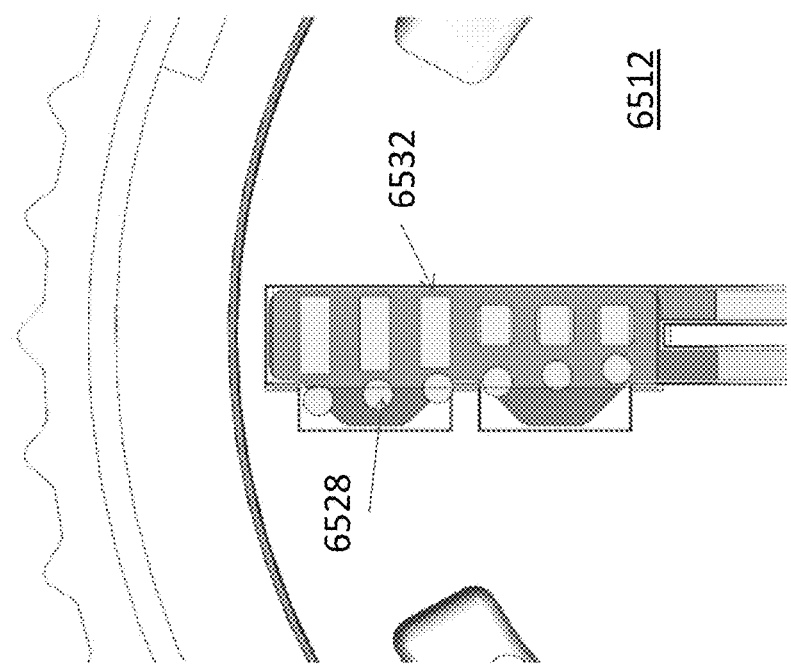

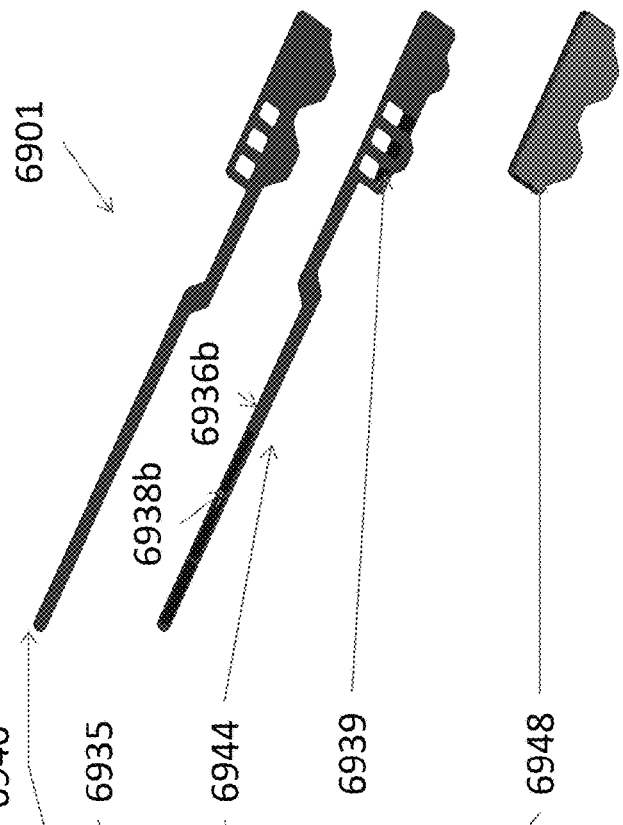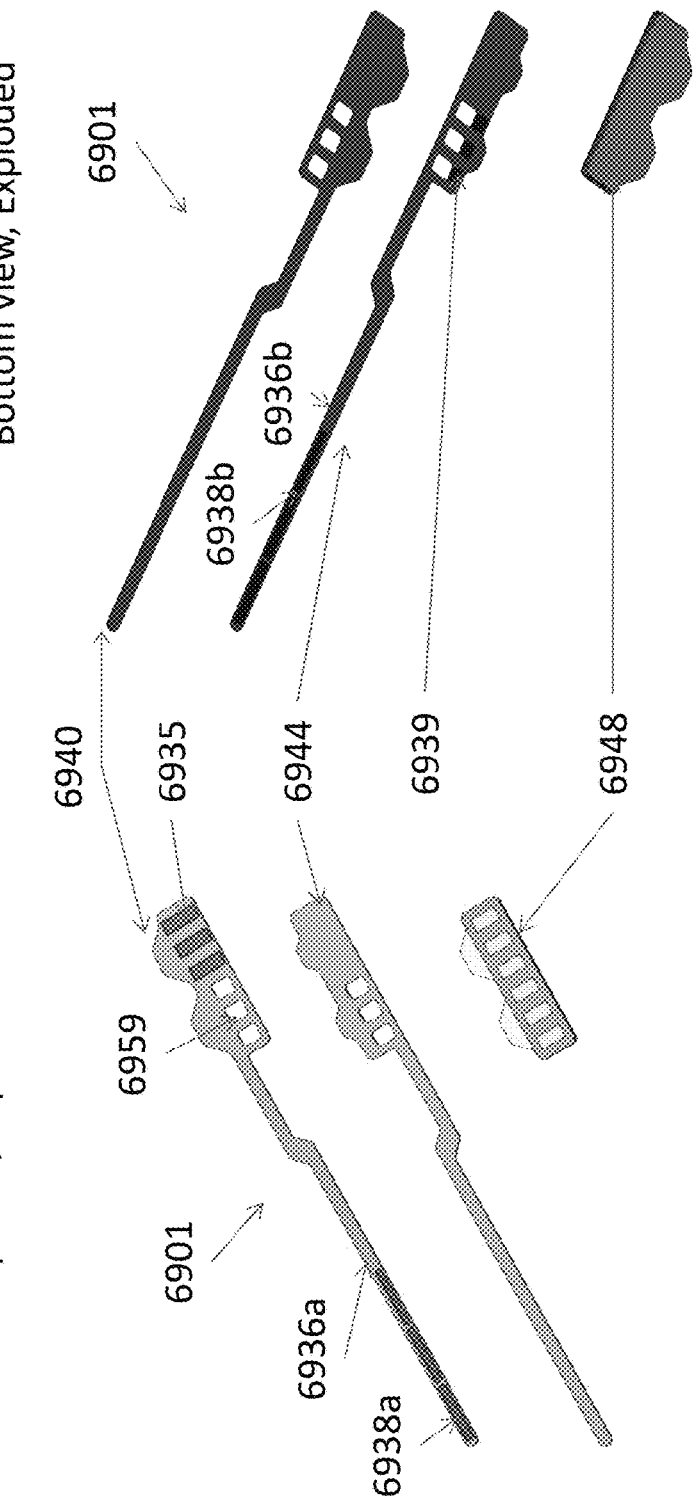

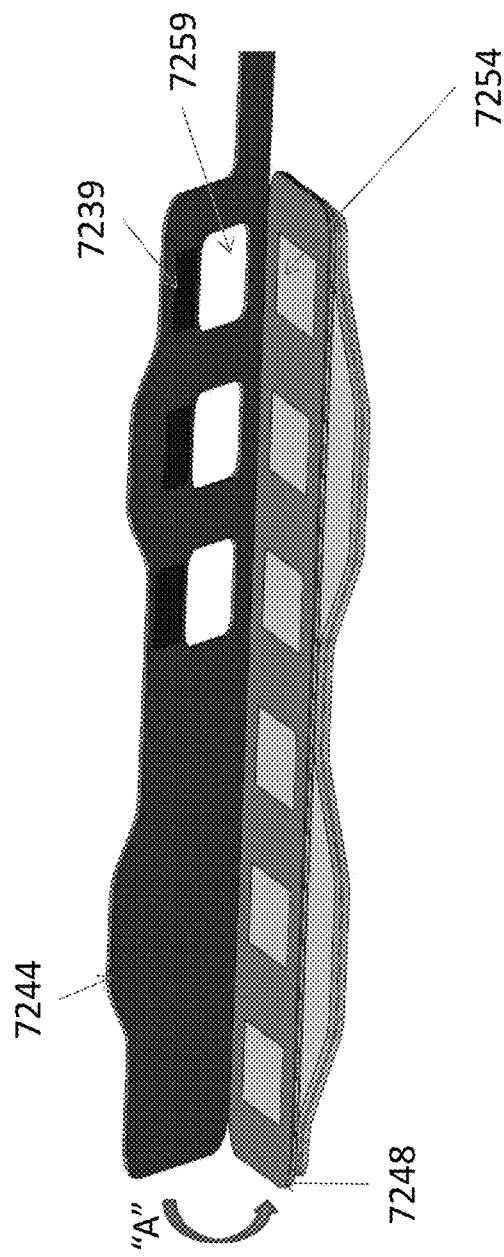
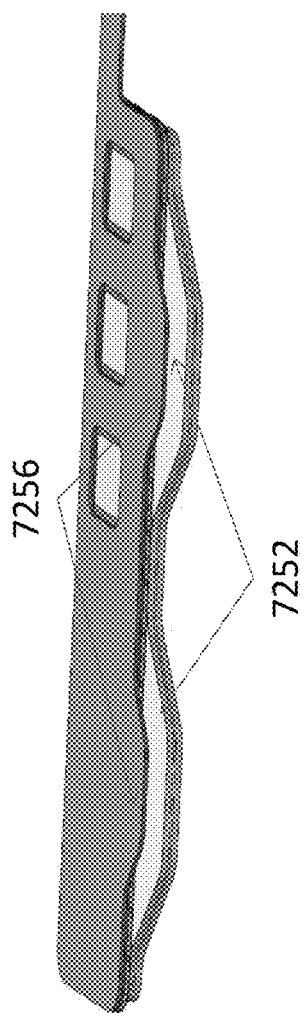
FIG. 72A
FIG. 72B

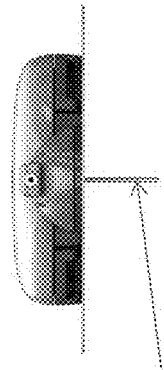
FIG. 83A—Top View
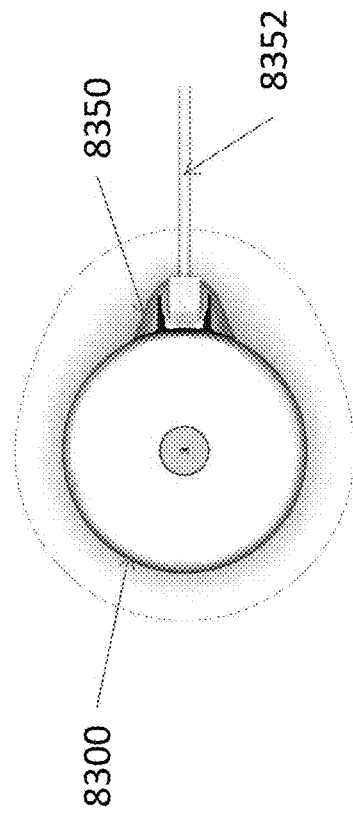
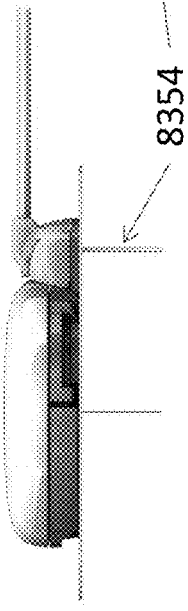
FIG. 83C—Side View
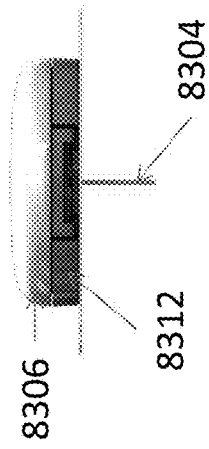
FIG. 83B—Front View
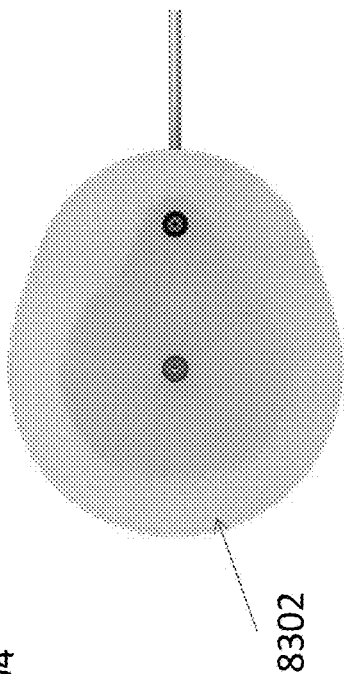
FIG. 83D—Back View
FIG. 83E—Bottom View

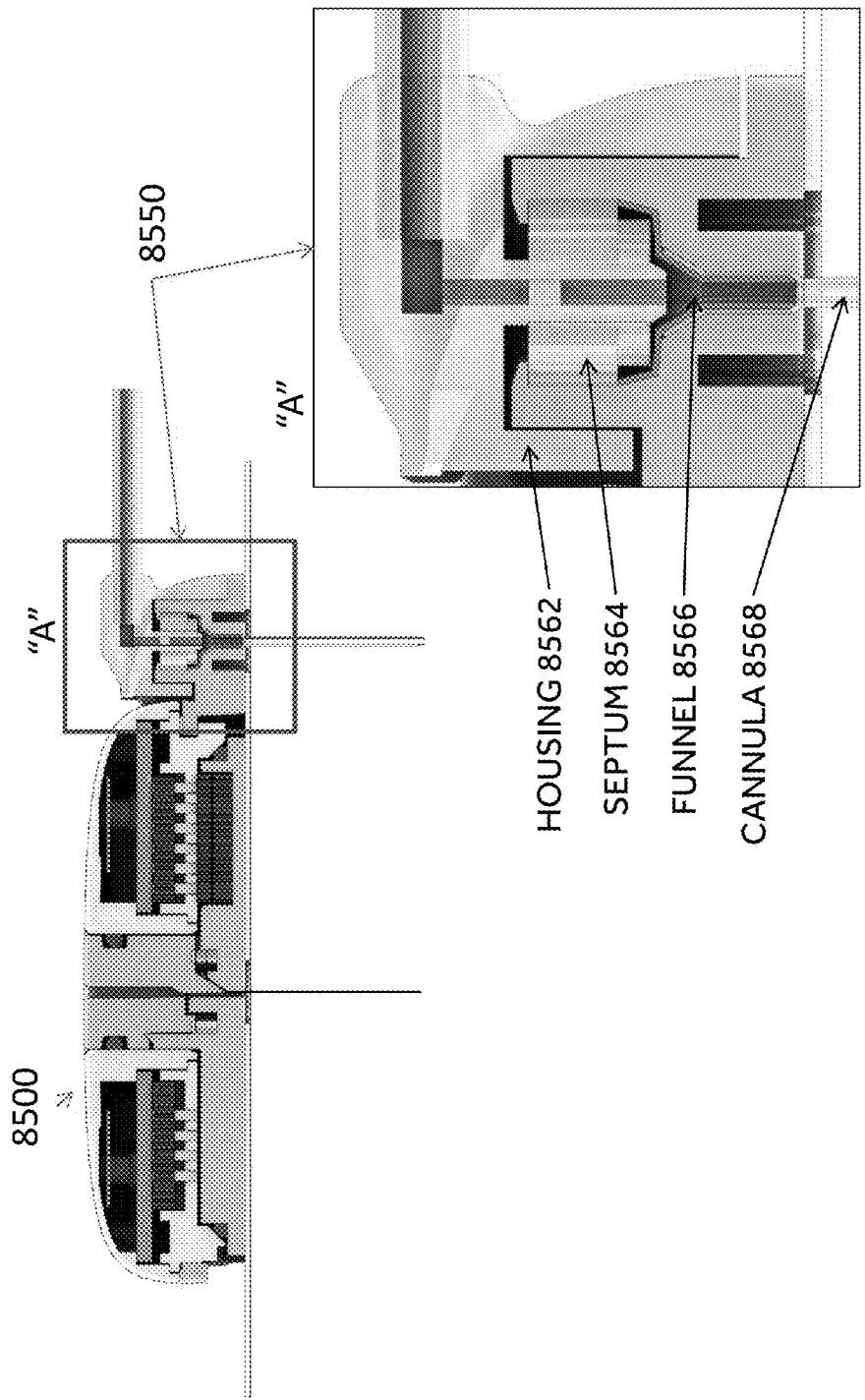

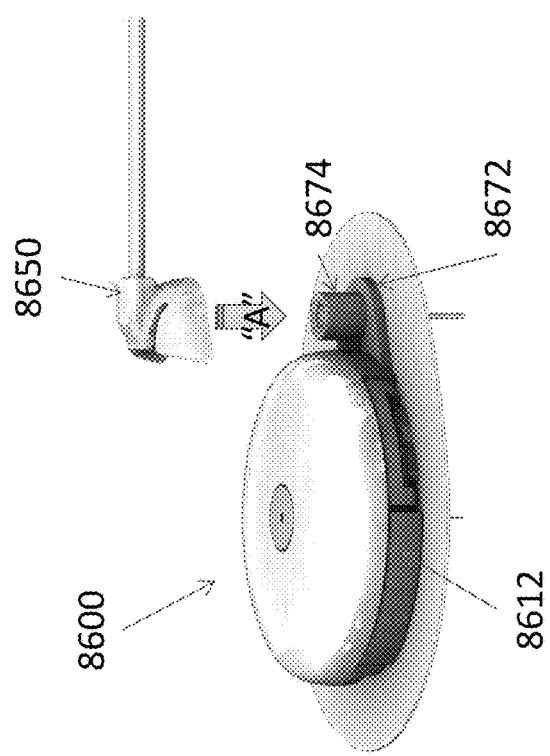

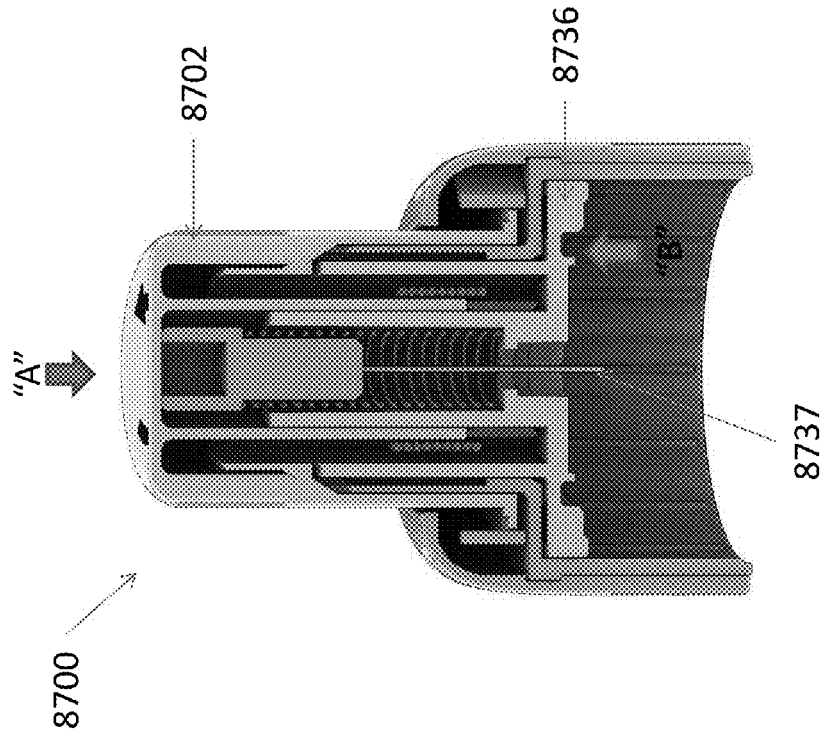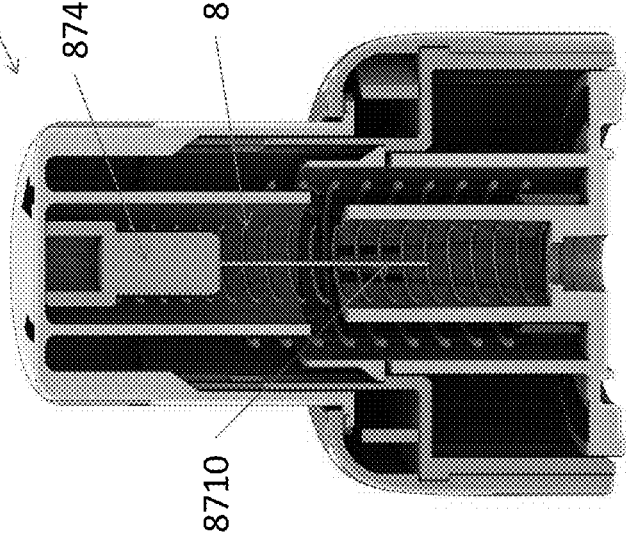

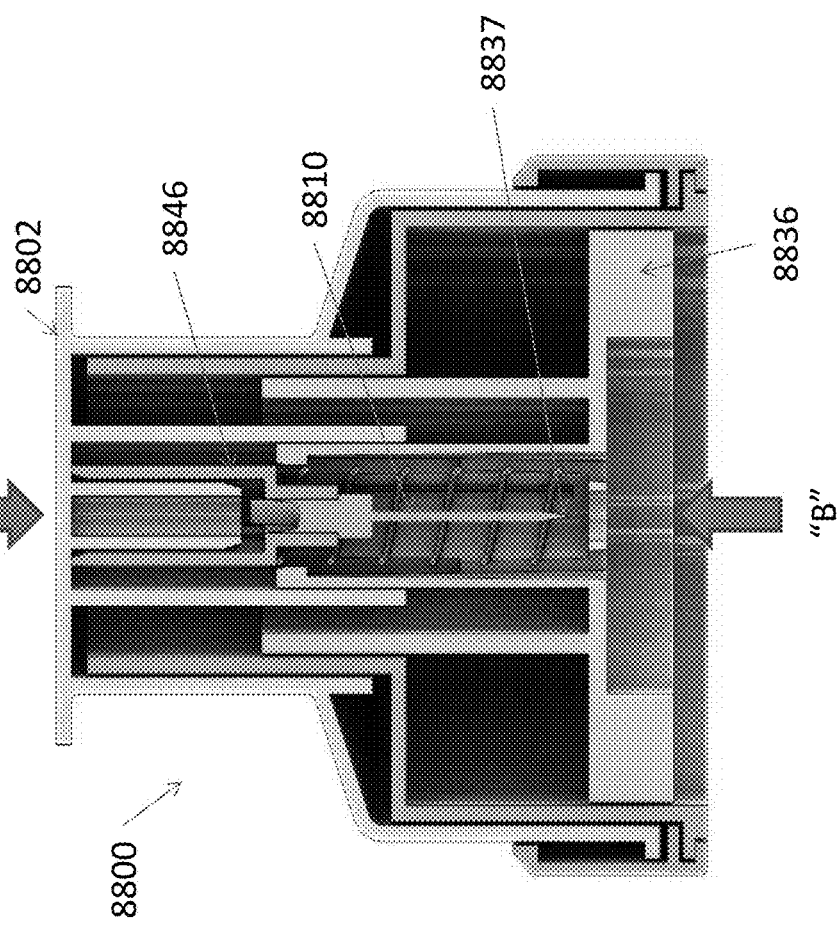

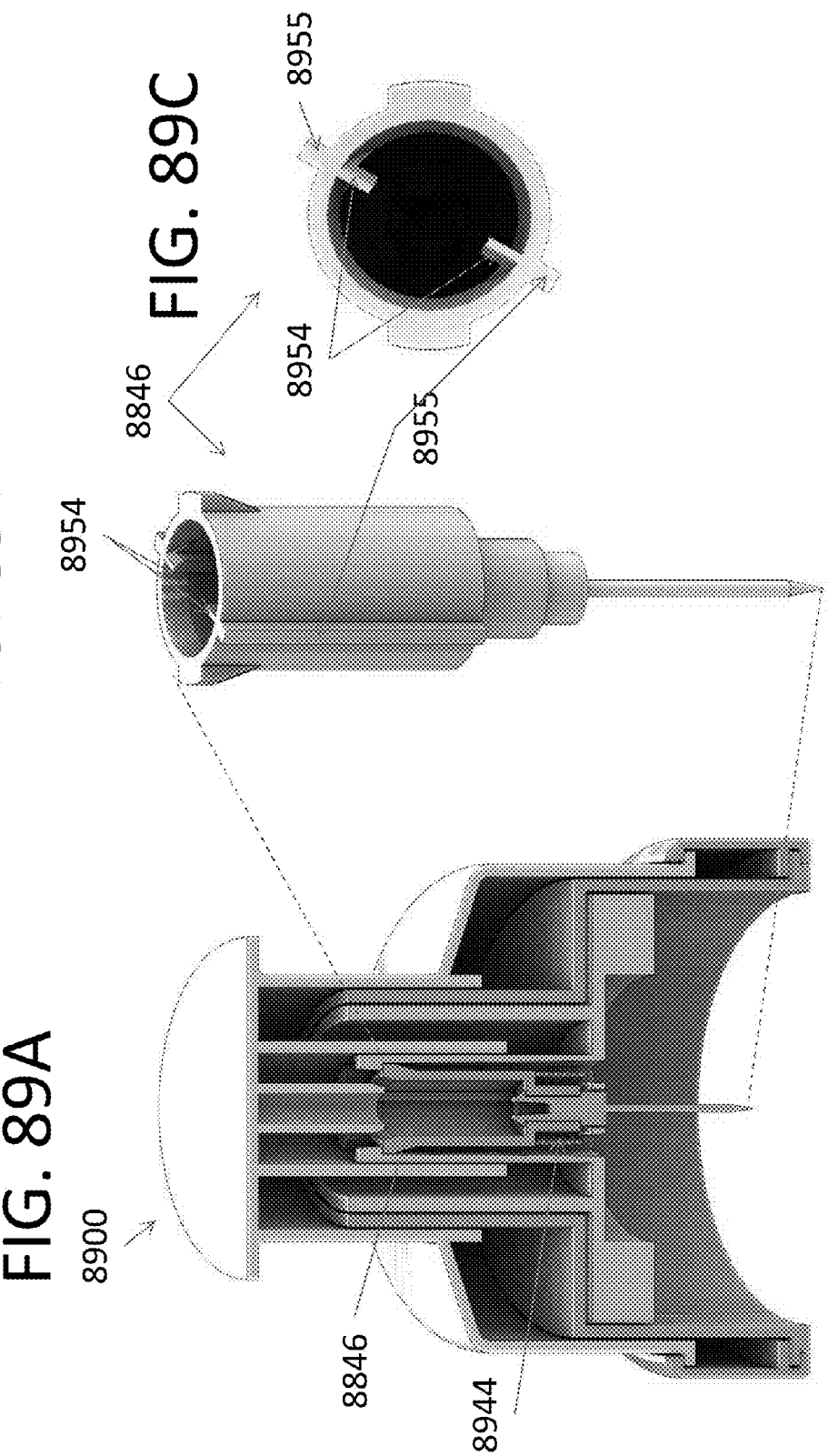

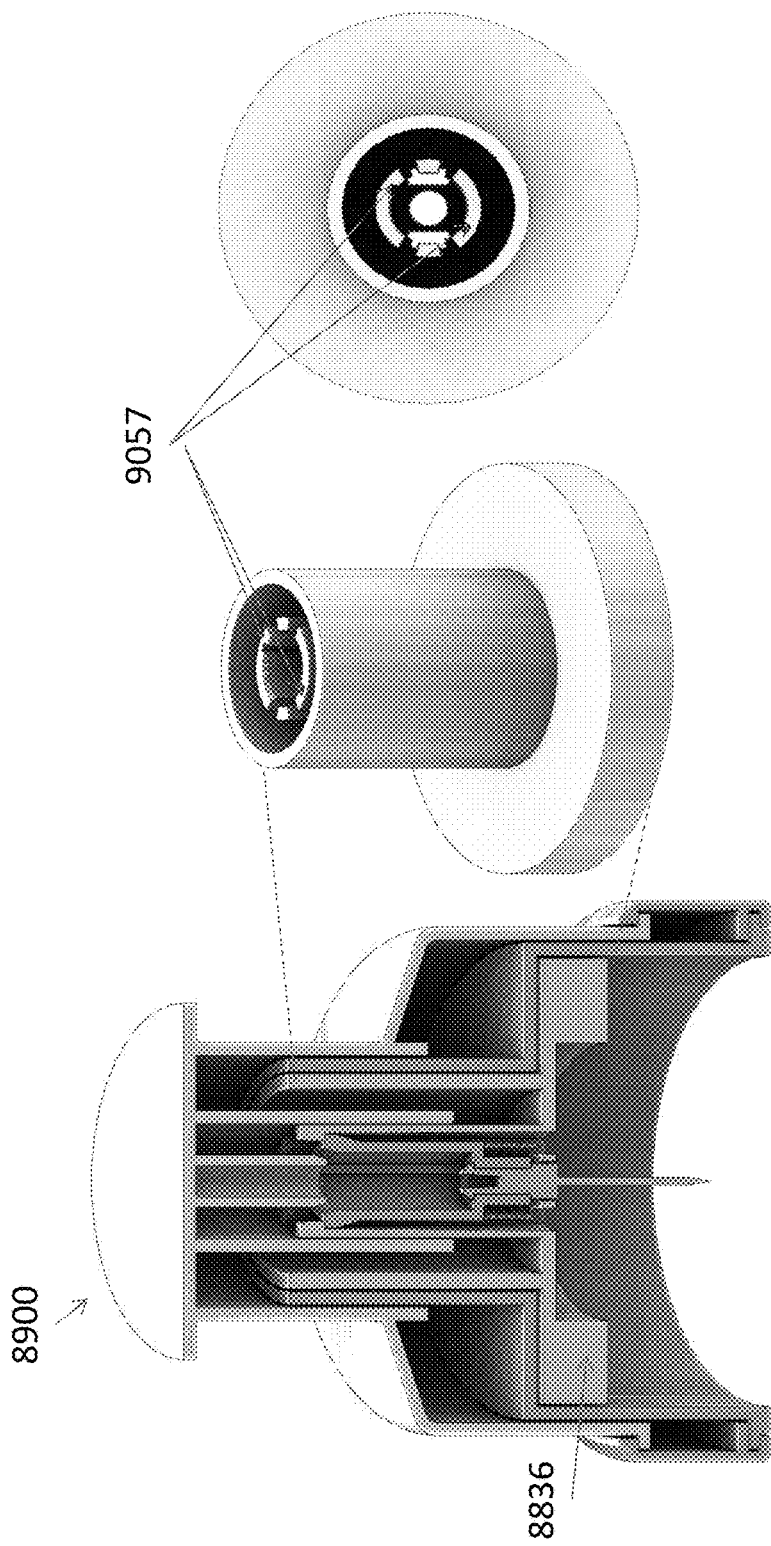

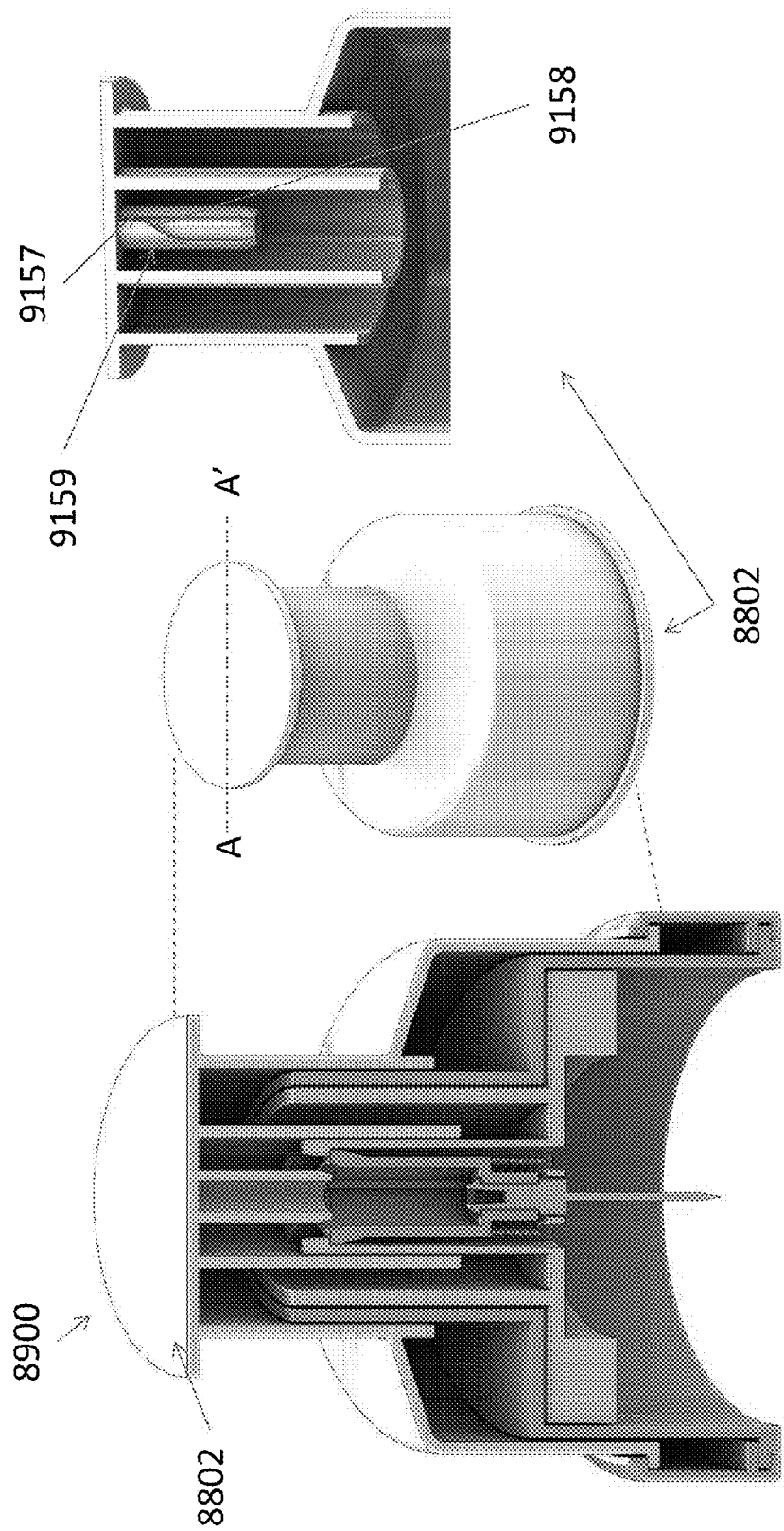

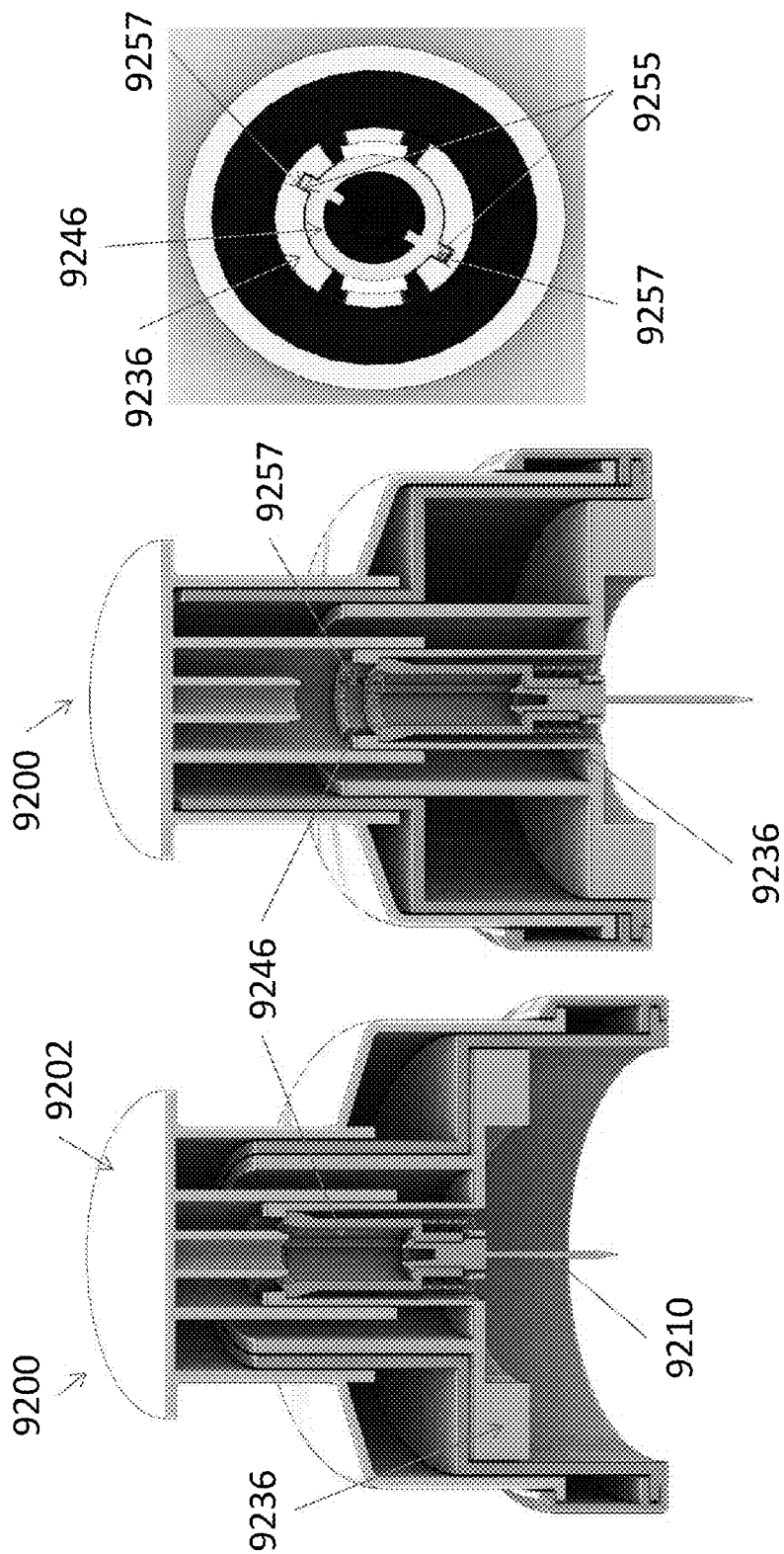

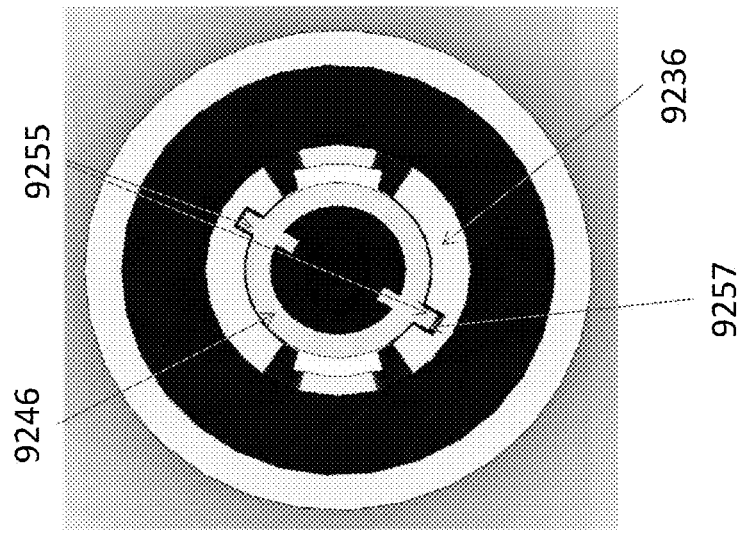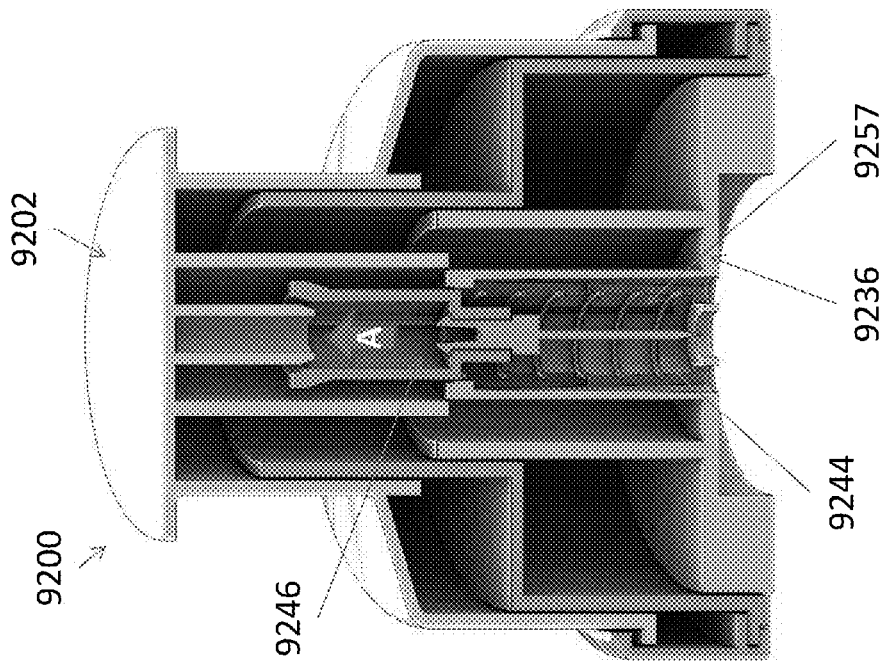

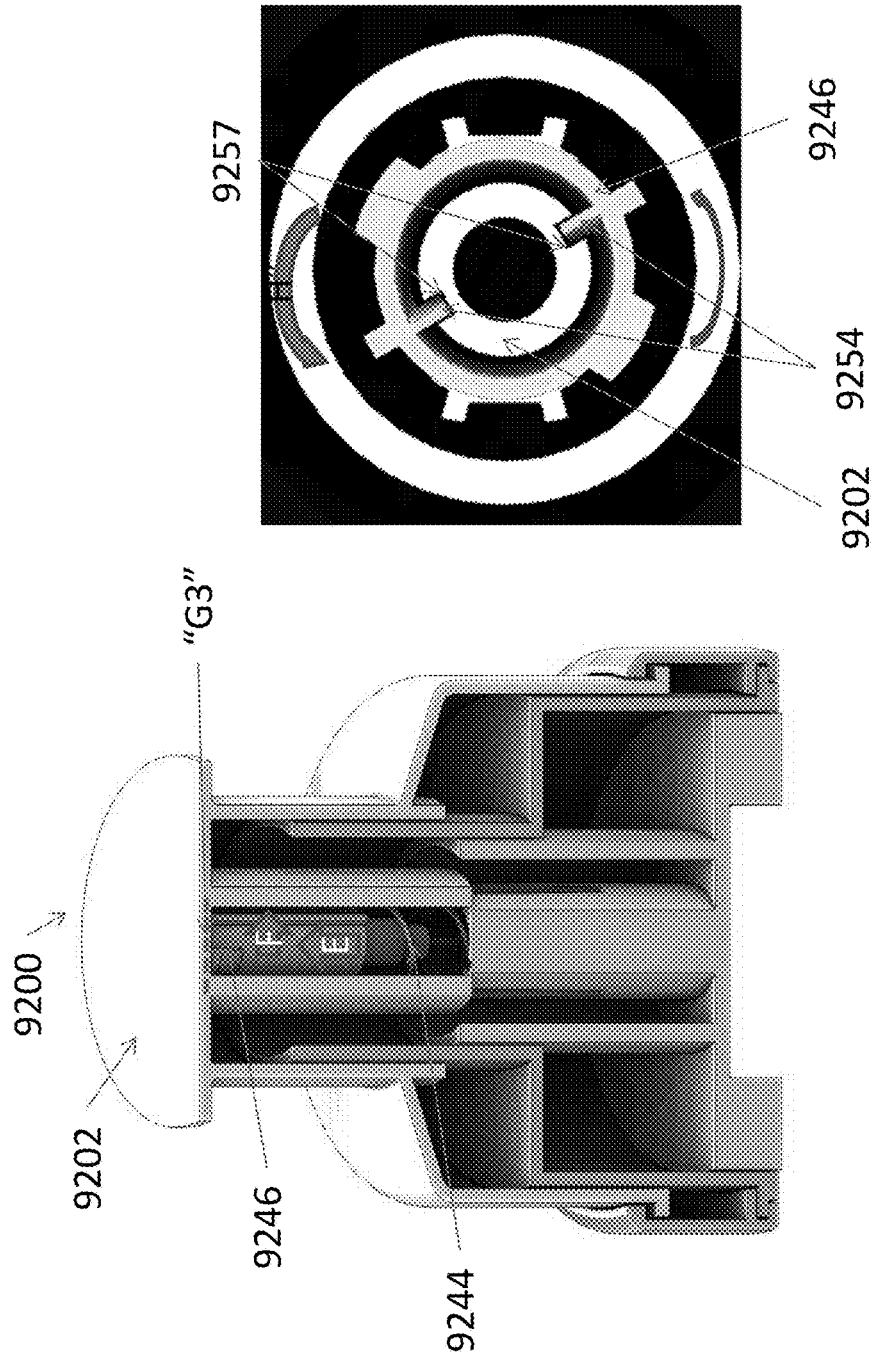

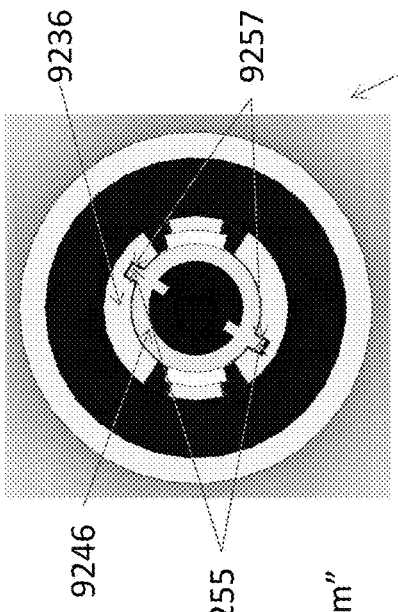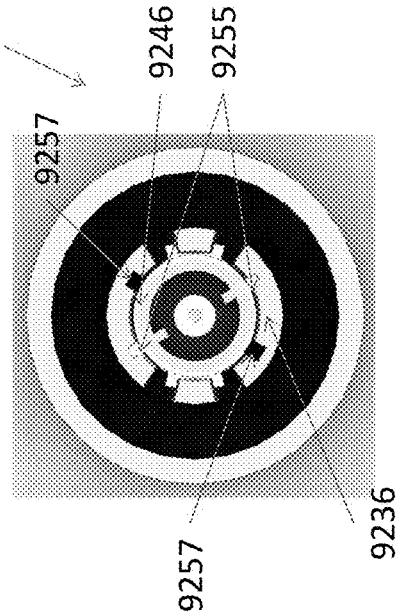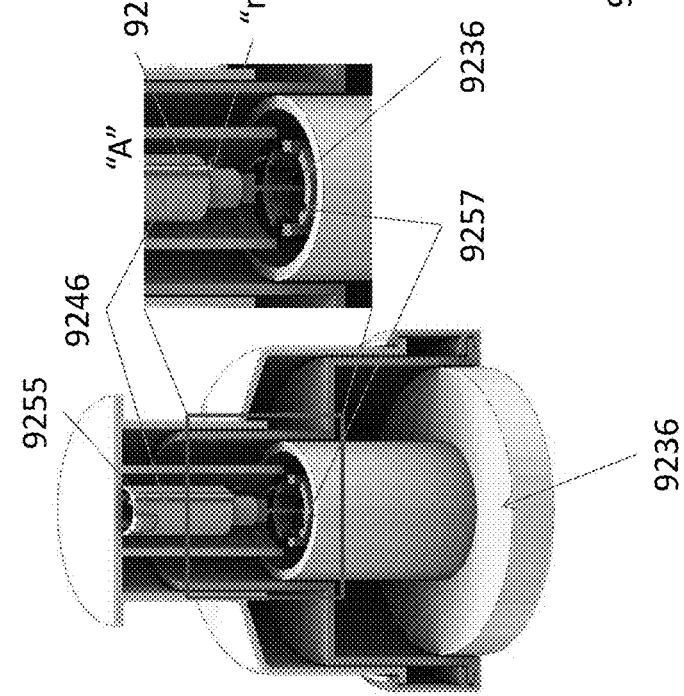

INSERTION DEVICE

RELATED APPLICATIONS

The present disclosure claims priority to and the benefit of U.S. Provisional Patent Application Ser. No. 62/320,290 filed on Apr. 8, 2016, U.S. Provisional Application Ser. No. 62/344,847 filed on Jun. 2, 2016, U.S. Provisional Patent Application Ser. No. 62/344,852 filed on Jun. 2, 2016, and U.S. Provisional Patent Application Ser. No. 62/402,676 filed on Sep. 30, 2016, the contents of which are incorporated herein by reference in their entirety.

TECHNICAL FIELD

Embodiments of the present disclosure generally relate to medical devices, and more particularly, to medical devices or products having a sensor and a transmitter and their associated components, connections and arrangement techniques.

BACKGROUND

Diabetes is a disease in which the body does not produce or properly use insulin. Millions of people in the United States and around the world have been diagnosed with some form of diabetes. Type 1 diabetes results from the body's failure to produce insulin. Type 2 diabetes results from insulin resistance in which the body fails to properly use insulin. In order to effectively manage the disease, diabetics must closely monitor and manage their blood glucose levels through exercise, diet and medications. In particular, both Type 1 and Type 2 diabetics rely on insulin delivery and blood glucose monitoring to control their diabetes.

External infusion devices have been used to deliver medication to a patient as generally described in U.S. Pat. Nos. 6,554,798 and 6,551,276 which are specifically incorporated by reference herein. In addition to delivering medication to a patient, other medical devices have been used to determine body characteristics by obtaining a sample of bodily fluid. A variety of implantable electrochemical sensors have been developed for detecting and/or quantifying specific agents or compositions in a patient's blood. For instance, glucose sensors have been developed for use in obtaining an indication of blood glucose levels in a diabetic patient. Such readings can be especially useful in monitoring and/or adjusting a treatment regimen that typically includes the regular administration of insulin to the patient. Thus, blood glucose readings are particularly useful in improving medical therapies with semi-automated medication infusion pumps of the external type and/or implantable type.

Monitoring blood glucose levels plays an integral role in the management and control of diabetes. Finger stick measurements, glucose sensors and monitors have traditionally been used to check the blood glucose levels of diabetic patients. In recent years, continuous glucose monitoring systems have been developed utilizing the latest sensor technologies incorporating both implantable and external sensors as generally described in U.S. Pat. No. 5,391,250 entitled "Method of Fabricating Thin Film Sensors", U.S. Pat. No. 6,484,046 entitled "Electrochemical Analyte Sensor," and U.S. Pat. Nos. 5,390,671, 5,568,806 and 5,586,553, entitled "Transcutaneous Sensor Insertion Set," all of which are specifically incorporated by reference herein. Newer systems deliver the preciseness of finger stick measurements coupled with the convenience of not having to repeatedly prick the skin to obtain glucose measurements. These newer systems provide the equivalent of over 200 finger stick readings per day. Additionally, continuous glucose monitoring systems allow physicians and patients to monitor blood glucose trends of their body and suggest and deliver insulin based on each patient's particular needs. Accordingly, physicians and medical device companies are always searching for more convenient ways to keep diabetic patients aware of their blood glucose levels throughout the day.

As such, physiological characteristic (or analyte) sensors may be generally used to test analyte levels in patients. For example, thin film sensors may be used for obtaining an indication of blood glucose levels and monitoring blood glucose levels in a diabetic patient. In these instances, a portion of a glucose sensor is positioned subcutaneously/transcutaneously in direct contact with patient extracellular fluid. Glucose sensor readings can be especially useful in adjusting a treatment regimen that typically includes regular administration of insulin to the patient.

A glucose sensor may be packaged and sold as a product that includes certain features or components that allow the patient to position and subcutaneously/transcutaneously implant the sensor. For example, thin film glucose sensors are often implanted subcutaneously/transcutaneously using an introducer needle, which is packaged with the glucose sensor. The introducer needle is used to puncture the skin of a patient at the same time as the sensor is introduced. The introducer needle is then withdrawn, leaving the sensor in the skin of the patient. The introducer needle is used and then discarded after inserting the sensor at the sensor site. Currently, some sensor platforms use a multiple-use, durable insertion device. This type of durable insertion device presents various issues. For example, the use model for this type of durable insertion device is generally complex, that is, the current process requires many complex steps, some of which may require fine motor skills for the user. Current durable insertion devices are also prone to wear and damage. Also, in general, current sensor platforms require users to carry both packaged sensors and an insertion device. If the user is not carrying the insertion device, the user cannot insert the sensor. In addition, durable insertion devices generally require disinfection or cleaning such as in a clinical setting.

Once a continuous glucose sensor is inserted, the continuous glucose sensor is designed to monitor glucose concentration of the patient and a sensor signal is produced that is representative of the glucose concentration. The continuous glucose sensor may use wireless data communication techniques to transmit data indicative of the blood glucose levels to a receiving device such as a portable infusion pump, a glucose monitor device, and/or the like. For example, the transmitted sensor signal may be used to generate a controller input for a controller to generate commands that affect the operation of a delivery system to infuse a liquid, which includes insulin, into the patient.

Typical devices or products generally include a sensor and a transmitter that are placed side by side.

SUMMARY

Embodiments of the present disclosure generally relate to medical devices that include a sensor assembly and a transmitter assembly, for example, a transmitter assembly positioned on top of a sensor assembly. This arrangement addresses issues created by typical side-by-side arrangements including, for example, issues with on-body device stability, robustness of connections, comfort, overall use model, etc.

According to an embodiment, a device includes a sensor assembly that includes: a sensor base having a top surface and a bottom surface, at least one interface disposed on the top surface of the sensor base, where the interface(s) accommodates a sensor stack, the sensor stack including at least one sensor head having at least one electrical contact pad adapted to connect to at least one elastomeric connector. The sensor assembly also includes a mounting base having a first side that attaches to at least a portion of the bottom surface of the sensor base, and a second side that is adapted to adhere to a user's skin. The device also includes a transmitter assembly adapted to connect with the top surface of the sensor base of the sensor assembly, the transmitter assembly including: a transmitter shell and a transmitter cap having an interface adapted to engage with the sensor base; and at least one electronics module including at least one electrical contact disposed on the transmitter cap, where the at least one electrical contact connects with the at least one electrical contact pad of the sensor assembly, where the sensor assembly and the transmitter assembly connect at one or more areas as a single unit in response to a rotating motion by a user.

In a further embodiment, the sensor assembly further includes a sensor extension coupled to the sensor base on a substantially centered location.

In a further embodiment, the sensor extension is an integral part of the sensor base of the sensor assembly.

In a further embodiment, the sensor extension includes a glucose sensor that monitors blood glucose levels in a diabetic patient.

In a further embodiment, the mounting base covers an entire outline of the bottom surface of the sensor base.

In a further embodiment, the electrical contact(s) disposed on the transmitter cap is solid and inflexible.

In a further embodiment, the device further includes a substantially symmetrical round shape.

In a further embodiment, the top surface of the sensor base further includes a sensor base cap extending therefrom that is substantially centered on the top surface of the sensor base.

In a further embodiment, the transmitter cap further comprises an opening substantially centered on the transmitter cap, wherein the opening is fitted to engage with the sensor base cap.

In a further embodiment, the one or more areas where the sensor assembly and the transmitter assembly connect are evenly spaced apart along an outline of the device.

In a further embodiment, the at least one interface that accommodates the sensor stack further includes a cavity disposed on the top surface of the sensor base.

In a further embodiment, the transmitter assembly further includes a wireless transmitter that communicates with a remote device.

In a further embodiment, the at least one electrical contact of the at least one electronics module of the transmitter cap further includes four charging or communications contacts.

In a further embodiment, the at least one electrical contact of the at least one electronics module of the transmitter cap further comprises six sensor contacts.

In a further embodiment, the six sensor contacts further comprise 1 reference electrode (RE), 1 counter electrode (CE) and 4 working electrodes (WE).

In a further embodiment, the at least one electrical contact of the at least one electronics module is substantially flush with a bottom surface of the transmitter cap.

In a further embodiment, the sensor base further includes at least one tab adapted to engage with at least one slot disposed on the transmitter cap to lock the sensor assembly and the transmitter assembly together axially.

In a further embodiment, the sensor base further includes at least one snap arm adapted to lock the transmitter assembly and the sensor assembly together rotationally.

In a further embodiment, the sensor base further includes at least one interface having at least one feature that matches at least one corresponding interface of the transmitter cap to lock the sensor assembly and the transmitter assembly together axially or rotationally.

In a further embodiment, the at least one interface of the sensor base further includes at least one slot having features that match the at least one corresponding interface of the transmitter cap.

In a further embodiment, the at least one corresponding interface of the transmitter cap further includes at least one rail.

In a further embodiment, the elastomeric connector further includes a top square cross section.

In a further embodiment, the elastomeric connector further includes a connector that includes alternating conductive and insulating regions.

In a further embodiment, the elastomeric connector further includes a ZEBRA connector.

In a further embodiment, the transmitter cap further includes a shell subassembly including a housing for a custom battery adjoining a substrate portion on which a PCB board is disposed, where the housing and the substrate portion are compressed to fit together without requiring solder or other connections.

In a further embodiment, the sensor assembly and the transmitter assembly include respective clocking features that do not have rotational symmetry and prevent the transmitter assembly from being connected to the sensor assembly in a particular orientation where the at least one electrical contact disposed on the transmitter cap does not align with the at least one electrical contact pad of the sensor assembly.

In a further embodiment, the clocking features further include at least one lug positioned along an outline of the transmitter cap and at least one corresponding opening positioned along an outline of the sensor base of the sensor assembly.

According to another embodiment, a device comprises: a sensor assembly including: a sensor base having a top surface and a bottom surface, and a mounting base having a first side that attaches to at least a portion of the bottom surface of the sensor base, and a second side that is adapted to adhere to a user's skin. The device also includes a transmitter assembly adapted to connect with the top surface of the sensor base of the sensor assembly, the transmitter assembly including: a transmitter shell and a transmitter cap having at least one interface adapted to engage with the sensor base; where the sensor assembly and the transmitter assembly connect at one or more compression areas as a single unit in response to a rotating motion by a user.

In a further embodiment, the two compression areas are automatically squeezed or compressed in response to the user applying the rotating motion in a first direction to lock the sensor assembly into place.

In a further embodiment, the sensor assembly and the transmitter assembly are disconnected in response to the user squeezing or compressing the two compression areas while applying a rotating motion in a second direction opposite from the first direction.

Sensor Connections

According to an embodiment, a sensor transmitter assembly includes: a sensor assembly including a sensor module where a first sensor including a first sensor head having at least one first sensor contact pad is combined with a second sensor including a second sensor head having at least one second sensor contact pad. The sensor transmitter assembly also includes a transmitter assembly positioned on a top of the sensor assembly to form a single unit, the transmitter assembly having at least one transmitter contact disposed on a base of the transmitter assembly, where the at least one first sensor contact pad and the at least one second sensor form a connection path with the at least one transmitter contact.

In a further embodiment, the first sensor and the second sensor are discrete single-sided sensors.

In a further embodiment, each of the first sensor and the second sensor includes 1 RE, 1CE and 2 pairs of independent WE s that correspond to six contacts disposed on the base of the transmitter assembly.

In a further embodiment, each RE of the first sensor and the second sensor are shorted together and connected to a shared RE transmitter contact.

In a further embodiment, each CE of the first sensor and the second sensor are shorted together and connected to a shared CE transmitter contact.

In a further embodiment, each of the first sensor contact pads and the second sensor contact pads include a window cut therethrough.

In a further embodiment, the first sensor head and the second sensor head each have staggered windows cut through respective contact pads where at least one contact pad for each WE remains active.

In a further embodiment, each of the first sensor contact pads and the second sensor contact pads includes at least one trace leading to a respective electrode.

In a further embodiment, the trace(s) of each contact pad runs to a first side, where a contact pad is deactivated as a result of cutting a window on the first side of the contact pad.

In a further embodiment, the sensor module is assembled together before installation into a sensor base of the sensor assembly.

In a further embodiment, the first sensor head or the second sensor head further includes a sensor head extension on which at least one conducting pad is integrated.

In a further embodiment, the first sensor head or the second sensor head is adapted to be folded along a line that places the at least one conducting pad in contact with at least one contact pad.

In a further embodiment, the first sensor head further includes at least one conducting pad integrated on it.

In a further embodiment, the first sensor and the second sensor are interlaced, where a distal end of the first sensor is on top and the second sensor head is on bottom such that the second sensor contact pad(s) are placed against the conducting pad(s) integrated on the first sensor.

In a further embodiment, a signal from the at least one first sensor contact pad travels directly through an elastomeric connector to the at least one transmitter contact.

In a further embodiment, a signal from the at least one second sensor contact pad travels through the at least one conducting pad integrated on the first sensor head and through an elastomeric connector to the at least one transmitter contact.

According to another embodiment, a sensor transmitter assembly includes: a sensor module where a first sensor including a first sensor head having at least one first sensor contact pad is combined with a second sensor including a second sensor head having at least one second sensor contact pad, where the sensor module further includes a flex connector, where the first sensor and the second sensor are assembled to the flex connector. The sensor transmitter assembly also includes: a transmitter assembly positioned on a surface of the sensor module, the transmitter assembly having at least one transmitter contact disposed on a base of the transmitter assembly, where the at least one first sensor contact pad and the at least one second sensor form a connection path with the at least one transmitter contact.

In a further embodiment, the flex connector includes at least one conducting pad(s) that are isolated from each other, where the conducting pads of the flex connector conduct a signal from at least one of the first sensor contact pad(s) or the second sensor contact pad(s) to an elastomeric connector.

In a further embodiment, the flex connector further includes a double-sided adhesive on a top side and a bottom side, where the flex connector is adapted to be bonded to the first sensor and the second sensor on the top side and to a sensor base of the sensor assembly on the bottom side.

According to yet another embodiment, a method for connecting a sensor transmitter assembly includes: forming a back to back sensor combination for a sensor transmitter assembly including: creating windows through a first contact pad head of a first sensor where at least one window results in at least one active WE contact pad on the first sensor; creating windows through a second contact pad head of a second sensor where at least one window of the second contact pad results in at least one active WE contact pad on the second sensor, where the first sensor and the second sensor have mirrored window patterns across each respective contact pad head. The method also includes placing the first sensor back to back with the second sensor where the windows of the first sensor and the windows of the second sensor are aligned and provide a signal path between contact pads of the first contact pad head and the second contact pad head. The method further includes forming a sensor connector stack by placing the back to back sensor combination between a first elastomeric connector and a second elastomeric connector. And the method also includes connecting a transmitter assembly to the sensor assembly, where the sensor connector stack is compressed between at least one transmitter contact and a sensor base of the sensor assembly, where the signal path extends to the at least one transmitter contact.

Sensor Lockouts

According to an embodiment, a device includes: a sensor assembly having at least one sensor lockout having at least one feature particular to a generation of the sensor assembly; and a transmitter assembly having at least one transmitter lockout having at least one feature particular to a generation of the transmitter assembly, where the sensor assembly and the transmitter assembly connect with each other as a result of the at least one feature of the at least one sensor lockout matching the at least one feature of the transmitter lockout.

In a further embodiment, the sensor assembly and the transmitter assembly are functionally incompatible with each other, where the sensor assembly and the transmitter assembly do not connect with each other as a result of the at least one feature of the at least one sensor lockout not matching the at least one feature of the at least one transmitter lockout.

In a further embodiment, the at least one sensor lockout and the at least one transmitter lockout are included in an interchangeable mold insert adapted to be changed independently.

In a further embodiment, the at least one sensor lockout and the at least one transmitter lockout further include at least one slot and at least one rail on respective surfaces of the sensor assembly and the transmitter assembly that do not match and block the transmitter assembly from fully rotating onto and making a connection with a non-compatible sensor assembly.

In a further embodiment, the at least one sensor lockout and the at least one transmitter lockout further include at least one slot and at least one rail on respective surfaces of the sensor assembly and the transmitter assembly that match each other and allows the transmitter assembly to fully rotate onto and make a connection with a compatible sensor assembly.

In a further embodiment, the at least one feature particular to the generation of the sensor assembly and the at least one feature particular to the generation of the transmitter assembly further include at least one of a length, a width, a shape or a positioning.

In a further embodiment, the at least one feature particular to the generation of the sensor assembly further includes a placement along a predetermined diameter dimension on a sensor assembly surface, and the at least one feature particular to the generation of the transmitter assembly further includes a placement along a predetermined diameter dimension on a transmitter assembly surface.

According to another embodiment, a device comprises: a first assembly including a first interface, and a second assembly comprising a second interface, where the second assembly is incompatible for use with the first assembly, and where the first interface and the second interface block the first assembly from connecting with the incompatible second assembly.

In a further embodiment, the first interface and the second interface block the second assembly from fully rotating onto and making a connection with the incompatible second assembly.

In a further embodiment, the first interface and the second interface further include lockout features including at least one of a length, a width, a depth, a shape or a positioning on a corresponding first assembly or second assembly.

In a further embodiment, the first interface further includes a slot, and the second interface further includes a rail that does not match the slot.

In a further embodiment, the device includes an interchangeable mold insert adapted to be changed such that lockout features of the first interface or the second interface are changed.

In a further embodiment, the first interface and the second interface are located on respective noncritical surfaces of the first assembly and the second assembly.

According to yet another embodiment, a device comprises: a sensor assembly having sensor mechanical lockouts including a first sensor mechanical lockout feature and a second sensor mechanical lockout feature; and a transmitter assembly having transmitter mechanical lockouts, where the first sensor mechanical lockout feature defines a generation of the sensor assembly, and the second sensor mechanical sensor feature determines a generation of transmitter assembly that will fit with the sensor assembly.

In a further embodiment, the first sensor mechanical lockout feature includes a first slot and a second sensor mechanical lockout feature includes a second slot.

In a further embodiment, the transmitter mechanical lockouts further include at least one rail.

In a further embodiment, the transmitter mechanical lockouts further include a first transmitter mechanical lockout feature that defines a generation of the transmitter assembly, and a second transmitter mechanical lockout feature that determines which generation of sensor assembly will fit with the transmitter assembly.

In a further embodiment, the transmitter assembly initially engages with the sensor assembly by lowering down the transmitter assembly onto the sensor assembly and rotating the transmitter assembly on the sensor assembly, wherein the transmitter mechanical lockouts rotate through the sensor mechanical lockouts.

In a further embodiment, the second sensor mechanical lockout features match the transmitter mechanical lockouts so that full rotation of the transmitter mechanical lockouts is allowed and a connection is completed.

In a further embodiment, wherein the second sensor mechanical lockout features do not match the transmitter mechanical lockouts so that full rotation of the transmitter mechanical lockouts is prevented and a connection is not completed.

Duo

According to an embodiment, a device includes: a sensor transmitter assembly including a transmitter assembly placed on top of a sensor assembly to form a single unit, where a sensor portion extends from the sensor assembly and is adapted to be positioned in direct contact with a user's extracellular fluid. The device also includes an infusion set combined with the sensor transmitter assembly, where the infusion set is connected to a connection portion that extends from the sensor assembly, where a cannula extends from the infusion set, and the cannula is adapted to be introduced into a body of the user for infusing fluids.

In a further embodiment, the sensor portion extends from the sensor assembly from a substantially centered location.

In a further embodiment, the sensor assembly provides structural support to the sensor portion and facilitates entry into the body of the user.

In a further embodiment, the infusion set further includes an insertion conduit adapted to be connected to a reservoir or other supply device.

In a further embodiment, the device includes a mounting base for fastening the combined sensor transmitter assembly and infusion set, where the mounting base adheres to the user's skin.

In a further embodiment, the infusion set further includes a housing that engages with the connection portion, a septum, and a funnel.

In a further embodiment, the septum is compressed between the funnel and the connection portion.

In a further embodiment, when the housing is connected to the connection portion, the septum forms a radial seal around a needle contained in the housing, creating a sealed fluid path between tubing of the housing and the cannula, and the funnel compresses the cannula against the connection portion, where the cannula is mechanically retained within the connection portion, and a fluid tight seal is created between the funnel, the cannula, and the connection portion.

According to another embodiment, a combined sensor and infusion set include: a sensor assembly including a sensor extending from a substantially centered location on a bottom side of the sensor assembly; a connection portion extending from a base of the sensor assembly; and an infusion set including a cannula extending from a bottom side of the infusion set, a housing that engages with the connection portion, and a septum compressed between a funnel and the connection portion.

In a further embodiment, the combined sensor and infusion set include a transmitter assembly positioned on top of the sensor assembly as a single unit.

In a further embodiment, the sensor assembly provides structural support to the sensor and facilitates entry of the sensor into a body of a patient.

In a further embodiment, the cannula is adapted to be introduced into a body of a patient for infusing fluids to the patient.

In a further embodiment, the infusion set includes an insertion conduit adapted to be connected to a reservoir or other supply device.

In a further embodiment, the combined sensor and infusion set is fastened by a mounting base or patch that adheres to a patient's body.

In a further embodiment, when the housing is engaged, the septum forms a radial seal around a needle included in the housing, creating a sealed fluid path between tubing of the housing and the cannula.

In a further embodiment, the funnel compresses the cannula against the connection portion thus mechanically retaining the cannula within the connection portion and creating a fluid tight seal between the funnel, the cannula and the connection portion.

According to yet another embodiment, a combined sensor and infusion set include: a sensor assembly including a connector portion that extends from a portion of the sensor assembly, where the connection portion comprises a connector cap; and an infusion set including a cannula adapted to fittingly engage with the connector cap of the connection portion, where the sensor assembly and the infusion snap mechanically at at least one interface of the connection portion.

In a further embodiment, the at least one interface of the connection portion further includes at least one notch.

In a further embodiment, the sensor assembly and the infusion set snap mechanically as a result of a top down connection.

In a further embodiment, the combined sensor and infusion set further include a transmitter assembly positioned on top of the sensor assembly as a single unit.

Insertion Device

According to an embodiment, an insertion device includes: a plunger coupled with a lock collar, where the insertion device houses contents including at least one component including: a striker including at least one self-locking striker snap arm configured to keep the insertion device in a cocked position while not in use such that the striker is kept from firing by a striker spring captured between the plunger and the striker when the insertion device is in the cocked position; a sensor assembly including a sensor disposed on a bottom surface of the sensor assembly, where a mounting base having a first side attaches to the bottom surface of the sensor assembly, and a second side of the mounting base is exposed; and a needle carrier adapted to hold a piercing member, the needle carrier captured between the striker and a needle carrier spring where at least one self-releasing snap keeps the needle carrier cocked, where the plunger prevents the self-releasing snap(s) from repositioning and releasing the needle carrier; such that when the insertion device is fired in response to a user depressing at least a portion of the plunger, the striker fires the needle carrier holding the piercing member such that the self-locking striker snap arm(s) are positioned to enter a groove to allow the striker to snap down, where after the insertion device is fired, the needle carrier is retracted in response to the user releasing the plunger such that the piercing member is encapsulated within the housing of the insertion device.

In a further embodiment, the insertion device is single use and disposable.

In a further embodiment, the insertion device includes a lid that completely covers a bottom surface of the lock collar to protect the contents within the insertion device.

In a further embodiment, the insertion device is unlocked by the user using two unlocking directional forces including performing a rotation motion while applying a downward force on the plunger to prevent the lock collar from accidentally unlocking.

In a further embodiment, the sensor assembly is fastened to a user's skin via the mounting base and the sensor is introduced into a body of the user upon firing of the needle carrier and the piercing member of the insertion device.

In a further embodiment, the sensor is introduced into a body of the user upon the user pushing on the plunger using a minimum pushing force for a certain minimum travel or distance.

In a further embodiment, the sensor assembly is automatically left behind on an insertion site upon the user pulling away the insertion device away from the insertion site after the insertion device is fired.

In a further embodiment, after the insertion device is used to insert the sensor extension into a body of a user, a transmitter assembly is connected to the sensor assembly at one or more areas as a single unit in response to a rotating motion by the user.

In another embodiment, a method for an insertion device mechanism includes: unlocking an insertion device that includes a plunger having at least one clearance slot coupled to a lock collar having at least one rib in response to a user rotating the plunger such that the clearance slot(s) align with the rib(s) of the lock collar; upon unlocking the insertion device, firing the insertion device at an insertion site in response to the user pressing the plunger; upon firing of the insertion device, causing a piercing member to insert a sensor of a sensor assembly into a body of the user and causing the sensor assembly to adhere to the body of the user; and retracting a needle carrier having the piercing member in response to the user releasing the plunger such that the piercing member is encapsulated inside the insertion device.

In a further embodiment, the firing the insertion device further includes compressing a striker spring in response to the user pressing the plunger wherein the rib(s) of the plunger deflect at least one self-locking striker snap arm.

In a further embodiment, once the sensor assembly is adhered to the body of the user, releasing the sensor assembly in response to the user pulling away the insertion device.

According to yet another embodiment, an insertion device includes: a plunger coupled to a lock collar, where the insertion device houses contents including: a striker; a sensor assembly; a needle carrier holding a piercing member, where, upon the insertion device being used or fired, the sensor assembly adheres to a user's body released from the insertion device in response to the user pulling away the insertion device, where the piercing member is retracted such that it is encapsulated inside the insertion device; and where a piercing member protection mechanism is adapted to prevent the insertion device from being fully depressed again once it has been used or fired. The piercing member protection mechanism includes: at least one cam rail disposed on an inner surface of the needle carrier; at least one outer guide rail disposed on an outer surface of the needle carrier; at least one guide slot disposed on an inner wall of the striker; a shaft extending from a top surface of the plunger, the shaft including a cammed surface that includes at least one locking slot from a first end proximate to the top surface of the plunger and extending along a surface of the shaft into a corresponding cam. During insertion of the insertion device into the user's body, the guide rail(s) of the needle carrier fit inside the guide slot(s) of the striker. After insertion, and during retraction of the needle carrier, the guide slot(s) of the striker guide the needle carrier. And where, as the needle carrier continues to retract, the needle carrier pulls free from the striker and is guided by the cammed surface of the shaft of the plunger such that the cam rail(s) of the needle carrier contact the corresponding cam of the plunger; and where once the needle carrier is fully retracted into the insertion device, the locking slot(s) of the shaft of the plunger engage the cam rail(s) of the needle carrier, permanently locking the retracted needle carrier into a rotated position.

In a further embodiment, the needle carrier includes two outer guide rails on opposite sides along an outer surface of the needle carrier.

In a further embodiment, the striker includes two guide slots disposed on opposite sides along an outline of an inner surface or wall of the striker.

In a further embodiment, when the cam rail(s) of the needle carrier contact the corresponding cam of the plunger, the needle carrier rotates in a direction guided by the corresponding cam.

In a further embodiment, the corresponding cam of the plunger includes an angle that guides the needle carrier along the angle.

In a further embodiment, the angle of the corresponding cam is approximately 60 degrees.

In a further embodiment, the needle carrier further includes a spring that holds the fully retracted needle carrier against the plunger.

In a further embodiment, when the needle carrier is permanently locked into the rotated position, the outer guide rail(s) of the needle carrier do not line up with the guide slot(s) of the striker.

In a further embodiment, the outer guide rail(s) of the needle carrier interfere with at least a portion of a top surface of the striker such that the needle carrier acts as a barrier between the plunger and the striker thus preventing the plunger and the striker from being fully depressed keeping a tip of the piercing member protected within the insertion device.

Other features and advantages of the embodiments of the present disclosure will become apparent from the following detailed description, taken in conjunction with the accompanying drawings which illustrate, by way of example, various features of embodiments of the present disclosure.

BRIEF DESCRIPTION OF THE DRAWINGS

A more complete understanding of the embodiments of the present disclosure may be derived by referring to the detailed description and claims when considered in conjunction with the following figures, where like reference numbers refer to similar elements throughout the figures.

FIG. 2A is an exploded top perspective view of the sensor transmitter assembly illustrated in FIGS. 1A and 1B according to an embodiment of the present disclosure;

FIG. 2B is an exploded bottom perspective view of the sensor transmitter assembly illustrated in FIGS. 1A and 1B according to an embodiment of the present disclosure;

FIG. 4 is an exploded view of a sensor assembly according to an embodiment of the present disclosure;

FIGS. 5A-5C illustrate views for affixing a sensor head and an elastomeric connector to a sensor base of a sensor assembly according to an embodiment of the present disclosure;

FIGS. 7A-7C illustrate views of an interface for a sensor assembly including a sensor base, a sensor portion, a needle, a pedestal base and a pedestal cap according to an embodiment of the present disclosure;

FIG. 10A is a bottom side perspective view of a transmitter shell subassembly according to an embodiment of the present disclosure;

FIG. 10B is a top side perspective view of a transmitter shell subassembly according to an embodiment of the present disclosure;

FIG. 11A is a partial plane view of a transmitter assembly layout according to an embodiment of the present disclosure;

FIG. 11B is another partial plane view of a transmitter assembly according to an embodiment of the present disclosure;

FIGS. 12A-D are perspective views of transmitter cap contacts overmolding according to an embodiment of the present disclosure;

FIG. 15A is a partial top side perspective view of a back-to-back sensor connection according to an embodiment of the present disclosure.

FIG. 15B is a partial bottom side perspective view of a back-to-back sensor connection according to an embodiment of the present disclosure.

FIG. 15C is a partial top view of a bottom surface of a transmitter assembly according to an embodiment;

FIG. 16 is a top view of a sensor having at least one contact pad according to an embodiment of the present disclosure;

FIG. 20 illustrates a back-to-back sensor connection to a transmitter assembly according to an embodiment of the present disclosure;

FIGS. 31A-31B are top views of a sensor transmitter assembly with mechanical lockouts according to yet another embodiment of the present disclosure;

FIGS. 33A-33B illustrate lockouts for different generations of transmitter assemblies and sensor assemblies according to another embodiment of the present disclosure;

FIG. 40 illustrates top views of a sensor assembly and a transmitter assembly having features that do not have rotational symmetry according to an embodiment of the present disclosure;

FIG. 45A is a perspective outer view of a single-use, disposable insertion tool according to an embodiment of the present disclosure.

FIG. 45B is a perspective inner view of the single-use, disposable insertion tool of FIG. 45A according to an embodiment of the present disclosure.

FIGS. 47A-47B are perspective views of an insertion device illustrating a second step for a use model of the insertion device according to an embodiment of the present disclosure.

FIG. 48 is a perspective view of an insertion device illustrating a third step for a use model of the insertion device according to an embodiment of the present disclosure.

FIGS. 49A-49B are perspective views of an insertion device illustrating a fourth step for a use model of the insertion device according to an embodiment of the present disclosure.

FIGS. 52A-52B are cutout views of the insertion device of FIGS. 50A-50B in an insertion position according to an embodiment of the present disclosure.

FIG. 55 is a flow chart illustrating a method for an insertion device mechanism according to an embodiment of the present disclosure.

FIG. 57A is an exploded top perspective view of the sensor transmitter assembly illustrated in FIGS. 56A and 56B according to an alternative embodiment of the present disclosure;

FIG. 57B is an exploded bottom perspective view of the sensor transmitter assembly illustrated in FIGS. 56A and 56B according to an embodiment of the present disclosure;

FIG. 59 is an exploded view of a sensor assembly according to an alternative embodiment of the present disclosure;

FIGS. 62A-62C illustrate views of an interface for a sensor assembly including a sensor base, a sensor portion, a piercing member or needle, a pedestal base and a pedestal cap according to an alternative embodiment of the present disclosure;

FIG. 65A is a bottom side perspective view of a transmitter shell subassembly according to an alternative embodiment of the present disclosure;

FIG. 65B is a top side perspective view of a transmitter shell subassembly according to an alternative embodiment of the present disclosure;

FIG. 66A is a partial plane view of a transmitter assembly layout according to an alternative embodiment of the present disclosure;

FIG. 66B is another partial plane view of a transmitter assembly according to an alternative embodiment of the present disclosure;

FIG. 66C is a partial perspective view of a transmitter assembly layout illustrating details of external contacts to a PCB according to an alternative embodiment of the present disclosure;

FIG. 68 is a partial top view of an electrical connection of a sensor assembly and at least one contact of a transmitter assembly according to an embodiment of the present disclosure;

FIG. 69A is an exploded top view of a sensor module having a back to back sensor connection with a rigid flex connector according to an embodiment of the present disclosure;

FIG. 69B is an exploded bottom view of the sensor module of FIG. 69A according to an embodiment of the present disclosure;

FIGS. 72A-72D illustrate an assembly process for a sensor module according to an embodiment of the present disclosure;

FIG. 83A is a top orthogonal view of a combined sensor and infusion set according to an embodiment of the present disclosure;

FIG. 83B is a front orthogonal view of the combined sensor and infusion set of FIG. 69A according to an embodiment of the present disclosure;

FIG. 83C is a side orthogonal view of the combined sensor and infusion set of FIG. 69A according to an embodiment of the present disclosure;

FIG. 83D is a back orthogonal view of the combined sensor and infusion set of FIG. 69A according to an embodiment of the present disclosure;

FIG. 83E is a bottom orthogonal view of the combined sensor and infusion set of FIG. 69A according to an embodiment of the present disclosure.

FIG. 85 is a section view of a combined sensor and infusion set according to an embodiment of the present disclosure;

FIG. 86A illustrates a perspective view of a connection for a sensor and infusion set according to an embodiment of the present disclosure;

FIG. 87A illustrates a used insertion device according to an embodiment of the present disclosure;

FIG. 87B illustrates the used insertion device of FIG. 87A with a depressed plunger and striker according to an embodiment of the present disclosure;

FIG. 88 illustrates a cutout section view of an insertion device having a piercing member protection mechanism according to an embodiment of the present disclosure;

FIG. 89A illustrates a section view of an insertion device having a piercing member protection mechanism including a needle carrier disposed therein according to an embodiment of the present disclosure;

FIG. 89B illustrates a perspective view of the needle carrier of FIG. 89A according to an embodiment of the present disclosure;

FIG. 89C illustrates a top view of the needle carrier of FIGS. 89A and 89B according to an embodiment of the present disclosure;

FIG. 90A illustrates a section view of an insertion device having a piercing member protection mechanism including a striker disposed therein according to an embodiment of the present disclosure;

FIG. 90B illustrates a perspective view of the striker of FIG. 90A according to an embodiment of the present disclosure;

FIG. 90C illustrates a top view of the striker of FIGS. 90A and 90B according to an embodiment of the present disclosure;

FIG. 91A illustrates a section view of an insertion device having a piercing member protection mechanism including a plunger according to an embodiment of the present disclosure;

FIG. 91B illustrates a perspective view of the plunger of FIG. 90A according to an embodiment of the present disclosure;

FIG. 91C illustrates a section view cutout along line A-A' of the striker of FIG. 91B according to an embodiment of the present disclosure;

FIG. 92A illustrates a section view of an insertion tool having a piercing member protection mechanism that has not been used or fired according to an embodiment of the present disclosure;

FIG. 92B illustrates a section view of an insertion tool having a piercing member protection mechanism during insertion according to an embodiment of the present disclosure;

Figure 94B:
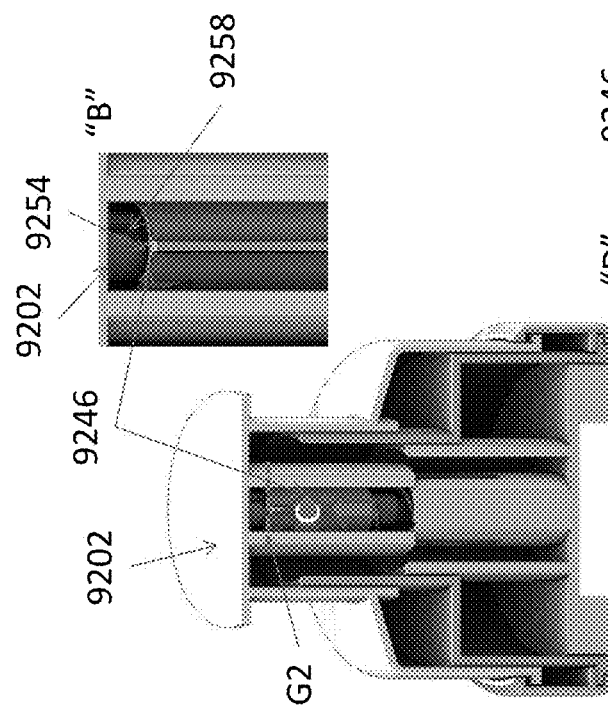
Figures 1, 94B:
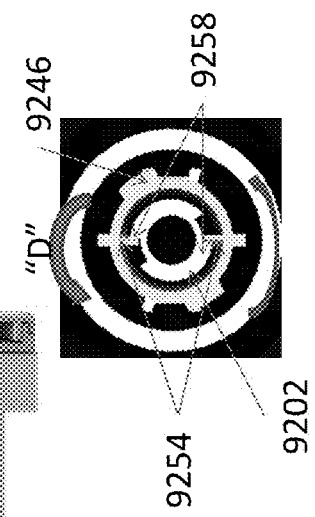
Figure 94A:
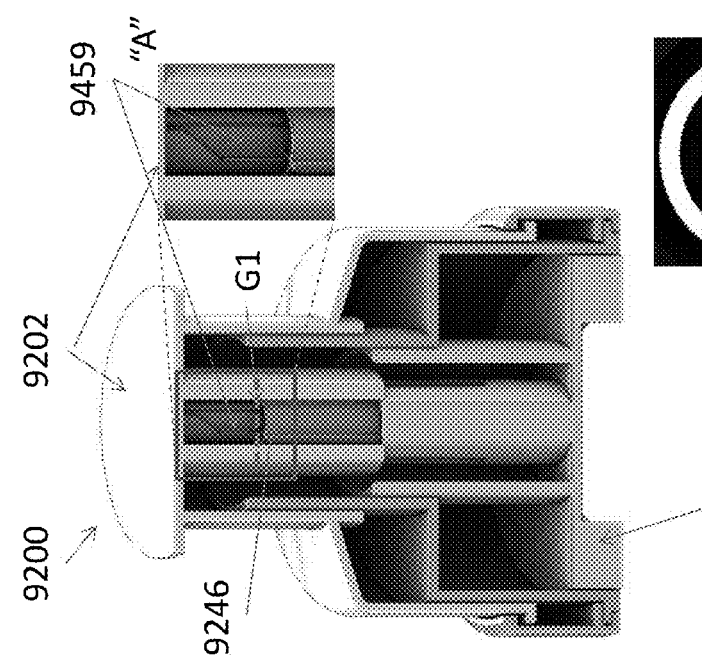
Figures 1, 94A:
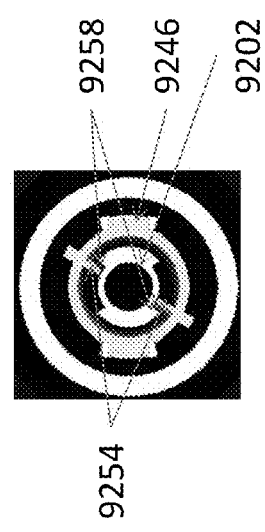

FIG. 92C illustrates a top section view of a needle carrier and a striker of the insertion tool of FIG. 92B during insertion according to an embodiment of the present disclosure;

FIG. 93A is a section view illustrating a first half of a retraction of a needle carrier of an insertion tool having a piercing member protection mechanism according to an embodiment of the present disclosure;

FIG. 93B illustrates a top section view of a needle carrier and a striker of the insertion tool of FIG. 93A during retraction according to an embodiment of the present disclosure;

FIG. 94A illustrates a section view of an insertion tool having a piercing member protection mechanism with a needle carrier retracted about halfway into a top portion of the insertion tool according to an embodiment of the present disclosure;

FIG. 94A-1 illustrates a top view of the needle carrier retracted about halfway into the top portion of the insertion tool of FIG. 94A according to an embodiment of the present disclosure.

Figure 96:
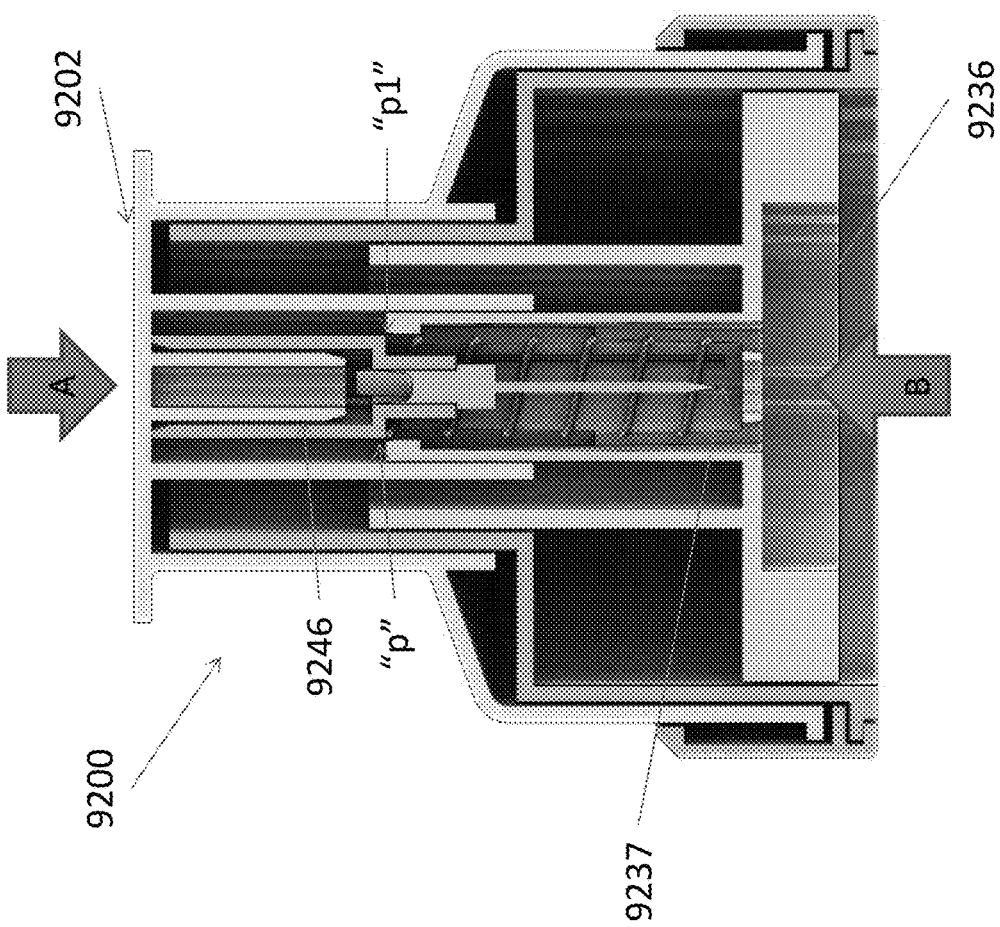

FIG. 94B illustrates a section view of an insertion tool having a piercing member protection mechanism with a needle carrier substantially in mid rotation within the insertion tool according to an embodiment of the present disclosure;

FIG. 94B-1 is a top section view illustrating the needle carrier substantially in mid rotation within the insertion tool of FIG. 94B;

FIG. 94C illustrates a section view of an insertion tool having a piercing member protection mechanism with a needle carrier fully retracted and rotated within the insertion tool according to an embodiment of the present disclosure;

FIG. 94C-1 is a top section view of the needle carrier fully retracted and rotated within the insertion tool of FIG. 94C;

FIGS. 95A-95C illustrate section views of a locking or piercing member protection mechanism for an insertion tool according to one or more embodiments of the present disclosure; and FIG. 96 illustrates a section view of a used or fired inserter tool having a locking or piercing member protection mechanism with a plunger and striker depressed according to an embodiment of the present disclosure.

DETAILED DESCRIPTION

Embodiments of the present disclosure generally relate to the design and arrangement techniques of a medical device, component or product. In particular, embodiments relate to a device, component or product that includes a sensor (e.g., an analyte sensor) and a transmitter. In various embodiments, an analyte sensor may refer to, without limitation, a substance or chemical constituent in a biological fluid (e.g., blood, interstitial fluid, cerebral spinal fluid, lymph fluid or urine) that can be analyzed. Non-limiting exemplary embodiments are described below that may relate to a continuous glucose sensor and transmitter of the type used by diabetic patients. It should be appreciated that the design and arrangement techniques described according to one or more embodiments are not limited for use with glucose sensors. Indeed, the concepts and technology described with reference to glucose sensors may also be used with other medical devices, components or products, other sensor types, other medical supplies, or the like.

According to one or more embodiments of the present disclosure, a device or product having a platform including a new design and arrangement technique of placing a transmitter on top of a sensor, for example, for use in the indication or monitoring of blood glucose levels in a diabetic patient, may address issues created by conventional platforms having a sensor and a transmitter placed side-by-side. For example, platforms according to one or more embodiments address issues and provide benefits to a patient (also referred to as "user") including increased on-body device stability, increased robustness of connection, improved on-body comfort during wear, a simplified use model, etc. Likewise, platforms according to one or more embodiments provide opportunities to resolve issues associated with device performance or assembly including, for example, sensor pullouts or pullups, adhesion to the body, disconnects (e.g., electrical, mechanical, RF, etc.), damage to transmitter pins or contacts, adhesive backfill, cap/needle interference, and cost reduction.

As such, a device having a sensor transmitter assembly according to one or more embodiments of the present disclosure has many features that provide many benefits to a patient as well as to performance and assembly of the device. Below are listed various non-limiting features of a device according to one or more embodiments along with corresponding benefits.

1) A large mounting base—a device according to one or more embodiments includes a transmitter assembly positioned on a first surface or base of a sensor assembly. A first side of a mounting base is disposed on a second or bottom surface of the sensor assembly. A second side of the mounting base attaches to a user's skin. In one or more embodiments, the mounting base is large enough to cover an entire outline of the sensor assembly so that an external load applied to the device is distributed across the large surface area, thus increasing on-body stability and comfort and minimizing the need for other inconvenient attachment techniques such as overtape. Increased on-body stability leads to increased sensor accuracy. In embodiments where the mounting base includes a large stretchy pad, items such as clothing are not caught between the patch and the user's skin.

2) A low profile and reduced volume—the arrangement techniques for the sensor transmitter assembly according to one or more embodiments such as positioning a transmitter assembly on top of a sensor assembly, as opposed to side by side, allow the assembly to have a low profile. A low profile increases on-body stability, on-body comfort and is aesthetically better than a larger device with a higher profile. A patient avoids issues associated with larger devices such as bulkiness, lack of comfort, potential device visibility under clothes, etc. In addition, the transmitter components are arranged more efficiently, allowing for a significant size reduction over conventional platforms or devices.

3) A centered sensor—a device having a sensor transmitter assembly according to one or more embodiments has a substantially round shape where a sensor is positioned substantially in the center of the device. As a result, on-body stability is improved because the sensor is positioned, for example, in the center of a patch that attaches to a patient's body. Also, the use model is simple for a patient when introducing the sensor into the body.

4) Multi-point connection—in one or more embodiments, a device having a sensor assembly that connects with a transmitter assembly at multiple points (e.g., 2, 3, etc. points) along an outline of the device provides connection robustness and use model simplicity. In that regard, the multi-point connections make the attachment stronger without increasing difficulty for connecting to a user. Multi point connections are generally stronger than, for example, having only one connection point.

5) Solid transmitter contacts—a mechanical interface between a sensor and a transmitter is robust, preventing disconnects such as electrical disconnects. In one or more embodiments, because the transmitter is a durable device, electrical contacts on the transmitter are solid and inflexible, thus increasing the robustness of the contacts.

Furthermore, the transmitter contacts are not inside the transmitter assembly but instead, they are substantially flush with a bottom surface of the transmitter, which provides easy access for cleaning and avoids potential corrosion of the contacts.

6) Elastomeric sensor contacts—because the sensor is disposable, flexible electrical contacts, which are more prone to damage, can be used in the sensor. In various embodiments, elastomeric gaskets create a mechanical seal of a sensor substrate path, thus eliminating the need for a fluid seal, for example an adhesive seal. As such, a fluid seal is replaced by a more reliable mechanical seal.

7) Smooth, continuous surfaces and edges—a device according to one or more embodiments has smooth, continuous surfaces and edges that improve on-body comfort and aesthetics. A patient avoids having to wear a device with uncomfortable pointy or rough surfaces or edges. Smooth surfaces and edges can also be better concealed under clothing without potential snagging or visibility.

8) Radial symmetry and no-look twist connection—in one or more embodiments, radial symmetry provides use model simplicity and better aesthetics. Connection and disconnection between the transmitter and the sensor are intuitive to a patient. For example, the patient can connect (or disconnect) the transmitter to the sensor through an intuitive twisting motion. The patient can connect (or disconnect) the transmitter and the sensor single-handedly without the patient having to look at the device, thus enabling the device to be worn in more locations on the patient's body. That is, the patient can easily connect or disconnect the transmitter to the sensor even in body locations where the patient does not have visibility, for example, on the patient's back.

In addition, according to one or more embodiments of the present disclosure, mechanical lockouts between non-compatible transmitter/sensor combinations may be made easily through, for example, interchangeable mold inserts. In certain embodiments, it is likely that some generations of devices or products include a transmitter assembly and a sensor assembly that are functionally incompatible with each other. For example, a device includes a transmitter assembly using a new transmitter algorithm paired with an older sensor assembly. In some embodiments, it is necessary to provide ways to prevent incompatible transmitter assemblies and sensor assemblies from connecting to each other both mechanically and electrically. One or more embodiments allow lockouts to prevent incompatible transmitter and sensor assemblies from connecting. The lockouts are changed easily and independently of other potentially critical features. In an embodiment, slots and rails on respective sensor or transmitter assemblies are used to block a transmitter from fully rotating onto and making a connection with a non-compatible sensor.

It should be noted that a device can include components having a combination of one or more features as described according to one or more embodiments, and the features are interchangeable between components of the device.

In addition, one or more embodiments relate to a single-use, disposable insertion device or product that includes a sensor (e.g., an analyte sensor), an insertion needle and related packaging into the one combined single-use, disposable device. It should be appreciated that the design and arrangement techniques of the insertion device described according to one or more embodiments are not limited for use with glucose sensors. Indeed, the concepts and technology described with reference to glucose sensors may also be used with other medical devices, products, components, supplies, other sensor types, or the like.

While current platforms use multiple-use, durable insertion devices, which makes for a complex use model of the insertion devices requiring many steps and fine motor skills as well as being prone to wear and damage, platforms according one or more embodiments of the present disclosure integrate a sensor, an insertion needle, a needle hub and sensor packaging into an all-in-one, single-use disposable device with a greatly simplified use model. In that regard, an insertion device according to one or more embodiments of the present disclosure reduces the number of steps for insertion, makes those steps simple and intuitive, and requires only gross motor skills for the user. This increases the likelihood of successful insertion and reduces the number of replacement sensors needed by users. Also, it decreases the need for in-depth training such as in-person training on how to use the device. Furthermore, because insertion devices according to one or more embodiments are single-use, the need for disinfection or cleaning in a clinical setting is eliminated.

While current platforms require users to carry packaged sensors plus a separate insertion device such that users cannot insert a sensor if the user does not have the insertion device, embodiments of the present disclosure allow users to carry only one device. For example, users only need to carry one device instead of carrying both, packaged sensors and an insertion device. This results in less waste that needs to be disposed after each insertion.

An insertion device according to one or more embodiments provides tension-loaded, e.g., spring-loaded, sensor insertion into the body of a user. To remove a needle after insertion of the sensor, the device automatically retracts the tension-loaded, e.g., spring-loaded needle in response to the user pulling the insertion device away from the body. The device also shields the used needle to prevent accidental needle sticks or other potential safety or hygiene issues. Also, in various embodiments, the device includes a locking mechanism to prevent it from being accidentally fired during various handling stages such as transportation, storage, etc.

In one or more embodiments, the insertion device is axially symmetrical, thus eliminating the need for the user to orient the device to the body in a particular way during insertion. Also, the device can be used one-handed such that the user utilizes it without looking. This enables the sensor to be easily inserted in hard-to-reach places such as the back of the arm. The firing mechanism of the insertion device guarantees that sufficient pressure is applied to the insertion site, which ensures full needle insertion and sensor adhesion to the skin of the user.

According to one or more embodiments, after the insertion device has been used or fired, for example to insert a sensor into the body of a user, and the needle has been retracted back into an inner volume of the insertion device, a needle protection mechanism is used to prevent the needle from being exposed by preventing a plunger and a striker of the insertion device from being fully depressed again. Advantageously, the needle is protected from exposure without adding excessive volume to the insertion device.

Overview of Device with Sensor/Transmitter Assembly

Figure 1B:
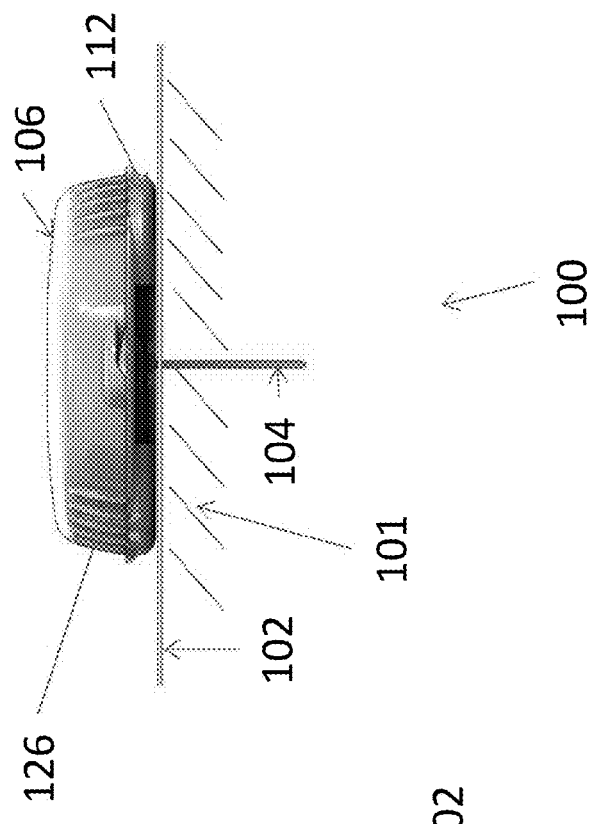
FIG. 1B is a side view of the sensor transmitter assembly of FIG. 1A according to an embodiment of the present disclosure.
Figure 1A:
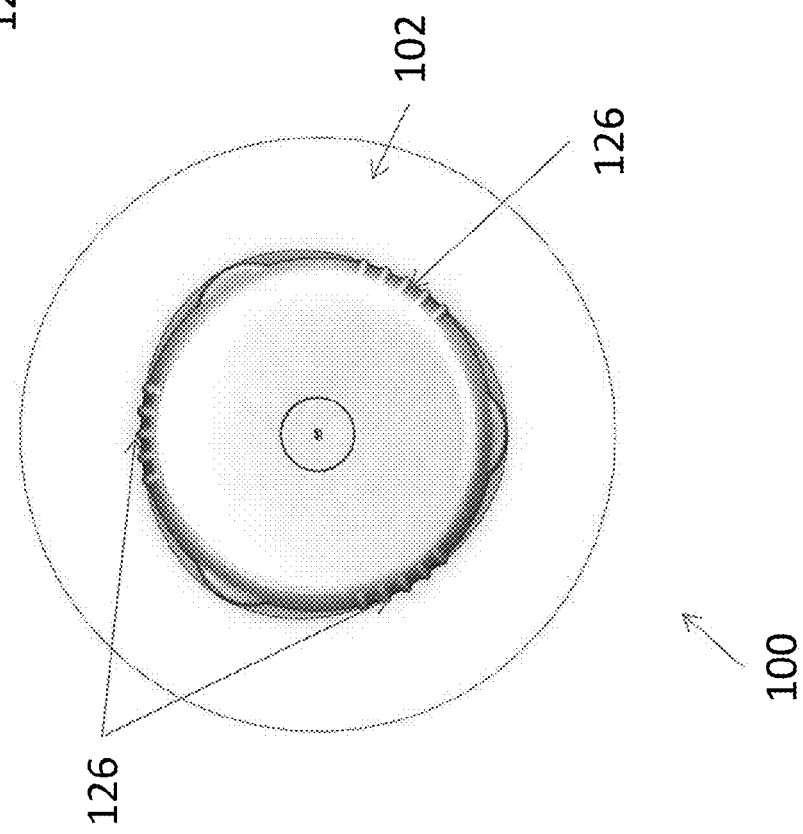
FIG. 1A is a top view of a sensor transmitter assembly as a single unit having at least one outer edge according to an embodiment of the present disclosure.

FIG. 1A is a top view of a sensor transmitter assembly as a single unit according to an embodiment of the present disclosure. FIG. 1B is a side view of the sensor transmitter assembly of FIG. 1A according to an embodiment of the present disclosure.

FIG. 1A and FIG. 1B illustrate a sensor transmitter assembly 100 as a single unit as may be worn on-body by a patient. Sensor transmitter assembly 100 may be fastened by a mounting base or patch 102 that adheres to the patient's skin. As illustrated in the embodiment of FIG. 1A, the sensor transmitter assembly 100 may have a substantially symmetrical round shape. Radial symmetry of the sensor transmitter assembly 100 avoids having to orient the assembly in a certain way on the patient's body, as compared to, for example, other shapes such as rectangular shapes that may require a certain orientation on the body. The shape of the sensor transmitter assembly 100 according to one or more embodiments has smooth outer edges, which prevent potential wear issues such as snagging on the patient's clothing that may be caused by, for example, sharp, pointy edges. Also, smooth footprint edges help improve comfort of wear.

As illustrated in the embodiment of FIG. 1B, sensor transmitter assembly 100 includes a transmitter assembly 106 positioned on top of a sensor assembly 112. Transmitter assembly 106 and sensor assembly 112 attach at one or more edges or points, for example at three outer edges 126 that are spaced apart, for example, evenly spaced apart around an outline of the sensor transmitter assembly. It should be noted that transmitter assembly 106 and sensor assembly 112 may attach at any number of points or edges as appropriate, for example, at three edges as illustrated in FIG. 1A, or at 2 edges, 4 edges, 5 edges, etc. A sensor extension or portion 104 is coupled to a sensor base of sensor assembly 112 on a substantially centered location. Sensor portion 104 may be an integral part of the sensor base of sensor assembly 112. The sensor base of sensor assembly 112 provides structural support to sensor portion 104 and facilitates entry of sensor portion 104 into the body of the patient. Sensor portion 104 may be introduced into the body of the patient using a needle. In various embodiments, the needle and the sensor assembly 112 may be pre-connected as part of a sensor set. In other embodiments, the needle, sensor assembly 112, and sensor portion 104 may be packaged and provided together. In further embodiments, a disposable insertion device, which is an integrated, single unit device (for example as described below according to one or more embodiments with respect to FIGS. 45A-55), allows the user to position and subcutaneously implant a sensor into the user's body. As such, in various embodiments, sensor portion 104 may be positioned subcutaneously/transcutaneously in direct contact with a patient's extracellular fluid 101.

In various embodiments, sensor portion 104 is an electrochemical sensor that includes a glucose oxidase enzyme, as known in the art by those familiar with glucose sensor technology. The glucose oxidase enzyme enables sensor portion 104 to monitor blood glucose levels in a diabetic patient by effecting a reaction of glucose and oxygen. It should be understood that although one or more embodiments relate to glucose sensors, the concepts and technology described herein may be adapted for use with any one of a wide variety of sensors known in the art.

Alternative embodiments for a sensor transmitter assembly are illustrated in at least FIGS. 56A-56B, 57A-57B, 58A-58C, which will be described in more detail below, where a sensor transmitter assembly is shown having two compression areas instead of one or more outer edges (e.g., 3 outer edges 126 as illustrated in FIG. 1A and FIG. 1B). For example, two compression areas 142a, 142b illustrated in FIGS. 56A and 56B for a sensor transmitter assembly shown as a single unit allow a user to easily rotate in a first direction the transmitter assembly onto the sensor assembly in order to lock the sensor assembly to the transmitter assembly. To unlock the transmitter assembly from the sensor assembly, the user can easily press or squeeze at the compression areas while rotating in an opposite second direction. This provides a double fail safe mechanism (e.g., simultaneously squeezing and rotating) that is easy and intuitive for a user.

FIG. 2A is an exploded top perspective view of the sensor transmitter assembly 100 illustrated in FIGS. 1A and 1B according to an embodiment of the present disclosure. FIG. 2B is an exploded bottom perspective view of the sensor transmitter assembly 100 illustrated in FIGS. 1A and 1B according to an embodiment of the present disclosure. As illustrated in FIGS. 1A and 1B, the components of the sensor transmitter assembly 100 may be coupled together as a single unit.

The embodiment of FIG. 2A illustrating an exploded top view of the sensor transmitter assembly generally includes a transmitter assembly 106 and a sensor assembly 112. Sensor assembly 112 includes electrical and physical interfaces and elements that accommodate an electronics module that includes at least one electronics component 208 as will be described in more detail below for example at least with respect to the embodiment of FIG. 4. At least one electronics component 208 is disposed on a cavity of a sensor base 219 of sensor assembly 112. A mounting base or patch 102 is attached to an entire bottom surface or outline of sensor assembly 112. Transmitter assembly 106 includes an opening 216 that is adapted to engage with a cap 209 of sensor assembly 112. In that regard, transmitter assembly 106 is initially lowered into sensor assembly 112 such that opening 216 of transmitter assembly 106 is positioned to fit cap 209 of sensor assembly 112. A solid connection of transmitter assembly 106 to sensor assembly 112 is completed by an intuitive rotation motion as will be described in more detail below.

In certain embodiments, portions of the sensor transmitter assembly are formed at least in part of a plastic material. In various embodiments, the bulk of the sensor transmitter assembly is formed as molded plastic components. In other embodiments, the sensor transmitter assembly is formed from ABS, nylon, an ABS/PC blend, PVC, polytetrafluoroethylene (PTFE), polypropylene, polyether ether ketone (PEEK), polycarbonate, or the like.

As illustrated in FIG. 2B, transmitter assembly 106 includes a bottom surface 211 that is substantially flat and accommodates various components including at least one electronics module having a set of contacts 217a and 217b. In general, after insertion of sensor portion 104 into the body of a patient, transmitter assembly 106 is connected to sensor assembly 112 where contacts 217a and 217b of transmitter assembly 106 are adapted to connect to corresponding contact pads on sensor assembly 112 (e.g., at least one electronics component 208) as will be described in more detail below, for example, with respect to the embodiment illustrated in FIGS. 15A-15C. Transmitter assembly 106 includes a wireless transmitter that communicates with a remote device such as an infusion pump, a monitor device, or the like. In that regard, contacts 217b are charging/communication contacts. Contacts 217a are sensor contacts. In this embodiment, there are 4 charging/communication contacts 217b and 6 sensor contacts 217a that can include 1 reference electrode (RE), 1 counter electrode (CE) and 4 working electrodes (WE). Advantageously, contacts 217a and 217b are not inside transmitter assembly 106, but instead, they are substantially flush with bottom surface 211 which provides easy access for cleaning and avoids potential corrosion.

In particular embodiments, a mounting base (or patch) 102 is a large, stretchy patch that affixes the sensor assembly 112 to the skin of the patient. Mounting base or patch 102 has a bottom surface 102a (as shown in FIG. 2B) that is adapted to be attached to the skin of the patient using appropriate attachment techniques, for example, an adhesive (e.g., a fluid adhesive, a spray adhesive, etc.), staples, or the like. In one or more embodiments, mounting base or patch 102 is made of a flexible and breathable material with adhesive properties, such as cloth, a bandage-like material, and the like. For example, suitable materials include polyurethane, polyethylene, polyester, polypropylene, polytetrafluoroethylene (PTFE), or other polymers. In other embodiments, mounting base or patch 102 is made of solid materials, for example, plastic, etc. A top surface 102b of mounting base 102 (as shown in FIG. 2A) is adapted to be bonded or otherwise attached to an entire bottom surface of sensor assembly 112. As such, in various embodiments, mounting base or patch 102 is bonded to the entire device outline, not just to certain edges of the device, thus providing on-body stability. In various embodiments, glue, ultrasonic welding, etc. can be used for bonding. By applying pressure to the device, the pressure load spreads on the entire surface of patch 102 creating a secure, stable adhesion to the body without the need for fold-over tape, overtape, or other inconvenient attachment techniques. In this way, items such as clothing may not be caught underneath the surfaces of mounting base or patch 102. Additional adhesive layers, liners, etc. can also be provided on the bottom of the mounting base 102 to temporarily secure the mounting base 102 as necessary.

Advantageously, the design and arrangement techniques of the sensor transmitter assembly according to one or more embodiments herein allow for a reduction in size compared to conventional assemblies as shown in the examples of Table 1 below.

TABLE 1

|  | Conventional Sensor Assembly | Sensor Transmitter Assembly According to One or More Embodiments | % Reduction |
| --- | --- | --- | --- |
| Height (in) | 0.37 | 0.31 | 16% |
| Width (in) | 1.40 | 1.10 | 22% |

TABLE 1-continued

|  | Conventional Sensor Assembly | Sensor Transmitter Assembly According to One or More Embodiments | % Reduction |
| --- | --- | --- | --- |
| Length (in) | 1.56 | 1.10 | 30% |
| Footprint (in$^2$) | 1.51 | 0.95 | 37% |
| Volume (in$^3$) | 0.39 | 0.26 | 33% |

Sensor/Transmitter Connection, Mechanical

According to one or more embodiments, one or more interface components are used to mechanically connect the sensor assembly 112 and the transmitter assembly 106. The interface component(s) include, for example, at least one snap arms, tabs, slots, latches, etc. that correspond or are adapted to engage with each other. In alternative embodiments, the interface components have features such as a size, a shape, a length, a cross-section, a depth, a positioning, etc. that allows them to engage with each other. FIG. 2A illustrates sensor assembly 112, which includes at least one snap arm 222 and at least one tab 224. In this embodiment, three snap arms 222 and three tabs 224 are positioned spaced along an outer rim or outline of a sensor base 219. FIG. 2B illustrates a transmitter assembly 106 including at least one slot 218 and at least one latch 233. In this embodiment, three slots 218 and three latches 233 are located spaced along an outer rim or outline of transmitter assembly 106. In other embodiments, sensor assembly 112 has a number of interfaces such as snap arms 222 and/or tabs 224 that can correspond to a number of interfaces such as slots 218 and/or latches 233 of transmitter assembly 106 as appropriate, for example, 1, 2, 4, 5, etc. Tabs 224 of sensor base 219 and slots 218 of transmitter assembly 106 are adapted to engage with each other in order to lock the transmitter assembly and the sensor assembly together axially. For example, each of tabs 224 fits into at least a portion of a corresponding slot 218 when transmitter assembly 106 is lowered onto sensor assembly 112. Snap arms 222 lock the transmitter assembly and the sensor assembly together rotationally. For example, latches 233 engage or receive corresponding snap arms 222 when transmitter assembly 106 is rotated onto sensor assembly 112. In various embodiments, transmitter assembly 106 and sensor assembly 112 are not connected simply by pushing them together, but a rotation motion is also used for completing the connection as will be described in more detail below for example with respect to the embodiments of FIGS. 3A-3C. Lock forces are generally symmetrical about the center of the sensor transmitter assembly.

In this embodiment, interface components, e.g., snap arms and tabs, can be flexible and less robust, and have been placed on sensor base 219 at least in part because sensor assembly 112 is disposable. Interface components that are more robust, e.g., slots 218 and latches 233, have been placed on transmitter assembly 106 at least in part because it is durable or inflexible. However, it should be noted that, conversely, in various embodiments, snap arms 222 and tabs 224 are located on transmitter assembly 106 and slots 218 and latches 233 are located on sensor assembly 112. That is, one or more interface components, e.g., snap arms, tabs, slots and latches are interchangeable between the sensor assembly and the transmitter assembly.

Figures 3A, 3B, 3C:
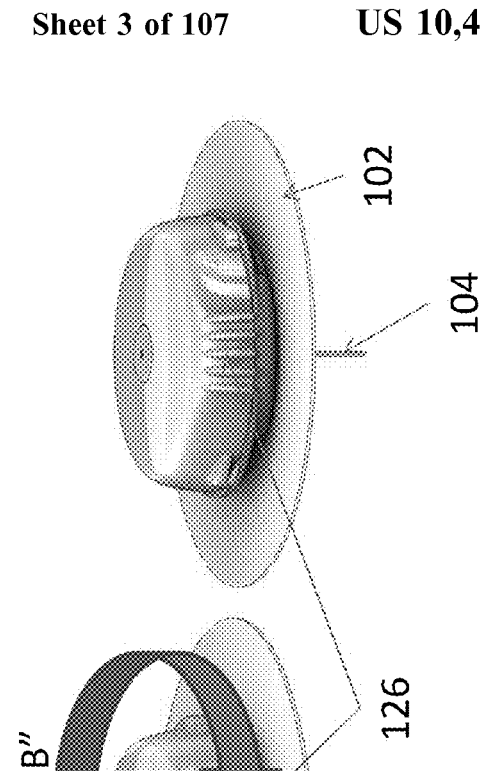
FIGS. 3A-3C illustrate side perspective views for mechanically connecting a sensor assembly to a transmitter assembly according to an embodiment of the present disclosure.

Referring to FIGS. 3A-3C, side perspective views for mechanically connecting a sensor assembly to a transmitter assembly are illustrated according to an embodiment of the present disclosure. Initially, as illustrated in the embodiment of FIG. 3A, a transmitter assembly 106 is positioned, for example, lowered onto a sensor assembly 112 as indicated by downward arrow "A". In that regard, an interface such as an opening 216 of transmitter assembly 106 is lined up with, fits, or otherwise matches an interface such as a cap 209 of sensor assembly 112. In this embodiment, opening 216 may be a hole having a round shape. In other embodiments opening 216 may have different sizes or shapes such as a square, a hexagon, etc., that fits or otherwise engages with a corresponding interface (e.g., cap 209) of sensor assembly 112. As described above according to one or more embodiments, one or more slots of transmitter assembly 106 engage into one or more corresponding tabs 224 of sensor assembly 112 to lock the transmitter and the sensor together axially (see, e.g., FIGS. 2A-2B). In this embodiment, there are three tabs and three corresponding slots that provide a keyed structure such that the transmitter assembly drops in and lines up in a particular way (not randomly), locks, and does not move around.

As illustrated in FIG. 3B, once transmitter assembly 106 is locked together axially with sensor transmitter 112, a push or twist action (e.g., a clockwise rotating motion), as indicated by arrow "B", is used to connect transmitter assembly 106 to sensor assembly 112 together rotationally. Conversely, a counterclockwise rotation motion is used to disconnect transmitter assembly 106 from sensor assembly 112. It should be noted that in other embodiments, a clockwise rotating motion disconnects the transmitter assembly to the sensor assembly, and a counterclockwise rotation motion connects the transmitter assembly to the sensor assembly. Snap arms 222 and latches 233 (see, e.g., FIGS. 2A-2B) lock the transmitter and the sensor assemblies together rotationally. As such, according to embodiments herein, transmitter assembly 106 rests completely on top of sensor assembly 112. The sensor and transmitter assemblies are mechanically connected at the outermost edges, for example at three edges 126 (also illustrated in FIG. 1A) where tabs 224 and slots 218 lock the transmitter and the sensor assemblies together axially, and snap arms 222 and latches 233 lock the transmitter and the sensor assemblies together rotationally. This results in little relative movement being possible between the sensor and transmitter assemblies. Stable electrical connections are also ensured.

Advantageously, a twisting action is generally intuitive to a patient and allows the patient to connect (or disconnect) the transmitter assembly 106 to/from the sensor assembly 112 with one hand without the patient having to look, thus allowing the patient to place and wear the sensor transmitter assembly on more locations on the body, even on locations where the patient has no visibility such as on the patient's back. FIG. 3C illustrates the sensor transmitter assembly as would be worn by the patient on-body as one unit. In this regard, mounting base 102 can be bonded to the patient's body and sensor portion 104 can be positioned subcutaneously/transcutaneously in direct contact with a patient's extracellular fluid.

Sensor Assembly

Referring to FIG. 4, an exploded view of a sensor assembly is illustrated according to an embodiment of the present disclosure. A sensor assembly 112 has components including without limitation a mounting base 102, a sensor base 219 having a sensor head cavity 415 and a cap cavity 418, a sensor pad fastener 407, a sensor 404, an elastomeric connector 402, at least one inner square ring 406, an O-ring 405, a cap 409 and an outer square ring 403. Mounting base 102 is adapted to be bonded to at least a portion of a bottom surface area of sensor base 219. In various embodiments, mounting base 102 is bonded to cover an entire bottom surface area or an entire outline of sensor base 219. Sensor base 219 includes sensor head cavity 415 adapted to fittingly receive sensor pad fastener 407 (e.g., an adhesive or the like). As such, sensor base 219 and sensor pad fastener 407 provide support to a sensor 404 and an elastomeric connector 402 as will be described in more detail below, for example, with respect to the embodiments of FIGS. 5A-5C. Cap cavity 418 is adapted to fit at least one square ring 406 that also provides a fluid seal for sensor 404. O-ring 405 fits around a cap 409 that is adapted to connect with cap cavity 418. An outer square ring 403 fits around an outline of sensor base 219 and provides water tightness for the sensor assembly.

FIG. 59 is an alternative embodiment of an exploded view of a sensor assembly that includes a sensor base having one or more interfaces, e.g., two slots, adapted to engage with one or more corresponding interfaces, e.g., two rails, of a transmitter assembly as will be described in more detail below according to one or more embodiments.

Referring to FIGS. 5A-5C, top views for affixing a sensor head and an elastomeric connector to a sensor base of a sensor assembly are illustrated according to an embodiment of the present disclosure. In FIG. 5A, sensor base 219 has a sensor head cavity (illustrated in FIG. 4) formed thereon that holds in place a sensor head 504 on a sensor pad fastener by using suitable fastening techniques such as double sided tape, adhesive, molded glue, a snap fit, or the like.

In FIG. 5B, an elastomeric connector 402 is placed on top of sensor head 504. In various embodiments, elastomeric connector 402 is retained by a rib structure 506 or by any other suitable structure such as a spring, a snap fit, etc. Rib structure 506 provides dead volume for elastomeric connector 402 to expand into in response to a transmitter assembly being connected to the sensor assembly as will be described in more detail below.

FIG. 5C is a side perspective view of the elastomeric connector fitted into the sensor head cavity of sensor base 219. In this embodiment, a top cross section of elastomeric connector 402 is square, which avoids having to orient the elastomeric connector in any particular direction. In an embodiment, it has approximately a 13% nominal compression.

In various embodiments, elastomeric connector 402 is an elastomeric z-axis connector, for example, a ZEBRA connector (manufactured by FUJIPOLY) or other equivalent connector that includes alternating conductive and insulating regions in a rubber or elastomer matrix that produce overall anisotropic conductive properties. In general, ZEBRA connectors provide high-density redundant electrical paths for high reliability connections. ZEBRA connectors are generally flexible and create a gasket-like seal for harsh environments. The length, width and height may be specified as well as the stripe pitch to fit an application. In various embodiments, a recess with ribs is specified that captures and provides an elastomer reference surface for alignment (while allowing a lateral dimension of the elastomer to increase as it is compressed) with a deflection stop to control the final part separation, and alignment pins for substrate alignment. In some aspects, a "matrix" elastomeric connector includes short, fine, metallic wires, for example 300-2000 wires per square centimeter, aligned in parallel without touching each other, embedded in a rubber sheet. The wires either protrude slightly from the top and bottom of the rubber sheet, or they are curved and flush with the top and bottom planes. It should be noted that other type of Z-connectors may be used as well as leaf spring type connectors or the like. Elastomeric connectors used in various embodiments have alternating conductive and nonconductive layers supported by nonconductive supports, e.g., Silicone nonconductive supports. Inner conductive layers of an elastomeric connector create signal paths. Outer nonconductive layers prevent shorting between contacts.

Sensor Base/Sensor Portion/Needle/Cap Interface

Figure 6:
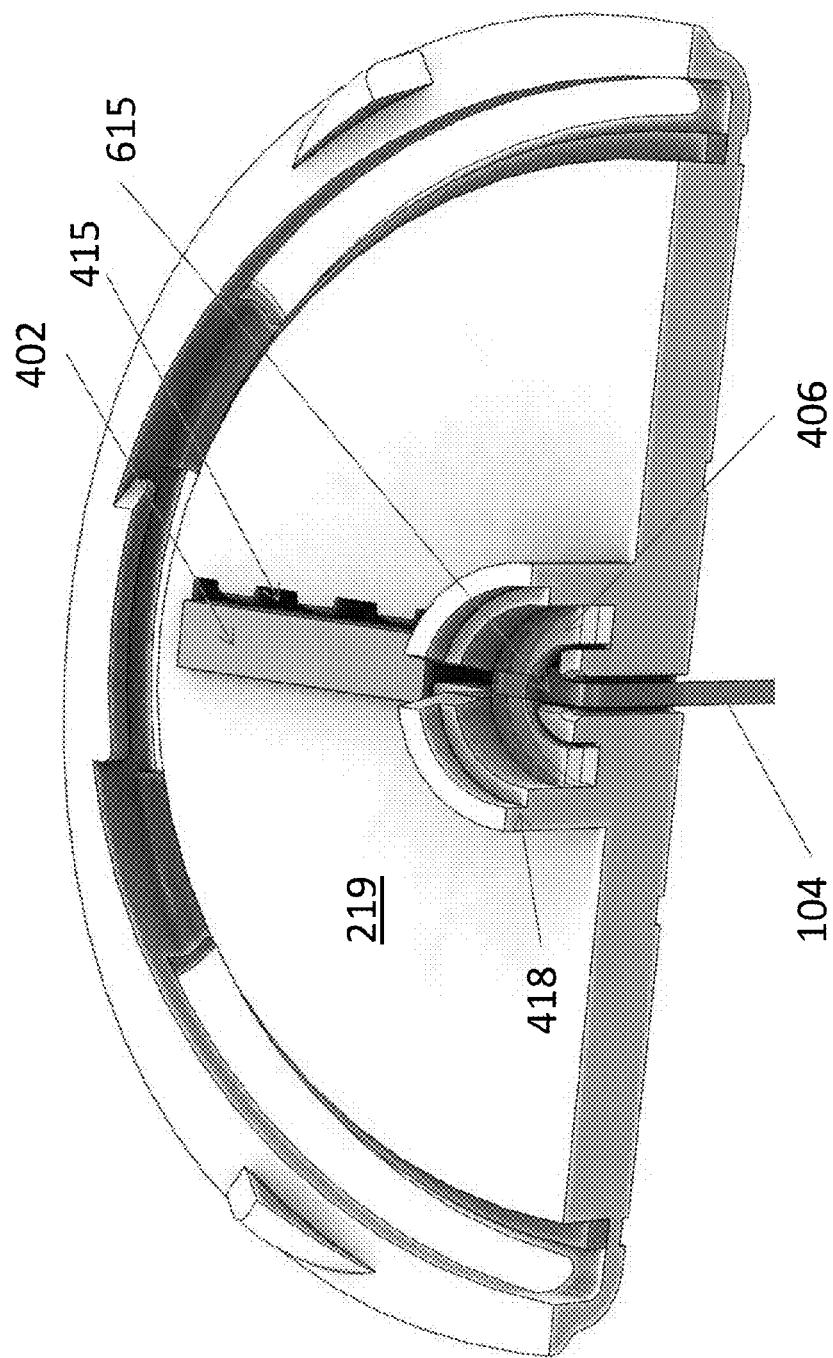
FIG. 6 is a partial top perspective view of a sensor assembly according to an embodiment of the present disclosure.

FIG. 6 illustrates a partial top perspective view of a sensor assembly according to an embodiment of the present disclosure. As described above according to an embodiment, a sensor base 219 includes a sensor head cavity 415 adapted to receive a sensor pad fastener, a sensor and an elastomeric connector 402. A top portion 615 of sensor portion 104 extends into an opening of cap cavity 418. Two identical inner square rings 406 sandwich a portion of substrate of the sensor, e.g., top portion 615 of sensor portion 104 as will be described in more detail below according to one or more embodiments.

Figure 7E:
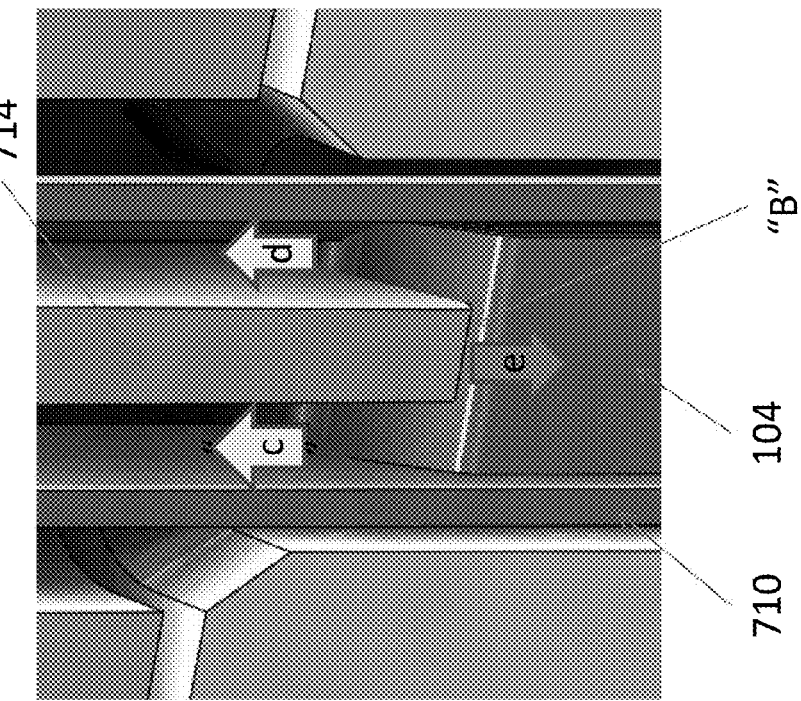
FIG. 7E is a detail of the interface illustrated in FIG. 7D according to an embodiment of the present disclosure.

FIGS. 7A-7E illustrate views of an interface for a sensor assembly including a sensor base, a sensor portion, a needle, and a cap according to an embodiment of the present disclosure. In FIG. 7A, a top part of sensor portion 104 is disposed in an opening 706 extending along a sensor base 219. Identical inner square rings 406 sandwich a portion of the sensor substrate, i.e., at least a portion 715 of a top of sensor portion 104. Top sensor portion 715 is angled at an angle "A°" (see also FIG. 7B). In alternative embodiments, angle "A°" has different angle values other than 90 degrees, for example 33°, 45°, or any other suitable angle. As such, this part of the sensor portion does not have a straight or sharp bend. Inner square rings 406 have a substantially square cross section when they are not compressed, which avoids slipping over each other. In an embodiment, they have a 5% OD compression.

As illustrated in FIG. 7B, upon compression for example by positioning a cap 409 on top of sensor base 219 (i.e., into cap cavity 418) with for example a 20% axial compression, inner square rings 406 may expand so that a sensor fold is on a fluid side of a seal thus, there is no polyimide-against-polyimide gap to seal against. No glue, curing or other fastening techniques are needed. That is, in this embodiment, the two inner square rings 406 sandwich an area of the sensor, e.g., top sensor portion 715, that is not folded back onto itself. This results in the inner square rings 406 compressing against only one layer of the sensor. If the inner square rings were to compress against a folded region of the sensor, they would not seal a leak path created by a gap between two layers of the sensor. In this embodiment, everything is compressed together and supported. As illustrated in FIG. 7C, an insertion device such as a needle 710 is positioned though opening 706 of sensor base 219. Notably, opening 706 extends fittingly into a hole or opening 711 of cap 409 of the sensor assembly to accommodate needle 710.

Figure 7D:
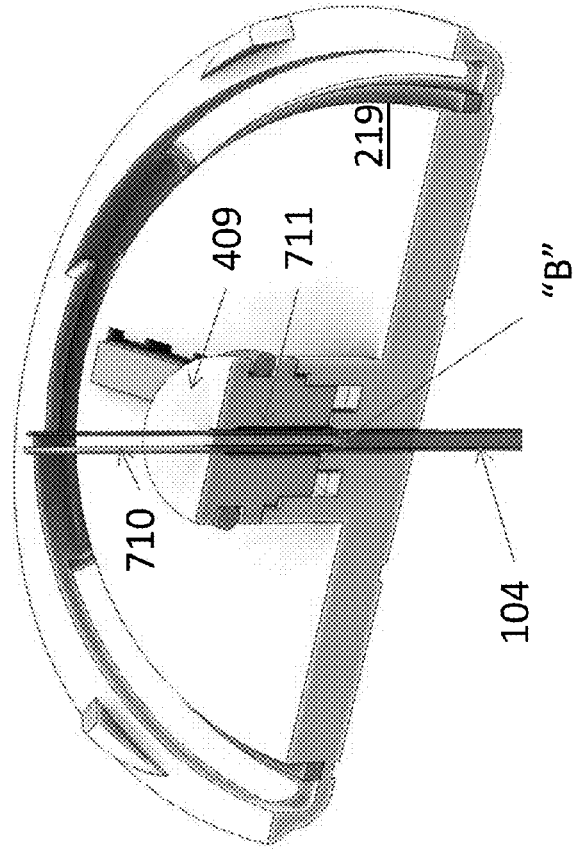
FIG. 7D is a partial side perspective view of a sensor assembly showing an interface of a sensor portion, a sensor base, a needle and a pedestal cap according to an embodiment of the present disclosure.

Referring to FIG. 7D, a partial side perspective view of a sensor assembly showing an interface of a sensor portion, a sensor base, a needle and a cap is illustrated according to an embodiment of the present disclosure. FIG. 7D illustrates an interface of a sensor portion 104, a sensor base 219, a needle 710 and a cap 409. Cap 409 includes a hole or opening 711 adapted to accommodate needle 710 through cap 409. In this embodiment, opening 711 is substantially centered on cap 409. The needle hole or opening 711 is relieved for example with approximately a 3.5:1 aspect ratio for tool strength and to prevent over constraint between cap 409 and sensor base 219. Needle hole or opening 711 can be designed to fit needles of any profile. FIG. 7E is a detail of the interface illustrated in FIG. 7D according to an embodiment of the present disclosure. FIG. 7E illustrates the interface at a point "B". A sensor clamp 714 is located in an interior of needle 710 to resist sensor pullups. Sensor clamp 714 clamps down on sensor portion 104. Needle 710 does not touch sensor portion 104. In various embodiments, after insertion into a patient's body, when needle 710 is pulled out of sensor base 219, it pulls sensor portion 104 upwards at areas indicated by arrows "c" and "d". Sensor clamp 714 holds sensor portion 104 down at an area indicated by arrow "e". This puts the length of the sensor portion that is between upward pulling arrows "c" and "d" and downward pulling arrow "e" in tension. Because the sensor portion is in tension, needle 710 slips past sensor portion 104, allowing sensor portion 104 to stay in place as needle 710 retracts. Without clamp 714, sensor portion 104 would be carried along needle 710 when needle 710 is retracted, pulling sensor portion 104 out of the patient's body.

Figure 8:
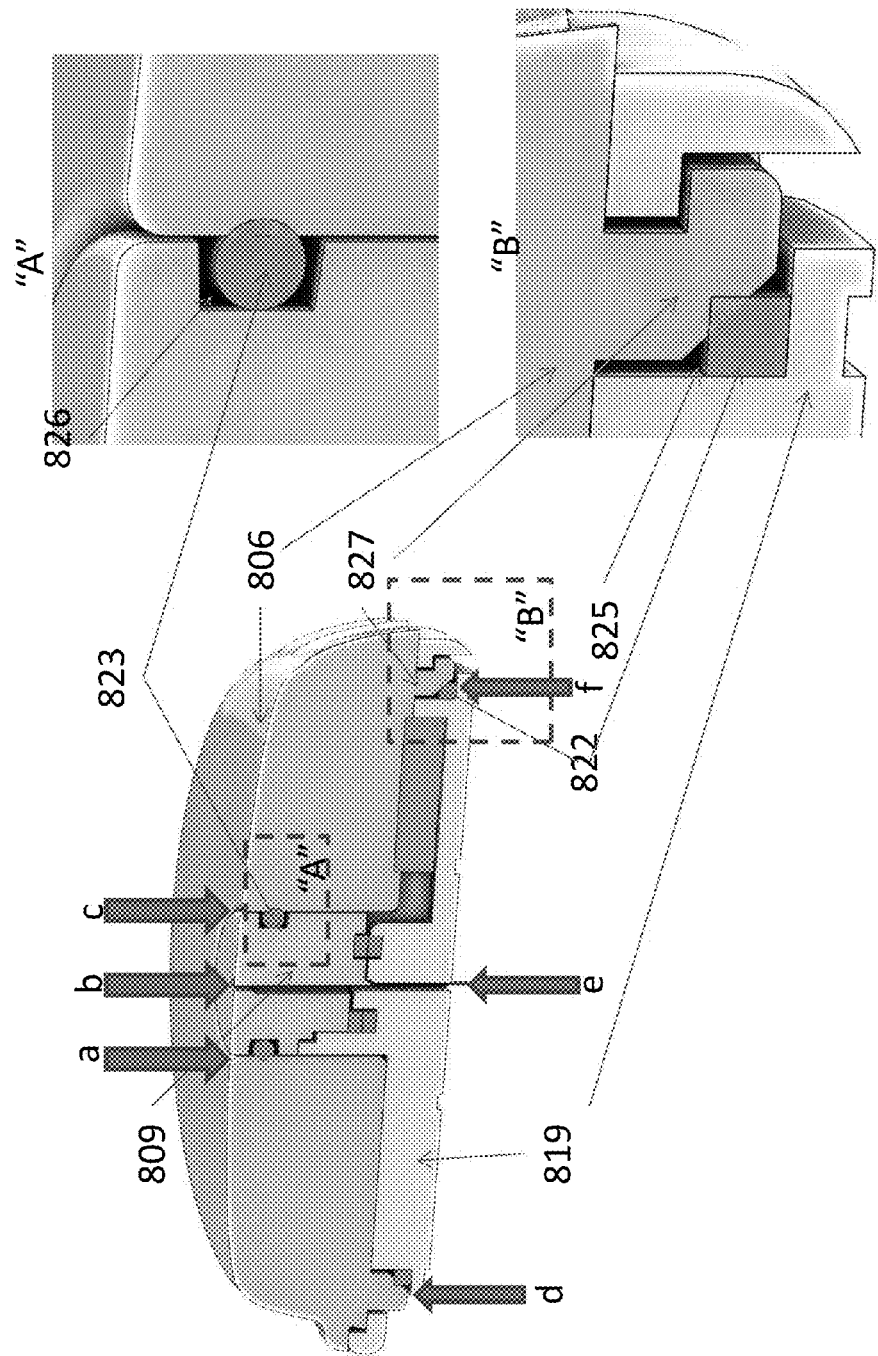
FIG. 8 illustrates a sensor transmitter assembly with seals that improve water tightness according to an embodiment of the present disclosure.

FIG. 8 illustrates a sensor transmitter assembly with seals that improve water tightness according to an embodiment of the present disclosure. A cap 809 of a sensor assembly has at least one cavity 826 formed at each lateral side as further illustrated in detail "A". A radial seal 823 is placed in a respective cavity 826. In one or more embodiments, radial seals 823 are self-lubricated. In some embodiments, radial seals 823 are made of elastomeric materials. In a particular embodiment, radial seals 823 are made of Nitrile or buna-n rubber. In various embodiments, radial seals 823 have a round shape, but may have any appropriate shape. In various embodiments, a side portion of sensor base 819 further includes at least one cutout 825 cut for example in an "L" shape or at a 90 degree angle, or at any other appropriate shape or angle adapted to receive a portion 827 of a transmitter assembly 806. A crush seal 822 is placed in a respective cutout 825 formed at a connection between portion 827 of transmitter assembly 806 and sensor base 819 as further illustrated in detail "B". Crush seals 822 are held in place with friction. In various embodiments, crush seals 822 have a square cross section to prevent any rolling or other type of movement. In various embodiments, crush seals 822 are self-lubricated. In some embodiments, crush seals 822 are made of elastomeric materials. In a particular embodiment, crush seals 822 are made of Nitrile or buna-n rubber. In this way, potential leak paths (as represented by arrows a and c) are sealed by radial seals 823 and potential leaks (as represented by arrows d and f) are sealed by crush seals 822. Potential leaks (as represented by arrows b and e) are sealed by inner square rings 406 described in the embodiments of FIG. 7A-7C. As such, water (or other liquid) tightness of the sensor transmitter assembly is ensured.

Transmitter Assembly

Figure 9:
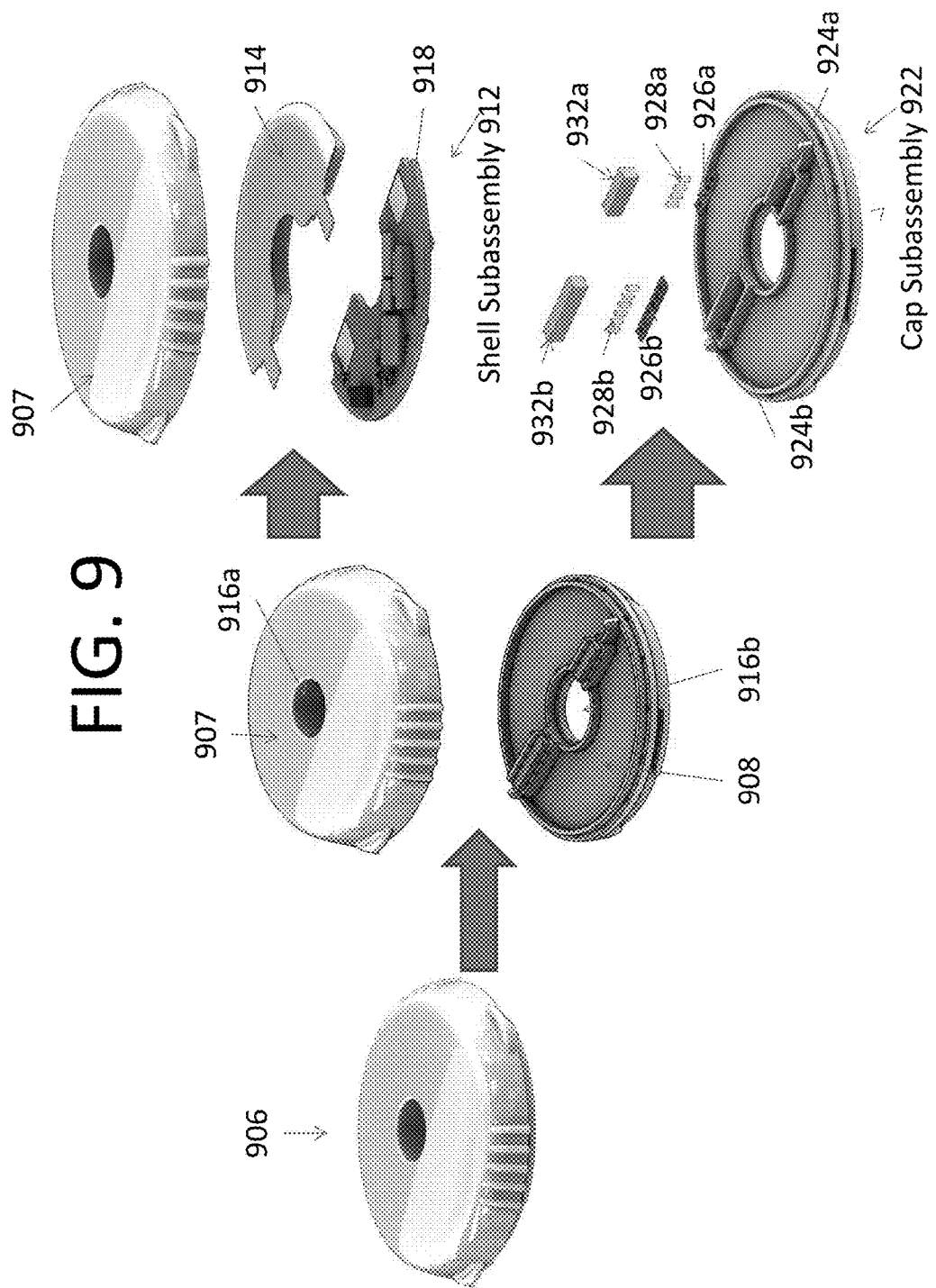
FIG. 9 is an exploded view of a transmitter assembly according to an embodiment of the present disclosure.

Referring to FIG. 9, an exploded view of a transmitter assembly is illustrated according to an embodiment of the present disclosure.

A transmitter assembly 906 includes without limitation a transmitter shell 907 adapted to be connected or otherwise be positioned on a transmitter cap 908. Transmitter shell 907 and transmitter cap 908 each include respective openings 916a and 916b adapted to be engaged with a sensor assembly cap as described above according to one or more embodiments. Transmitter shell 907 includes a shell subassembly 912 including a custom portion 914 that houses, for example, a custom battery. Also, transmitter shell 907 includes a substrate portion 918 on which a PCB board having various electronic components is disposed. Transmitter cap 908 includes a cap subassembly 922 having recesses or openings 924a and 924b that are adapted to respectively accommodate various components including fastening devices or materials, e.g., epoxy 926a and 926b, contacts 928a (e.g., 4 contacts) and 928b (e.g., 6 contacts), and elastomeric connectors 932a and 932b. Notably, no spring or other support components are necessary.

Referring to FIGS. 10A and 10B, side perspective views of a transmitter shell subassembly are illustrated according to an embodiment of the present disclosure. FIG. 10A illustrates a bottom side perspective view of a transmitter shell subassembly according to an embodiment. A transmitter shell subassembly 1012 includes, without limitation, components including a custom battery 1014, for example a custom D-shaped battery (e.g., 36 mAh) adjoining a PCB 1018 disposed therein. In various embodiments, PCB 1018 is disposed on approximately one half portion of shell subassembly 1012 and custom battery 1014 is disposed on approximately the other half portion of the subassembly. Advantageously, the components are compressed or otherwise fit together such that no solder or other connections are necessary for the subassembly. In this way, the arrangement minimizes dead volume and reduces the height of the subassembly. FIG. 10B illustrates a top side perspective view of the transmitter shell subassembly 1012. In one or more embodiments, custom battery 1014 is custom made to fit together with PCB 1018. In various embodiments, PCB 1018 includes a chip antenna 1032. Advantageously, chip antenna 1032 is moved away from custom battery 1014 for a more efficient layout. It should be noted that in various embodiments the subassembly fits various components as necessary, which are designed in various shapes or sizes to fit in the subassembly. For example, in alternative embodiments, there are one or more custom batteries (e.g., 1, 2, etc.) that are of particular shapes to fit together with a PCB of a particular shape and occupy less than half or more than half (e.g., one quarter, three quarters, etc.) of the subassembly. In various embodiments, custom battery 1014 is a Lithium battery or it can be of any other appropriate chemistry. Also, in various embodiments, options for connecting the custom battery to the PCB include double sided tape, or adhesive to keep them in place or from shifting around.

Referring to FIG. 11A, a partial plane view of a transmitter assembly layout is illustrated according to an embodiment of the present disclosure. As described above, a shell subassembly of a transmitter assembly 1106 includes a PCB 1118 disposed on substantially one half portion and a custom battery 1114 disposed on substantially the other half portion of the shell subassembly of transmitter assembly 1106. FIG. 11B illustrates another partial plane view of a transmitter assembly according to an embodiment of the present disclosure. Elastomeric connectors 1132a and 1132b are connected to a PCB 1118. Elastomeric connector 1132a is adapted to accommodate four contacts 1128a and elastomeric connector 1132b is adapted to accommodate six contacts 1128b. No spring connectors are necessary. Contacts 1128a and 1128b are solid contacts that form a solid connection. It should be noted that in various embodiments the elastomeric connectors are adapted to accommodate different numbers of contacts as necessary for certain applications. For example, elastomeric connector 1132a accommodates any number of contacts such as 3, 5, 7, etc. and elastomeric connector 1132b accommodates any number of contacts such as 4, 8, 10, etc.

Figure 11C:
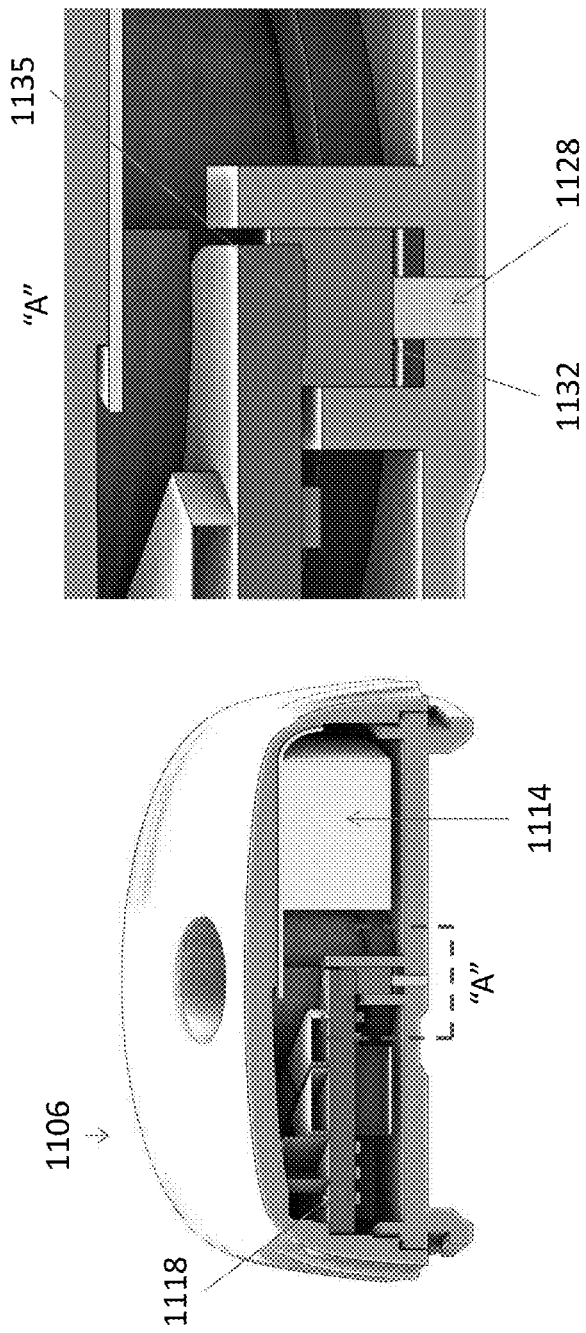
FIG. 11C is a partial perspective view of a transmitter assembly layout illustrating details of external contacts to a PCB according to an embodiment of the present disclosure.

FIG. 11C is a partial perspective view of a transmitter assembly layout illustrating details of external contacts to a PCB according to an embodiment of the present disclosure. As described above according to an embodiment, transmitter assembly 1106 includes a PCB 1118 disposed on substantially one half portion and a custom battery 1114 disposed on substantially the other half portion of transmitter assembly 1106. As illustrated in detail "A", a first side of an elastomeric connector 1132 is attached to or otherwise connects with a PCB contact pad 1135. External contacts 1128 are disposed on or otherwise connected to another side of elastomeric connector 1132, which includes conductive material. Such connection layout eliminates the need for more intrusive connection methods (e.g., soldering) of external contacts to the PCB.

In various embodiments as described above, elastomeric connector 1132 is a z-type connector, e.g. a ZEBRA connector that includes alternating conductive and insulating regions in a rubber or elastomer matrix that produce overall anisotropic conductive properties. It should be noted that other type of Z-connectors can be used as well as leaf spring type connectors.

Referring to FIGS. 12A-D, perspective views of transmitter cap contacts overmolding are illustrated according to an embodiment of the present disclosure.

In FIG. 12A, a mold 1221 of a transmitter cap for a transmitter assembly includes molded portions 1203*a* and 1203*b* each including at least one opening or hole formed thereon. In this embodiment, molded portion 1203*a* has four holes and molded portion 1203*b* has six holes. As illustrated in detail "A", molded portion 1203*a* of mold 1221 of the transmitter cap includes at least one hole 1205*a*. As illustrated in FIG. 12B, holes formed on molded portions 1203*a* and 1203*b* are adapted to accommodate contacts 1204, which are positioned in corresponding holes. In various embodiments, contacts 1204 are symmetric to avoid orientation issues inside a corresponding hole of molded portions 1203*a* and 1203*b*. As illustrated in detail "B", four contacts 1204 are positioned in corresponding holes formed on molded portion 1203*a*. In FIGS. 12C-12D, an overmolding 1209 is placed on top of mold 1221 (and contacts 1204). Contacts 1204 are insert molded into transmitter cap 1208. In various embodiments, mold 1221 represents one half of a mold for a transmitter assembly, and overmolding 1209 represents another half of the mold. First, contacts 1204 are captured between the two mold halves, that is, between mold 1221 and overmolding 1209. Then, transmitter cap 1208, for example, made of a plastic material, fills a mold cavity 1212 and encapsulates the contacts 1204.

Sensor/Transmitter Connection, Electrical

Figure 13:
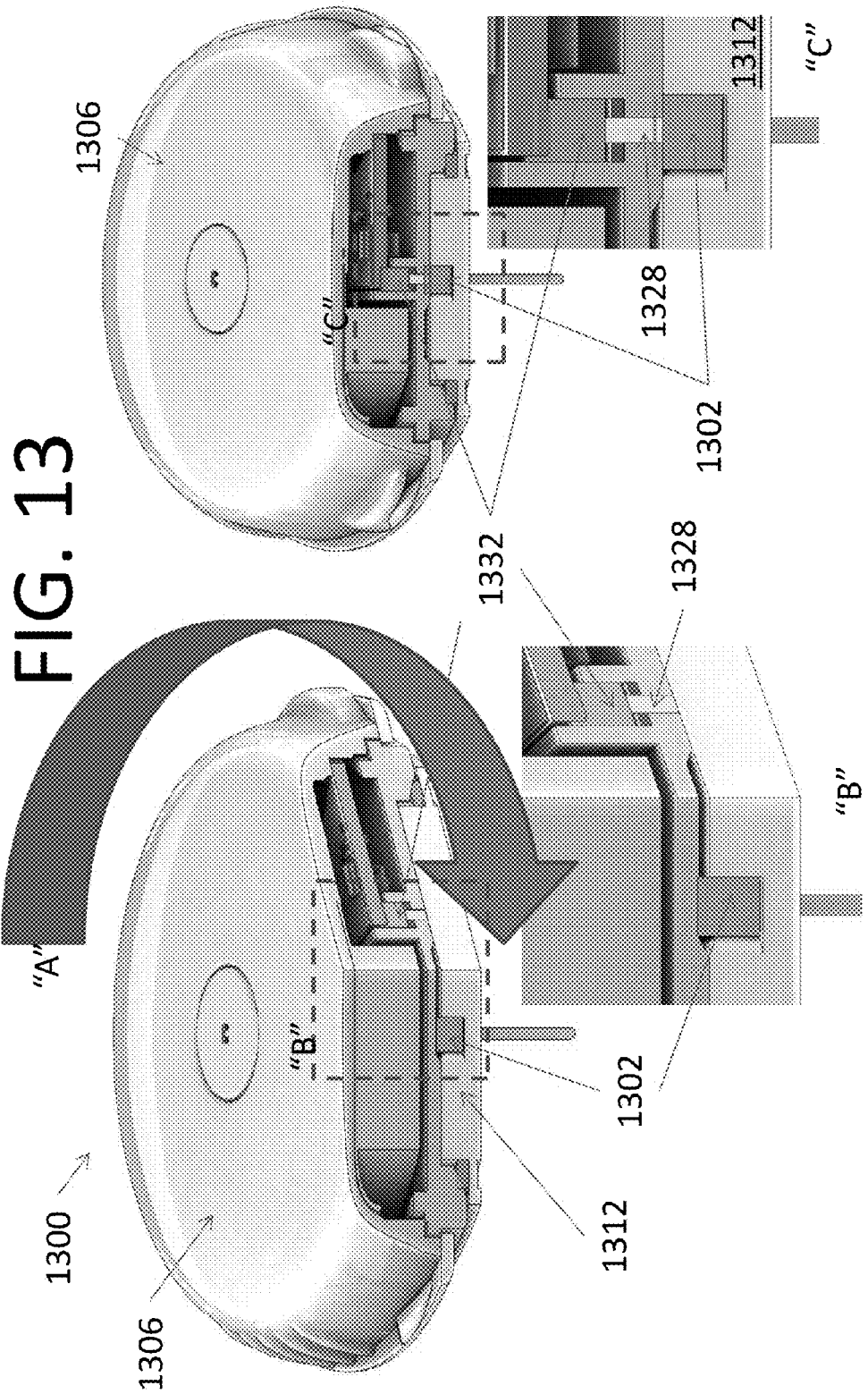
FIG. 13 illustrates side perspective views for electrically connecting a sensor assembly to a transmitter assembly according to an embodiment of the present disclosure.

FIG. 13 illustrates side perspective views for electrically connecting a sensor assembly to a transmitter assembly according to an embodiment.

A sensor transmitter assembly 1306 is connected to a sensor assembly 1312 by initially lowering down transmitter assembly 1306 into sensor assembly 1312. As illustrated in detail "B", at this stage, an elastomeric connector 1332 and a contact 1328 of transmitter assembly 1306 are not aligned with an elastomeric connector 1302 of sensor assembly 1312. A twisting or rotation motion, as indicated by arrow "A", is used to lock transmitter assembly 1306 and sensor assembly 1312. As a result of the rotation motion, as illustrated in detail "C", elastomeric connector 1332 and contact 1328 of transmitter assembly 1306 line up with elastomeric connector 1302 of sensor assembly 1312, thus competing the connection.

Figure 14:
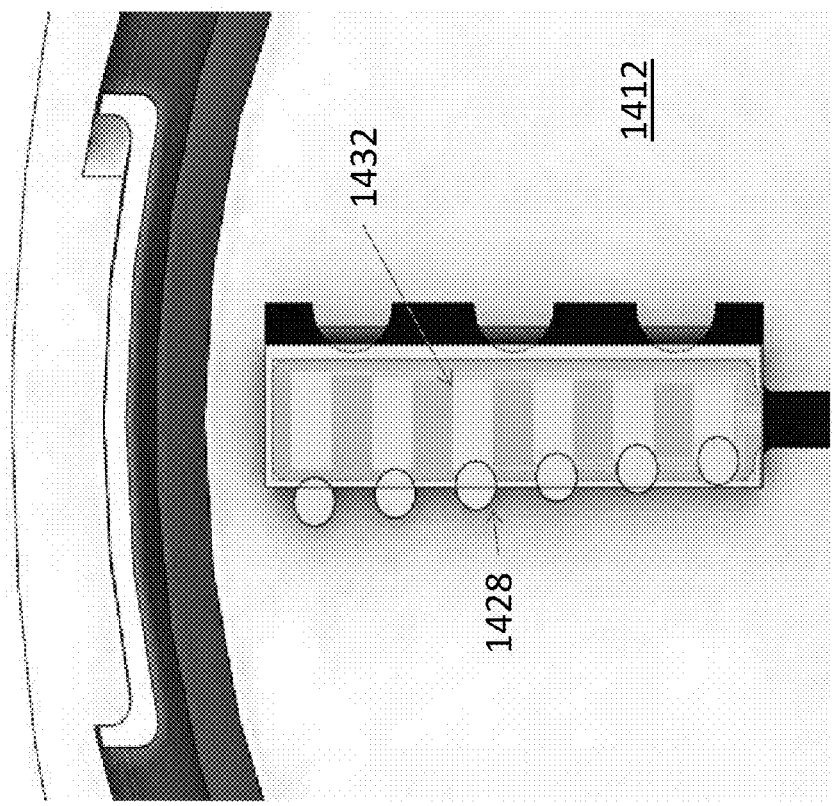
FIG. 14 is a partial top view of an electrical connection of a sensor assembly and at least one contact of a transmitter assembly according to an embodiment of the present disclosure.

Referring to FIG. 14, a partial top view of an electrical connection of a sensor assembly and at least one contact of a transmitter assembly is illustrated according to an embodiment of the present disclosure. As described above according to an embodiment, a sensor assembly 1412 has a cavity in which an elastomeric connector 1432 is disposed. When a transmitter assembly is connected to the sensor assembly, at least one contact of the transmitter assembly makes a connection with the elastomeric connection 1432. In this embodiment, six contacts 1428 of a transmitter assembly connect with elastomeric connector 1432. In some cases angular misalignment may occur between the contacts. In this embodiment, an angular misalignment of approximately 5° is shown between the contacts. Even though contacts 1428 do not line straight up, they still make electrical contact with elastomeric connector 1432. As such, in various embodiments, a tolerance of up to about 5° angular misalignment can occur without disrupting the connection between the contacts and the elastomeric connector and otherwise running into another area. Advantageously, the angular misalignment is within a margin of error such that even if the contacts are angularly misaligned, the design of the elastomeric connector ensures that an electrical connection is robust. If a transmitter assembly is mechanically connected to sensor assembly 1412, then an electrical connection is ensured.

Back to Back Sensor Connections

Referring now to FIGS. 15A-15C, back-to-back sensor connections are illustrated according to an embodiment of the present disclosure. FIG. 15A is a partial top side perspective view of a back-to-back sensor connection according to an embodiment of the present disclosure. FIG. 15B is a partial bottom side perspective view of a back-to-back sensor connection according to an embodiment of the present disclosure. FIG. 15C is a partial top view of a bottom surface of a transmitter assembly according to an embodiment.

As illustrated in FIGS. 15A and 15C, and as described above according to one or more embodiments (see, e.g., FIG. 2B), a transmitter assembly 1506 includes at least one transmitter contact 1517 disposed on a bottom surface 1511. In this embodiment, six transmitter contacts 1517 are illustrated. An upper sensor includes a sensor head 1543 having at least one upper sensor contact pad 1535. In this embodiment, six upper sensor contact pads 1535 are illustrated. The upper sensor extends into or is otherwise connected to upper sensor electrodes 1537. As illustrated in FIG. 15B, a lower sensor includes a sensor head 1545 having at least one lower sensor contact pad 1539. In this embodiment, six lower sensor contact pads 1539 are illustrated. Lower sensor head 1545 extends into or is otherwise connected to lower sensor electrodes 1541.

In particular embodiments, to create a double-sided sensor, two discrete single-sided sensors are placed back-to-back. For example, an upper sensor having sensor head 1543 is placed back-to-back with a lower sensor having lower sensor head 1545. As will be described in more detail below, for example, with respect to the embodiment of FIG. 16, each single-sided sensor has 1 Reference Electrode (RE), 1 Counter Electrode (CE), and 2 independent Working Electrodes (WE) that correspond to six contacts 1517 disposed on a transmitter cap 1511 of a transmitter assembly 1506 as illustrated in FIG. 15C. The REs of the two sensors are shorted together and connected to a shared RE transmitter contact. The CEs of the two sensors are shorted together and connected to a shared CE transmitter contact. Each WE on each of the two sensors is connected to its own independent WE transmitter contact (WE-A through WE-D).

Referring to FIG. 16, a top view of a sensor having at least one contact pad is illustrated according to an embodiment of the present disclosure. A single-sided sensor 1640 has 1 CE, 1 RE and at least one WE, for example, WE-1 and WE-2. As shown, the CE has one contact pad, the RE has one contact pad, and each of the WEs has two contact pads connected in parallel, for example. Each WE contact pad has one trace 1643 leading to its corresponding electrode. The CE and RE pads each have two traces 1647 leading to their respective electrodes.

Figure 17:
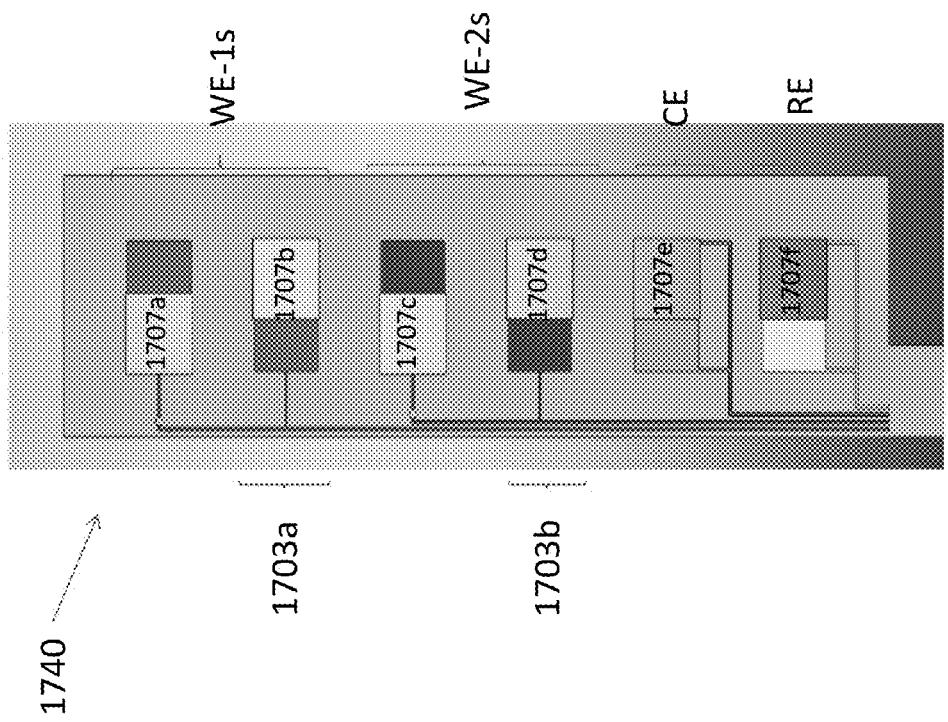
FIG. 17 is a top view of a sensor having windows cut through each of the sensor contact pads according to an embodiment of the present disclosure.

Referring now to FIG. 17, a top view of a sensor having windows cut through each of the sensor contact pads is illustrated according to an embodiment of the present disclosure. A sensor 1740 is fabricated so that during fabrication, windows may be cut out through each of the sensor contact pads. In this embodiment, windows 1707a-1707f are cut out through each corresponding sensor contact pad as illustrated. In various embodiments, windows 1707a-1707f are cut out using, for example, laser cutting or any other suitable cutting techniques. Traces from the contact pads leading to their respective electrodes run to one side, for example, the left side. In this embodiment, because the traces from the WE-1 and WE-2 contact pads run to the left side, cutting out windows on the left side of the contact pad deactivates that contact pad. Cutting out windows on the right side keeps the contact pad active. In this embodiment, as a result of window 1707b of WE-1 and window 1707d of WE-2 being cut out (on the right side), contact pad 1703a of WE-1 and contact pad 1703b WE-2 remain active. Conversely, cutting windows 1707a and 1707c on the left side of the respective WE contact pads, deactivates those contact pads. That is, cutting out a window on a side of a WE contact pad where the traces run, deactivates the contact pad.

Notably, on each single-sided sensor, for example, sensor 1740, the windows cut through respective WE contact pads are staggered so that only one of the two contact pads for each WE remains active. For example, in this embodiment, each of WE-1s contact pads has a window 1707a cut on the left side and a window 1707b cut on the right side, so that only WE-1 contact pad 1703a having a window cut on the right side remains active. Similarly, WE-2s contact pads has a window 1707c cut on the left side and a window 1707d cut on the right side, so that only WE-2 contact pad 1703b having its window cut on the right side remains active. With respect to the RE contact pad and the CE contact pad, because the CE and RE contact pads each have two traces, one on each side of the corresponding contact pad, the CE and RE contact pads remain active regardless of which side the window is on.

Figure 18:
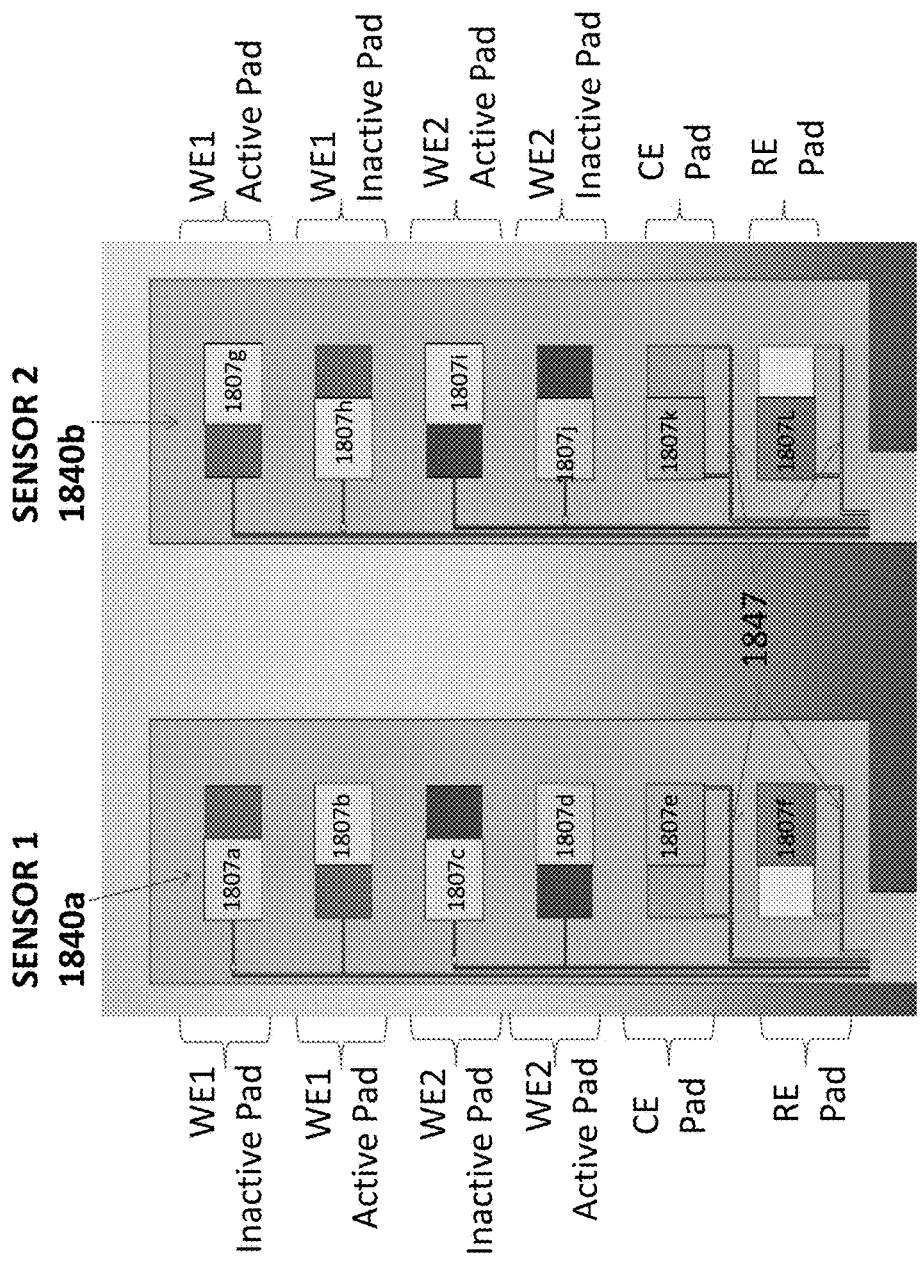
FIG. 18 illustrates a back-to-back sensor combination according to an embodiment of the present disclosure.

FIG. 18 illustrates a back-to-back sensor combination according to an embodiment of the present disclosure. A first sensor 1840a and a second sensor 1840b are combinable to form a back-to-back sensor. In this embodiment, first sensor 1840a and second sensor 1840b each has 6 contact pads including 4 WE pads (2 WE1 pads and 2 WE2 pads each). Each of the 6 contact pads of first sensor 1840a has windows 1807a-1807f created or cut out through a contact pad head of first sensor 1840a, and each of the 6 contact pads of second sensor 1840b has windows 1807g-1807L created or cut out through a contact pad head of second sensor 1840b. In various embodiments, windows 1807a-1807L are cut by using an appropriate cutting technique such as are laser cutting. Windows 1807a-1807f of first sensor 1840a are mirror images of windows 1807g-1807L of second sensor 1840b. By mirroring a cut pattern for windows 1807a-1807L, active WE pads are staggered between the two sensors 1840a and 1840b. In that regard, a window 1807a cut on a left side of WE1 contact pad in first sensor 1840a results in an inactive pad, and a window 1807g cut on a right side of WE 1 contact pad in second sensor 1840b results in an active pad. A window 1807b cut out on a right side of WE1 contact pad in first sensor 1840a results in an active pad, and a window 1807h cut on a left side of WE1 contact pad in second sensor 1840b results in an inactive pad. A window 1807c cut out on a left side of WE1 contact pad in first sensor 1840a results in an inactive pad, and a window 1807i cut on a right side of WE1 contact pad in second sensor 1840b results in an active pad. A window 1807d cut out on a right side of WE1 contact pad in first sensor 1840a results in an active pad, and a window 1807j cut on a left side of WE1 contact pad in second sensor 1840b results in an inactive pad. It should be understood that the cut-out parts on the contact pads can be done on alternative sides (left or right) to mirror each other as appropriate.

In addition, first sensor 1840a and second sensor 1840b each have a CE contact pad and an RE contact pad. Each respective CE contact pad and RE contact pad of first sensor 1840a and second sensor 1840b have two traces 1847. In that regard, CE contact pad of first sensor 1840a has a cut out window 1807e having one trace, and another trace is on the non-cut out part of the contact pad. Similarly, CE contact pad of second sensor 1840b has a cut out window 1807k having one trace, and another trace is on the non-cut out part of the contact pad. RE contact pad of first sensor 1840a also has a cut out window 1807f on one trace, and another trace is on the non-cut out part of the contact pad. Similarly, RE contact pad of second sensor 1840b has a cut out window 1807L on one trace, and another trace is on the non-cut out part of the contact pad. Because the CE and RE contact pads each have two traces, one on each side of the corresponding contact pad, the CE and RE contact pads remain active regardless of which side the window is on.

Figure 19A:
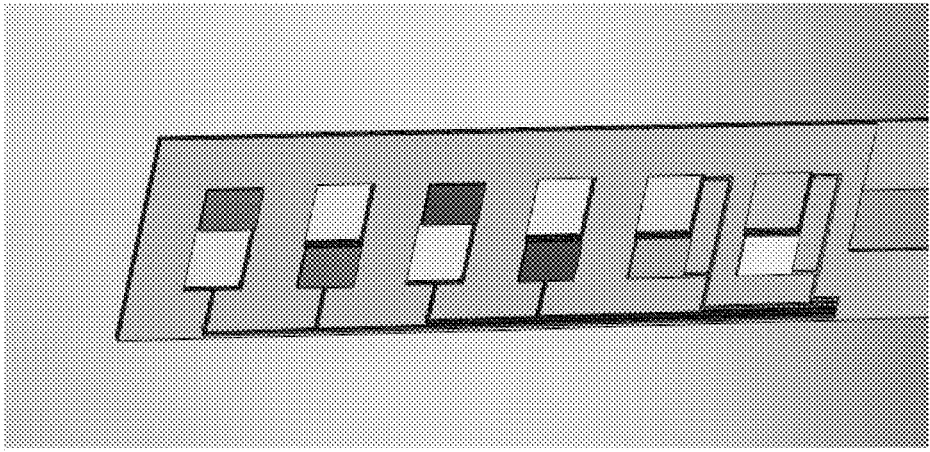
FIGS. 19A-19C illustrate views for placing a first sensor and a second sensor back to back and creating a signal path according to an embodiment of the present disclosure.
Figure 19B:
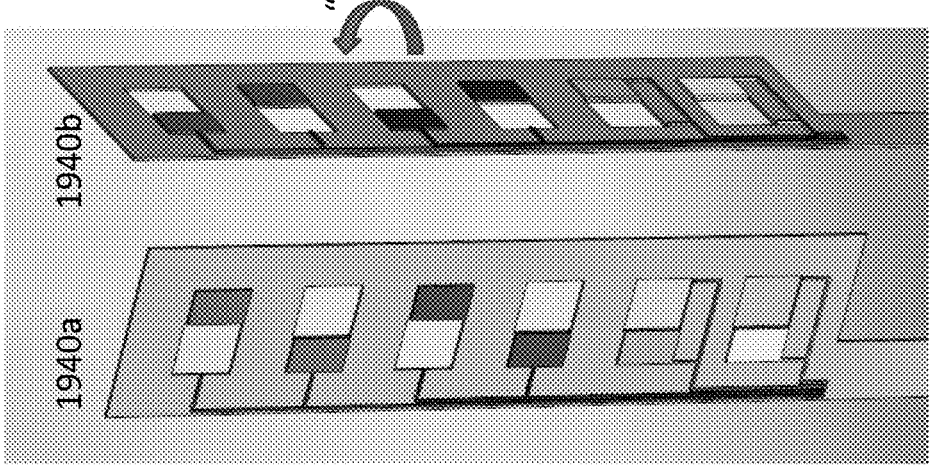
Figure 19C:
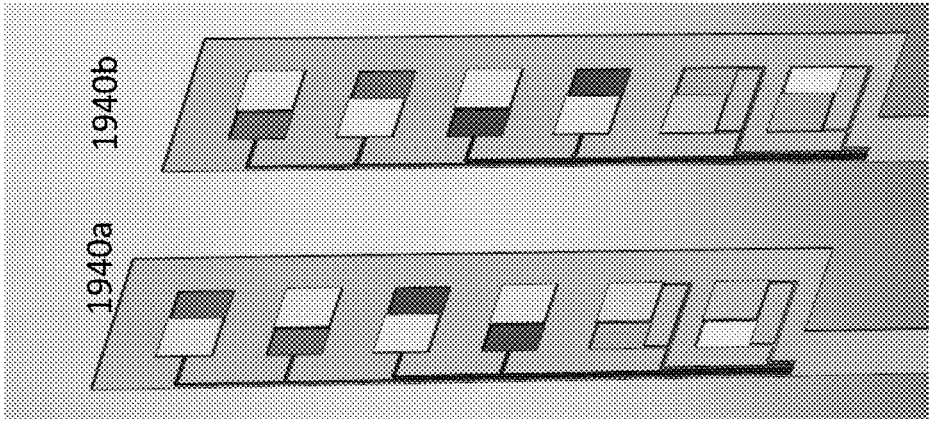

FIGS. 19A-19C illustrate views for placing a first sensor and a second sensor back to back and creating a signal path according to an embodiment of the present disclosure. As illustrated in FIG. 19A, a first sensor 1940a and a second sensor 1940b have mirrored window cut patterns across each respective sensor pad head as described above, for example with respect to the embodiment of FIG. 18. As illustrated in FIG. 19B, first sensor 1940a is placed back to back with second sensor 1940b, for example, by placing or turning second sensor 1940b as indicated by arrow "A" into first sensor 1940a. Because first sensor 1940a and second sensor 1940b have mirrored window cut patterns, the windows of each respective sensor are aligned as illustrated in FIG. 19C. As a result, a signal path is provided between the contact pads of first sensor 1940a and a transmitter as will be described in more detail below.

FIG. 20 illustrates a back-to-back sensor connection to a transmitter assembly according to an embodiment of the present disclosure. A transmitter assembly 2006 includes at least one contact 2017, for example 6 contacts: one RE, one CE, and 4 WEs (WE-D, WE-C, WE-B and WE-A). A first sensor head 2040a includes 6 contact pads having cut out windows, for example as described above with respect to the embodiments of FIGS. 17-18. In this embodiment contact pads corresponding to WE-D and WE-B are active, and contact pads corresponding to WE-C and WE-A are inactive. A sensor assembly 2012 includes a second sensor 2040b. Second sensor 2040b has 6 contact pads having cut out windows as described above for example with respect to the embodiments of FIGS. 17-18. In this embodiment, contact pads corresponding to WE-C and WE-A are active, and contact pads corresponding to WE-D and WE-B are inactive.

When first sensor 2040a is combined with second sensor 2040b (for example as described above according to the embodiments of FIGS. 19A-19C), a signal path to transmitter contacts 2017 is created through active contact pads WE-D and WE-B of first sensor 2040a and through active contact pads WE-C and WE-A of second sensor 2040b. In this embodiment, first sensor 2040a is an upper sensor and second sensor 2040b is a lower sensor. In alternative embodiments, because the pattern of active/inactive pads are interchangeable, the upper sensor has a pattern similar to second sensor 2040b of this embodiment, and the lower sensor has a pattern similar to first sensor 2040a of this embodiment.

Figure 21:
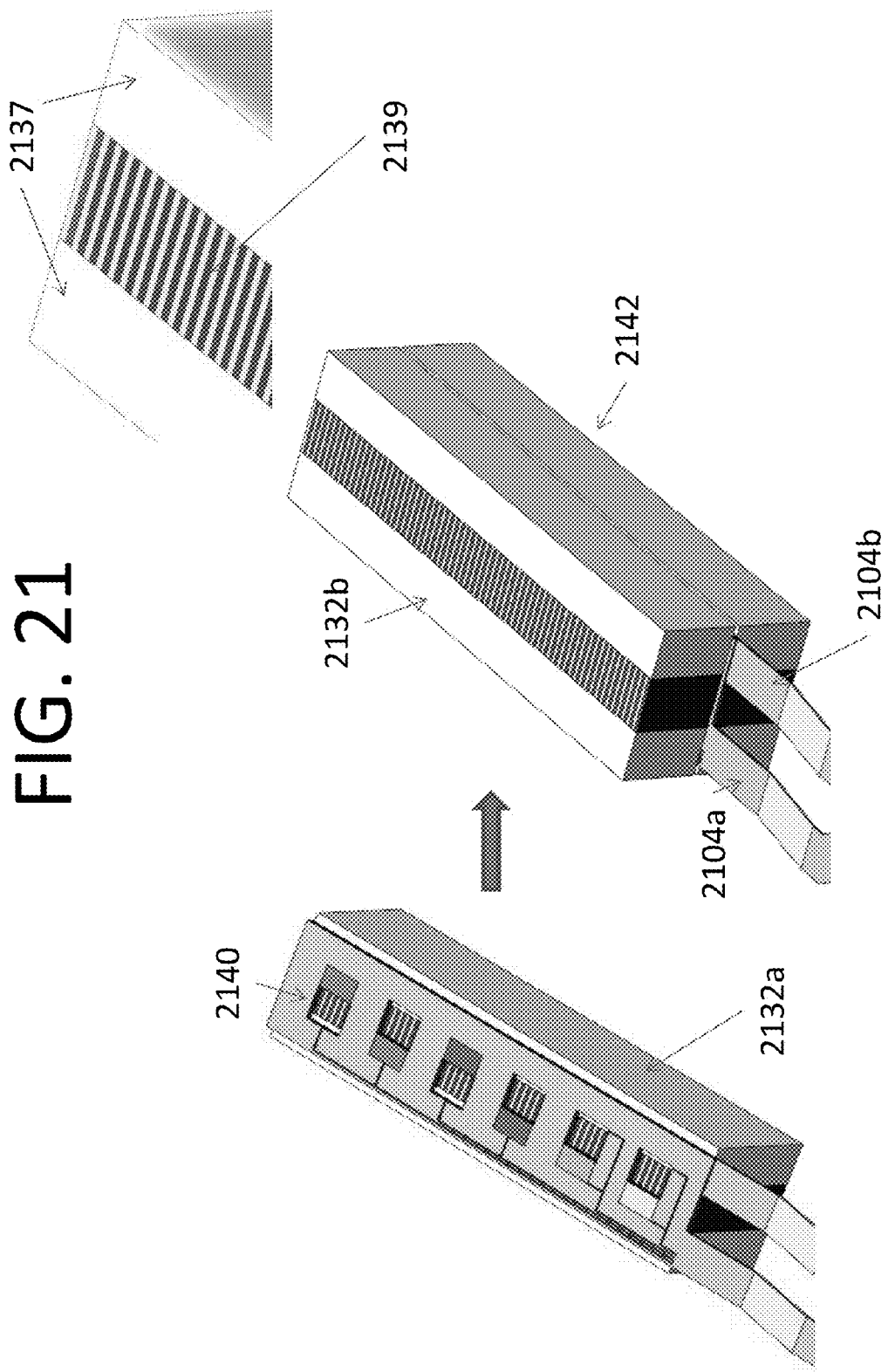
FIG. 21 illustrates a back-to-back sensor disposed in between elastomeric connectors according to an embodiment of the present disclosure.

FIG. 21 illustrates a back-to-back sensor disposed in between elastomeric connectors according to an embodiment of the present disclosure. A back-to-back sensor 2140 as described above for example with respect to the embodiments of FIGS. 19A-19C is placed on a lower elastomeric connector 2132a. Then, an upper elastomeric connector 2132b is positioned on top of back-to-back sensor 2140 to form a sensor/connector stack 2142. As such, sensor connector stack 2142 includes the back-to-back sensor 2140 sandwiched or otherwise placed in between two elastomeric connectors. Electrodes 2104a and 2104b extend from or are otherwise connected to respective sensor heads (e.g., lower sensor head and upper sensor head) of back-to-back sensor 2140. In various embodiments, lower elastomeric connector 2132a and/or upper elastomeric connector 2132b are z-axis elastomeric connectors. For example, they are ZEBRA connectors. The upper and lower elastomeric connectors 2132a and 2132b have alternating conductive and nonconductive layers 2139 supported by nonconductive supports 2137, e.g., Silicone nonconductive supports. In various embodiments, an inner conductive layer of an elastomeric connector creates signal paths. Outer nonconductive layers prevent shorting between contacts.

Figure 22:
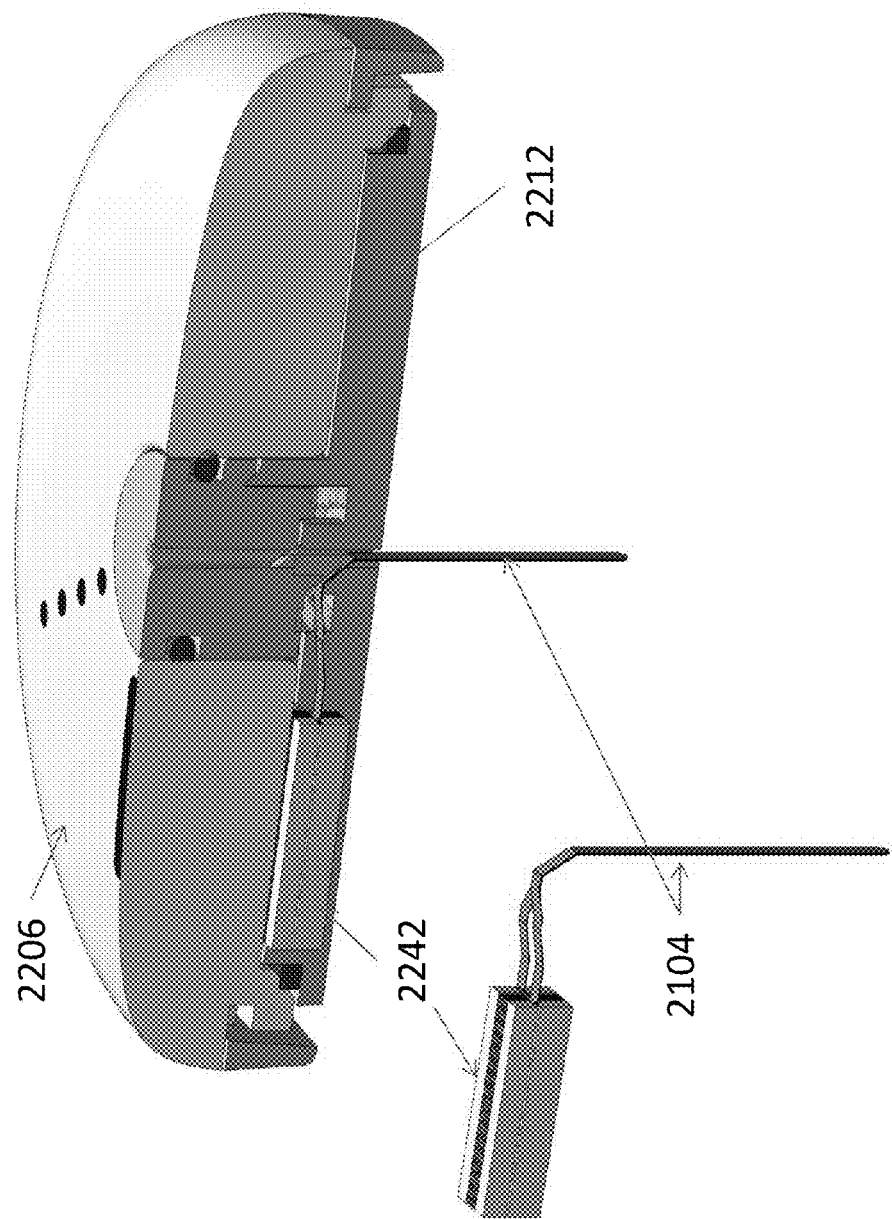
FIG. 22 is a partial side perspective view of a sensor transmitter assembly having a back-to-back sensor connected to a transmitter according to an embodiment of the present disclosure.

FIG. 22 is a partial side perspective view of a sensor transmitter assembly having a back-to-back sensor connected to a transmitter according to an embodiment of the present disclosure. A transmitter assembly 2206 is connected to a sensor assembly 2212. A connector stack 2242 includes a back-to-back sensor sandwiched or otherwise placed in between two elastomeric connectors as described above for example with respect to the embodiment of FIG. 21. When transmitter assembly 2206 is connected to sensor assembly 2212, sensor-connector stack 2242 is compressed between transmitter contacts (not shown) and a sensor base of sensor assembly 2212. A sensor portion 2104 extends from or is otherwise connected to connector stack 2242.

Figure 23:
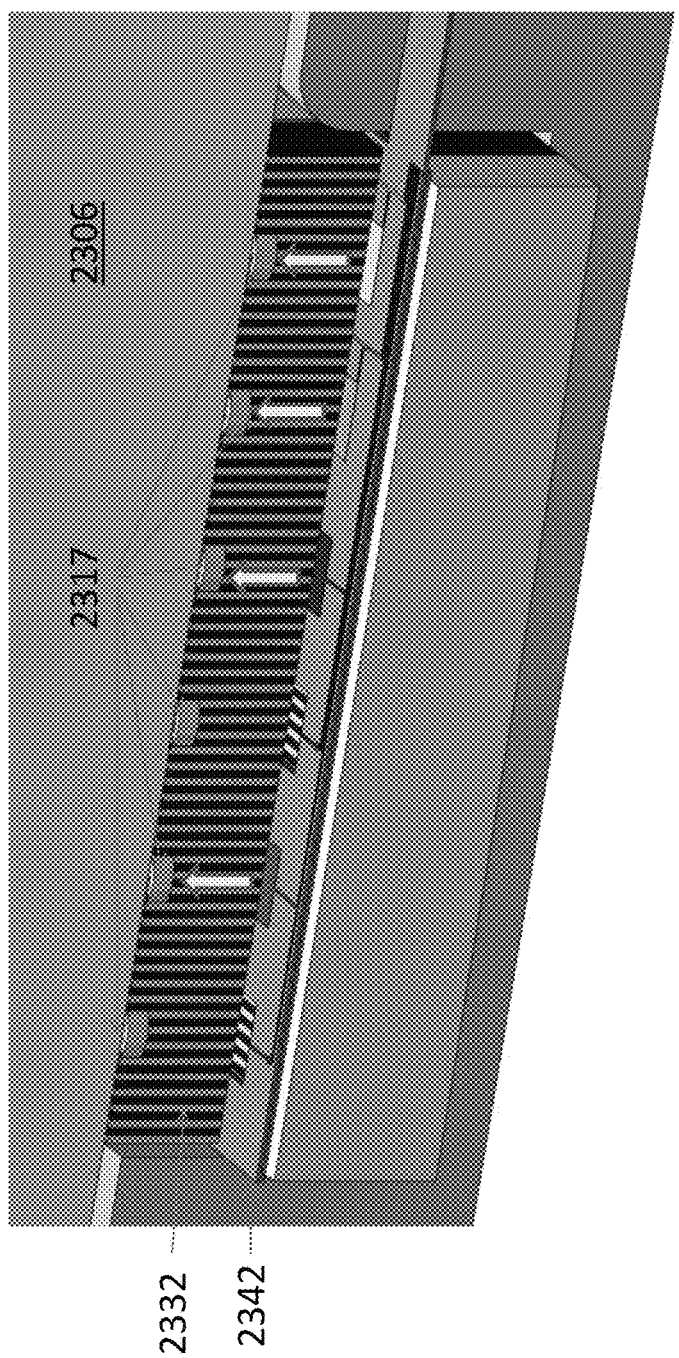
FIG. 23 is a perspective view of a connection between sensor contact pads and transmitter contacts according to an embodiment of the present disclosure.

Referring to FIG. 23, a perspective view of a connection between sensor contact pads and transmitter contacts is illustrated according to an embodiment of the present disclosure. A transmitter assembly 2306 includes at least one contact 2317. In this embodiment, transmitter assembly 2306 includes 6 contacts 2317. A sensor connector stack 2342 includes six contact pads of back-to-back sensors that connect to transmitter contacts 2317 through conductive layers of an upper elastomeric connector 2332.

Figure 24:
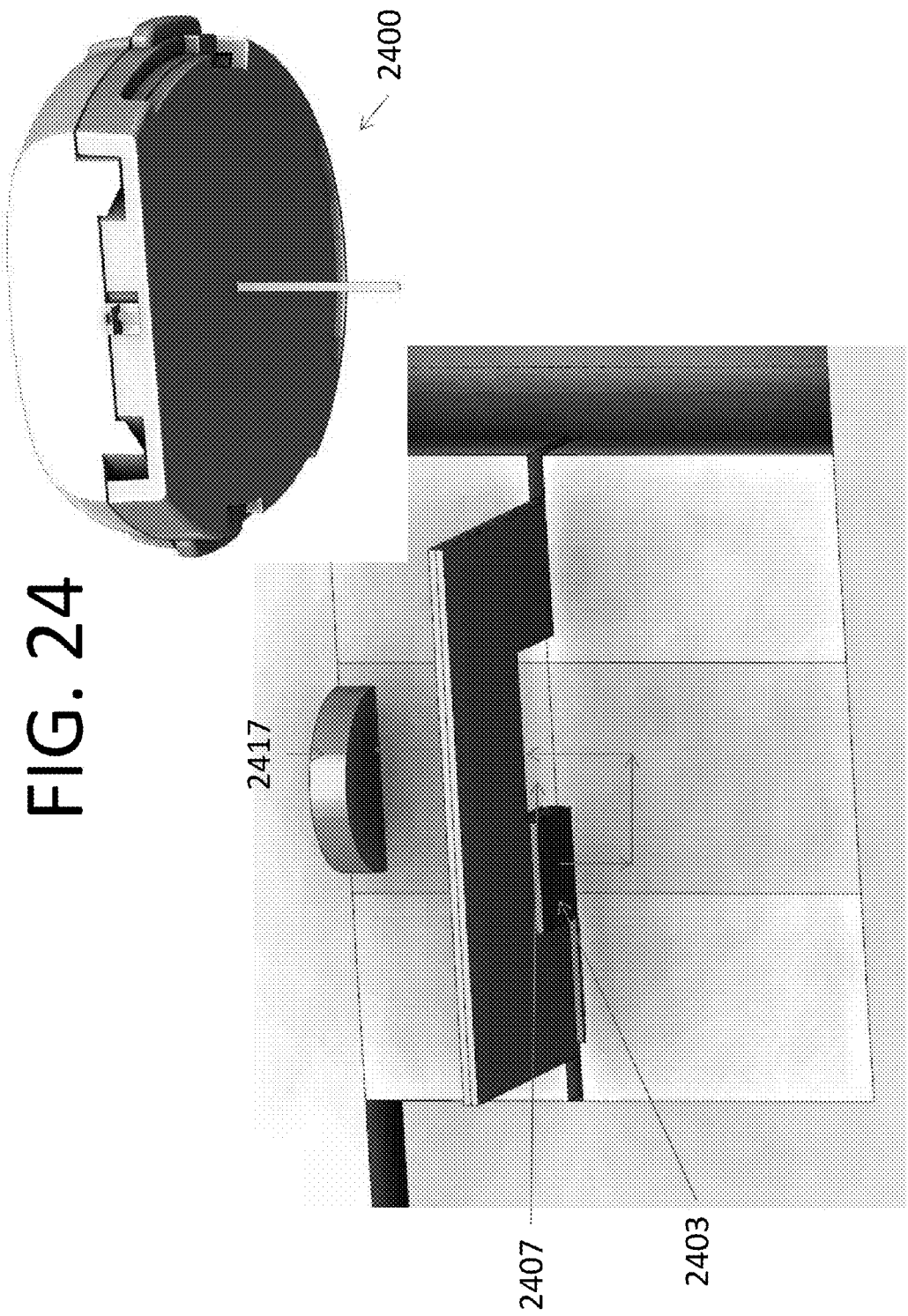
FIG. 24 is a bottom perspective view of a connection of a sensor contact pad to a transmitter contact according to an embodiment of the present disclosure.

FIG. 24 is a bottom perspective view of a connection of a sensor contact pad to a transmitter contact according to an embodiment of the present disclosure. In forming sensor transmitter assembly 2400, a transmitter assembly is connected to a sensor assembly as described above according to one or more embodiments. As a result of the connection, an upper elastomeric connector and a lower elastomeric connector are compressed and extrude into sensor windows such as window 2407 of a contact pad. The upper and lower elastomeric connectors also compress against each other, i.e., they may overlap. Lower sensor contact pads, for example a lower sensor contact pad 2403, is connected to the transmitter contacts, for example transmitter contact 2417, as a result of an overlap of at least one conductive layer of an upper elastomeric connector with at least one conductive layer of a lower elastomeric connector.

Figure 25:
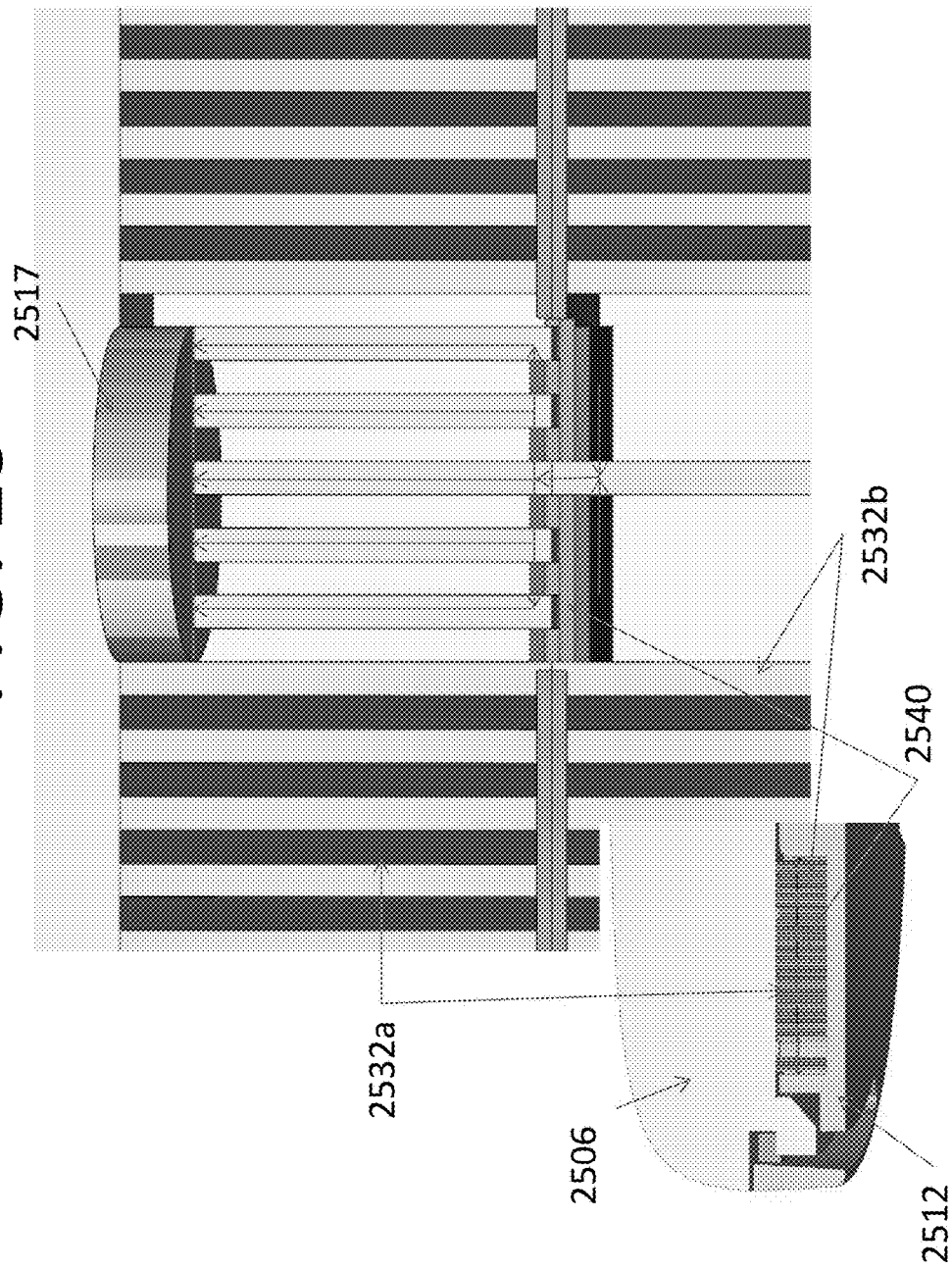
FIG. 25 illustrates a detailed connection of at least one sensor contact pad to a transmitter contact according to an embodiment of the present disclosure.

FIG. 25 illustrates a detailed connection of at least one sensor contact pad to a transmitter contact according to an embodiment of the present disclosure. A transmitter assembly 2506 connects with a sensor assembly 2512 compressing lower and upper elastomeric connectors 2532a and 2532b. Elastomeric connectors 2532a and 2532b sandwich upper and lower sensors 2540 as described above according to one or more embodiments. An inactive contact pad of the upper sensor that is located directly above an active contact pad on the lower sensor acts as a conductor. As a result, contact resistance is minimized between the lower sensor contact pad and a transmitter contact, for example, transmitter contact 2517, in case there is overlap between only one pair of conductive layers of an upper elastomeric connector and a lower elastomeric connector. That is, even if only one pair of conductive layers of the upper and lower elastomeric connectors line up, that is all that is needed for making contact with transmitter contact 2517. This is facilitated by the spreading of or compression of the elastomeric connectors when connecting transmitter assembly 2506 to sensor assembly 2512.

Figure 26:
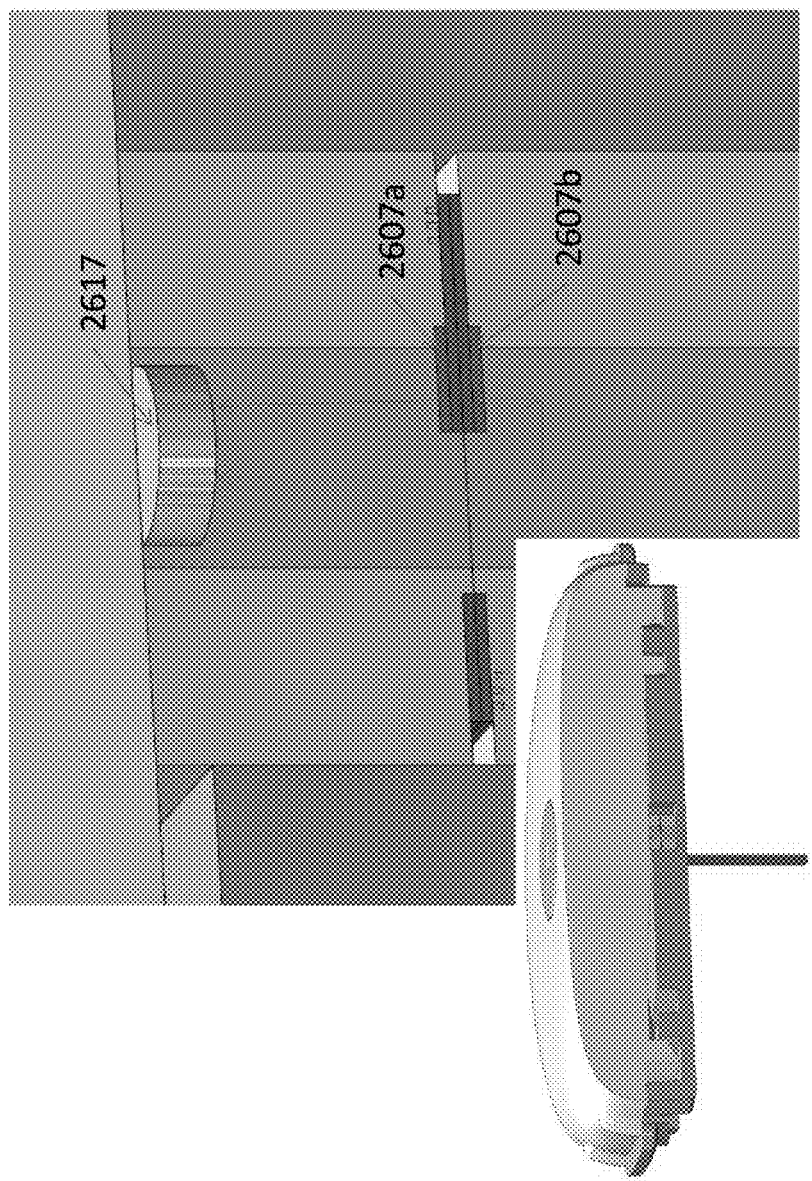
FIG. 26 illustrates a connection of a CE or RE to a transmitter contact according to an embodiment of the present disclosure.

Referring to FIG. 26, a connection of a CE or RE to a transmitter is illustrated according to an embodiment of the present disclosure. A contact pad 2607a of an upper sensor, for example a contact pad of a CE or RE, and a contact pad 2607b of a lower sensor, for example a corresponding CE or RE are both connected to their common transmitter contact 2617. As indicated, both the contact pad 2607a and the contact pad 2607b are connected via an elastomeric connector.

Figure 27A:
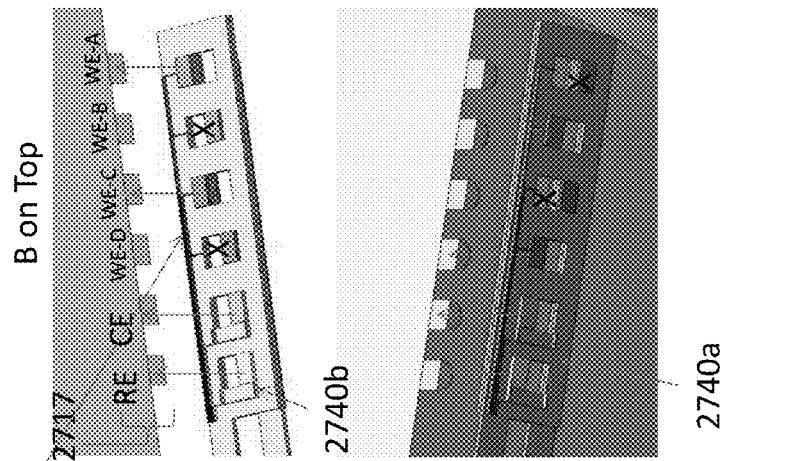
FIGS. 27A-27C are views of a first sensor and a second sensor having mirrored contact pads and respective connections to a transmitter according to an embodiment of the present disclosure.
Figure 27B:
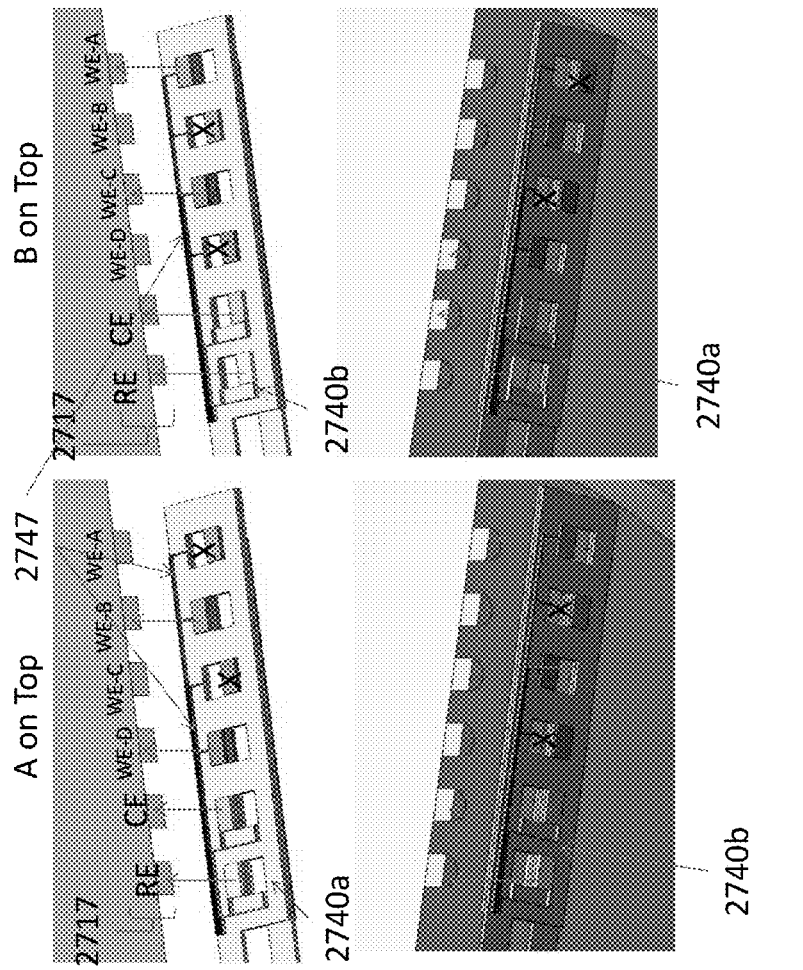
Figure 27C:
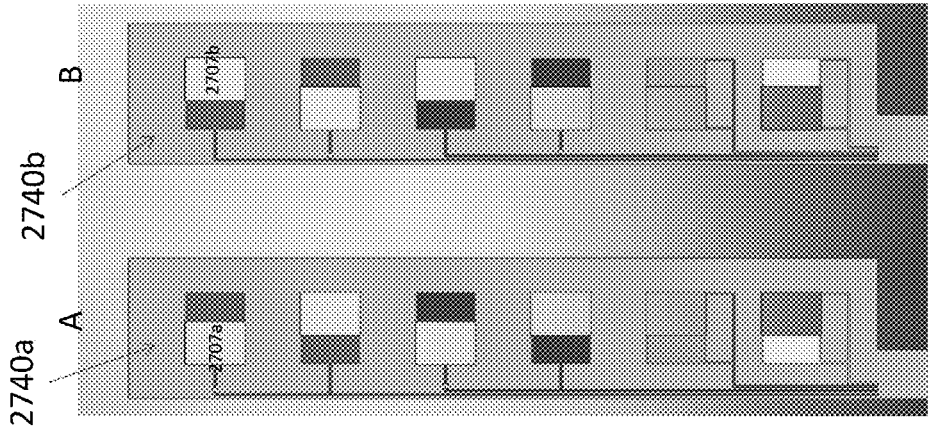

Referring now to FIGS. 27A-27C, views of a first sensor and a second sensor having mirrored contact pads and respective connections to a transmitter are illustrated according to an embodiment of the present disclosure. As illustrated in the embodiment of FIG. 27A, a first sensor and a second sensor having mirrored contact pad windows are illustrated according to an embodiment of the present disclosure. A first sensor 2740a "A" and a second sensor 2740b "B" each has a windows pattern cut through each sensor head as described above according to one or more embodiments. The cut pattern of one sensor mirrors the cut pattern of the other sensor. That is, the cut patterns of first sensor "A" and second sensor "B" mirror each other. For example, a contact pad of the first sensor "A" having a window 2707a cut on the left side mirrors a contact pad of the second sensor "B" having a window 2707b cut on the right side. In this way, the contact pads of each sensor line up when they are connected to corresponding transmitter contacts. Advantageously, it is unnecessary in manufacturing to control which sensor is on top. The device functions regardless of which sensor is on top as a result of the contact pad windows lining up.

FIG. 27B illustrates an embodiment where a first sensor "A" is on top of a second sensor "B". In this embodiment, a first sensor "A" may be positioned or otherwise connected between second sensor "B" and transmitter contacts 2717. Transmitter contacts include an RE, a CE and 4 WEs (WE-D, WE-C, WE-B and WE-A). Because the windows cut on each contact pad of first sensor "A" mirror contact pads of second sensor "B", they line up and the sensor functions. For example, the contact pad of the first sensor "A" that corresponds to transmitter contact WE-D has a window cut on a side where its trace 2747 does not connect thus making the contact pad active. Even though the corresponding contact pad of second sensor "B" has a window cut on a side where its trace connects thus making the contact pad inactive, a connection with transmitter contact WE-D is established by the active contact pad of first sensor "A" lining up with the inactive pad of second sensor "B". Similarly, the contact pads of first sensor "A" line up with the contact pads of second sensor "B" such that the mirrored cut windows line up to establish a connection with each transmitter contact WE-C, WE-B and WE-A. As described above, the CE and RE for both the first sensor "A" and the second sensor "B" have two traces each and are connected to their common transmitter contact.

FIG. 27C illustrates an embodiment where the second sensor "B" is on top of the first sensor "A". In this embodiment, the second sensor "B" is positioned or otherwise connected between the first sensor "A" and transmitter contacts 2717. As described above, because the windows cut on each contact pad of second sensor "B" mirror contact pads of first sensor "A", they line up and the sensor functions. For example, the contact pad of the second sensor "B" that corresponds to transmitter contact WE-D has a window cut on a side where its trace 2747 connects thus making the contact pad inactive. However, the corresponding contact pad on first sensor "A" has a mirrored window cut on a side where its trace does not connect thus making the contact pad active. As such, a connection with transmitter contact WE-D is established by the active contact pad of first sensor "A" lining up with the inactive contact pad of second sensor "B". Similarly, the contact pads of second sensor "B" line up with the contact pads of first sensor "A" such that the mirrored cut windows line up to establish a connection with each transmitter contact WE-C, WE-B and WE-A. As described above, the CE and RE for both the first sensor "A" and the second sensor "B" have two traces each and are connected to their common transmitter contact.

Alternative embodiments for back to back sensor connections are described below with respect to FIGS. 69A-82.

Mechanical Lockouts

As described above according to one or more embodiments, a device or product includes a transmitter assembly positioned on top of a sensor assembly. In certain embodiments, it is likely that some generations of devices or products include a transmitter assembly and a sensor assembly that are functionally incompatible with each other. For example, a device includes a transmitter assembly using a new transmitter algorithm paired with an older sensor assembly. In particular examples, an assembly meant for pediatric use may be incompatible with an assembly meant for adult use, or an assembly meant for a heavy person's use may be incompatible with an assembly meant for a small person's use. In some embodiments, it is necessary to provide ways to prevent incompatible transmitter assemblies and sensor assemblies from connecting to each other both mechanically and electrically. One or more embodiments allow lockouts to prevent incompatible transmitter and sensor assemblies from connecting. The lockouts are changed easily and independently of other potentially critical features. In an embodiment, interfaces such as slots and rails on respective sensor or transmitter assemblies are used to block a transmitter from fully rotating onto and making a connection with a non-compatible sensor.

In some embodiments, mutually exclusive generations of sensor assemblies and transmitter assemblies are created by changing lockout features, e.g., a length, a width, a depth, a shape, a positioning, etc. of interfaces such as slots in a sensor base and the corresponding mating features, e.g., the mating rails in the transmitter assembly. Changing the features of the sensor base and the corresponding mating features in the transmitter assembly is accomplished by using interchangeable mold inserts, or by other appropriate techniques such as adding interfaces e.g., slots or rails to the respective assembly by carving, soldering, adhering, etc.

In particular embodiments, the lockout features are located on non-critical surfaces of, for example, a sensor base of a sensor assembly and/or a transmitter cap or shell of a transmitter assembly. For instance, these surfaces are not cosmetic and are not sealing surfaces. Because these surfaces are non-critical, it is functionally acceptable if they have visible mold parting lines. As such, in various embodiments, this allows different lockout configurations to be created by using, for example, interchangeable mold inserts rather than by creating entirely new molds for each configuration.

Figure 28:
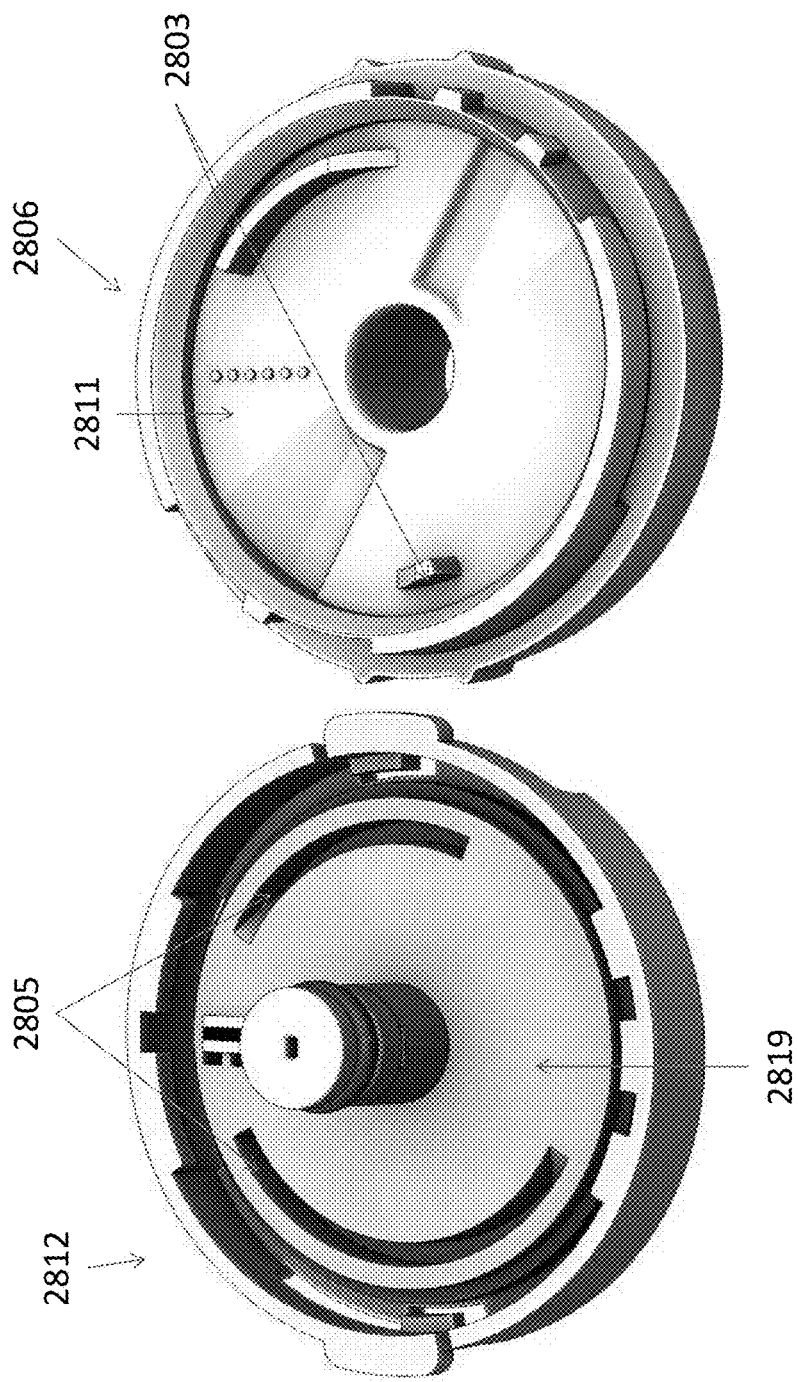
FIG. 28 illustrates perspective side views of a sensor assembly and a transmitter assembly having mechanical lockouts according to an embodiment of the present disclosure.

Referring now to FIG. 28, perspective side views of a sensor assembly and a transmitter assembly having mechanical lockouts are illustrated according to an embodiment of the present disclosure. To create lockout features, a sensor assembly 2812 includes a sensor base 2819 to which at least one slot 2805 is added. In this embodiment, sensor base 2819 has two slots 2805. One slot defines the generation of the sensor assembly. The other slot determines which transmitter generations will fit with that sensor assembly. Similarly, a transmitter assembly 2806 includes a transmitter cap 2811 to which at least one rail 2803 is added. In this embodiment, two rails are added to transmitter cap 2811. One rail defines the generation of the transmitter. The other rail determines which sensor generations will fit with that transmitter.

Figure 29B:
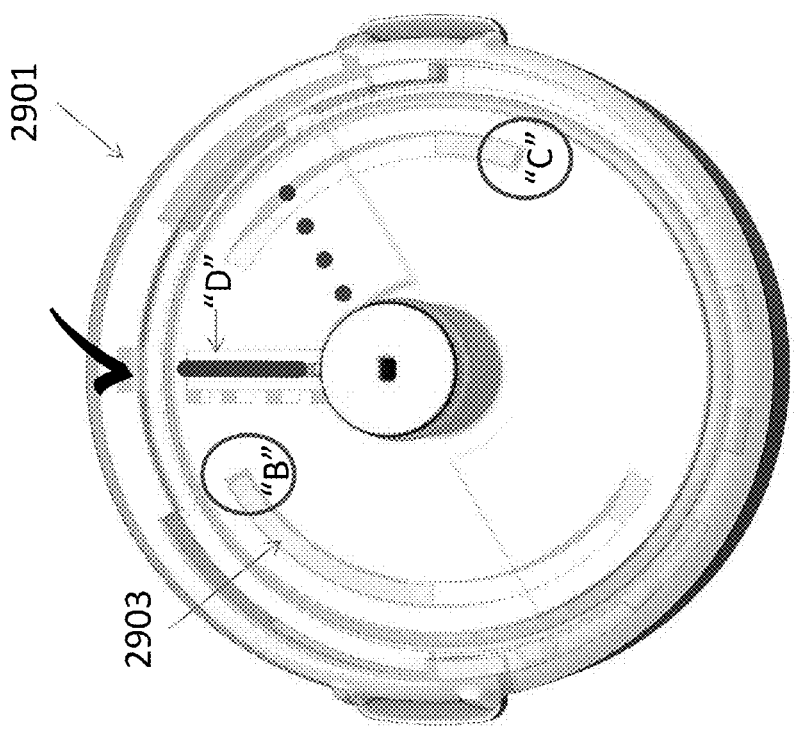
FIGS. 29A-29B are top views of a sensor transmitter assembly having mechanical lockouts according to an embodiment of the present disclosure.
Figure 29A:
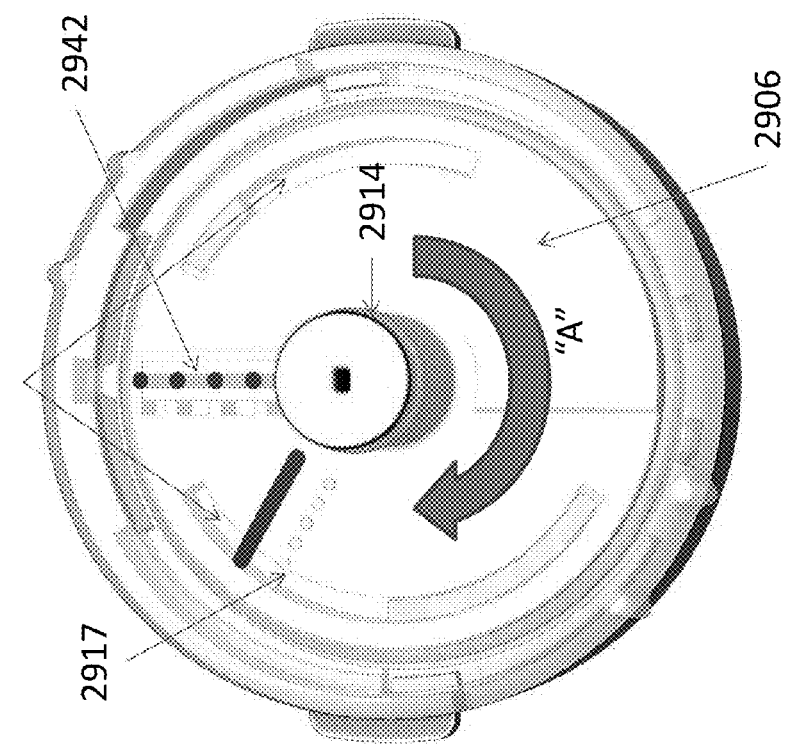

Referring to FIGS. 29A-29B, top views of a sensor transmitter assembly with mechanical lockouts are illustrated according to an embodiment of the present disclosure. As described above according to one or more embodiments, a transmitter assembly 2906 is initially engaged to a sensor assembly by lowering down the transmitter assembly onto the sensor assembly guided by a cap 2914 disposed on the sensor assembly. To complete a connection of the transmitter assembly to the sensor assembly, the transmitter assembly is rotated, for example, in a clockwise manner as indicated by arrow "A" in FIG. 29A. In this way, rails disposed on transmitter assembly 2906 (for example as illustrated in FIG. 28), rotate through slots 2905 disposed on the sensor assembly (see for example FIG. 28). In FIG. 29B, the slots of the sensor assembly are long enough to allow the rails 2903 to rotate all the way through as shown at points "B" and "C". As a result of the slots being long enough to allow full rotation of the rails, the transmitter assembly locks into the sensor assembly and makes contact, for example, contacts 2917 of the transmitter assembly align with contact pads of a sensor stack 2942 of the sensor assembly as shown at point "D". It should be noted that in various embodiments, the sensor assembly and the transmitter assembly will connect with each other even when the contacts are misaligned by a certain angle, for example a 5 degree misalignment (see for example the embodiment of FIG. 14).

Figures 30A, 30B:
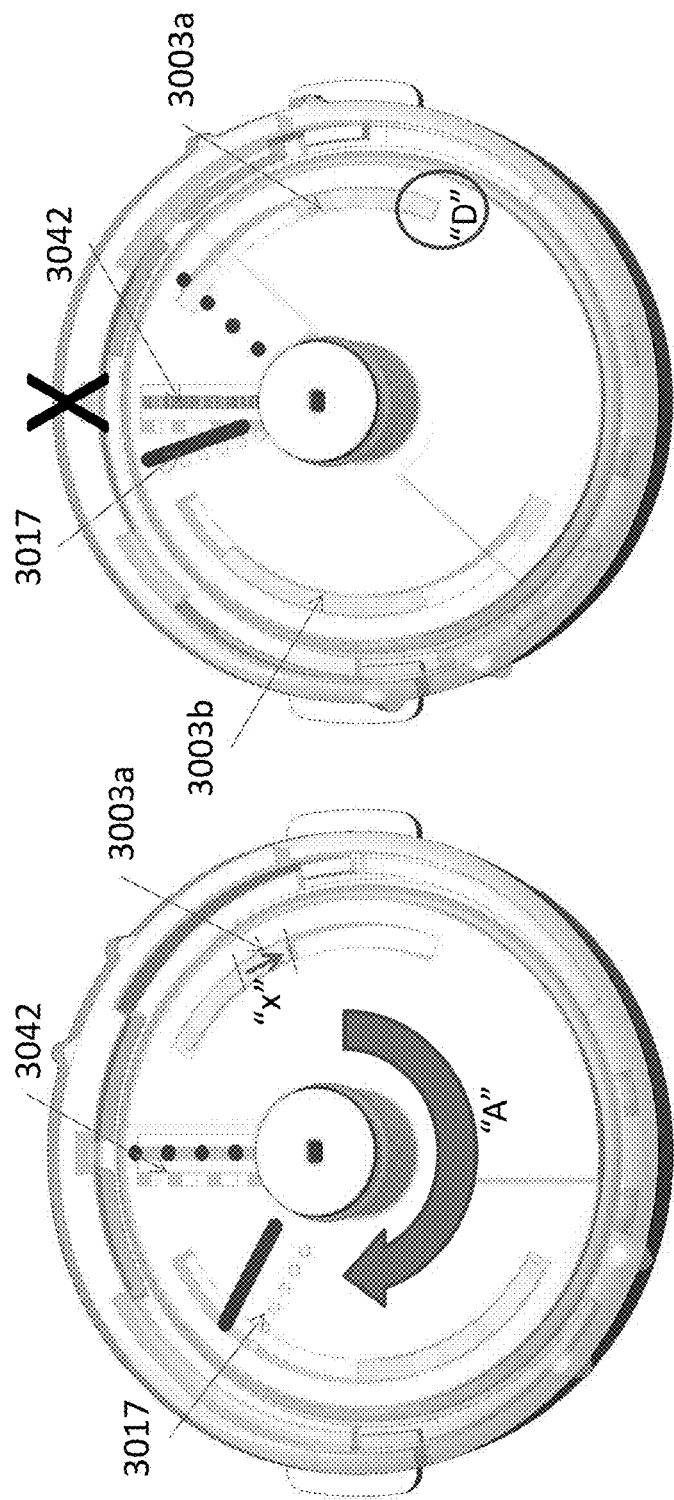
FIGS. 30A-30B are top views of a sensor transmitter assembly with mechanical lockouts according to another embodiment of the present disclosure.

FIGS. 30A-30B are top views of a sensor transmitter assembly with mechanical lockouts according to another embodiment of the present disclosure. According to one or more embodiments, new generation transmitter assemblies are incompatible with older-generation sensor assemblies. For example, a new generation transmitter assembly includes a new transmitter algorithm that is incompatible with an older generation sensor assembly. In this case the new-generation transmitter assembly is made to lock out the older-generation sensor. As illustrated in FIG. 30A, to make a new generation transmitter lock out an older-generation sensor, a rail 3003a disposed e.g., on a right side of a transmitter cap of the transmitter assembly is extended, that is, the length of the rail is increased by a length "x". In various embodiments, the length of rail 3003a is extended by an appropriate "x" amount such as 2 mm, 5 mm, 10 mm, etc. The transmitter assembly is engaged with the sensor assembly and the transmitter assembly is rotated, for example, in a clockwise direction as indicated by arrow "A" such that the rails 3003a and 3003b disposed on the transmitter assembly rotate through the slots disposed on the sensor assembly. However, as illustrated in FIG. 30B, because rail 3003a has been extended (e.g., its length has been increased by an "x" amount), rail 3003a reaches the end of its corresponding slot at point "D". As such, because rail 3003a is extended, it prevents full rotation of the transmitter assembly. In this case, contacts 3017 of the transmitter assembly do not line up or connect with contact pads of a sensor stack 3042 of the sensor assembly. The transmitter assembly locks out the sensor assembly. It should be noted that in various embodiments, because the sensor assembly and the transmitter assembly would connect even when misaligned, for example misaligned by about 5 degrees, the levels of lockouts would differ from each other by a much larger angle to prevent a connection. In this embodiment, each level of lockout is about 20 degrees. The angular misalignment in this case (e.g., 20 degrees) exceeds a particular maximum level of lockout that would allow a connection.

FIGS. 31A-31B are top views of a sensor transmitter assembly with mechanical lockouts according to yet another embodiment of the present disclosure. In the embodiments of FIG. 31A-31B, a new generation sensor assembly is made to lock out an older-generation transmitter. As illustrated in FIG. 31A, a slot 3105a disposed for example on a left side of a sensor base of a new generation sensor assembly is shortened, that is, the length of the slot is decreased by an amount "Z". In various embodiments, the length of slot 3105a is shortened by an appropriate amount such as 2 mm, 5 mm, 10 mm, etc. The sensor assembly is engaged with a transmitter assembly, which is rotated, for example, in a clockwise direction as indicated by arrow "A" such that the rails 3103a and 3103b disposed on the transmitter assembly rotate through the slots disposed on the sensor assembly. However, as illustrated in FIG. 31B, because slot 3105a has been shortened (i.e., its length has been decreased by a "Z" amount), rail 3103a reaches the end of its corresponding slot at point "B". As a result, full rotation of the transmitter assembly is prevented. In this case, contacts 3117 of the transmitter assembly do not line up or connect with contact pads of a sensor stack 3142 of the sensor assembly. The sensor assembly locks out the transmitter assembly. It should be noted that in various embodiments, because the sensor assembly and the transmitter assembly would connect even when misaligned, for example misaligned by about 5 degrees, the levels of lockouts would differ from each other by a much larger angle to prevent a connection. In this embodiment, each level of lockout is about 20 degrees. The angular misalignment in this case (e.g., 20 degrees) exceeds a particular maximum level of lockout that would allow a connection.

Figure 32B:
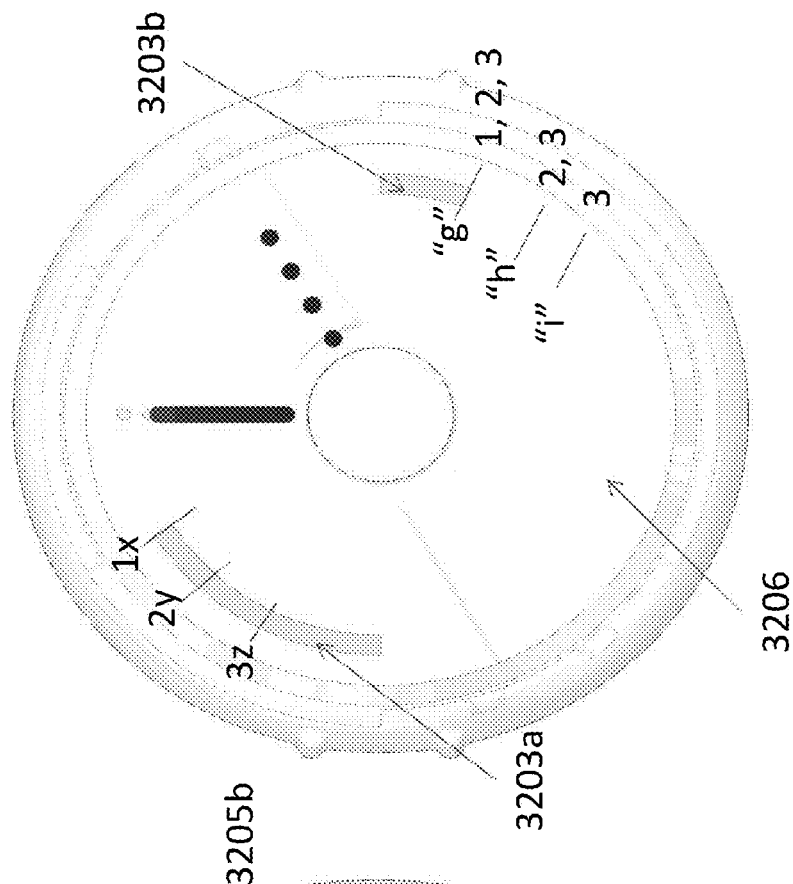
FIGS. 32A-32B illustrate lockouts for different generations of a transmitter assembly and a sensor assembly according to an embodiment of the present disclosure.
Figure 32A:
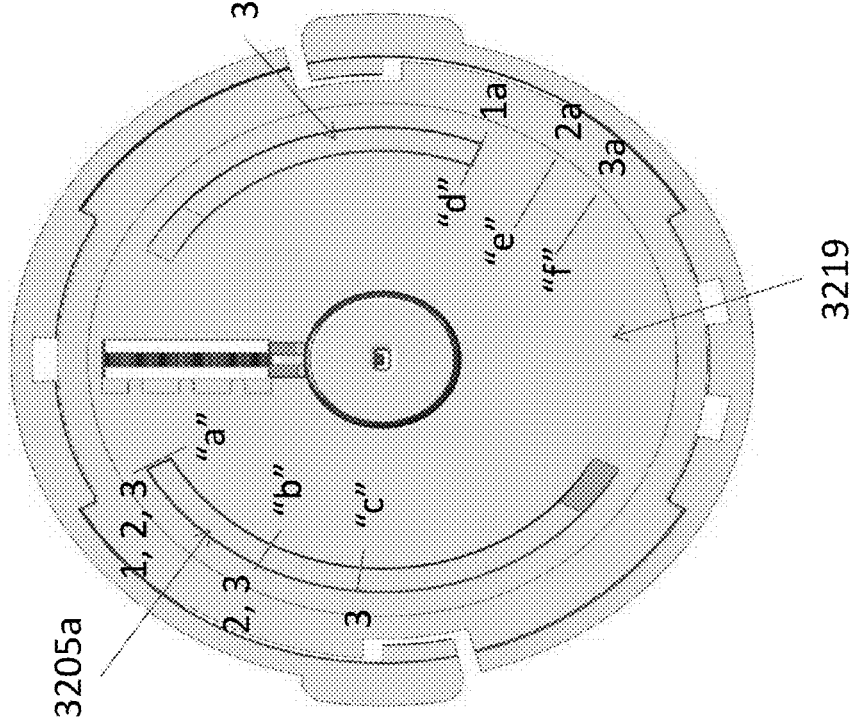

Referring to FIGS. 32A-32B, lockouts for different generations of transmitter assemblies and sensor assemblies are illustrated according to an embodiment of the present disclosure. In FIG. 32A, a sensor assembly base 3219 has a slot 3205a and a slot 3205b. As described above according to one or more embodiments, slots 3205a and 3205b are adapted to engage or otherwise receive a corresponding rail of a transmitter assembly. To determine which transmitter generation(s) are received or accepted by the sensor assembly, one or more features of slots 3205a and 3205b are adjusted. For example, the length of slot 3205a determines which transmitter generation(s) the sensor assembly will accept. It should be noted that transmitter assembly generations are designated by numeral references 1, 2, 3. For example, an old generation transmitter is designated by numeral reference "1", a newer generation transmitter is designated by numeral reference "2", and an even newer generation transmitter is designated by numeral reference "3". In this embodiment, slot 3205a of a length "a" determines that the sensor assembly will accept transmitter generation(s) 1, 2, 3. A shorter length "b" of slot 3205a results in the sensor assembly accepting transmitter generation(s) 2 and 3. And a shorter length "c" of slot 3205a results in the sensor assembly only receiving a transmitter generation 3. In alternative embodiments, it should be noted that mechanical lockouts have a variety of corresponding features including, for example, a different shape, width, depth, positioning, etc.).

With respect to slot 3205b, its length determines the generation of the sensor assembly, for example, slot 3205b for an old generation sensor (designated by a numeral reference "1a") has a length "d", slot 3205b for a newer generation sensor (designated by a numeral reference "2a") has a length "e", and slot 3205b for an even newer generation sensor (designated by a numeral reference "3a") has a length "f". That is, the length of slot 3205b is extended to length "e" for a newer generation sensor 2a and the length of slot 3205b is extended to length "f" for an even newer generation sensor 3a.

In FIG. 32B, a transmitter assembly base 3206 has a rail 3203a and a rail 3203b. As described above according to one or more embodiments, rails 3203a and 3203b are adapted to engage or otherwise connect with a corresponding slot of a sensor assembly. To determine which sensor generation(s) engages with the transmitter assembly, one or more features of rails 3203a and 3203b are adjusted. For example, the length of rail 3203b determines which sensor generation(s) the transmitter assembly will accept. It should be noted that sensor assembly generations are designated by numeral references 1, 2, 3. For example, an old generation sensor is designated by numeral reference "1", a newer generation sensor is designated by numeral reference "2", and an even newer generation sensor is designated by numeral reference "3". In this embodiment, rail 3203b is of a length "g", which determines that the transmitter assembly will accept sensor generation(s) 1, 2, 3. A length "h" of rail 3203b determines that the transmitter assembly will accept sensor generation(s) 2 and 3. And a length "i" of rail 3203b determines that the transmitter assembly will only receive a sensor generation 3.

With respect to rail 3203a, its length determines the generation of the transmitter assembly, for example, rail 3203a for an old generation transmitter has a length "1x", rail 3203a for a newer generation transmitter has a length "2y", and rail 3203a for an even newer generation transmitter has a length "3z". That is, a newer generation transmitter assembly has a slot 3203a of a shorter length "2y", and an even newer generation transmitter assembly has a slot 3203a of an even shorter length "3z". It should be noted that in general, generations of transmitters and sensors are fabricated based on various factors including for example: as needed by an application, at a given time frequency (e.g., every year, every quarter, etc.), based on a release of a new product, in response to a design improvement, etc.

Referring now to FIGS. 33A-33B, lockouts for different generations of transmitter assemblies and sensor assemblies are illustrated according to another embodiment of the present disclosure. In various embodiments, each sensor assembly includes at least one mechanical lockout having features that determine the generation of the sensor assembly and what transmitters the sensor assembly will accept. Similarly, each transmitter assembly includes at least one mechanical lockout having features that determine the generation of the transmitter assembly and what sensors the transmitter assembly will accept. The features of the mechanical lockouts include, for example, a length, a shape, a width, a depth, a positioning, etc. In one or more embodiments, each sensor assembly includes two slots. One slot defines which generation that sensor is. The other slot determines which transmitter generations will fit with that sensor. Similarly, each transmitter assembly includes two rails. One rail defines which generation that transmitter is. The other rail determines which sensor generations will fit with that transmitter.

In FIG. 33A, a sensor base 3319 of a sensor assembly includes a slot 3305b that defines the generation the sensor assembly, and a slot 3305a that defines which generations of transmitters that sensor assembly will accept. In this case, slot 3305b defines the generation of the sensor assembly as being a Generation 1 sensor assembly. Slot 3305a determines that Generations 1, 2, 3 transmitters will be accepted. Similarly, a transmitter cap of transmitter assembly 3306 includes a rail 3303a that defines the generation of the transmitter assembly, and a rail 3303b that defines which generations of sensors that transmitter will accept. In this case, rail 3303a defines the generation of the transmitter assembly as being a Generation 1 transmitter. Rail 3303b determines that Generations 1, 2, 3 sensors will be accepted.

In the first pair "I" of corresponding slots and rails, slot 3305a, which determines that Generations 1, 2, 3 transmitters will be accepted, pairs with rail 3303a, which defines a Generation 1 transmitter. And in the second pair II, slot 3305b, which determines a Generation 1 sensor assembly, pairs with rail 3303b, which determines that Generations 1, 2, 3 sensors will be accepted.

As such, as illustrated in FIG. 33B, when transmitter assembly 3306 is connected to sensor base 3319, a connection is completed because there is overlap in both pairs of corresponding slots and rails. In this regard, features such as the length of corresponding slots and rails do not prevent the sensor assembly and the transmitter assembly from connecting as indicated at points "A" and "B". Contacts 3317 of transmitter assembly 3306 line up (or are within a certain angular misalignment) with contact pads of sensor stack 3342 as indicated at point "C".

Figures 34A, 34B:
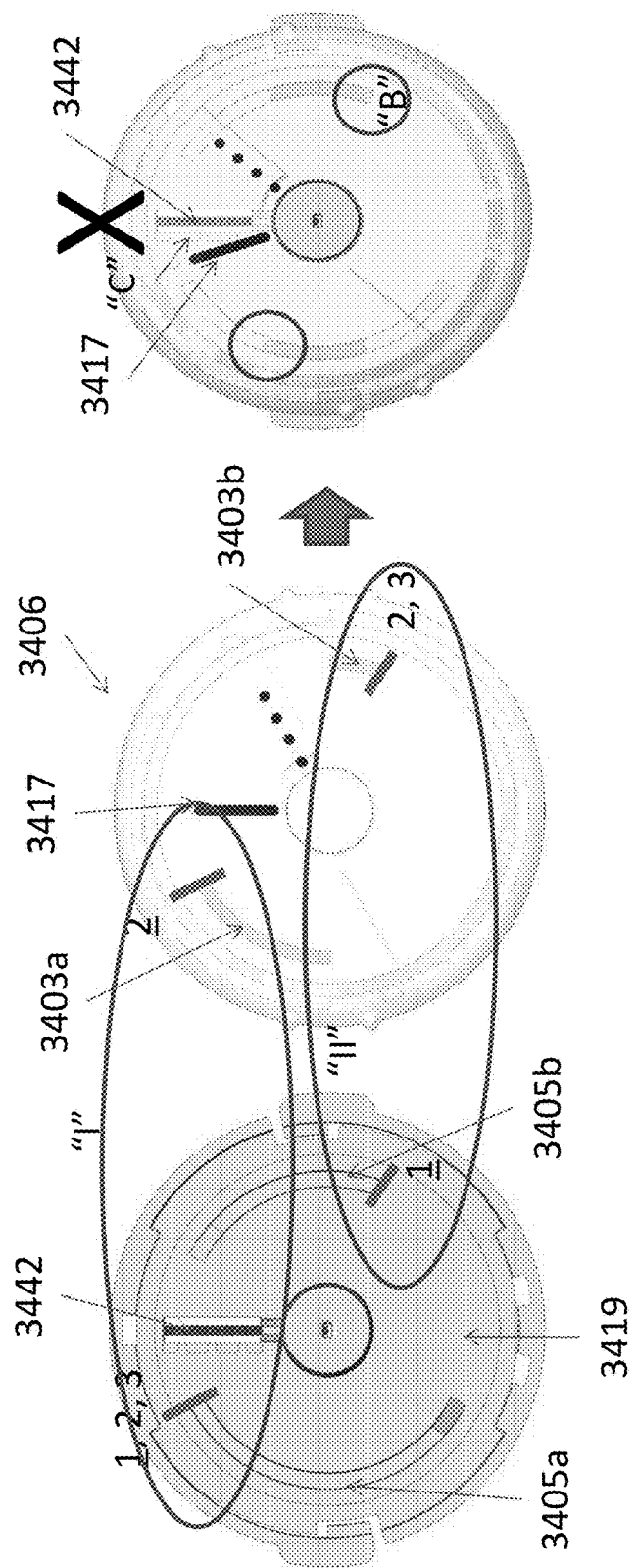
FIGS. 34A-34B illustrate lockouts for different generations of transmitter assemblies and sensor assemblies according to yet another embodiment of the present disclosure.

Referring now to FIGS. 34A-34B, lockouts for different generations of a transmitter assembly and a sensor assembly are illustrated according to yet another embodiment of the present disclosure. In FIG. 34A, a sensor base 3419 of a sensor assembly includes a slot 3405b that defines the generation the sensor assembly, and a slot 3405a that defines which generations of transmitters that sensor assembly will accept. In this case, slot 3405b defines the generation of the sensor assembly as being a Generation 1 sensor assembly. Slot 3305a determines that Generations 1, 2, 3 transmitters will be accepted. Similarly, a transmitter cap of transmitter assembly 3406 includes a rail 3403a that defines the generation of the transmitter assembly, and a rail 3403b that defines which generations of sensors that transmitter will accept. In this case, rail 3403a defines the generation of the transmitter assembly as being a Generation 2 transmitter. Rail 3403b determines that Generations 2, 3 sensors will be accepted. In the first pair "I" of corresponding slots and rails, slot 3405a, which determines that Generations 1, 2, 3 transmitters will be accepted, pairs with rail 3403a, which defines a Generation 2 transmitter. However, in the second pair II, slot 3405b, which determines a Generation 1 sensor assembly, does not pair with rail 3403b, which determines that only Generations 2, 3 sensors will be accepted.

As such, as illustrated in FIG. 34B, when transmitter assembly 3406 is connected to sensor base 3419, a connection is not completed because both pairs of corresponding slots and rails do not overlap. In this regard, features such as the length of corresponding slots and rails prevent the sensor assembly and the transmitter assembly from connecting, for example, when rail 3403b reaches the end of slot 3405b at point "B", the transmitter assembly is prevented from rotating all the way through. Contacts 3417 of transmitter assembly 3406 do not line up (or are not within a certain angular misalignment) with contact pads of sensor stack 3442 as indicated at point "C".

Figure 35:
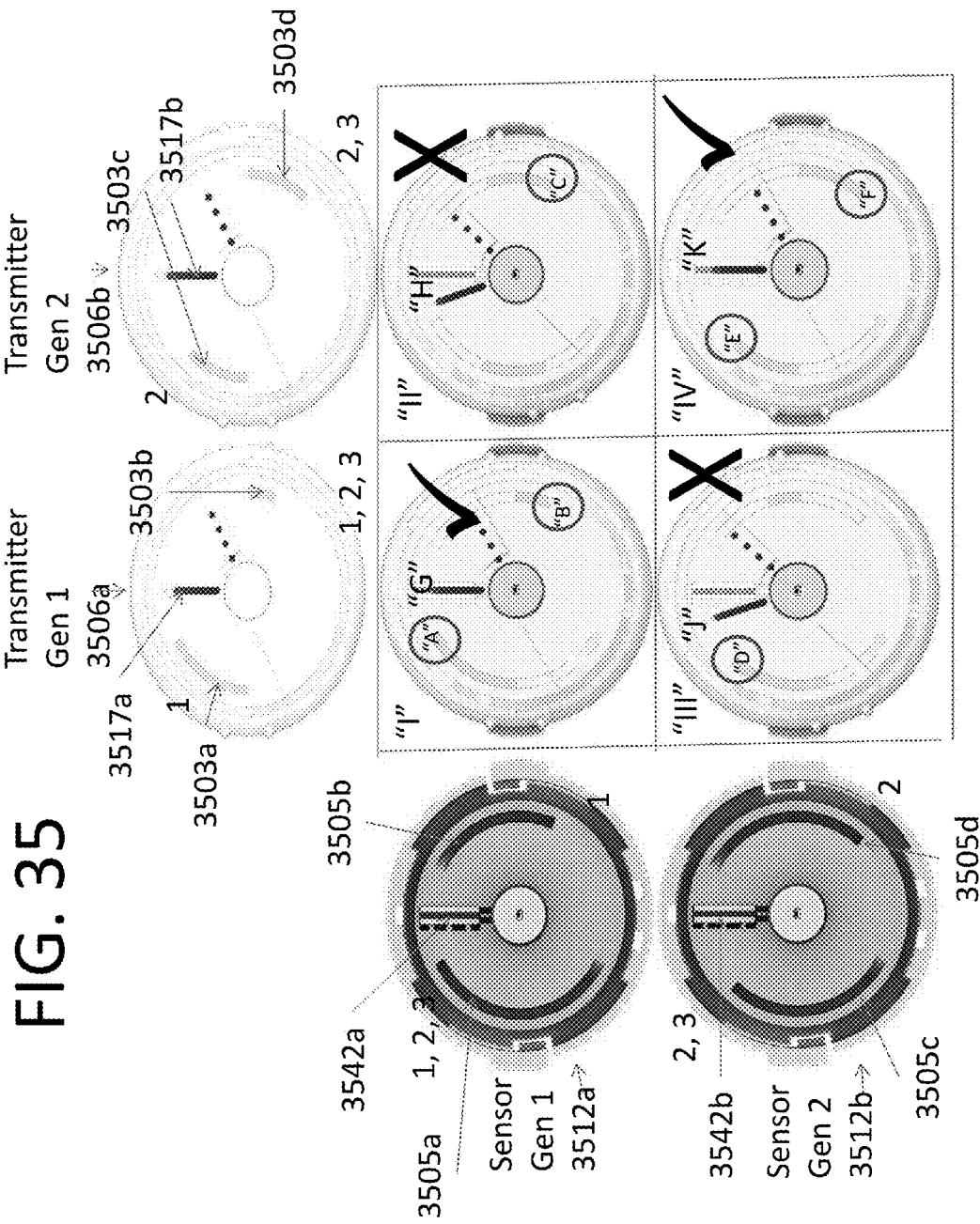
FIG. 35 illustrates top views of different generations of sensor and transmitter assemblies with different mechanical lockouts according to an embodiment of the present disclosure.

Referring now to FIG. 35, top views of different generations of sensor and transmitter assemblies with different mechanical lockouts are illustrated according to one or more embodiments of the present disclosure. Mechanical lockouts, for example slots and rails, are used to make sensor and transmitter generations mutually exclusive. For example, a Generation 1 sensor will connect only with a Generation 1 transmitter, and a Generation 2 sensor will connect only with a Generation 2 transmitter as illustrated in the embodiment of FIG. 35. In that regard, in some embodiments, the relative features of the mechanical lockouts, for example, the relative lengths of the slots and rails are made to prevent the transmitter assembly from rotating enough so that a connection with the sensor assembly is not completed. In other embodiments, the relative lengths of the slots and rails are made to allow the transmitter assembly to rotate enough to connect with the sensor assembly.

A transmitter assembly 3506a includes a Generation 1 transmitter and has a rail 3503a and a rail 3503b. Rail 3503a is made to correspond to Generation 1 of the transmitter assembly. Rail 3503b is made to correspond to Generations 1, 2 and 3 of a sensor assembly. A transmitter assembly 3506b includes a Generation 2 transmitter and has a rail 3503c and a rail 3503d. Rail 3503c is made to correspond only to Generation 2 of the transmitter assembly. Rail 3503d is made to correspond only to Generations 2 and 3 of a sensor assembly. A sensor assembly 3512a includes a Generation 1 sensor and has a slot 3505a and a slot 3505b. Slot 3505a is made to correspond to Generations 1, 2 and 3 of a transmitter assembly. Slot 3505b is made to correspond only to Generation 1 of the sensor assembly. A sensor assembly 3512b includes a Generation 2 sensor and has a slot 3505c and a slot 3505d. Slot 3505c is made to correspond to Generations 2 and 3 of a transmitter assembly. Slot 3505d is made to correspond only to Generation 2 of the sensor assembly.

In case "I", sensor assembly 3512a has a slot 3505a that accepts Generations 1, 2, 3 of transmitters and is paired with a rail 3503a of transmitter assembly 3506a, which has a Generation 1 transmitter. Slot 3505b, which defines a Generation 1 sensor, is paired with rail 3503b that determines that sensor Generations 1, 2, 3 will be accepted. As such, there is overlap in both pairs of corresponding slots and rails such that a connection of the sensor assembly and the transmitter assembly is completed. In this regard, the relative lengths of the slots and rails allow the transmitter to rotate enough as indicated by points "A" and "B" so that transmitter contacts 3517a align with sensor contact pads of sensor stack 3542a as indicated at point "G". A Generation 1 sensor connects with a Generation 1 transmitter.

However, in case "II", sensor assembly 3512a including a Generation 1 sensor will not connect with a transmitter assembly 3506b having a Generation 2 transmitter. Rail 3503d runs into the end of slot 3505b at point "C" before the transmitter contacts 3517b line up with sensor contact pads of sensor stack 3542a as indicated at point "H". In other words, the contact of rail 3503d into the end of slot 3505b at point "C" blocks the transmitter assembly from rotating all the way into the connection position. A Generation 1 sensor does not connect with a Generation 2 transmitter.

In case "III", sensor assembly 3512b including a Generation 2 sensor does not connect with a transmitter assembly 3506a having a Generation 1 transmitter. When sensor assembly 3512b is connected to transmitter assembly 3506a, there is no overlap in both pairs of corresponding slots and rails. No connection is made because rail 3503a runs into the end of slot 3505c at point "D" before the transmitter assembly 3506a can be rotated all the way, blocking the connection. Contacts 3517a of the transmitter assembly do not connect with contact pads of sensor stack 3542b as indicated at point "J". A Generation 2 sensor does not connect with a Generation 1 transmitter.

In case "IV", sensor assembly 3512b has a slot 3505c that accepts Generations 2, 3 of transmitters and is paired with a rail 3503c of transmitter assembly 3506b, which has a Generation 2 transmitter. Slot 3505d, which defines a Generation 2 sensor, is paired with rail 3503d that determines that sensor Generations 2, 3 will be accepted. As such, there is overlap in both pairs of corresponding slots and rails such that a connection of the sensor assembly and the transmitter assembly is completed. In this regard, the relative lengths of the slots and rails allow the transmitter to rotate enough as indicated by points "E" and "F" so that transmitter contacts 3517b align with sensor contact pads of sensor stack 3542b as indicated at point "K". A Generation 2 sensor connects with a Generation 2 transmitter.

Figure 36:
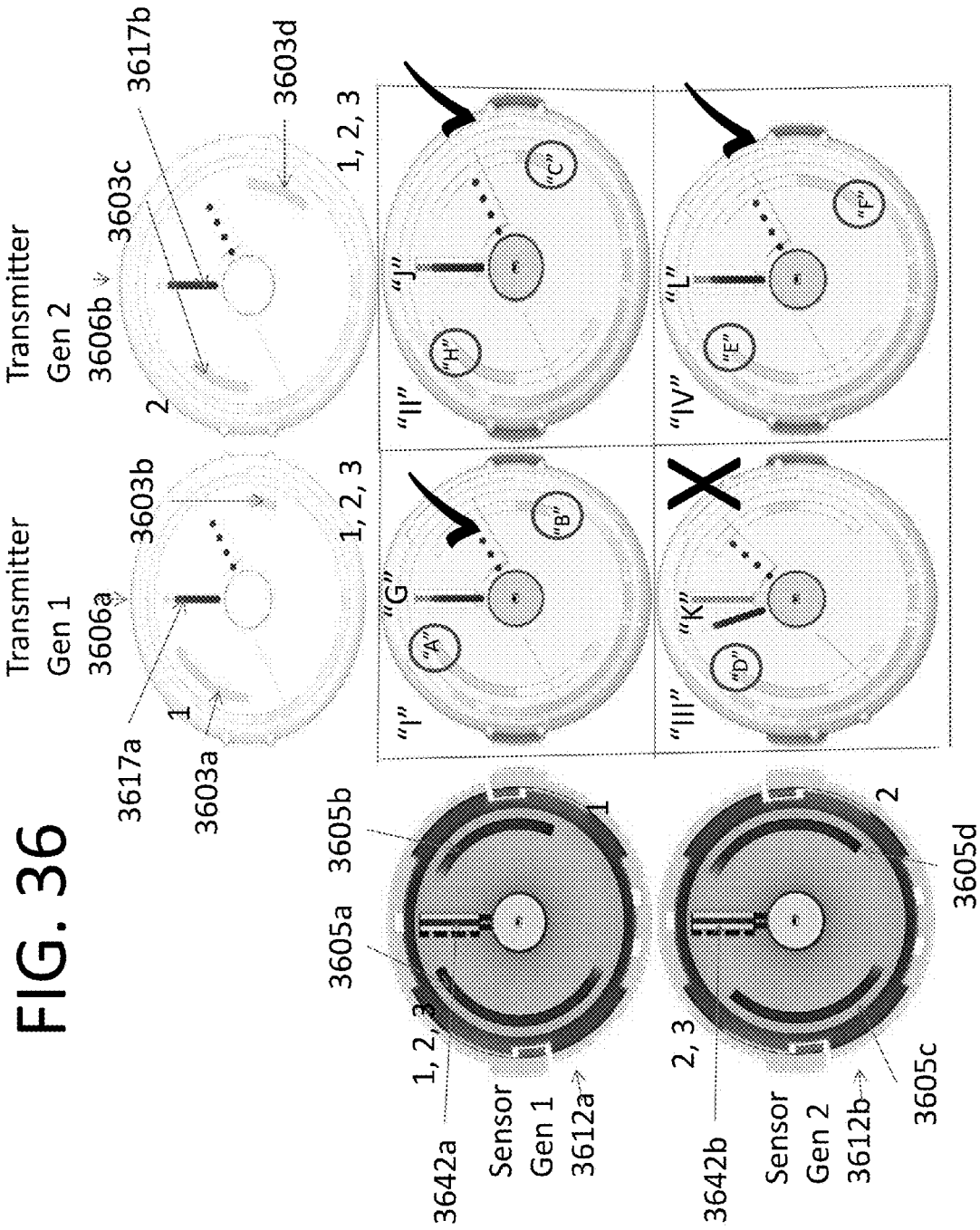
FIG. 36 illustrates top views of different generations of sensor and transmitter assemblies with different mechanical lockouts according to another embodiment of the present disclosure.

Referring now to FIG. 36, top views of different generations of sensor and transmitter assemblies with different mechanical lockouts are illustrated according to another embodiment of the present disclosure. Mechanical lockouts, for example interfaces such as slots and rails, are used to make sensor or transmitter generations backwards compatible. For example, a Generation 2 sensor will only connect with a Generation 2 transmitter. However, the Generation 2 transmitter is backwards compatible and will connect with both a Generation 1 and a Generation 2 sensor as illustrated in the embodiment of FIG. 36.

A transmitter assembly 3606a includes a Generation 1 transmitter and has a rail 3603a and a rail 3603b. Rail 3603a is made to have features (e.g., length) that determine the transmitter's generation, here, the transmitter is a Generation 1. Rail 3603b is made to have features that determine which generations of sensors the transmitter will accept, here, Generations 1, 2, 3, of sensors will be accepted. A transmitter assembly 3606b includes a Generation 2 transmitter and has a rail 3603c and a rail 3603d. Rail 3603c is made to have features (e.g., length) that determine the transmitter's generation, here, the transmitter is a Generation 2. Rail 3603d is made to have features that determine which generations of sensors the transmitter will accept, here, Generations 1, 2, 3, of sensors will be accepted.

A sensor assembly 3612a includes a Generation 1 sensor and has a slot 3605a and a slot 3605b. Slot 3605a is made to have features (e.g., length) that determine which transmitter generation(s) the sensor will accept, here, Generations 1, 2, 3 of transmitters will be accepted. Slot 3605b is made to have features that determine the sensor's generation, here, the sensor is a Generation 1. A sensor assembly 3612b includes a Generation 2 sensor and has a slot 3605c and a slot 3605d. Slot 3605c is made to have features (e.g., length) that determine which transmitter generation(s) the sensor will accept, here, Generations 2, 3 of transmitters will be accepted. Slot 3605d is made to have features that determine the sensor's generation, here, the sensor is a Generation 2.

As such, as illustrated in case "I", sensor assembly 3612a has a slot 3605a that accepts Generations 1, 2, 3 of transmitters and is paired with a rail 3603a of transmitter assembly 3606a, which has a Generation 1 transmitter. Slot 3605b, which defines a Generation 1 sensor, is paired with rail 3603b that determines that sensor Generations 1, 2, 3 will be accepted. As such, there is overlap in both pairs of corresponding slots and rails such that a connection of the sensor assembly and the transmitter assembly is completed. In this regard, the relative lengths of the slots and rails allow the transmitter to rotate enough as indicated by points "A" and "B" so that transmitter contacts 3617a align with sensor contact pads of sensor stack 3642a as indicated at point "G". A Generation 1 sensor connects with a Generation 1 transmitter.

Likewise, in case "II", sensor assembly 3612a including a Generation 1 sensor connects with a transmitter assembly 3506b having a Generation 2 transmitter. Rail 3603c rotates into slot 3605a and rail 3603d rotates into slot 3605b. The rails and the slots, as indicated at points "H" and "C", do not prevent the full rotation of the transmitter assembly such that the transmitter assembly and the sensor assembly connect with each other. In this regard, the relative lengths of the slots and rails allow the transmitter assembly to rotate enough so that transmitter contacts 3617b align with sensor contact pads of sensor stack 3642a as indicated at point "J". A Generation 1 sensor connects with a Generation 2 transmitter.

In case "III", sensor assembly 3612b including a Generation 2 sensor will not connect with a transmitter assembly 3606a having a Generation 1 transmitter. Rail 3603a runs into the end of slot 3605c at point "D" before the transmitter contacts 3617a line up with sensor contact pads of sensor stack 3542b as indicated at point "K". In other words, the contact of rail 3603a into the end of slot 3505c at point "D" blocks the transmitter assembly from rotating all the way into the connection position. A Generation 2 sensor does not connect or is otherwise not compatible with a Generation 1 transmitter.

However, in case "IV", sensor assembly 3612b including a Generation 2 sensor connects with a transmitter assembly 3606b having a Generation 2 transmitter. Rail 3603c rotates into slot 3605d and rail 3603d rotates into slot 3605d. The rails and the slots, as indicated at points "E" and "F", do not prevent the full rotation of the transmitter assembly such that the transmitter assembly and the sensor assembly connect with each other. In this regard, the relative lengths of the slots and rails allow the transmitter assembly to rotate enough so that transmitter contacts 3617b align with sensor contact pads of sensor stack 3642b as indicated at point "L". A Generation 2 sensor connects with a Generation 2 transmitter.

It should be noted that although lockouts comprised of slots and rails are illustrated according to one or more embodiments herein, other types of lockouts may be created for respective transmitters and sensors with other, shapes, forms, additions, protrusions, etc. For example, lockouts may be of any form, shape, size, depth, etc. and may be positioned on different surface areas of the respective sensor and transmitter assemblies.

Figure 37:
FIG. 37 illustrates perspective views of sensor assemblies and transmitter assemblies with different lockout features according to an embodiment of the present disclosure.

FIG. 37 illustrates perspective views of sensor assemblies and transmitter assemblies with different lockout features according to an embodiment of the present disclosure. Different generations of sensors and transmitters are created by changing one or more features of their corresponding lockouts. For example, additional generations are created by changing a diameter measured from the center between the lockout features.

In various embodiments, a sensor assembly 3712a has a diameter having a dimension "A" between its lockout features, i.e., between slots. A sensor assembly 3712b, which is a different generation than sensor assembly 3712a, has a diameter "B" between its slots such that diameter dimension "B" is smaller than "A". Likewise, a sensor assembly 3712c has a diameter "C", which is smaller than diameters "B" and "A" of sensors 3712a and 3712b, respectively, which corresponds to different generations of sensors. Dimensions "A", "B" and "C" may have values appropriate to fit the sensor assembly, for example, dimension "A" is approximately 5 mm, dimension "B" is approximately 10 mm, and dimension "C" is approximately 15 mm. In other embodiments, dimension "A" is approximately 16.1 mm, dimension "B" is approximately 13.8 mm, and dimension "C" is approximately 11.5 mm.

Figure 38:
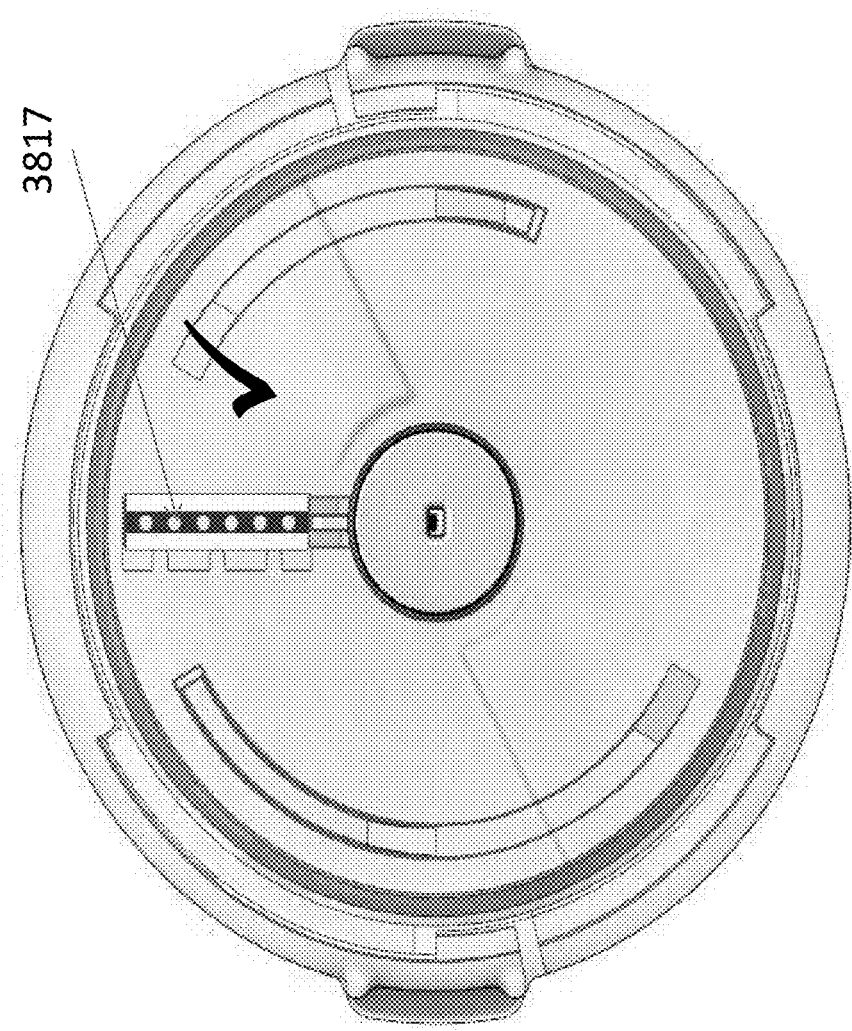
FIG. 38 is a top view of a sensor transmitter assembly with aligned contacts according to an embodiment of the present disclosure.

A transmitter assembly 3706a has a diameter having a dimension "A'" between its lockout features, i.e., between rails. A transmitter assembly 3706b, which is a different generation than transmitter assembly 3706a, has a diameter "B'" between its rails such that diameter dimension "B'" is smaller than dimension "A'". Likewise, a transmitter assembly 3706c has a diameter "C'", which is smaller than diameters "B'" and "A'" of transmitters 3706a and 3706b, respectively, which are different generations of transmitters. Dimensions "A'", "B'" and "C'" have values appropriate to fit the transmitter assembly, for example, dimension "A'" is approximately 5 mm, dimension "B'" is approximately 10 mm, and dimension "C'" is approximately 15 mm. In other embodiments, dimension "A" is approximately 16.1 mm, dimension "B" is approximately 13.8 mm, and dimension "C" is approximately 11.5 mm Clocking Lugs Referring to FIG. 38, a top view of a sensor transmitter assembly with aligned contacts is illustrated according to an embodiment of the present disclosure. As described according to one or more embodiments (see, e.g., the embodiments of FIGS. 3A-3C, 58A-58C), to connect a transmitter assembly to a sensor assembly, the transmitter assembly is first lowered on to the sensor assembly. Then, the transmitter assembly is rotated, for example in a clockwise direction by approximately 60° to lock it in place. In the embodiment of FIG. 38, rotating the transmitter assembly aligns the transmitter assembly's contacts 3817 with the sensor assembly's contacts.

Figure 39:
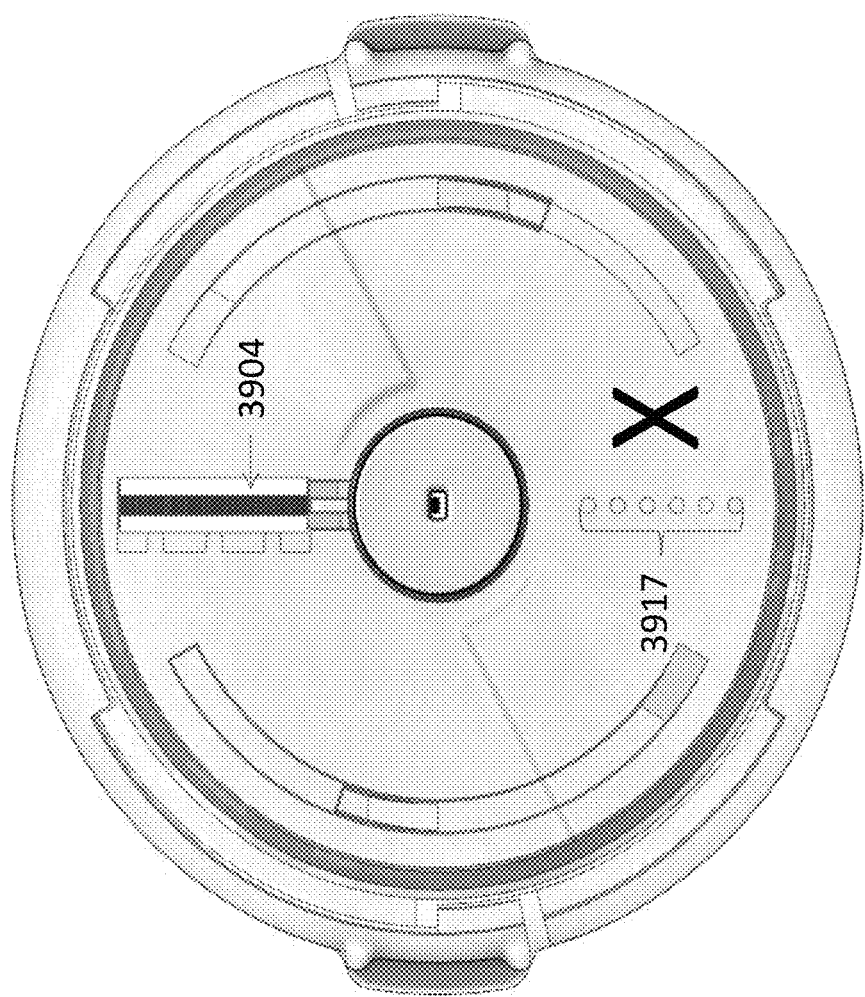
FIG. 39 is a top view of a sensor transmitter assembly with non-aligned contacts according to an embodiment of the present disclosure.

FIG. 39 illustrates a top view of a sensor transmitter assembly with non-aligned contacts according to an embodiment of the present disclosure. In some embodiments, because the mechanical mating features of a sensor base of a sensor assembly have 180° rotational symmetry, it is possible to connect the transmitter assembly in an incorrect orientation. In this embodiment, transmitter contacts 3917 do not line up with sensor contacts of a sensor stack 3904.

FIG. 40 illustrates top views of a sensor assembly and a transmitter assembly having features that do not have rotational symmetry according to an embodiment of the present disclosure. A sensor assembly 4012 and a transmitter assembly 4006 have features such as clocking features that do not have rotational symmetry. For example, sensor assembly 4012 has a hole or opening 4031 positioned on a first side along a rim or an outline of sensor assembly 4012. Also, an opening 4032 and an opening 4033 are positioned on a substantially opposite side of opening 4031 along the rim or outline of the sensor assembly 4012. Transmitter assembly 4006 includes a lug 4034 positioned on a first side along a rim or an outline of the transmitter assembly 4006. Transmitter assembly 4006 also includes a lug 4035 and a lug 4036, which are positioned on a substantially opposite side of lug 4034 along the perimeter or outline of the transmitter assembly 4006. Opening 4031 of sensor assembly 4012 is adapted to receive, engage or connect with lug 4034 of transmitter assembly 4006. Openings 4032 and 4033 are adapted to receive, engage or connect with lugs 4035 and 4036, respectively, of transmitter assembly 4006. As such, to prevent the transmitter assembly 4006 from being connected with the sensor assembly 4012 in an incorrect orientation, a mechanical interface between a sensor base of sensor assembly 4012 and a transmitter cap of transmitter assembly 4006 includes features such as openings and lugs that do not have rotational symmetry.

It should be noted that although openings and lugs are illustrated in embodiments herein, features to prevent a transmitter form being connected with a sensor in an incorrect orientation can be added such that there is no rotational symmetry, for example, features such as openings and lugs with different depths, shapes or cross-sections, sizes, positioning, or a combination thereof can be used.

Figure 41C:
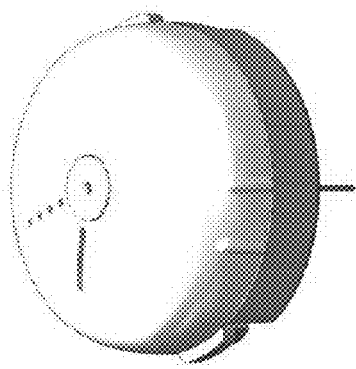
FIGS. 41A-41C illustrate perspective views of a sensor assembly and a transmitter assembly having clocking features according to an embodiment of the present disclosure.
Figure 41B:
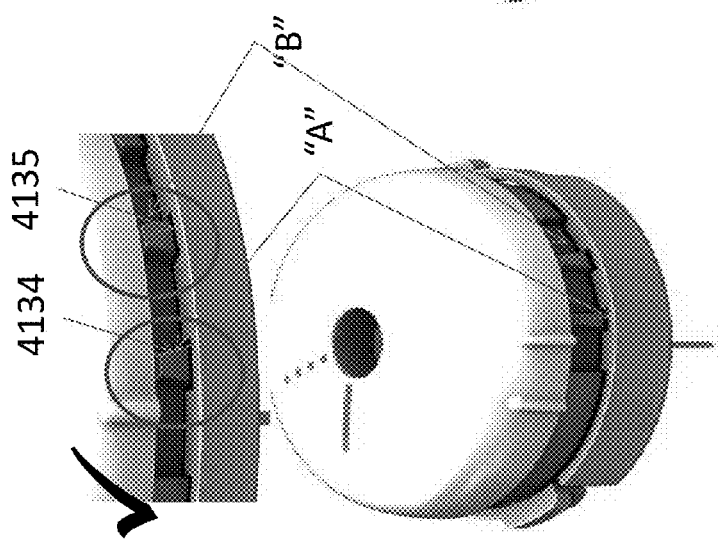
Figure 41A:
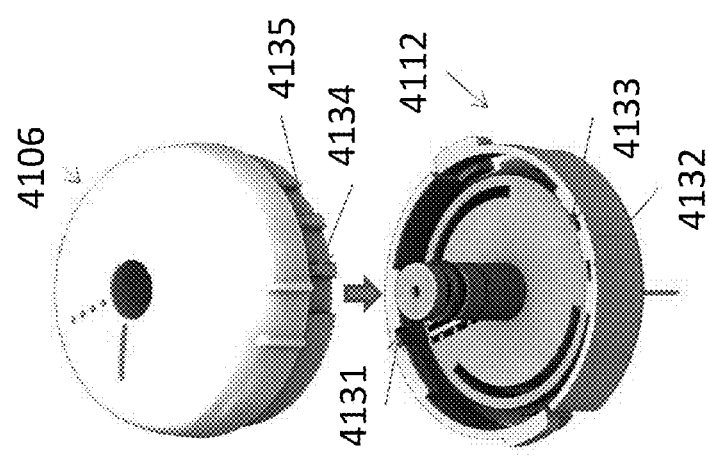

Referring to FIGS. 41A-41C, perspective views of a sensor assembly and a transmitter assembly having clocking features are illustrated according to an embodiment of the present disclosure. In FIG. 41A, as described above according to one or more embodiments, a transmitter assembly 4106 is lowered into a sensor assembly 4112. Transmitter assembly 4106 has clocking features such as a lug 4134 and a lug 4135 (not all lugs are shown). Sensor assembly 4112 has clocking features such as an opening 4131 disposed on a first side along an outline of sensor assembly 4112 and openings 4132 and 4133 disposed on a substantially opposite side from the first side along an outline of sensor assembly 4112. Sensor assembly openings 4131, 4132 and 4133 are adapted to receive lugs such as lugs 4134 and 4135 of transmitter assembly in a particular orientation. As illustrated in the embodiment of FIG. 41B, because the clocking features of the sensor assembly 4106 and the transmitter assembly 4112 do not have rotational symmetry, the transmitter assembly is lowered all the way onto a sensor base of the sensor assembly in only one correct orientation so that contacts of the transmitter assembly line up with contacts of the sensor assembly as illustrated at points "A" and "B". FIG. 41C illustrates a transmitter assembly fully lowered onto a sensor assembly.

In alternative embodiments, it should be noted that any appropriate number of clocking features may be used of any shape, depth, positioning or size. Also, in some embodiments, features such as lugs may be positioned on the sensor assembly instead of on the transmitter assembly, and openings may be positioned on the transmitter assembly instead of on the sensor assembly.

Figures 42A, 42B:
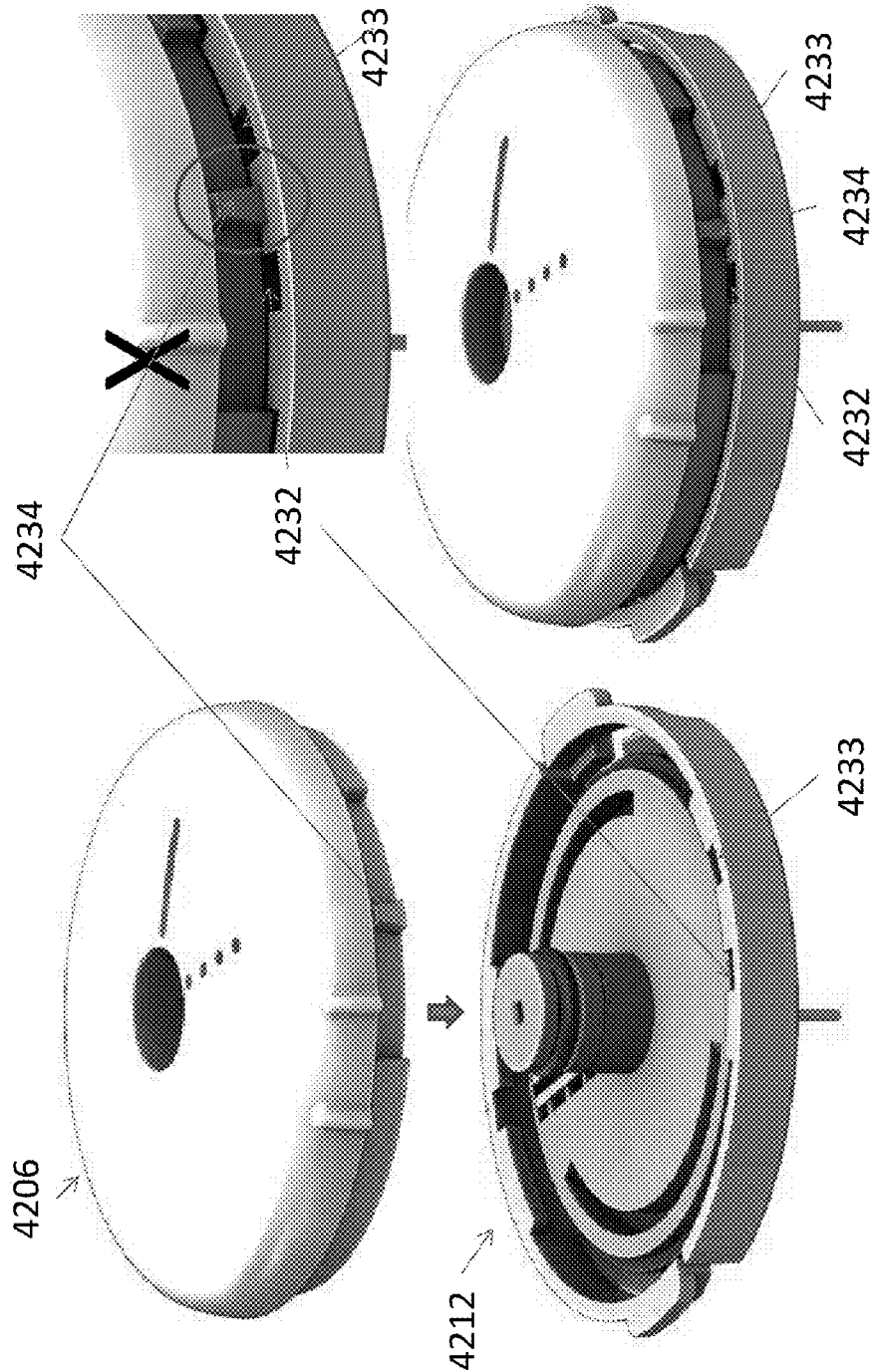
FIGS. 42A-42B illustrate perspective views of a sensor assembly and a transmitter assembly having clocking features according to another embodiment of the present disclosure.

Referring to FIGS. 42A-42B, a sensor assembly and a transmitter assembly having clocking features are illustrated according to another embodiment of the present disclosure. In FIG. 42A, as described above according to one or more embodiments, a transmitter assembly 4206 is lowered into a sensor assembly 4212. Transmitter assembly 4206 has clocking features such as a lug 4234 disposed on one side along a rim or an outline of transmitter assembly 4206. Sensor assembly 4212 has clocking features such as openings 4232 and 4233 disposed on a side along an outline of sensor assembly 4212. Sensor assembly openings 4232 and 4233 are adapted to receive lugs of transmitter assembly in a particular orientation. As illustrated in the embodiment of FIG. 42B, because the clocking features of the sensor assembly 4212 and the transmitter assembly 4206 do not have rotational symmetry, the transmitter assembly is not lowered all the way onto a sensor base of the sensor assembly 4212 in an orientation where lug 4234 of transmitter assembly 4206 does not line up with openings 4232 and 4233 of sensor assembly 4212. Transmitter assembly 4206 is only lowered onto sensor assembly 4212 in one correct orientation so that contacts of the transmitter assembly line up with contacts of the sensor assembly. Accordingly, in this embodiment, the clocking features physically block the transmitter assembly from being dropped all the way onto the sensor assembly base when it is in the incorrect orientation.

Methods

Figure 43:
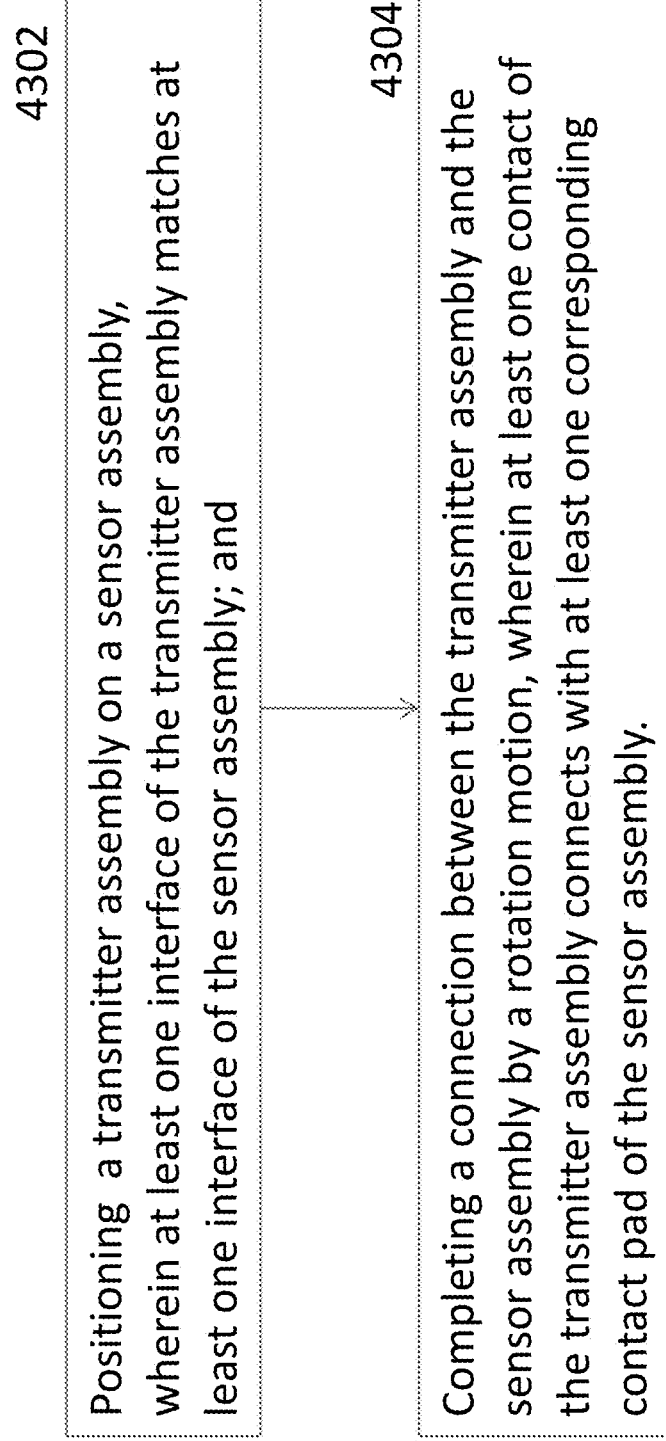
FIG. 43 is a flowchart illustrating a method for forming a sensor transmitter assembly according to an embodiment of the present disclosure.

Referring to FIG. 43, a flowchart illustrates a method for forming a sensor transmitter assembly according to an embodiment of the present disclosure. It should be noted that the method of FIG. 43 may be implemented by the sensor transmitter assembly illustrated, for example, at least in the embodiments of FIGS. 1A-1B, 3A-3C, 13, 15A-15C, 20, 22, 23, 27A-27C, 29A-29B, 33A-33B, 38, and 41A-41C, 56A-56B, 58A-58B, 67, 74 and 75.

In block 4302, a transmitter assembly is positioned on a sensor assembly, where at least one interface of the transmitter assembly matches at least one interface of the sensor assembly. For example, the transmitter assembly is initially lowered onto the sensor assembly where an opening substantially centered through the transmitter assembly fittingly engages with a cap extending from the sensor assembly. In various embodiments, interfaces such as clocking features are used to ensure that the transmitter assembly is positioned in a correct orientation on the sensor assembly such that contact pads of the sensor assembly match a location or line up with contacts of the transmitter assembly. The clocking features prevent the transmitter assembly from being lowered all the way down onto the sensor assembly if the transmitter is in the wrong orientation.

In block 4304, a connection between the transmitter assembly and the sensor assembly is completed by a rotation motion, wherein at least one contact of the transmitter assembly connects with at least one corresponding contact pad of the sensor assembly. In this regard, a patient uses an intuitive rotation motion (e.g., a clockwise motion) to lock the transmitter assembly to the sensor assembly. One or more interfaces, for example, tabs, slots and snap arms ensure that the transmitter assembly and the sensor assembly connect with each other axially and rotationally. In various embodiments, mechanical lockouts are used to prevent certain generations of sensor assemblies from connecting with certain generations of transmitter assemblies such that, for example, an interface of the transmitter assembly such as a rail having a certain length interferes with completing a connection as the transmitter assembly is rotated into a slot of the sensor assembly.

Figure 44:
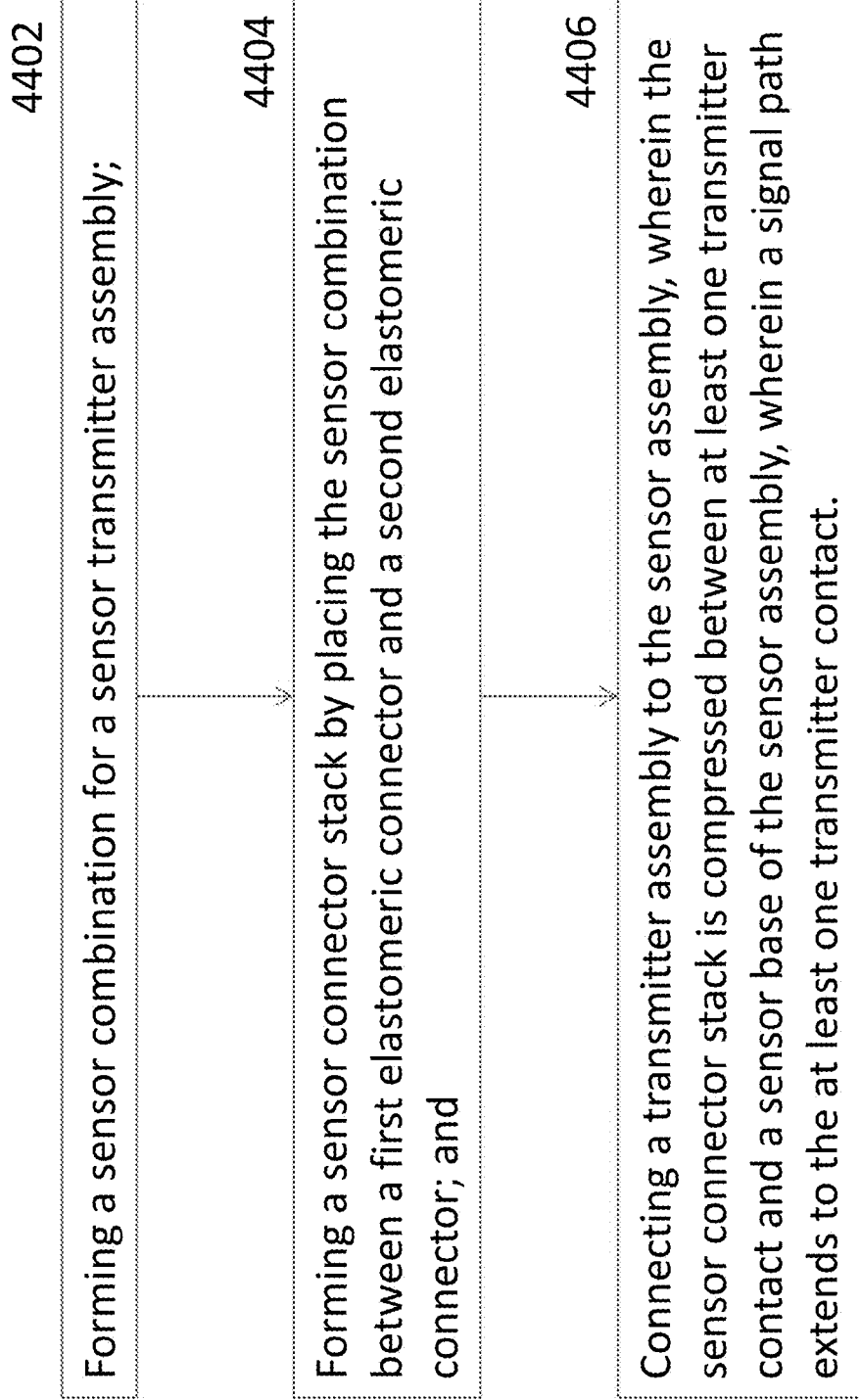
FIG. 44 is a flowchart illustrating a method for connecting a sensor transmitter assembly according to an embodiment of the present disclosure.

Referring now to FIG. 44, a flowchart illustrates a method for connecting a sensor transmitter assembly according to an embodiment of the present disclosure. It should be noted that the method of FIG. 44 may be implemented by the sensor transmitter assembly illustrated, for example, at least in the embodiments of FIGS. 5A-5C, 16-27, 60A-60C, 69A-82.

In block 4402, a sensor combination is formed for a sensor transmitter assembly. In an embodiment, windows are cut or otherwise created through a first contact pad head of a first sensor where at least one window results in at least one active WE contact pad on the first sensor. Also, windows are cut or otherwise created through a second contact pad head of a second sensor where at least one window of the second contact pad results in at least one active WE contact pad on the second sensor, where the first sensor and the second sensor have mirrored window patterns across each respective contact pad head. The first sensor is placed back to back with the second sensor where the windows of the first sensor and the windows of the second sensor are aligned and provide a signal path between contact pads of the first contact pad head and the second contact pad head.

In other embodiments, sensor combinations are created by using, for example, a rigid flex connector, a flex connector integrated with a lower sensor, or a flex connector integrated with a sensor where the sensors interlace as will be described in more detail below according to the embodiments illustrated in FIGS. 69A-82.

In block 4404, a sensor contact stack is formed by placing the sensor combination between a first elastomeric connector and a second elastomeric connector.

In block 4406, a transmitter assembly is connected to the sensor assembly, where the sensor connector stack is compressed between at least one transmitter contact and a sensor base of the sensor assembly, such that a signal path extends to the transmitter contact(s).

Benefits of Sensor Transmitter Arrangement

Advantageously, a device having a sensor transmitter assembly according to one or more embodiments of the present disclosure has many features that provide many benefits to a patient as well as to performance and assembly of the device. For example, Table 2 below summarizes various non-limiting features of the device along with corresponding potential benefits.

TABLE 2

| Feature | On-body Stability | Connection Robustness | On-body Comfort | Use Model Simplicity | Aesthetics |
|---|---|---|---|---|---|
| Large, stretch pad | X | | X | | |
| Patch bonded to entire device outline | X | | X | X | |
| Low profile | X | | X | | X |
| No overtape required | X | | X | X | X |
| Centered sensor | X | | | X | |
| Multi-point connection | | X | | X | |
| Solid transmitter contacts | | X | | | |
| Elastomeric sensor contacts | | X | | | |
| Smooth, continuous surfaces | | | | X | X |
| Smooth, continuous edges | | | | X | X |

TABLE 2-continued

| Feature | On-body Connection Stability | On-body Connection Robustness | On-body Comfort | Use Model Simplicity | Aesthetics |
|---|---|---|---|---|---|
| Reduced volume | | | X | | X |
| Radial symmetry | | | | X | X |
| No-look, twist connection | | | | X | |

Disposable Insertion Tool Use Model

Referring to FIG. 45A, a perspective outer view of a single-use, disposable insertion tool is illustrated according to an embodiment of the present disclosure. A disposable insertion tool 4500 (also referred to as "insertion device") according to one or more embodiments can be carried, shipped, or stored as an integrated, single unit as illustrated. Insertion device 4500 includes a top portion or plunger 4502 and a bottom portion or lock collar 4504 coupled to each other. Insertion device 4500 houses contents including one or more components, for example, a sensor assembly, a striker, a needle hub or carrier that holds a piercing member (e.g., a needle) and associated mechanisms and packaging. A lid 4506 is provided at an end of lock collar 4504 to keep the contents in place or otherwise protect the contents. For example, lid 4506 protects the contents against dirt, dust, debris, etc. Lid 4506 also protects against accidental firings of the contents such as the piercing member (e.g., needle). In various embodiments, lid 4506 seals an outline of a bottom surface of lock collar 4506. Lid 4506 covers an entire outline of lock collar 4504.

Referring to FIG. 45B, a perspective cutout view of the single-use, disposable insertion tool of FIG. 45A is illustrated according to an embodiment of the present disclosure. Insertion device 4500 includes a sensor assembly 4508 housed inside a top portion or plunger 4502 of insertion device 4500. Sensor assembly 4508 is in a pre-cocked position. A mounting base 4512 is disposed on a bottom surface of sensor assembly 4508. Mounting base 4512 covers at least an entire outline of the bottom surface of sensor assembly 4508. In various embodiments, mounting base 4512 is positioned to fit within an entire inner outline of bottom portion of lock collar 4504 of insertion device 4500. In particular embodiments, mounting base 4512 includes an exposed adhesive on a bottom side, that is, a first side of mounting base 4512 attaches to sensor assembly 4508 and a second side is exposed. In other embodiments, mounting base 4512 is made of a flexible material, a gauze-like material, or a solid material such as a plastic, a metal, etc.

Figure 46A:
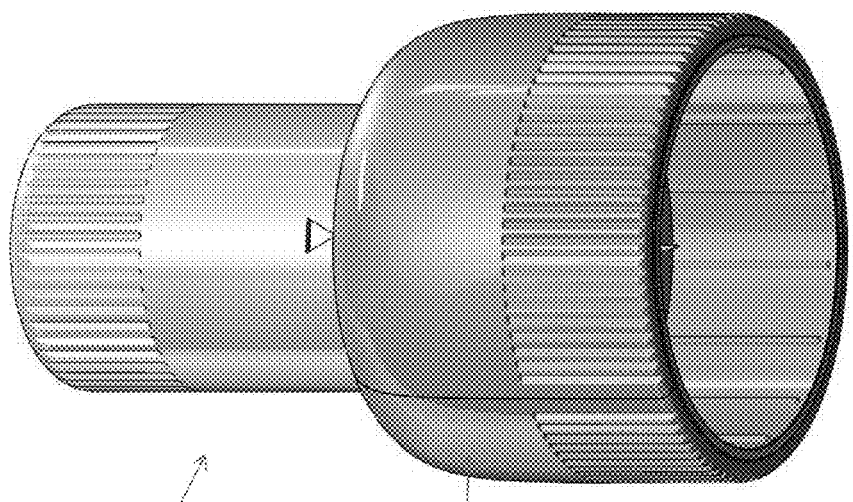
FIGS. 46A-46B are bottom perspective views of an insertion device illustrating a first step for a use model of the insertion device according to an embodiment of the present disclosure.
Figure 46B:
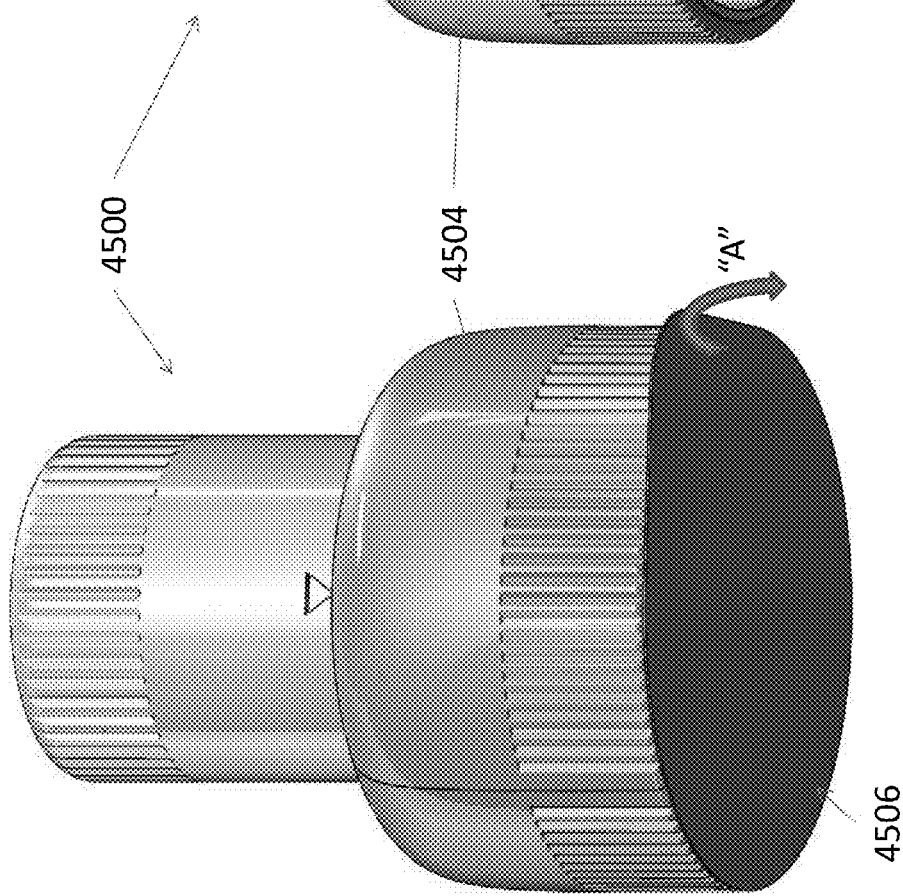

FIGS. 46A-46B are bottom perspective views of an insertion device illustrating a first step for a use model of the insertion device according to an embodiment of the present disclosure. In various embodiments, a user uses an insertion device 4500, which is an integrated, single unit device, to allow the user to position and subcutaneously implant a sensor into the user's body. For example, the user uses insertion device 4500 to implant a glucose sensor subcutaneously/transcutaneously.

First, as illustrated in FIG. 46A, a user of insertion device 4500 opens insertion device 4500 by peeling or otherwise removing a lid 4506 as indicated by arrow "A". For example, the user removes lid 4506 with a simple pulling with the hand or other appropriate tool. Lid 4506 can be of any appropriate material to provide protection or cover a bottom side of a lock collar 4504 of insertion device 4500, for example, plastic, paper, and/or the like. FIG. 46B illustrates insertion device 4500 having the bottom side of lock collar 4504 open, that is, without lid 4506 attached.

FIGS. 47A-47B are perspective views of an insertion device illustrating a second step for a use model of the insertion device according to an embodiment of the present disclosure. As illustrated in FIG. 47A, a rotation or twisting motion, for example in a counterclockwise direction as indicated by arrow "A" is used to align a marking 4716 (e.g., a downward arrow or other appropriate marking) of plunger 4502 with a corresponding marking 4718 (e.g., an upward arrow or other appropriate marking) of lock collar 4504. In various embodiments, the user performs the rotation motion as indicated by arrow "A" while applying a downward force (e.g., pushing) on plunger 4502. As such, two unlocking directional forces are used, one rotating force and one downward force (push). In this way, the two forces, for example, two concurrent moves of pushing and rotating, keep the lock collar from easily or accidentally rotating or unlocking so that an accidental trigger is prevented, for example an accidental trigger of a piercing member (e.g. a needle), thus increasing safety and avoiding wasting of an insertion device. FIG. 47B illustrates marking 4716 of plunger 4502 and marking 4718 of lock collar 4502 lined up in response to the user applying forces such as two concurrent moves to push and rotate to unlock lock collar 4502.

Referring now to FIG. 48, a perspective view of an insertion device illustrates a third step for a use model of the insertion device according to an embodiment of the present disclosure. Once plunger 4502 and lock collar 4504 are unlocked for example as indicated by markings 4716 and 4718 lining up as described above with respect to the embodiment of FIG. 47B, the user places insertion device 4500 against an insertion site. The user selects the insertion site to position and subcutaneously implant a sensor into the user's body. For example, the user uses insertion device 4500 to implant a glucose sensor subcutaneously/transcutaneously. Once the user positions insertion device 4500 on the selected insertion site, the user applies a downward force on at least of portion of plunger 4502, for example, the user depresses plunger 4502 at a top surface of plunger 4502 as indicated by arrow "A". Insertion device 4500 includes components including a sensor (not shown) that is inserted into the user's body as a result of the user pressing on plunger 4502 by a certain extent (i.e. travel or distance). In an embodiment, the sensor is inserted when plunger 4502 is depressed 0.30 inches. In other embodiments, the sensor is inserted when plunger 4502 is depressed 0.2 inches, 0.4 inches, 0.5 inches, or any other appropriate distance. In an embodiment, the user uses a predetermined minimum force to depress plunger 4502 so that the sensor is inserted into the user's body. For example, the user uses a minimum plunger spring force of 2.5 lbf. to insert the sensor. Notably, a force less than a certain minimum force does not allow the sensor to be implanted into the body. In this way, minimum plunger force and travel or distance prevent accidental firing or firing of the insertion device in mid-air. Due at least in part to the symmetrical shape of the insertion device (e.g., radially symmetrical), the user can insert a component such as a sensor using just one hand, without having to look at an insertion site, which allows more possible insertion sites such as the user's back, the back of the arm, etc. No orientation of the insertion device to the body is required.

Referring to FIGS. 49A-49B, perspective views of an insertion device illustrates a fourth step for a use model of the insertion device according to an embodiment of the present disclosure. After a user unlocks, positions an insertion device on an insertion site, depresses plunger 4502 of the insertion device with a certain force and/or for a certain distance so that a sensor is subcutaneously implanted into the user's body, the user then releases plunger 4502 and pulls the insertion device away from the insertion site. In this regard, as illustrated in the embodiment of FIG. 49A, the user releases plunger 4502 as indicated by arrow "A". For example, the user removes pressure from plunger 4502 by, for example, removing the user's finger or another tool from applying force on a top surface of plunger 4502. Then, as illustrated in FIG. 49B, the user removes the insertion device away from the insertion site as indicated by arrow "B". As illustrated in FIG. 49B, a sensor assembly 4508 is automatically left behind on the insertion site, and is ready for further use, for example, ready for transmitter connection. In various embodiments, a mounting base 4512 fastens sensor assembly 4508 to the user's body, for example, by using an adhesive that adheres to the user's body. It should be noted that as a result of the user releasing or pulling the insertion device away from the insertion site, a needle component housed in the insertion device automatically retracts as will be described in more detail below.

As such, embodiments of the present disclosure provide a simple use model for an insertion device. First, a user of an insertion device according to one or more embodiments simply opens the insertion device by removing a lid that covers or protects a bottom of the insertion device. Second, the user uses a rotation or twist action to unlock a lock collar of the insertion device. In an embodiment, unlocking is indicated by lining up a marking on a lock collar with a corresponding marking on a plunger of the insertion device. Third, the user positions the insertion device on a selected insertion site and pushes the plunger downward on the selected insertion site. In an embodiment, the user uses a minimum pushing force for a certain minimum travel or distance to insert a sensor into the body of the user at the insertion site. And fourth, the user releases the plunger and removes the insertion device away from the insertion site leaving behind the sensor at the insertion site, where the sensor remains fastened to the user's body via a mounting base.

Advantageously, embodiments of the present disclosure provide a simple use model for an insertion device for a user that requires only a few simple steps. For example, the user uses only a few steps to insert a sensor into a selected insertion site. No cocking is required. No removing liners is required, no buttons or other interfaces are required, no manually removing a needle hub is required, instead, a needle pops up and is retained automatically. No fine motor skills by the user are required. The user uses the insertion device to insert a component such as a sensor with one hand, without having to look at an insertion site, which allows more possible insertion sites such as the user's back, the back of the arm, etc. No orientation of the insertion device to the body is required. And no work surface is required.

In addition, embodiments of the present disclosure provide error-proof insertion. Push-to-fire mechanism guarantees that sufficient force is applied against an insertion site. Enough force is needed to trigger the insertion device. Also, full needle penetration is ensured. The sensor is fastened to the skin, e.g., the sensor is bonded with adhesive to the skin. Sequence of sensor insertion and needle retraction is guaranteed by the mechanism as will be described in more detail below.

Furthermore, embodiments of the present disclosure reduce the number of devices that a user carries to insert a sensor. For example, an insertion device according to one or more embodiments integrates components such as a sensor, a needle, a needle hub, packaging, etc. into one device instead of the user having to carry each component separately. Also, as a result, there is less waste produced with the use of a single integrated device than with multiple devices individually packaged.

Mechanism for Insertion Device

Figure 50B:
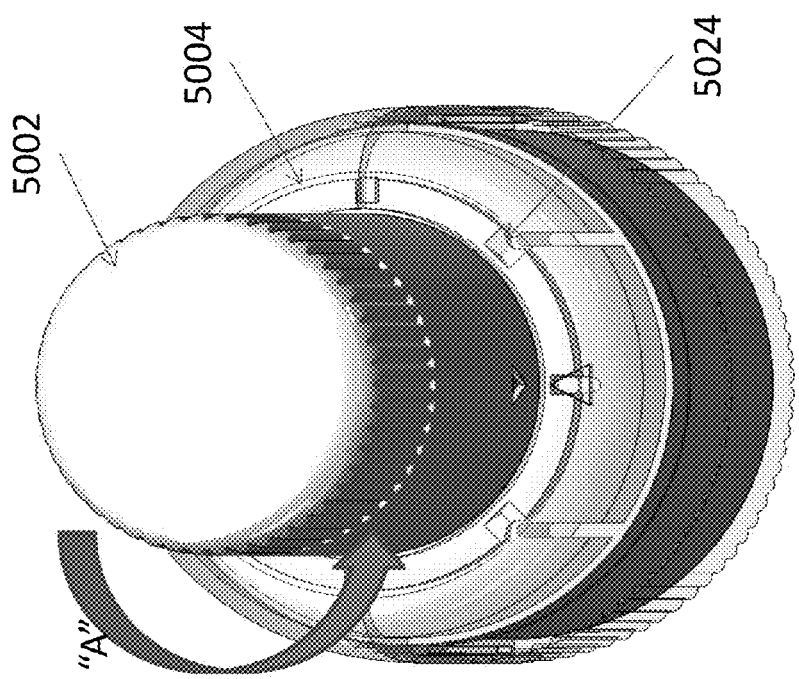
FIGS. 50A-50B are perspective views for unlocking an insertion device according to an embodiment of the present disclosure.
Figure 50A:
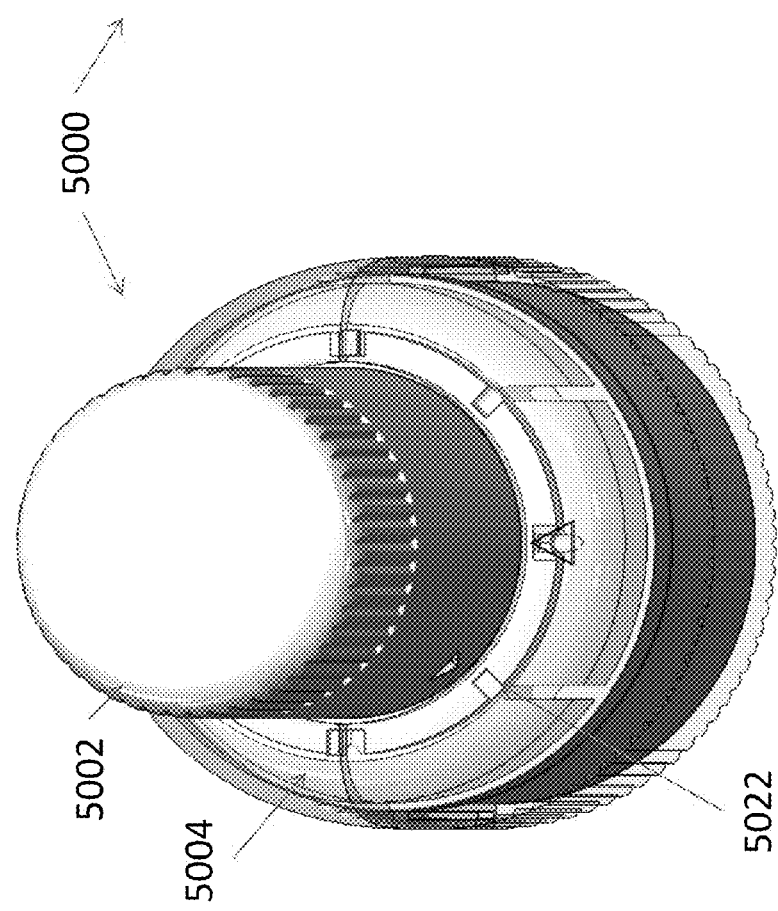

Referring to FIGS. 50A-50B, perspective views for unlocking an insertion device are illustrated according to an embodiment of the present disclosure. As described above according to one or more embodiments, an insertion device 5000 includes a plunger 5002 and a lock collar 5004. Plunger 5002 includes one or more ribs 5022 spaced along an outline of a side or a bottom surface of plunger 5002. For example, four, six, eight, or any appropriate number of ribs 5022 can be evenly spaced along the outline of the bottom surface of plunger 5002. Lock collar 5004 includes one or more clearance slots 5024 positioned around an outline of a side or a top surface of lock collar 5004. In FIG. 50A, plunger 5002 of insertion device 5000 is blocked or locked by at least one rib 5022. Insertion device 5000 is in such a locked position, for example, when the insertion device 5000 is being transported or stored. When a user desires to use the insertion device to implant a sensor, for example a glucose sensor at an insertion site on the body of a user, the user has to first unlock the insertion device. As illustrated in FIG. 50B, the user rotates plunger 5002 for example in a counterclockwise direction as indicated by arrow "A". As a result of the rotation, clearance slots 5024 align with ribs 5022 of lock collar 5004. The alignment of clearance slots 5024 with ribs 5022 unblocks or unlocks plunger 5002 so that the user can depress plunger 5002.

Figure 51:
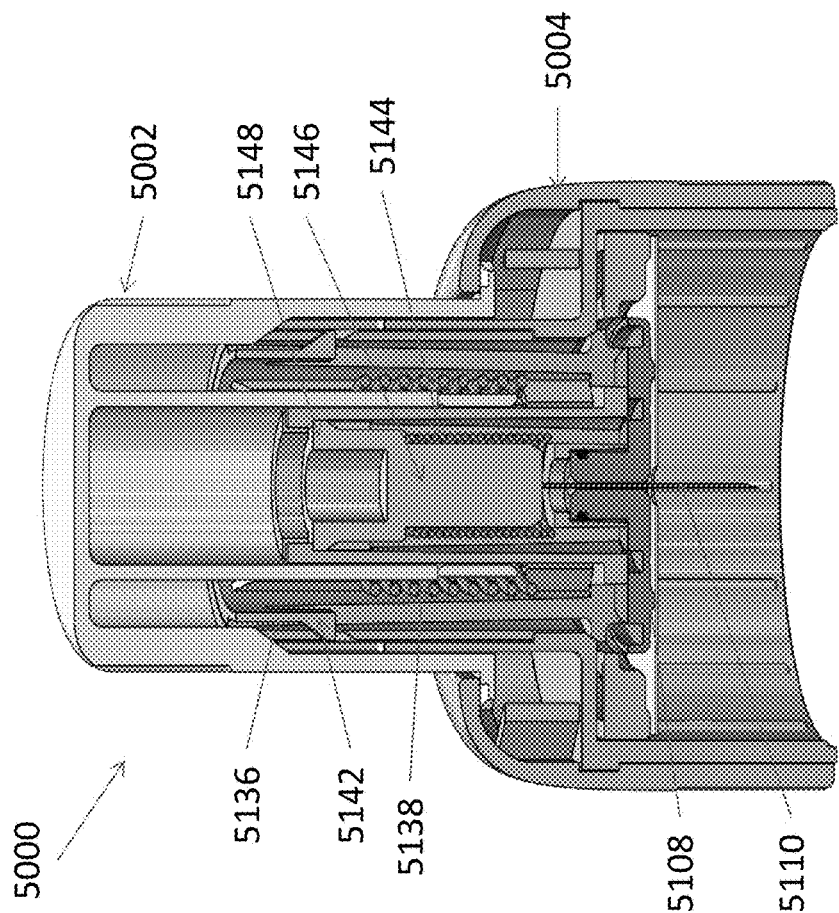
FIG. 51 is a cutout view of the insertion device of FIGS. 50A-50B in a cocked position according to an embodiment of the present disclosure.

Referring to FIG. 51, a cutout view of the insertion device of FIGS. 50A-50B is illustrated in a cocked position according to an embodiment of the present disclosure. Insertion device 5000 is configured to be in a cocked position, for example, when insertion device 5000 is transported, stored, or otherwise not in use. As described above according to one or more embodiments, insertion device 5000 includes a plunger 5002 coupled with a lock collar 5004. Insertion device 5000 also includes a striker 5136 that is configured to keep insertion device 5000 in a cocked position such that striker 5136 is kept from firing. In that regard, insertion device 5000 includes a striker spring 5138 that is captured between plunger 5002 and striker 5136 when it is in a cocked position. Self-locking striker snap arms 5142 keep striker 5136 cocked. To be fired, self-locking striker snap arms 5142 are positioned (e.g., turned) to enter a groove to allow striker 5136 to snap down as will be described in more detail below. A sensor assembly 5108 having or adapted to fit a piercing member 5110 (e.g., a needle) therethrough is also cocked and housed within insertion device 5000, for example, at a bottom side within an interior volume or portion of lock collar 5004. A needle carrier spring 5144 is captured between striker 5136 and a needle carrier 5146. Self-releasing snaps 5148 keep needle carrier 5146 cocked. Notably, plunger 5002 prevents snaps 5148 from re-positioning, e.g., flexing outwards, and releasing needle carrier 5146.

Referring to FIGS. 52A-52B, cutout views of the insertion device of FIGS. 50A-50B are illustrated in an insertion position according to an embodiment of the present disclosure. A user can use insertion device 5000 to insert a sensor at an insertion site on the user's body. In this regard, the user depresses plunger 5002 using the user's finger, hand or other appropriate tool. As illustrated in FIG. 52A, as a result of the user depressing plunger 5002, striker spring 5138 is compressed. Also, plunger ribs 5152 deflect self-locking striker snap arms 5142, for example, self-locking striker snap arms 5142 turn as indicated by arrows "A", allowing firing of insertion device 5000. FIG. 52B illustrates striker 5136 in the fired position with striker spring 5138 in a released position. Upon firing of insertion device 5000, piercing member 5110 of sensor assembly 5108 is inserted into a user's body.

Figure 53A:
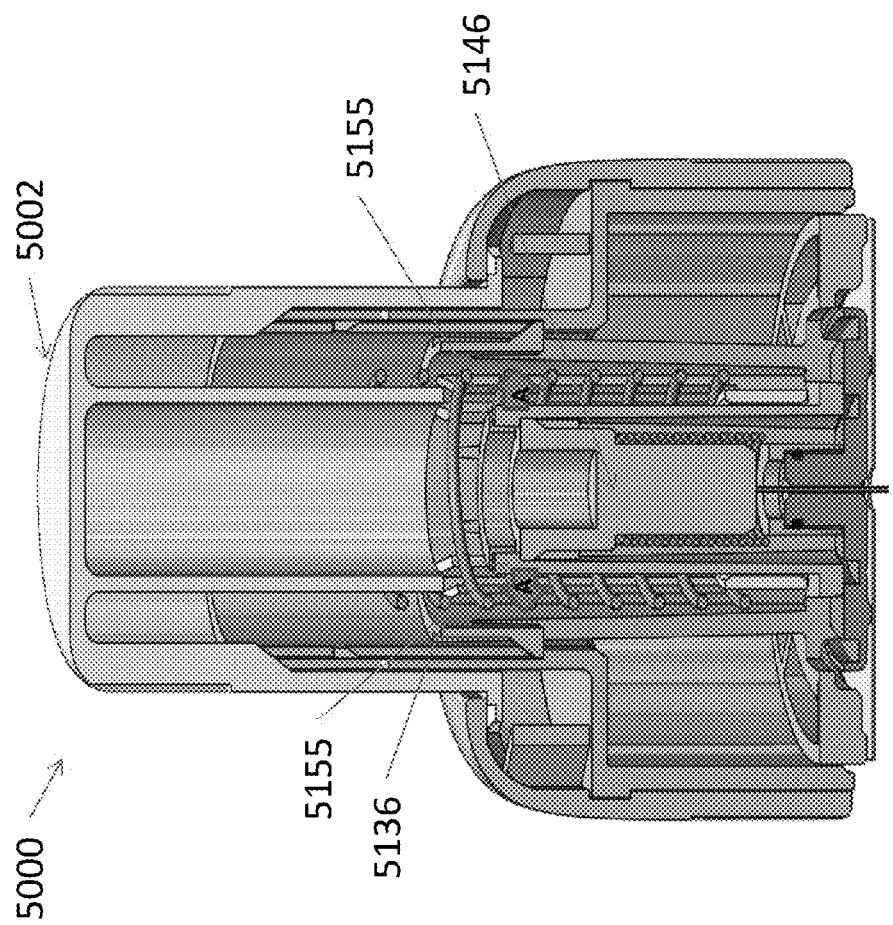
FIGS. 53A-53B are cutout views of the insertion device of FIGS. 50A-50B in a retraction position according to an embodiment of the present disclosure.
Figure 53B:
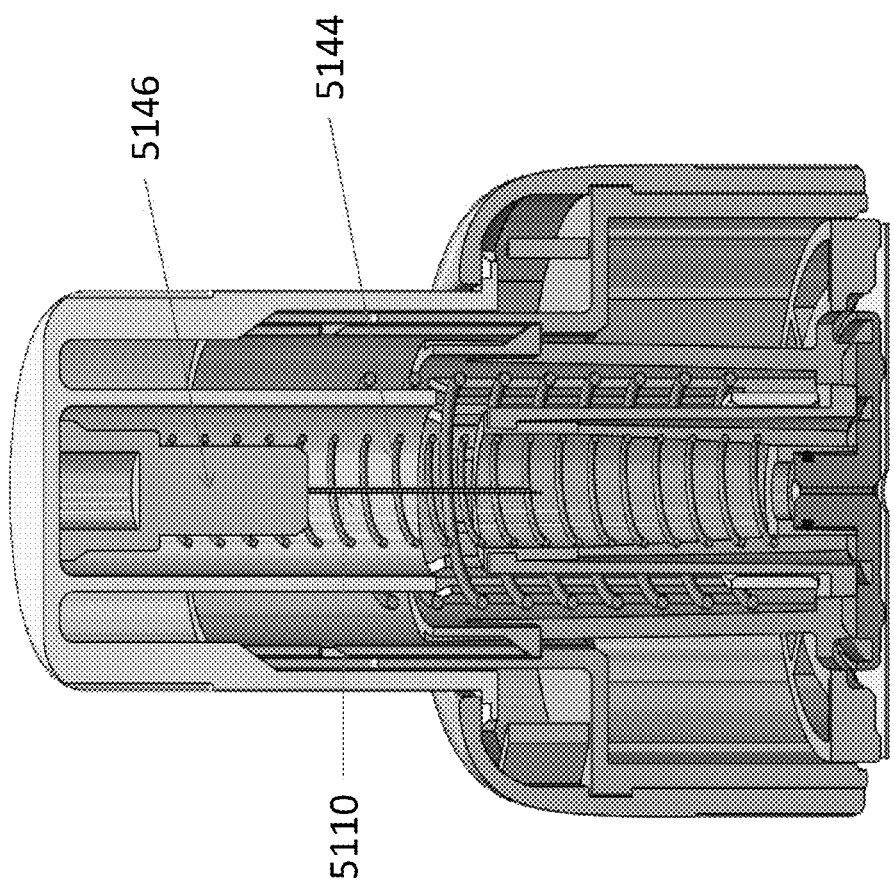

Referring to FIGS. 53A-53B, cutout views of the insertion device of FIGS. 50A-50B are illustrated in a retraction position according to an embodiment of the present disclosure. As illustrated in FIG. 53A, once a user fires insertion device 5000 at a selected insertion site, for example, by depressing plunger 5002 as described above, striker 5136 is in a fired position. With striker 5136 in the fired position, the user then releases plunger 5002, for example, by removing the user's finger, hand or other tool from plunger 5002. Releasing plunger 5002 frees snap arms 5155 to turn, for example flex outwards as indicated by arrows "A". As a result, as illustrated in FIG. 53B, needle carrier 5146 is retracted. In this regard, needle carrier spring 5144 expands and retracts needle carrier 5146. Needle carrier 5146 having piercing member 5110 is retracted such that it is encapsulated well inside inserter device 5000.

Figure 54:
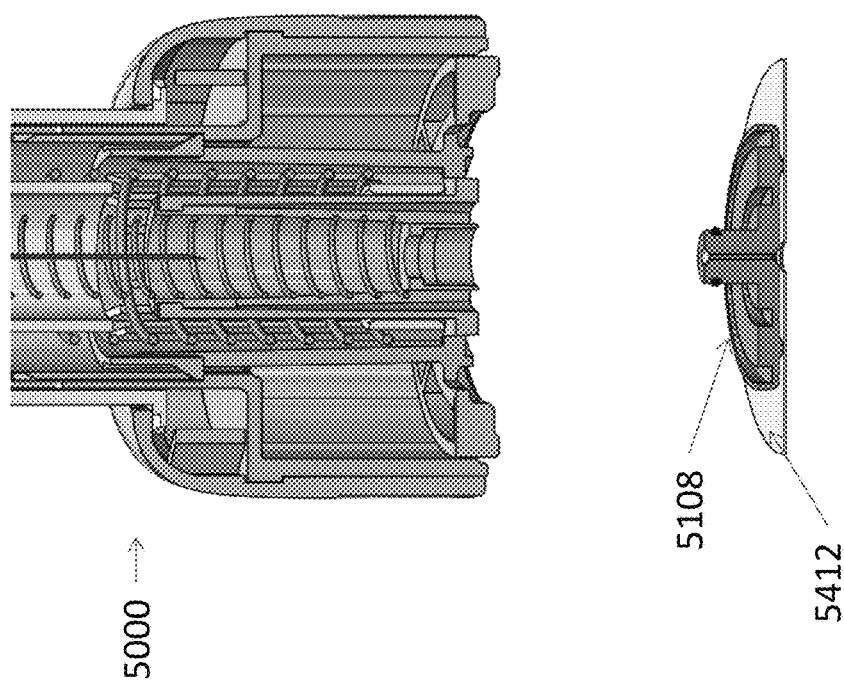
FIG. 54 is a cutout view of the insertion device of FIGS. 50A-50B in a released position according to an embodiment of the present disclosure.

Referring to FIG. 54, a cutout view of the insertion device of FIGS. 50A-50B is illustrated in a released position according to an embodiment of the present disclosure. Once a user fires insertion device 5000 such that a mounting base 5412 adheres sensor assembly 5108 to the user's body, the user pulls insertion device 5000 away from the body, thus releasing sensor assembly 5108.

Referring now to FIG. 55, a flow chart illustrates a method for an insertion device mechanism according to an embodiment of the present disclosure. In various embodiments, the method of FIG. 55 can be implemented by the insertion device illustrated in FIGS. 50A-54.

In block 5502, an insertion device includes a locking mechanism. The locking mechanism protects the insertion device from accidentally firing or other potential safety issues. As described above according to one or more embodiments, the insertion device includes a plunger having one or more clearance slots and a lock collar having one or more ribs. The one or more ribs on the lock collar block the plunger. Rotating the plunger aligns the clearance slots of the plunger with the ribs of the lock collar, thus unlocking the insertion device such that a user can depress the plunger.

In block 5504, upon unlocking of the insertion device, the insertion device is fired at an insertion site in response to a user pressing the plunger. In this regard, as described above according to one or more embodiments, pressing the plunger compresses a striker spring and plunger ribs deflect striker snaps, e.g., self-locking striker snap arms, thus firing the insertion device.

In block 5506, upon firing of the insertion device, a piercing member is caused to insert a sensor of a sensor assembly into the body of the user and a sensor assembly adheres to the body of the user.

In block 5508, a needle carrier having the piercing member is retracted in response to the user releasing the plunger. The piercing member is retracted such that it is encapsulated well inside the insertion device.

In block 5510, with the sensor assembly adhered to the user's body, releasing the sensor assembly in response to the user pulling away the insertion device.

In various embodiments, a disposable insertion tool piercing member protection mechanism may be provided as will be described in more detail below with respect to FIGS. 87A-96 according to one or more embodiments. Once the insertion device has been used, that is, released and pulled away from the user's body, a disposable insertion tool needle mechanism alleviates potential accidental exposure of a tip of a piercing member (e.g., needle). The piercing member remains protected inside the inserter device even if the user attempts to depress the plunger and striker on the used insertion device. That is, according to one or more embodiments, the piercing member (e.g., needle) is prevented from being exposed by preventing the plunger and striker from being fully depressed again once the insertion tool has been used.

Sensor Transmitter Assembly Alternative Embodiments

Figure 56A:
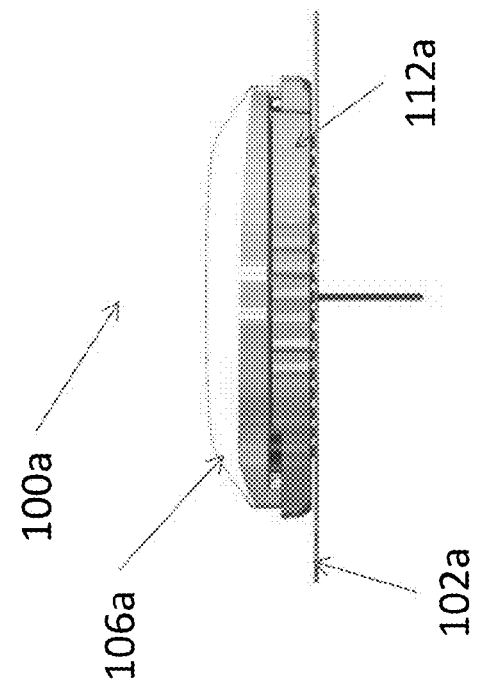
FIG. 56A is a top view of a sensor transmitter assembly as a single unit having two compression areas according to an alternative embodiment of the present disclosure.
Figure 56B:
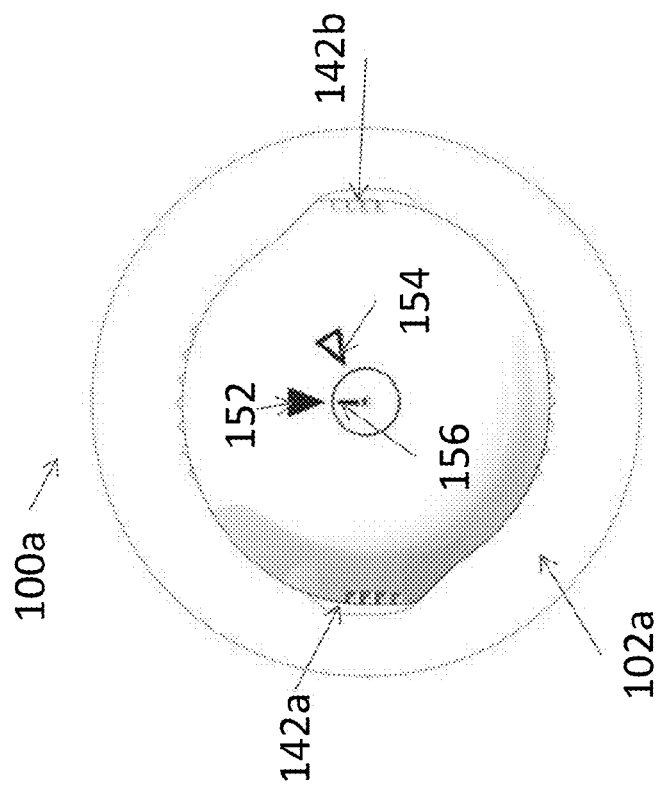
FIG. 56B is a side view of the sensor transmitter assembly of FIG. 56A according to an embodiment of the present disclosure.

FIG. 56A is a top view of a sensor transmitter assembly as a single unit having two compression areas according to an embodiment of the present disclosure. FIG. 56B is a side view of the sensor transmitter assembly of FIG. 56A according to an embodiment of the present disclosure.

Similar to the embodiment of FIG. 1A and FIG. 1B, the embodiment shown in FIG. 56A and FIG. 56B illustrates a sensor transmitter assembly 100a as a single unit as may be worn on-body by a patient. In this embodiment, however, instead of the sensor transmitter assembly having, for example, three outer edges 126 as illustrated in FIG. 1A and FIG. 1B, sensor transmitter assembly 100a includes two compression areas 142a and 142b, also referred to as "snap arms". As illustrated in the embodiment of FIG. 56B, sensor transmitter assembly 100a includes transmitter assembly 106a positioned on top of a sensor assembly 112a as a single unit. Transmitter assembly 106a and sensor assembly 112a attach at two edges, for example at two edges corresponding to compression areas 142a and 142b. In various embodiments, compression areas 142a and 142b (or snap arms) are included or located on either side of a base of sensor assembly 112a, for example evenly spaced apart substantially along an outer rim or outline of the base of sensor assembly 112a. A user can turn or apply a rotation motion to lock the sensor transmitter assembly into place. For example, the user can turn or rotate transmitter assembly 106a onto sensor assembly 112a in a first direction (for example, in a clockwise direction), which automatically squeezes or compresses compression areas 142a and 142b. Conversely, to disconnect, the user can squeeze (e.g., press inwards) the compression areas (or snap arms) while turning or applying a rotation motion. For example, when disconnecting transmitter assembly 106a from sensor assembly 112a, the user squeezes or compresses compression areas 142a and 142b while rotating in an opposite direction from the first direction, for example in a counterclockwise direction. Squeezing of compression areas 142a and 142b (or snap arms) and applying the rotation motion provides a double fail safe mechanism for disconnecting the sensor transmitter assembly 100a by using a mechanism that is intuitive to a user. Two compression areas make it easy for the user to squeeze and turn at the same time. However, it should be noted that transmitter assembly 106a and sensor assembly 112a can attach at any number of edges corresponding to respective compression areas or snap arms as appropriate, for example, at two edges corresponding to two compression areas as illustrated in FIG. 56A, or at 4 edges, 5 edges, 6 edges, etc. Compression areas 142a and 142b (or snap arms) on the base of sensor assembly 112a are designed to be self-locking. That is, if the user tries to disconnect transmitter assembly 106a just by rotating it and without manually squeezing the snap arms inwards, then the rotation motion causes the snap arms to flex outwards and lock even harder against transmitter assembly 106a. If compression areas 142 and 142*b* (or snap arms) were not self-locking, then it would be possible for the user to rotate transmitter assembly 106*a* hard enough to unlock the snap arms, which, in such case, would defeat the double fail-safe feature.

A surface, e.g., a top surface of sensor transmitter assembly 100*a* includes indicators 152, 154 and 156. Alignment of the indicators with respect to each other, e.g., as a result of a rotation motion, indicates whether the sensor transmitter assembly is in a locked or an unlocked position. For example, when indicator 152 is aligned with indicator 156, the sensor transmitter assembly is in a locked position. Whereas when indicator 152 is aligned with indicator 154, the sensor transmitter assembly is in an unlocked position. In this embodiment, indicator 152 is in the shape of a filled-in triangle, indicator 154 is in the shape of a clear triangle, and indicator 156 is in the shape of a dash or a line to indicate alignment with either indicator 152 or indicator 154. It should be noted that the characteristics of indicators 152, 154 and 156 can be of any shape, size, form, color, etc. to indicate alignment, and can be placed on any appropriate location on the sensor transmitter assembly such as on a side surface, etc.

The overall shape of sensor transmitter assembly 100*a* according to one or more embodiments is substantially round and has smooth footprint edges, which prevent potential wear issues such as snagging on the patient's clothing that may be caused by, for example, sharp, pointy edges. Also, smooth footprint edges help improve comfort of wear. Sensor transmitter assembly 100*a* is fastened by a mounting base or patch 102*a* that adheres to the user's skin.

FIG. 57A is an exploded top perspective view of the sensor transmitter assembly illustrated in FIGS. 56A and 56B according to an alternative embodiment of the present disclosure. FIG. 57B is an exploded bottom perspective view of the sensor transmitter assembly illustrated in FIGS. 56A and 56B according to an embodiment of the present disclosure. As illustrated in FIGS. 56A and 56B, the components of the sensor transmitter assembly 100 may be coupled together as a single unit.

As described above, the embodiment of FIG. 57A illustrating an exploded top view of the sensor transmitter assembly generally includes a transmitter assembly 106*a* and a sensor assembly 112*a*. Transmitter assembly 106*a* includes an opening 216*a* that is adapted to engage with a cap 214*a* of sensor assembly 112*a*. In that regard, transmitter assembly 106*a* is initially lowered onto sensor assembly 112*a* such that opening 216*a* of transmitter assembly 106 is positioned to fit cap 214*a* of sensor assembly 112*a*. In an embodiment, indicator 154 of transmitter assembly 106*a* can be aligned with indicator 156 of sensor assembly 112*a* when engaging opening 216*a* with cap 214*a*. A solid connection of transmitter assembly 106*a* to sensor assembly 112*a* is completed by applying an intuitive rotation motion, which automatically squeezes inward or compresses the snap arms or compression areas 142*a* and 142*b* that are positioned on a base of sensor assembly 112*a*.

As illustrated in FIG. 57B, transmitter assembly 106*a* includes a bottom surface 211*a* having at least one interface such as a rail, tab or snap arm 5703, and accommodates various components including at least one electronics module. Sensor assembly 112*a* includes at least one interface such as slot 5705 (illustrated in FIG. 57A) adapted to engage, match or otherwise receive corresponding interfaces such as rails, tabs or snap arms disposed on transmitter assembly 106*a*. It should be noted that there can be any number of interfaces such as rails, tabs or snap arms and corresponding interfaces such as slots (e.g., 3, 4, etc. on a corresponding surface) and can be positioned on respective surfaces of the transmitter assembly and the sensor assembly to allow engagement or attachment with each other. Also, the characteristics of the interfaces such as rails, tabs or snap arms and corresponding slots can be of any appropriate shape, size, depth, etc. to allow engagement or attachment with each other.

As described above for example with respect to the embodiments of FIGS. 2A-2B, a mounting base (or patch) 102*a* is a large, stretchy patch that affixes the sensor assembly 112*a* to the skin of the patient. Mounting base or patch 102*a* has a bottom surface (as shown in FIG. 57B) that is adapted to be attached to the skin of the patient using any appropriate attachment techniques, for example, an adhesive (e.g., a fluid adhesive, a spray adhesive, etc.), staples, or the like. In various embodiments, mounting base or patch 102*a* has a top surface that is bonded to the entire device outline, not just to certain edges of the device, thus providing on-body stability. In various embodiments, glue, ultrasonic welding, etc. can be used for bonding.

Figure 58C:
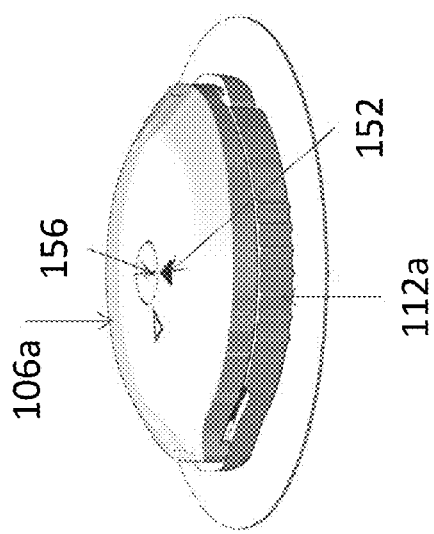
FIGS. 58A-58C illustrate side perspective views for mechanically connecting a sensor assembly to a transmitter assembly according to an alternative embodiment of the present disclosure.
Figure 58B:
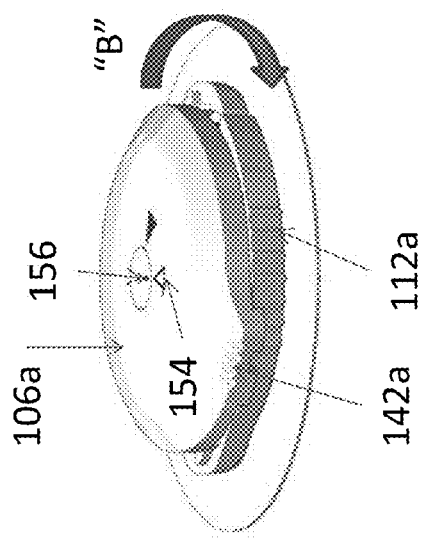
Figure 58A:
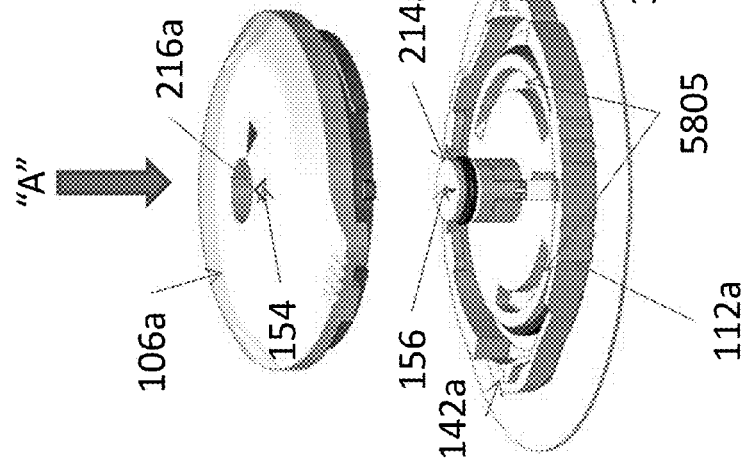

Referring to FIGS. 58A-58C, perspective side views for mechanically connecting a sensor assembly to a transmitter assembly are illustrated according to an alternative embodiment of the present disclosure. Initially, as illustrated in the embodiment of FIG. 58A, a transmitter assembly 106*a* is positioned, for example, lowered onto a sensor assembly 112*a* as indicated by downward arrow "A". In that regard, an interface such as an opening 216*a* of transmitter assembly 106*a* is lined up with, fits, or otherwise matches an interface such as a cap 214*a* of sensor assembly 112*a*. Also, an indicator 154 located on transmitter assembly 106*a* is aligned with an indicator 156 of sensor assembly 112*a*. As described above according to one or more embodiments, one or more interfaces, e.g., rails located on a bottom surface of transmitter assembly 106*a* engage into one or more corresponding interfaces, e.g., slots 5805 of sensor assembly 112*a*. In this embodiment, there are two rails and two corresponding slots that provide a keyed structure such that the transmitter assembly drops in and lines up (e.g., as indicated by aligning indicators 154 and 156) in a particular way (not randomly) so that it can be locked and does not move around.

As illustrated in FIG. 58B, after transmitter assembly 106*a* is initially positioned together axially with sensor transmitter 112*a* such that indicator 154 is aligned with indicator 156, a push or twist action (e.g., a clockwise rotating motion), as indicated by arrow "B", is used to connect transmitter assembly 106*a* to sensor assembly 112*a* together rotationally. As illustrated in FIG. 58C, the rotating motion aligns indicator 156 with indicator 152 indicating the locking of the sensor transmitter assembly in place. Conversely, a squeeze at the compression areas together with a rotation motion (e.g., in a counterclockwise direction) is used to disconnect transmitter assembly 106*a* from sensor assembly 112*a*. It should be noted that in other embodiments, a clockwise rotating motion disconnects the transmitter assembly to the sensor assembly, and a counterclockwise rotation motion connects the transmitter assembly to the sensor assembly. As such, according to embodiments herein, transmitter assembly 106*a* rests completely on top of sensor assembly 112*a*. This results in little relative movement being possible between the sensor assembly and the transmitter assembly. Stable electrical connections are also ensured.

Advantageously, a twist or rotating action along with compressing at the compression areas provides a double fail safe connection mechanism, is generally intuitive to a patient, and allows the patient to handle the sensor transmitter assembly with one hand without the patient having to look at an insertion site. This allows the patient to place and wear the sensor transmitter assembly on more locations on the body, even on locations where the patient has no visibility such as on the patient's back. FIG. 58C illustrates the sensor transmitter assembly as would be worn by the patient on-body as one unit.

Referring to FIG. 59, an exploded view of a sensor assembly is illustrated according to an alternative embodiment of the present disclosure.

As described above according to one or more embodiments, sensor assembly 112*a* includes a base 5919 having at least one interface such as slots 5905 adapted to engage with corresponding interfaces such as rails of a transmitter assembly. Sensor assembly 112*a* has components including without limitation a mounting base 102 such as an adhesive patch, sensor base 5919 having slots 5905, a sensor head cavity 5915 and a cap cavity 5918, an outer seal 5903, a sensor module 5904, an elastomeric connector 5902, at least one inner seal 5906, a cap 5909, an o-ring 5907 and a needle hub 5922. Sensor head cavity 5915 is adapted to fittingly receive and provide support to sensor module 5904 and elastomeric connector 5902 as will be described in more detail below, for example, with respect to the embodiments of FIGS. 60A-60C. Cap cavity 5918 is adapted to fit or accommodate at least one inner seal 5906 that also provides a fluid seal for sensor module 5904. An outer seal 5903 fits around sensor base 5919 and provides water tightness for sensor assembly 112*a*.

Figure 60C:
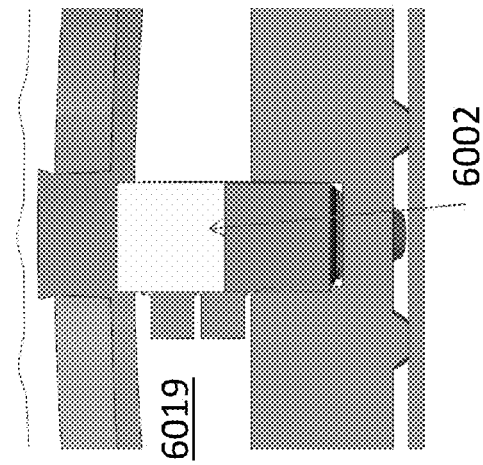
FIGS. 60A-60C illustrate views for affixing a sensor head and an elastomeric connector to a sensor base of a sensor assembly according to an alternative embodiment of the present disclosure.
Figure 60B:
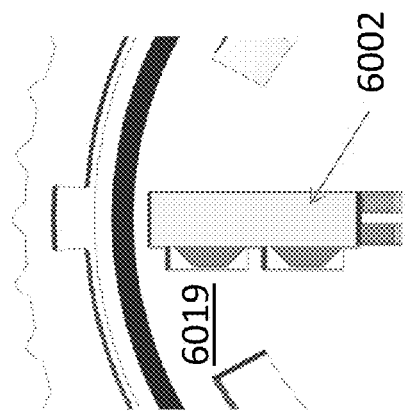
Figure 60A:
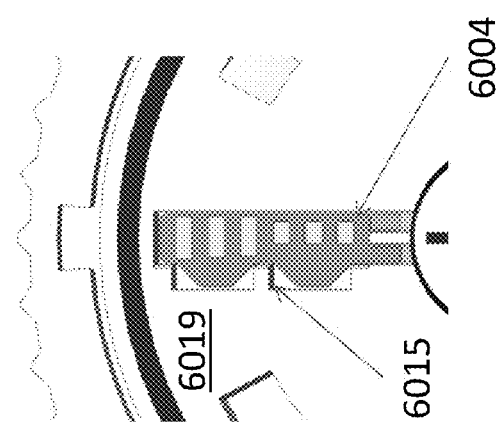

FIGS. 60A-60C illustrate views for affixing a sensor head and an elastomeric connector to a sensor base of a sensor assembly according to an alternative embodiment of the present disclosure. In FIG. 60A, sensor base 6019 includes a sensor head cavity 6015 (see also, FIG. 59) formed thereon that holds in place a sensor module 6004. Sensor module 6004 is positioned in sensor head cavity 6015 and can be fastened by using suitable fastening techniques such as double sided tape, adhesive, molded glue, a snap fit, laser weld, or the like. Configurations for sensor module 6004 will be described in more detail below according to one or more embodiments.

In FIG. 60B, an elastomeric connector 6002 is placed on top of sensor module 6004. In various embodiments, elastomeric connector 6002 is retained by any suitable structure such as a spring, a snap fit, etc. In one or more embodiments, the retaining structure provides dead volume for elastomeric connector 6002 to expand into in response to a transmitter assembly being connected to the sensor assembly.

FIG. 60C is a perspective side view of the elastomeric connector fitted into the sensor head cavity of sensor base 6019. In this embodiment, a top cross section of elastomeric connector 6002 is square, which avoids having to orient the elastomeric connector in any particular direction.

Figure 61:
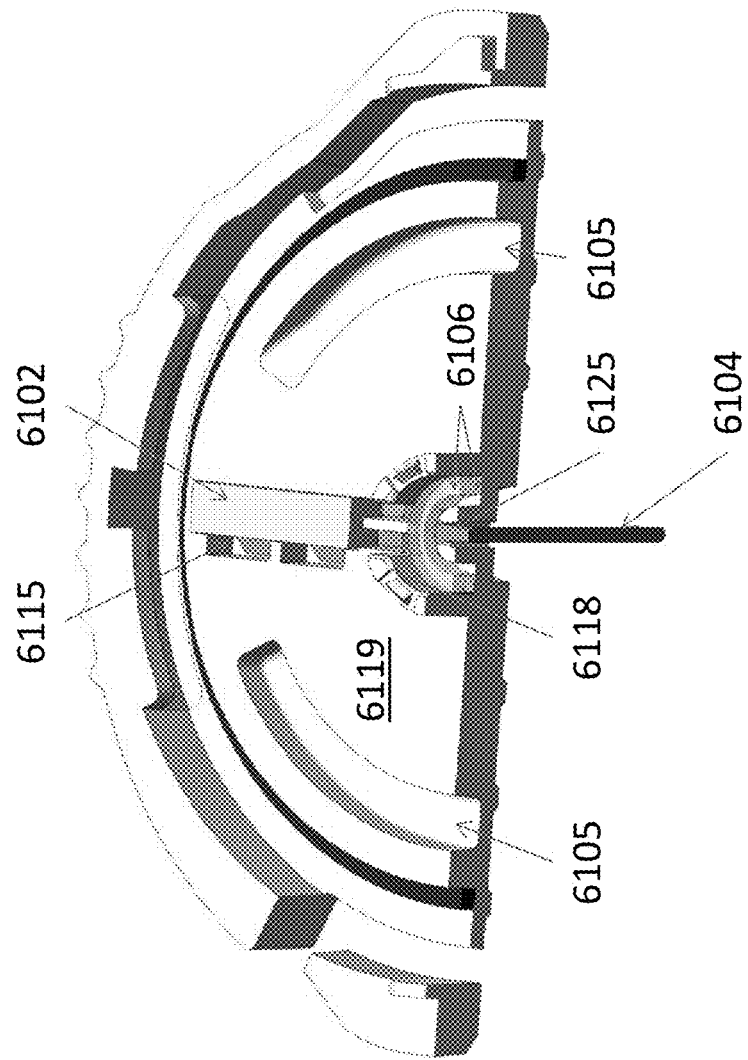
FIG. 61 is a partial top perspective view of a sensor assembly according to an alternative embodiment of the present disclosure.

FIG. 61 illustrates a perspective partial top view of a sensor assembly according to an alternative embodiment of the present disclosure. As described above according to one or more embodiments, a sensor base 6119 includes at least one interface such as sensor slot(s) 6105 and a sensor head cavity 6115 adapted to receive or accommodate (e.g., appropriately sized, shaped, positioned, etc.) a sensor module and an elastomeric connector 6102. A top portion 6125 of sensor portion 6104 extends directly straight at substantially a 90 degree angle (without further bending) into an opening of cap cavity 6118. Two identical inner seals or rings 6106 sandwich a portion of substrate of the sensor module, e.g., top portion 6125 of sensor extension or portion 6104 as will be described in more detail below according to one or more embodiments.

Figure 62D:
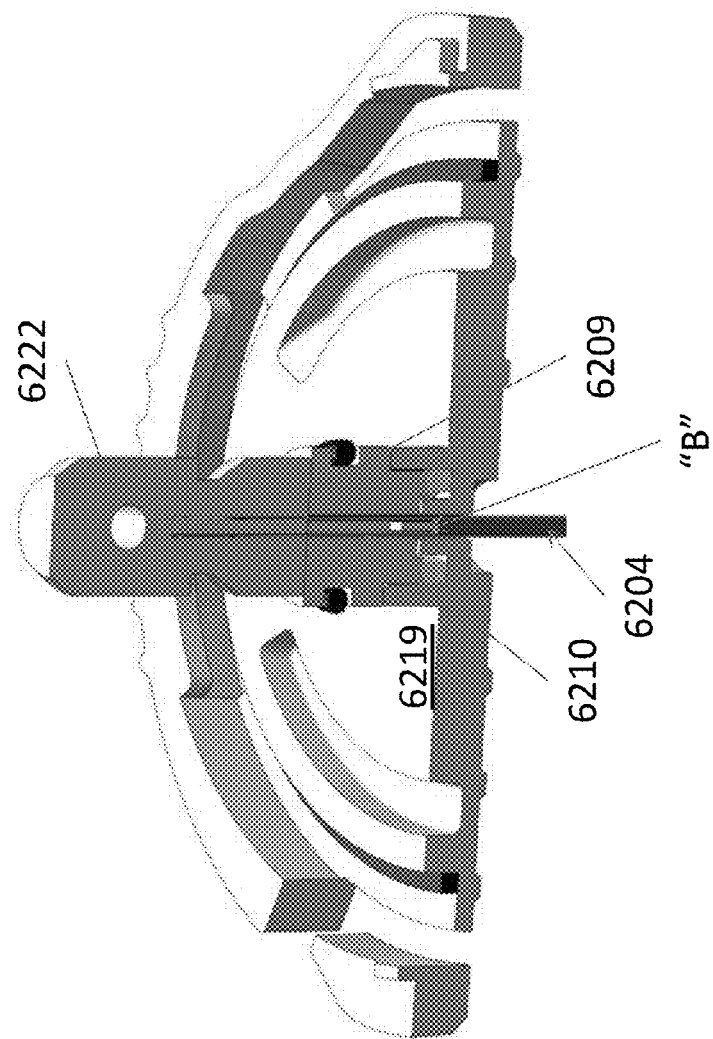
FIG. 62D is a partial side perspective view of a sensor assembly showing an interface of a sensor portion, a sensor base, a piercing member or needle and a pedestal cap according to an alternative embodiment of the present disclosure.

FIGS. 62A-62E illustrate perspective side views of an interface for a sensor assembly including a sensor base, a sensor portion, a piercing member or needle, a cap cavity and a cap according to an alternative embodiment of the present disclosure. In FIG. 62A, a top part of sensor portion 6204 is disposed in an opening 6206 extending along a sensor base 6219. Substantially identical inner rings 6207 sandwich a portion of the sensor substrate, i.e., at least a portion 6215 of a top of sensor portion 6204. Top sensor portion 6215 is angled at an angle "A'", for example approximately 90 degrees (see also FIG. 62B). As such, this part of the sensor portion has substantially a straight angle making this sensor portion easier to mold. Inner rings 6207 have a substantially square cross section when they are not compressed, which avoids slipping over each other.

As illustrated in FIG. 62B, upon compression for example by positioning a cap 6209 on top of sensor base 6219, inner square rings 6207 expand so that a sensor fold is on a fluid side of a seal, thus, there is no polyimide-against-polyimide gap to seal against. No glue, curing or other fastening techniques are needed. In this embodiment, everything is compressed together and supported. As illustrated in FIG. 62C, a piercing member such as a needle 6210 is positioned though opening 6206 of sensor base 6219.

Referring to FIG. 62D, a perspective partial side view of a sensor assembly showing an interface of a sensor portion, a sensor base, a piercing member or needle and a cap is illustrated according to an alternative embodiment of the present disclosure. FIG. 62D illustrates an interface of a sensor portion 6204, a sensor base 6219, a piercing member or needle 6210 and a cap 6209. Cap 6209 includes a hole or opening adapted to accommodate needle 6210 through cap 6209. The needle hole or opening extends through needle hub 6222 and is designed to fit all needle profiles including micro needles, HTI, and the like.

Figure 62E:
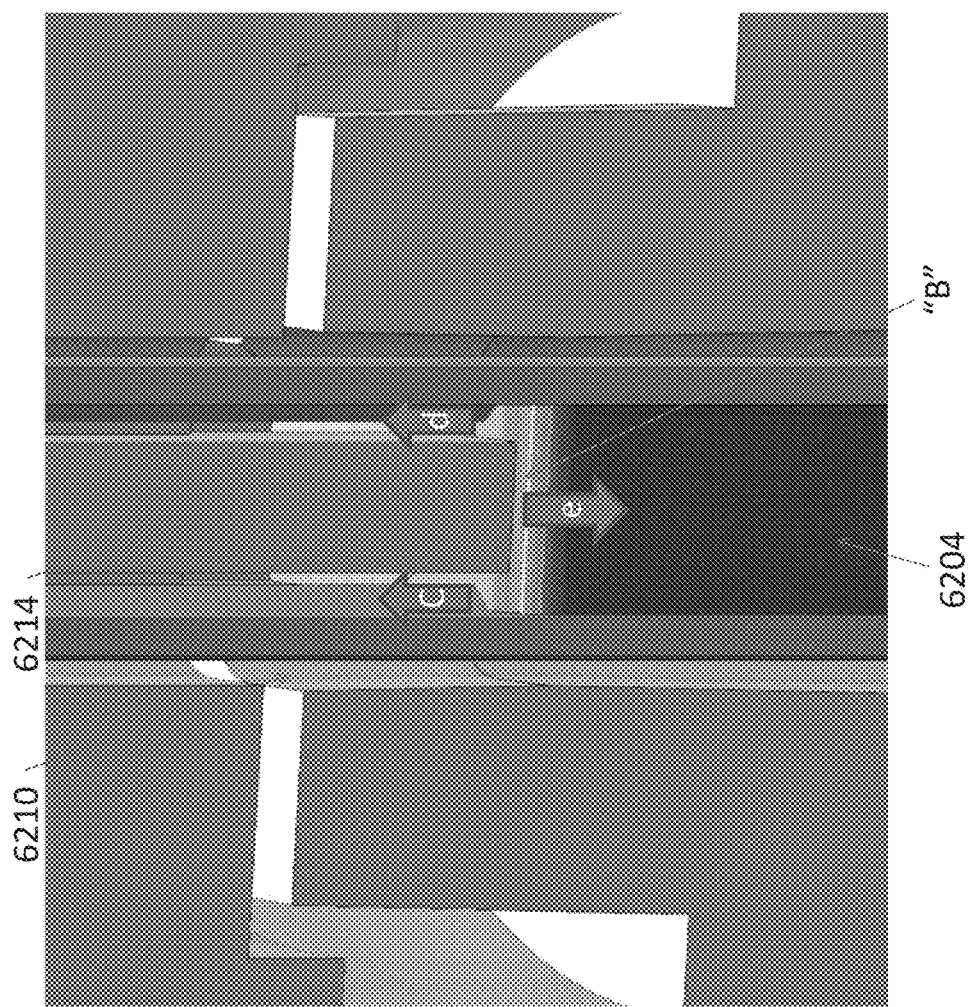
FIG. 62E is a detail of the interface illustrated in FIG. 62D according to an alternative embodiment of the present disclosure.

FIG. 62E is a detail of the interface illustrated in FIG. 62D according to an alternative embodiment of the present disclosure. FIG. 62E illustrates the interface at a point "B". A sensor clamp 6214 is located in an interior of needle 6210 to resist sensor pullups. Sensor clamp 6214 clamps down on sensor portion 6204. The needle does not touch sensor portion 6204. In various embodiments, after insertion into a patient's body, when the needle is pulled out of sensor base 6219, it pulls sensor portion 6204 upwards at areas indicated by arrows "c" and "d". Sensor clamp 6214 holds sensor portion 6204 down at an area indicated by arrow "e". This puts the length of the sensor portion that is between upward pulling arrows "c" and "d" and downward pulling arrow "e" in tension. Because the sensor portion is in tension, the needle slips past sensor portion 6204, allowing sensor portion 6204 to stay in place as the needle retracts. Without clamp 6214, sensor portion 6204 would be carried along with the needle when the needle is retracted, pulling sensor portion 6204 out of the patient's body.

Figure 63:
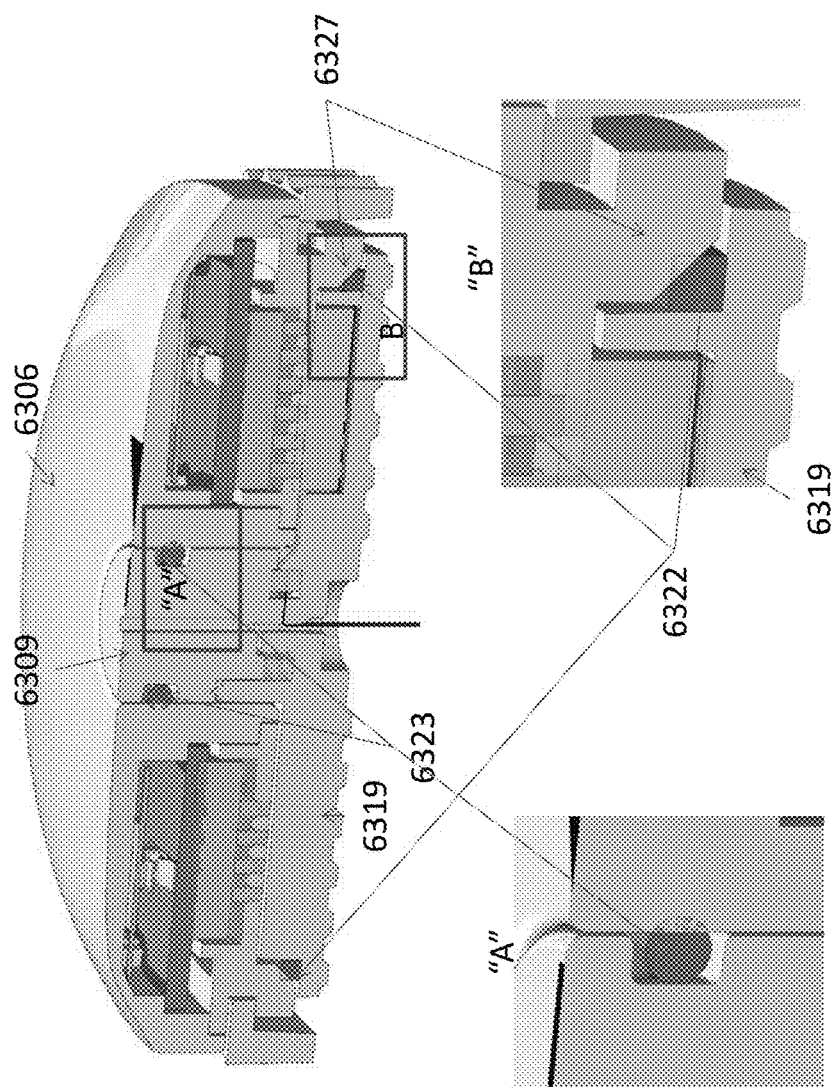
FIG. 63 is a perspective view of a sensor transmitter assembly with seals that improve water tightness according to an alternative embodiment of the present disclosure.

FIG. 63 illustrates a sensor transmitter assembly with seals that improve water tightness according to an alternative embodiment of the present disclosure. A cap 6309 of a sensor assembly has at least one cavity formed at each lateral side as further illustrated in detail "A". A radial seal 6323 is placed in a respective cavity formed on the cap. In various embodiments, radial seals 6323 have a round shape, but any appropriate shape can be used. In various embodiments, a side portion of sensor base 6319 further includes at least one cutout for example in an "L" shape or at substantially a 90 degree angle, or at any other appropriate shape or angle adapted to receive a portion 6327 of a transmitter assembly 6306. A crush seal 6322 is placed in a respective cutout formed at a connection between portion 6327 of transmitter assembly 6306 and sensor base 6319 as further illustrated in detail "B". In one or more embodiments, crush seals 6322 are held in place with friction. In various embodiments, crush seals 6322 have a square cross section to prevent any rolling or other type of movement. In this way, potential leak paths are sealed by radial seals 6323 and by crush seals 6322. As such, water (or other liquid or fluid) tightness of the sensor transmitter assembly is ensured.

Figure 64:
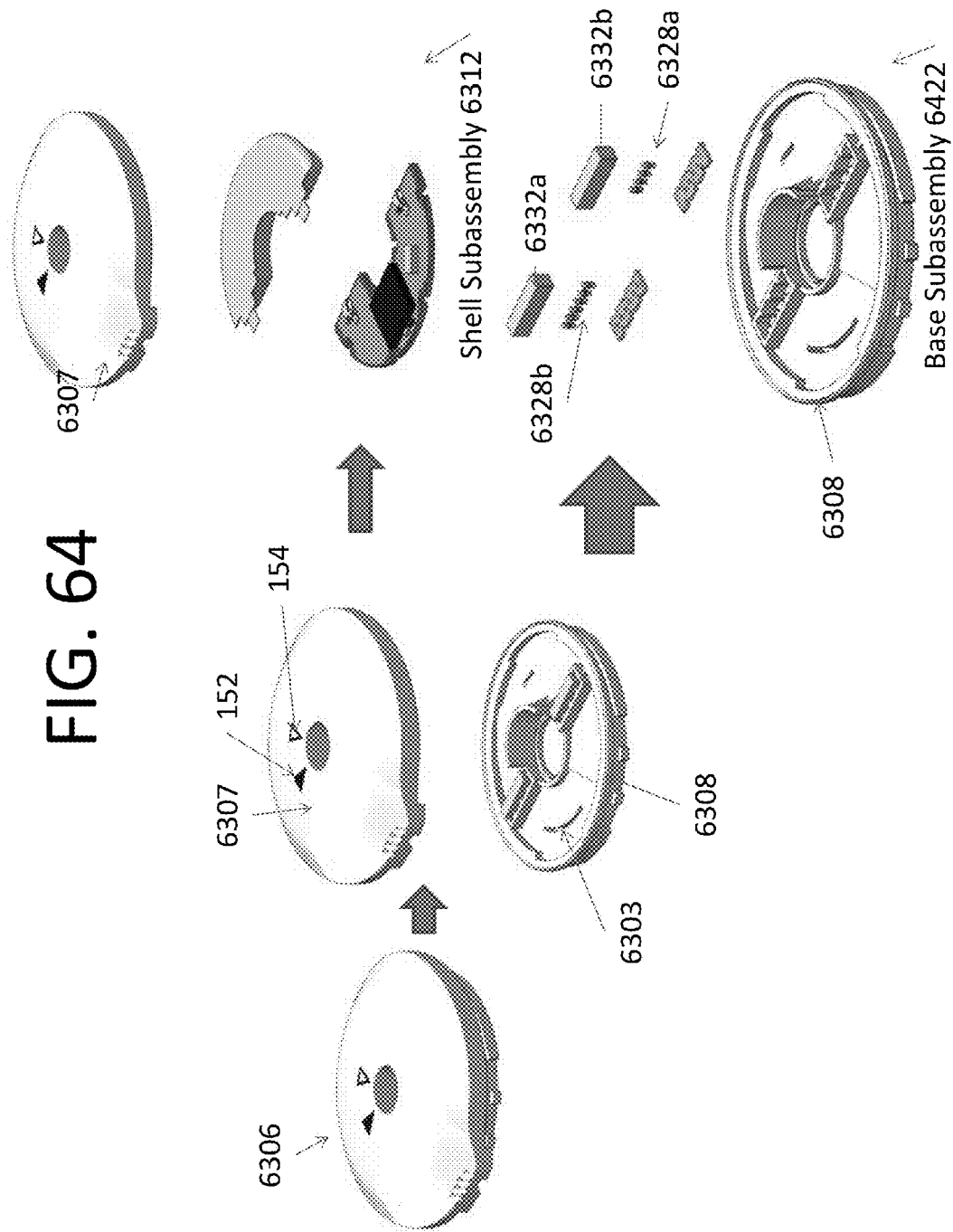
FIG. 64 is an exploded view of a transmitter assembly according to an alternative embodiment of the present disclosure.

Referring to FIG. 64, an exploded view of a transmitter assembly is illustrated according to an alternative embodiment of the present disclosure.

A transmitter assembly 6306 includes without limitation a transmitter shell 6307 adapted to be positioned, attached or otherwise connected with a transmitter cap 6308. Transmitter shell 6307 includes a top surface including markings or indicators 152 and 154 as described above according to one or more embodiments. Transmitter cap 6308 includes at least one interface, e.g., a rail 6303 adapted to engage with at least one corresponding interface, e.g., a slot of a second assembly such as a sensor assembly as described above according to one or more embodiments. Transmitter shell 6307 includes a shell subassembly 6312 including a custom portion that houses, for example, a custom battery and a substrate portion on which a PCB board having various electronic components is disposed as will be described in more detail below. Transmitter cap 6308 includes a cap subassembly 6422 having openings or cavities that are adapted to respectively accommodate various components including, e.g., substrates, contacts 6328a (e.g., 4 contacts) and 6328b (e.g., 6 contacts), and elastomeric connectors 6332a and 6332b.

Referring to FIG. 65A a perspective bottom view of a transmitter shell subassembly is illustrated according to an alternative embodiment of the present disclosure. A transmitter shell subassembly 6412 includes, without limitation, components including a custom battery 6414, for example a custom D-shaped battery (e.g., 36 mAh) adjoining a PCB base 6418 on which various components are disposed. In various embodiments, PCB base 6418 is disposed on a portion, for example approximately one half portion, of shell subassembly 6412 and custom battery 6414 is disposed on another portion, for example approximately the other half portion, of the subassembly. In various embodiments, connection points 6427 provide connection points for PCB base 6418. For example, connection points 6427 include materials such as plastic that can be heated and melted to connect the PCB base. In this embodiment, six connection points 6427 are illustrated, however, it should be noted that any number of connection points 6427 can be used as appropriate. Advantageously, the components e.g., battery 6414 and PCB base 6418 are compressed, are held together by friction, or otherwise fit together such that no solder or other connections are necessary for the subassembly. In this way, the arrangement minimizes dead volume and reduces the height of the subassembly.

FIG. 65B illustrates a perspective top view of the transmitter shell subassembly 6412. In one or more embodiments, custom battery 6414 is custom made to fit together with PCB 6418. It should be noted that in various embodiments the subassembly fits various components as necessary, which are designed in various shapes or sizes to fit in the subassembly. For example, in alternative embodiments, there are one or more custom batteries (e.g., 1, 2, etc.) that are of particular shapes to fit together with a PCB of a particular shape and occupy less than half or more than half (e.g., one quarter, three quarters, etc.) of the subassembly. In various embodiments, custom battery 6414 can be of any appropriate chemistry, for example, a Lithium battery. Also, in various embodiments, options for connecting the custom battery to the transmitter shell include various techniques such as using double sided tape, adhesive, etc. to keep them in place or from shifting around.

Referring to FIG. 66A, a partial plane view of a transmitter assembly layout is illustrated according to an embodiment of the present disclosure. As described above according to one or more embodiments, a shell subassembly of a transmitter assembly 6606 includes a PCB 6618 disposed on a portion, for example, substantially one half portion, and a custom battery 6614 disposed on another portion, for example, substantially the other remaining half portion of the shell subassembly of transmitter assembly 6606.

FIG. 66B illustrates another partial plane view of a transmitter assembly according to an embodiment of the present disclosure. Elastomeric connectors 6632a and 6632b are connected to a PCB 6618. In this embodiment, elastomeric connector 6632a is adapted to accommodate four contacts 6628a and elastomeric connector 6632b is adapted to accommodate six contacts 6628b. It should be noted that in various embodiments the elastomeric connectors are adapted to accommodate different numbers of contacts as necessary for particular applications.

FIG. 66C is a perspective partial view of a transmitter assembly layout illustrating details of external contacts to a PCB according to another embodiment of the present disclosure. As described above according to an embodiment, transmitter assembly 6606 includes a PCB 6618 disposed on substantially one half portion and a custom battery 6614 disposed on substantially the other half portion of transmitter assembly 6606. As illustrated in FIG. 66D, detail "A", a first side, e.g., a top side, of an elastomeric connector 6632 attaches to or otherwise connects with a PCB contact pad 6635. External contacts 6628 are disposed on or are otherwise connected to another side of elastomeric connector 6632, which includes conductive material.

Figure 67:
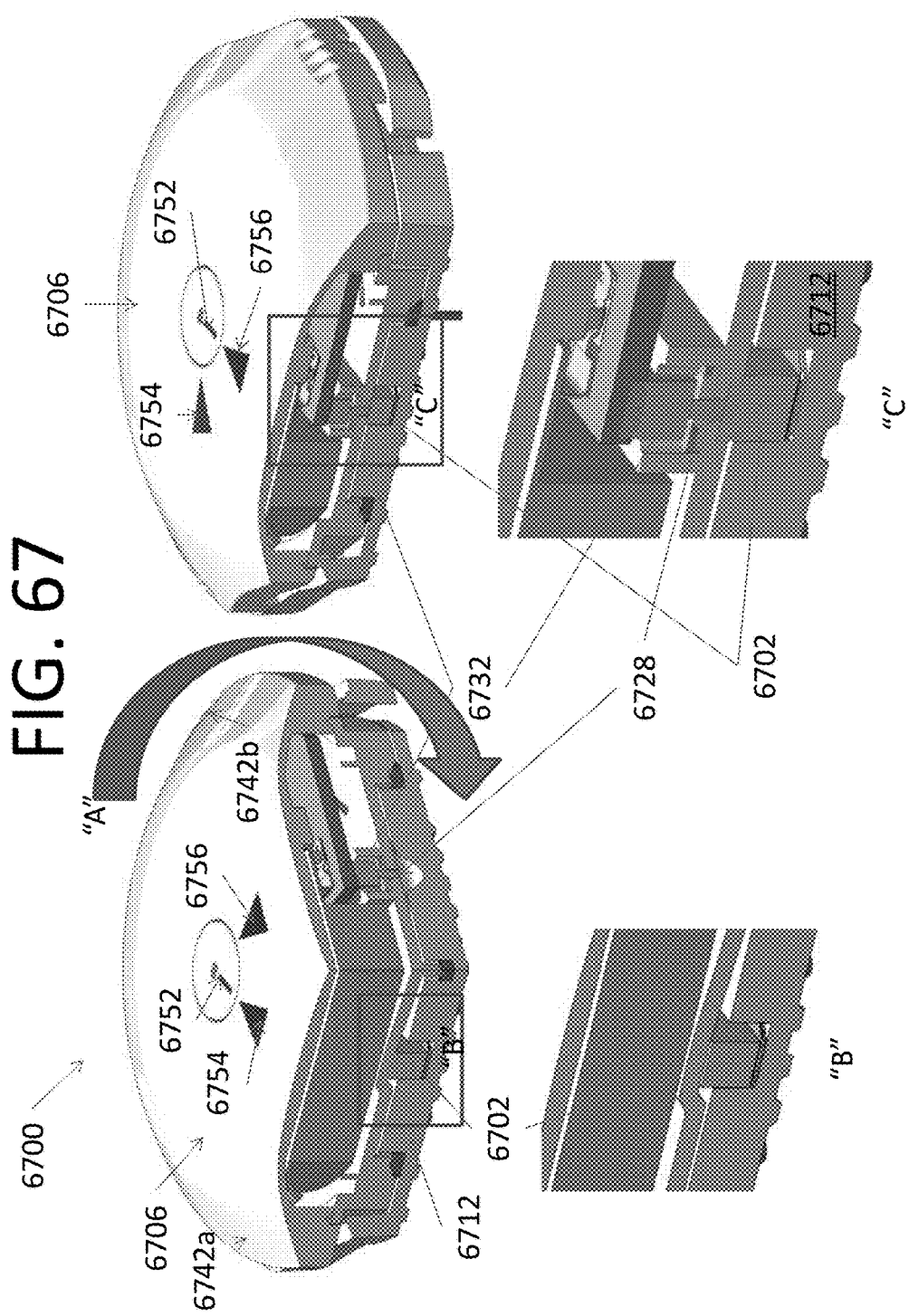
FIG. 67 illustrates side perspective views for electrically connecting a sensor assembly to a transmitter assembly according to an alternative embodiment of the present disclosure.

FIG. 67 illustrates perspective side views for electrically connecting a sensor assembly to a transmitter assembly according to an alternative embodiment.

A sensor transmitter assembly 6700 includes a transmitter assembly 6706 placed on a top surface of a sensor assembly 6712 by initially positioning, for example lowering down transmitter assembly 6706 into sensor assembly 6712. At this stage, an elastomeric connector 6732 and a contact 6728 of transmitter assembly 6706 are not aligned with an elastomeric connector 6702 of sensor assembly 6712 (see detail "B"). A twisting or rotation motion while squeezing on areas 6742a and 6742b, as indicated by arrow "A", is used to lock transmitter assembly 6706 and sensor assembly 6712. Indicators 6752, 6754 and 6756 indicate the locking position of sensor transmitter assembly 6700. For example, when indicator 6752 is aligned with indicator 6754, the sensor transmitter assembly is in an unlocked position, and when indicator 6752 is aligned with indicator 6756, the sensor transmitter assembly is in a locked position. As a result of the rotation motion, as illustrated in detail "C", elastomeric connector 6732 and contact 6728 of transmitter assembly 6706 line up with elastomeric connector 6702 of sensor assembly 6712, thus completing the connection.

Referring to FIG. 68, a partial top view of an electrical connection of a sensor assembly and at least one contact of a transmitter assembly is illustrated according to an alternative embodiment of the present disclosure. As described above according to one or more embodiments, a sensor assembly 6512 includes a sensor base having a cavity in which an elastomeric connector 6532 is disposed. When a transmitter assembly is connected to the sensor assembly, at least one contact of the transmitter assembly makes a connection with the elastomeric connector 6532. In this embodiment, six contacts 6528 of a transmitter assembly connect with elastomeric connector 6532. In some cases angular misalignment may occur between the contacts. In this embodiment, an angular misalignment of approximately 5° is shown between the contacts. Even though contacts 6528 do not line straight up, they still make electrical contact with elastomeric connector 6532. As such, in various embodiments, a tolerance of up to about 5° angular misalignment can occur without disrupting the connection between the contacts and the elastomeric connector and otherwise running into another area. Advantageously, the angular misalignment is within a margin of error such that even if the contacts are angularly misaligned, the design of the elastomeric connector ensures that an electrical connection is robust. If a transmitter assembly is mechanically connected to sensor assembly 6512, then an electrical connection is ensured.

Sensor Connections—Alternative Embodiments

Alternative Embodiment 1—Rigid Flex Connector

Referring to FIGS. 69A-69B, exploded views of a sensor module having a back to back sensor connection with a rigid flex connector are illustrated according to alternative embodiments of the present disclosure. FIG. 69A is an exploded top view of the sensor module having a back to back sensor connection with a rigid flex connector according to an alternative embodiment of the present disclosure, and FIG. 69B is an exploded bottom view of the sensor module of FIG. 69A according to an alternative embodiment of the present disclosure.

As illustrated in FIG. 69A and FIG. 69B, a sensor module 6901 includes a first sensor, e.g., an upper sensor 6940, a second sensor, e.g., a lower sensor 6944 and a flex circuit 6948. As illustrated in FIG. 69A, upper sensor 6940 includes a sensor head having at least one upper sensor contact pad 6935. In this embodiment, three upper sensor contact pads 6935 are illustrated. Also, three windows 6959 on the sensor head are illustrated. Upper sensor 6940 also includes at least one electrode 6938a (e.g., three electrodes 6938a as illustrated in FIG. 69A) on a leg 6936a extending from the upper sensor head. As illustrated in the exploded bottom view of FIG. 69B, lower sensor 6944 includes at least one lower sensor contact pad 6939. In this embodiment, three lower sensor contact pads 6939 are illustrated. Lower sensor 6944 also includes a leg 6936b having at least one electrode 6938b extending from the lower sensor head. It should be noted that upper sensor 6940 and lower sensor 6944 can have any number of contact pads in any appropriate placement, as well as windows and electrodes as appropriate for an application. Also, the upper and lower sensors may be alternatively positioned on a bottom or a top as part of the sensor module. Flex circuit 6948 will be described in more detail below for example with respect to the embodiment of FIGS. 71A-71B.

Figure 70A:
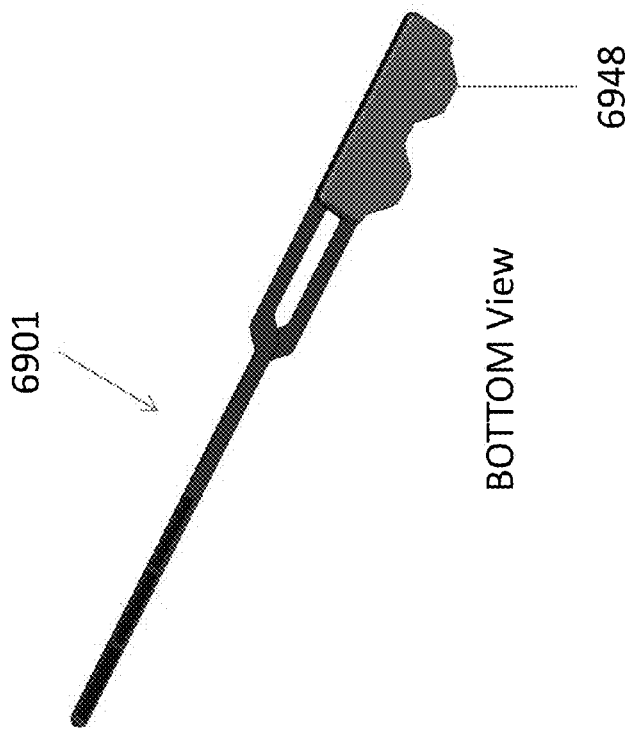
FIG. 70A is a perspective top view of a sensor module having a back to back sensor connection with a rigid flex connector according to an embodiment of the present disclosure.
Figure 70B:
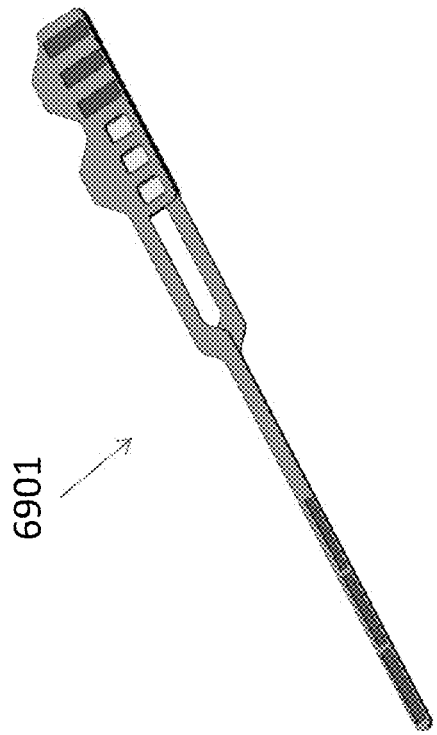
FIG. 70B is a perspective bottom view of the sensor module of FIG. 70A according to an embodiment of the present disclosure.

FIGS. 70A-70B illustrate perspective views of a sensor module having a back to back sensor connection with a rigid flex connector according to alternative embodiments of the present disclosure. FIG. 70A is a perspective top view of the sensor module having a back to back sensor connection with a rigid flex connector according to an alternative embodiment of the present disclosure. FIG. 70B is a perspective bottom view of the sensor module of FIG. 70A according to an alternative embodiment of the present disclosure.

Sensor module 6901 is formed by assembling a first sensor such as an upper sensor 6940 (illustrated in FIGS. 69A-69B) and a second sensor such as a lower sensor 6944 (illustrated in FIGS. 69A-69B) to a rigid flex circuit 6948. Assembly of the sensor module will be described in more detail below for example with respect to the embodiments of FIGS. 72A-72D.

Sensor module 6901 is assembled together before installation into a base, for example, a sensor base 6019 as illustrated in the embodiment of FIG. 60A. Advantageously, by assembling the sensor module before installation into a base, the sensor contact pads and sensor legs easily line up with each other, and it becomes possible to insert both sensor legs into the base at once, which is easier than inserting the sensor legs one at a time.

Figures 71A, 71B:
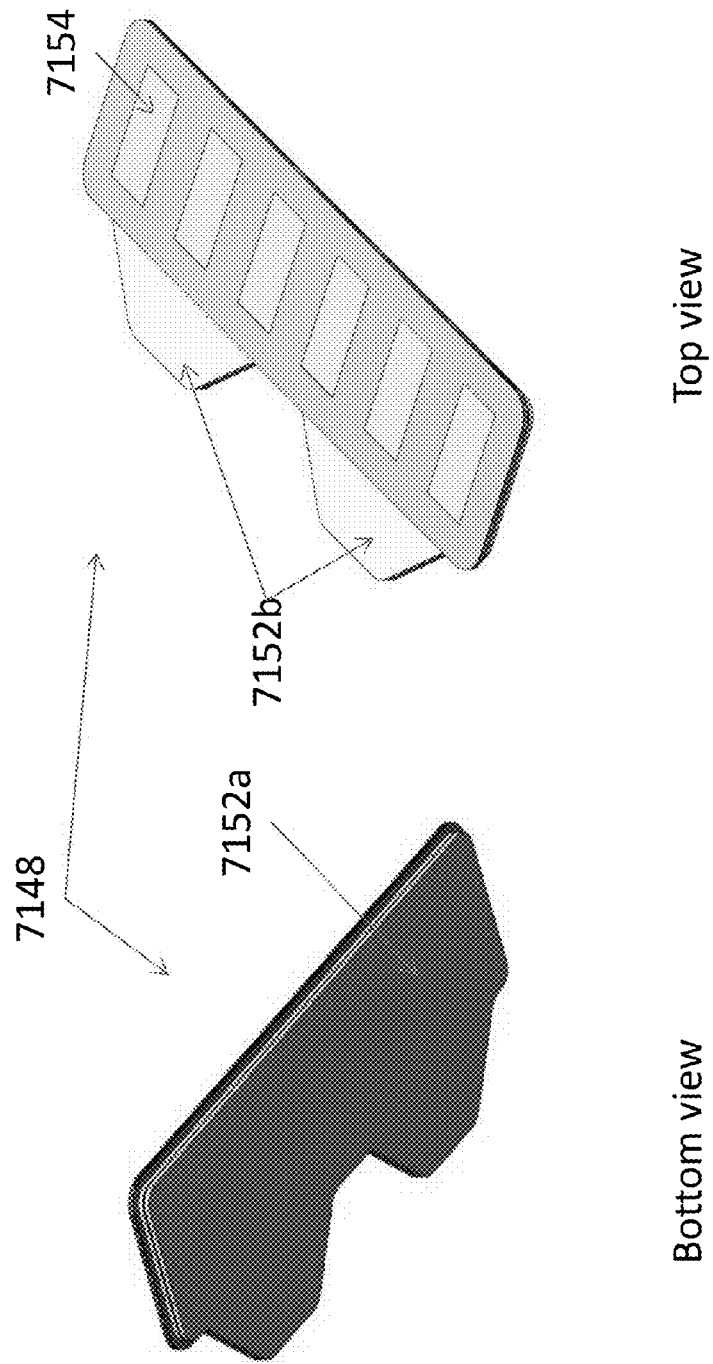
FIG. 71A is a perspective bottom view of a flex circuit according to an embodiment of the present disclosure.
FIG. 71B is a perspective top view of the flex circuit of FIG. 71A according to an embodiment of the present disclosure.

FIG. 71A is a perspective bottom view of a flex circuit according to an embodiment of the present disclosure. FIG. 71B is a perspective top view of the flex circuit of FIG. 71A according to an embodiment of the present disclosure.

A flex circuit 7148 includes at least one conducting pad on a first surface. In this embodiment, a top surface of flex circuit 7148 includes six conducting pads 7154 that are isolated from each other (illustrated in FIG. 71B). Conducting pads 7154 are adapted to conduct a signal from lower sensor contact pads to at least one elastomeric connector. A bottom surface 7152a and a top surface 7152b of flex circuit 7148 include fastening techniques such as double-sided adhesive on the top surface and the bottom surface respectively. Double-sided adhesive, for example, can bond the upper and lower sensors to the top side of the flex circuit, and the bottom side of the flex circuit to a base such as a sensor base. It should be noted that other types of fastening techniques such as solder, staples, etc. can be used to bond sensors to a first side of the flex circuit and bond a second side of the flex circuit to a base. Also, the flex circuit can be of any appropriate type, material or shape that fits into a base and accommodates appropriate sensors on a surface as needed for various applications. In various embodiments, the flex circuit construction includes a polyimide base layer, Copper conducting pads, and a polyimide cover layer, where the layers are bonded by appropriate bonding techniques such as with adhesive. In one or more embodiments, the flex circuit includes a single layer of conductor laminated to polyimide with circuitry or traces accessible from one side, and single-sided flex can be manufactured with or without coverlayers, which can act as a protective barrier or dielectric and are usually on a first or "top" side of the flex, depending on the intended application or requirement.

FIGS. 72A-72D illustrate an assembly process for a sensor module according to an embodiment of the present disclosure.

First, a lower sensor is assembled with a flex connector (also referred to as "flex circuit"). As illustrated in FIG. 72A, a lower sensor 7244 is positioned or rotated, for example as indicated by arrow "A" on a flex circuit 7248. Lower sensor contacts pads 7239 are positioned so that they are in contact with flex circuit contact pads 7254. Windows 7259 of lower sensor 7244 expose the flex connector contact pads 7254.

In FIG. 72B, tabs 7256 of lower sensor 7244 adhere or are otherwise fastened to flex circuit areas 7252, which include fastening techniques such as an adhesive. Notably, tabs 7256 are smaller than or fit within the surface area 7252 of the flex circuit having, for example, an adhesive. In this way, a portion of flex circuit areas 7252 having fastening techniques such as an adhesive are left exposed to allow bonding of an upper sensor.

Second, an upper sensor is assembled with the flex connector. As illustrated in FIG. 72C, an upper sensor 7240 is positioned or rotated, for example, as indicated by arrow "B" on the combination of a lower sensor 7244 and a flex connector as illustrated in the embodiment of FIG. 72B. Upper sensor 7240 includes tabs 7262 and at least one window 7269. These upper sensor tabs 7262 bond to a remaining portion of flex circuit areas 7252 having fastening techniques such as a double-sided adhesive (or other fastening techniques) on the flex connector. Windows 7269 of upper sensor 7240 align with windows 7259 of lower sensor 7244.

Figure 72D:
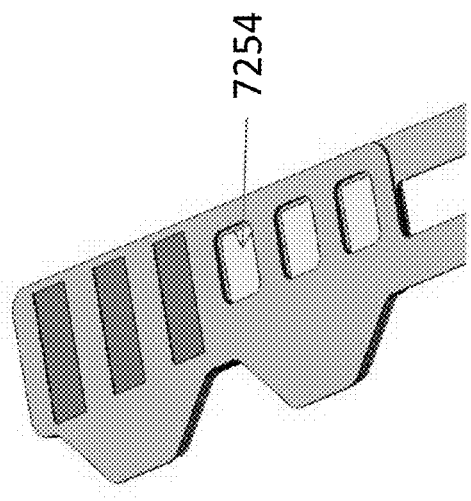
Figure 72C:
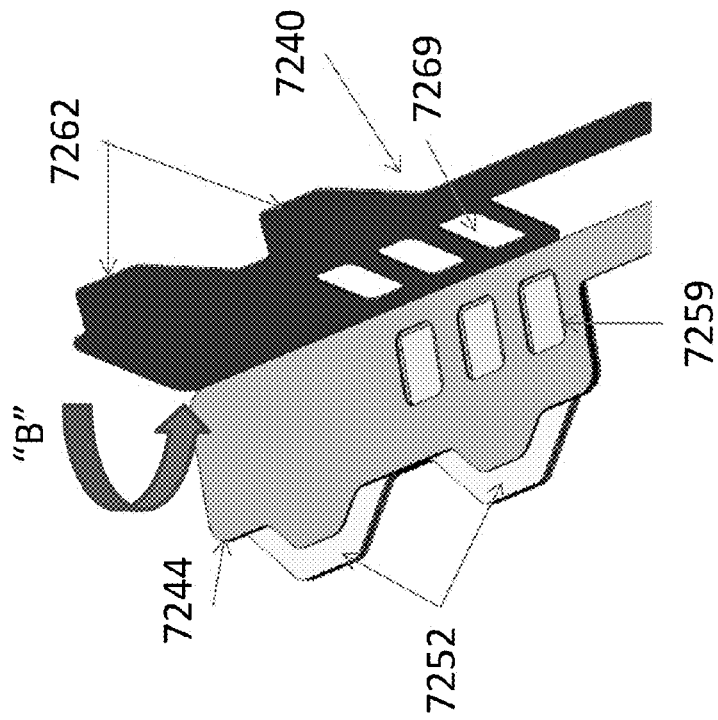

As illustrated in FIG. 72D, as a result of windows 7269 of upper sensor 7240 aligning with windows 7259 of lower sensor 7244, flex connector contact pads 7254 are left exposed.

Figure 73A:
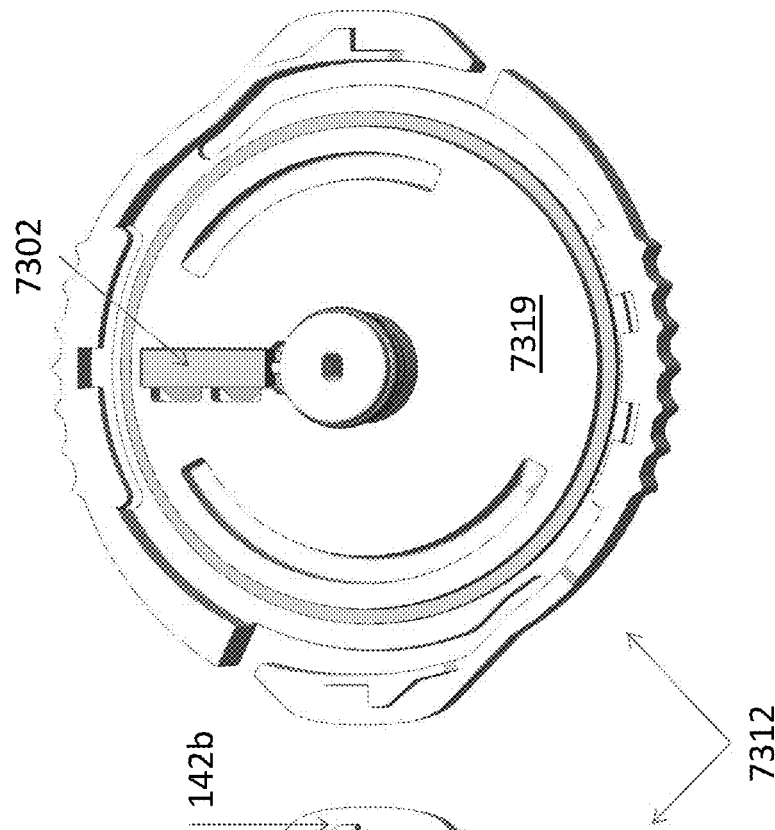
FIGS. 73A-73B illustrate a sensor module installed in a sensor subassembly according to an embodiment of the present disclosure.
Figure 73B:
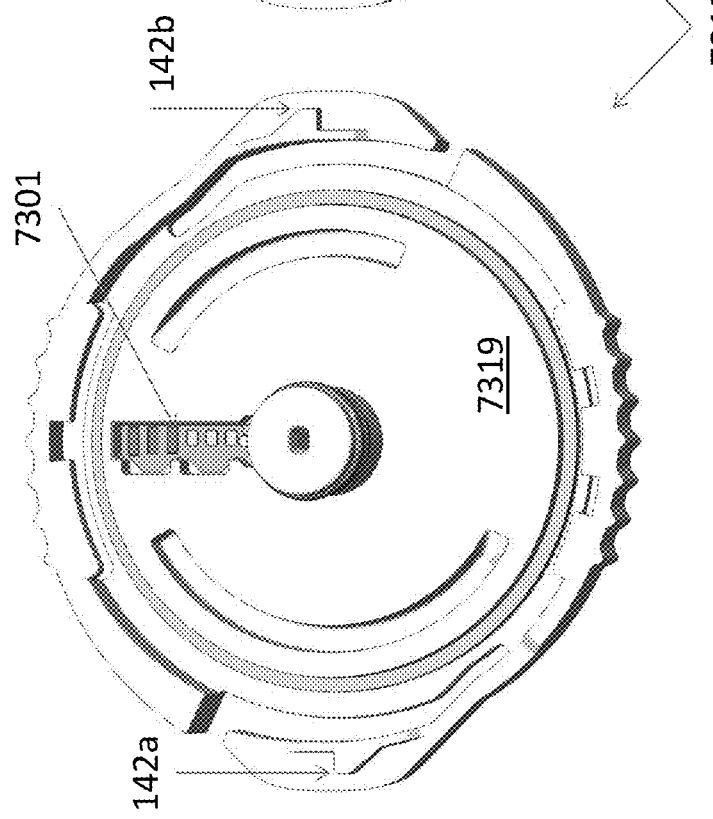

Referring now to FIGS. 73A-73B, a sensor module installed in a sensor subassembly is illustrated according to an alternative embodiment of the present disclosure.

In FIG. 73A, a sensor subassembly 7312 includes a sensor base 7319 having a recess or cavity in which a sensor module 7301 is installed. In various embodiments, sensor module 7301 has components as illustrated, for example, in the embodiments of FIGS. 69A-69B and 70A-70B. In FIG. 73B, a connector such as a z-axis elastomeric connector 7302 is installed on top of the sensor module.

As described above according to one or more embodiments, sensor base 7319 also includes at least one compression area or snap arm, for example, in this embodiment, two compression areas 142a and 142b or snap arms are located on either side of sensor base 7319. Also as described above, compression areas 142a and 142b or snap arms are designed to be self-locking. That is, if a user tries to disconnect a transmitter subassembly (not shown) from sensor subassembly 7312 just by rotating it and without manually squeezing compression areas 142a and 142b or snap arms inwards, then the rotation causes the compression areas 142a and 142b or snap arms to flex outwards and lock even harder against the transmitter subassembly. If the compression areas 142a and 142b or snap arms were not self-locking, then it would be possible to rotate the transmitter subassembly hard enough to unlock the compression areas 142a and 142b or snap arms, which would defeat a double fail-safe feature as described above, for example, with respect to the embodiments of FIGS. 56A and 56B.

Figure 74:
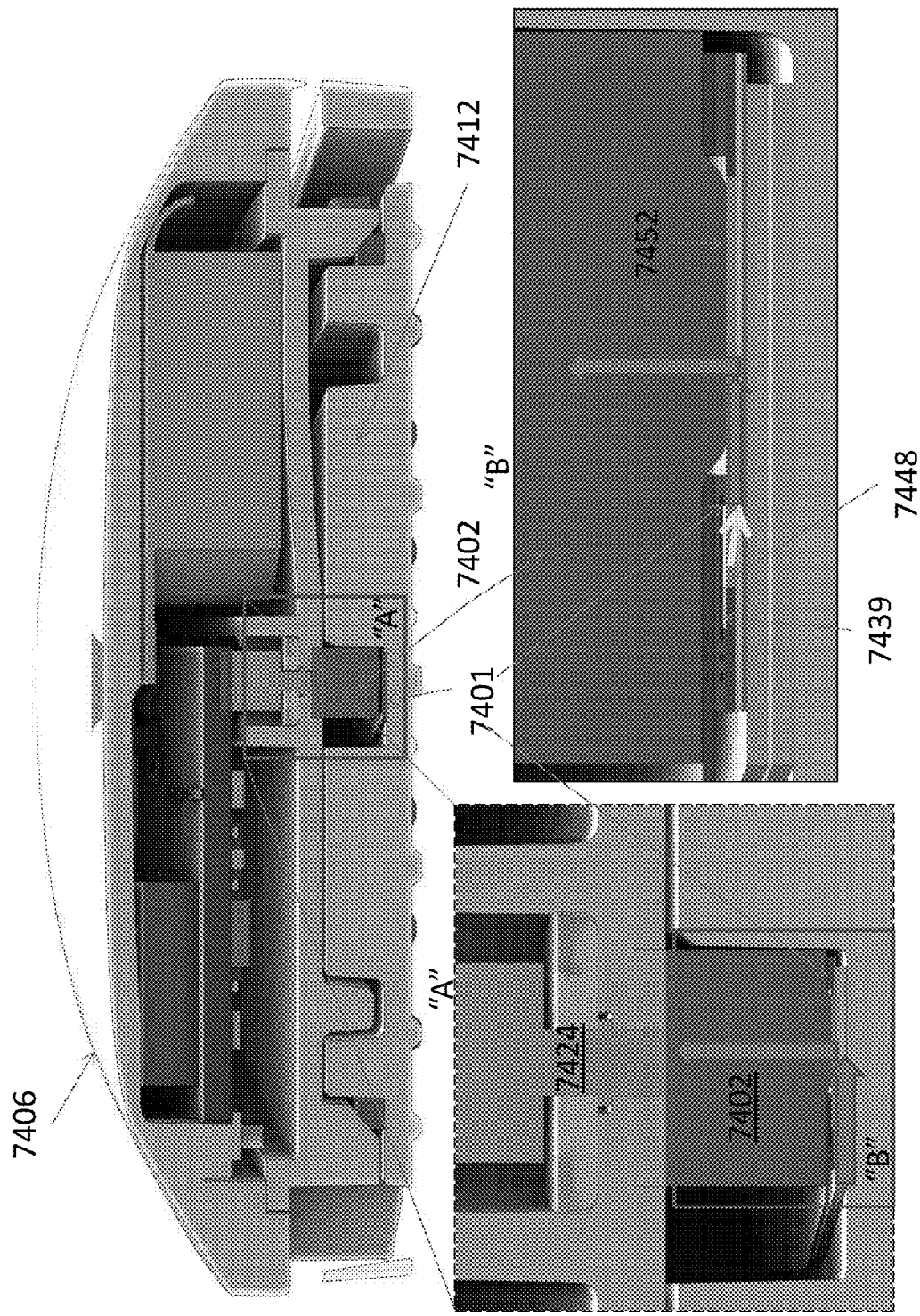
FIG. 74 illustrates a signal path to a transmitter from a lower sensor according to an embodiment of the present disclosure.

Referring now to FIG. 74, a signal path to a transmitter from a lower sensor is illustrated according to an embodiment of the present disclosure.

A transmitter assembly 7406 is connected to a sensor assembly 7412. As a result, at least a portion of a bottom surface of transmitter assembly 7406 compresses a connector, e.g., a z-axis elastomeric connector 7402 against a sensor module 7401.

As shown in details "A" and "B", elastomeric connector 7402 compresses lower sensor pads 7439 against flex circuit contact pads 7448. Elastomeric connector 7402 extrudes through windows 7452 in the sensor module 7401 and contacts the flex circuit contact pads. As a result, a signal path is created between the contact pads of the lower sensor of sensor module 7401 and transmitter contacts 7424.

Figure 75:
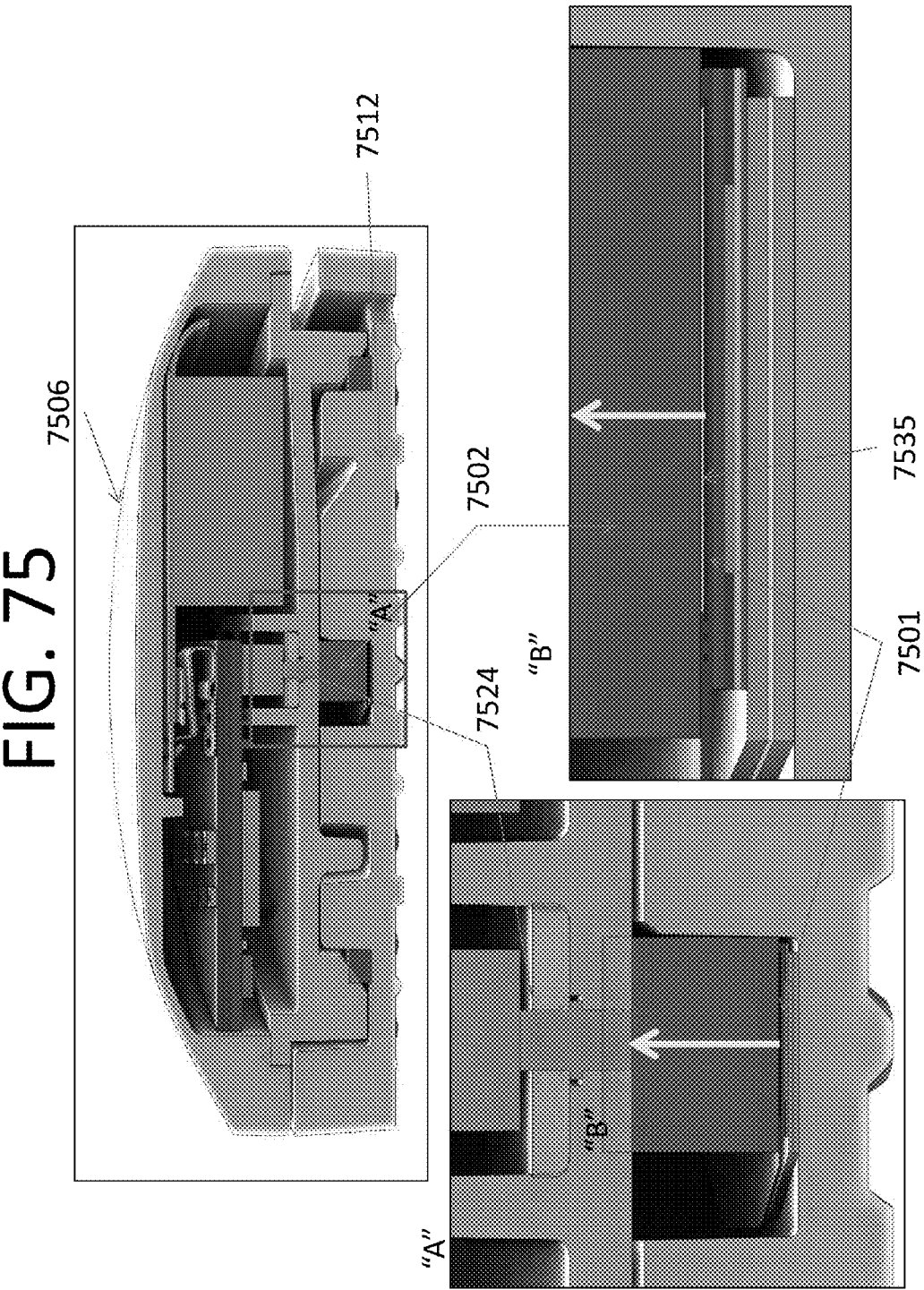
FIG. 75 illustrates a signal path to a transmitter from an upper sensor according to an embodiment of the present disclosure.

FIG. 75 illustrates a signal path to a transmitter from an upper sensor according to an embodiment of the present disclosure.

As a result of a transmitter assembly 7506 being connected to a sensor assembly 7512, a connector, e.g., a z-axis elastomeric connector 7502, is compressed against a sensor module 7501 as shown in details "A" and "B". A signal from an upper sensor contact pad 7535 travels directly through elastomeric connector 7502 to transmitter contacts 7524.

Alternative Embodiment 2—Flex Connector Integrated with Lower Sensor

Figure 76:
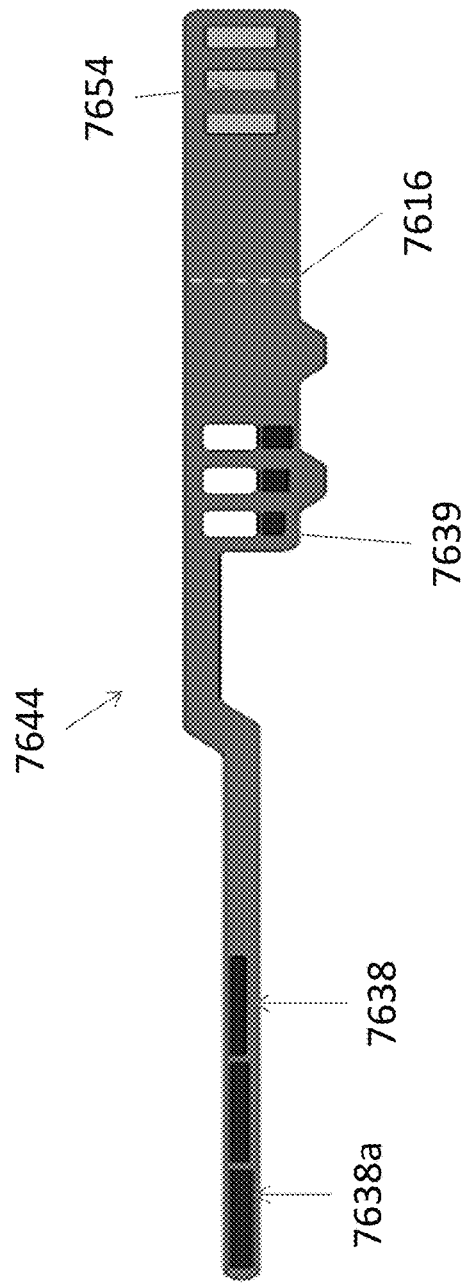
FIG. 76 illustrates a perspective view of a lower sensor with conducting pads and an integrated flex connector according to an embodiment of the present disclosure.

FIG. 76 illustrates a perspective view of a lower sensor with conducting pads and an integrated flex connector according to an embodiment of the present disclosure. A first sensor, e.g., a lower sensor 7644 is similar to lower sensor 6944 described above with respect to the embodiment of FIG. 69A-69B, except that conducting pads 7654 are integrated into a portion of an area such as on a side of lower sensor 6944 that extends from the lower sensor head. As such, lower sensor 7644 includes at least one lower sensor contact pad 7639. In this embodiment, three lower sensor contact pads 7639 are illustrated. Lower sensor 7644 also includes a leg 7638 extending from the lower sensor head. In one or more embodiments, at least one electrode 7638a, for example three electrodes 7638a as illustrated in this embodiment of FIG. 76, are placed on the extension or leg 7638. In various embodiments, lower sensor 7644 is foldable or otherwise flexible along a line 7616 that divides a head of the lower sensor into a portion or side where conducting pads 7654 are located. In various embodiments, line 7616 includes notches, perforations, or other techniques to facilitate folding or bending along line 7616. In various embodiments, perforations, notches, or the like can be made along line 7616 with laser techniques.

Figure 77B:
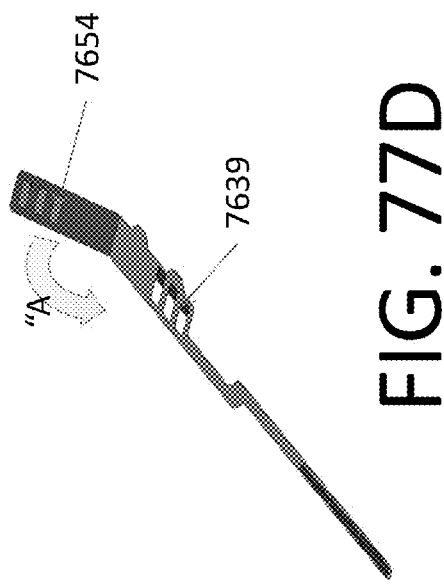
FIGS. 77A-77D illustrate perspective views for assembling the lower sensor of FIG. 76 according to an embodiment of the present disclosure.
Figure 77D:
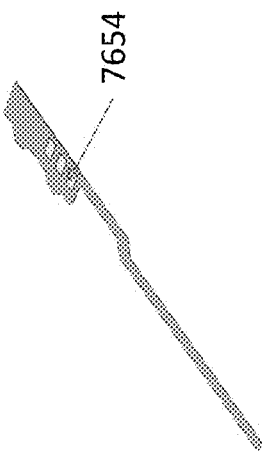
Figure 77A:
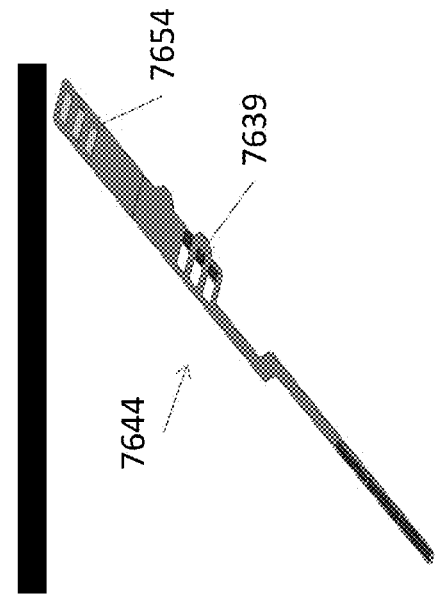
Figure 77C:
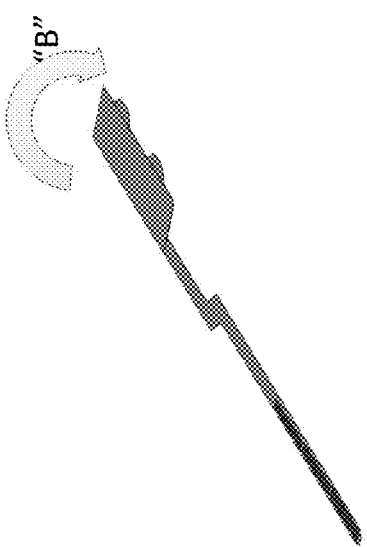

FIGS. 77A-77D illustrate perspective views for assembling the lower sensor of FIG. 76 according to an embodiment of the present disclosure. In the embodiment of FIG. 77A, lower sensor 7644 is illustrated having integrated conducting pads 7654 on a distal portion of a sensor head and contact pads 7639 on a proximate portion of the sensor head. As shown in FIG. 77B, lower sensor 7644 is assembled by first folding a portion of the sensor head as indicated by arrow "A". In that regard, the head of lower sensor 7644 is folded along an appropriate folding line such that conducting pads 7654 are placed in contact with lower sensor pads 7639. For example, lower sensor 7644 is folded at about a halfway point such that the conducting pads are placed in contact with the lower sensor contact pads. FIG. 77C illustrates a first surface after the lower sensor is folded. The first surface, for example, a bottom surface of the folded lower sensor can be flipped around as indicated by arrow "B". FIG. 77D illustrates a second surface of the folded lower sensor. The second surface, for example, a top surface of the folded lower sensor includes windows through which conducting pads 7654 are exposed.

Figure 78:
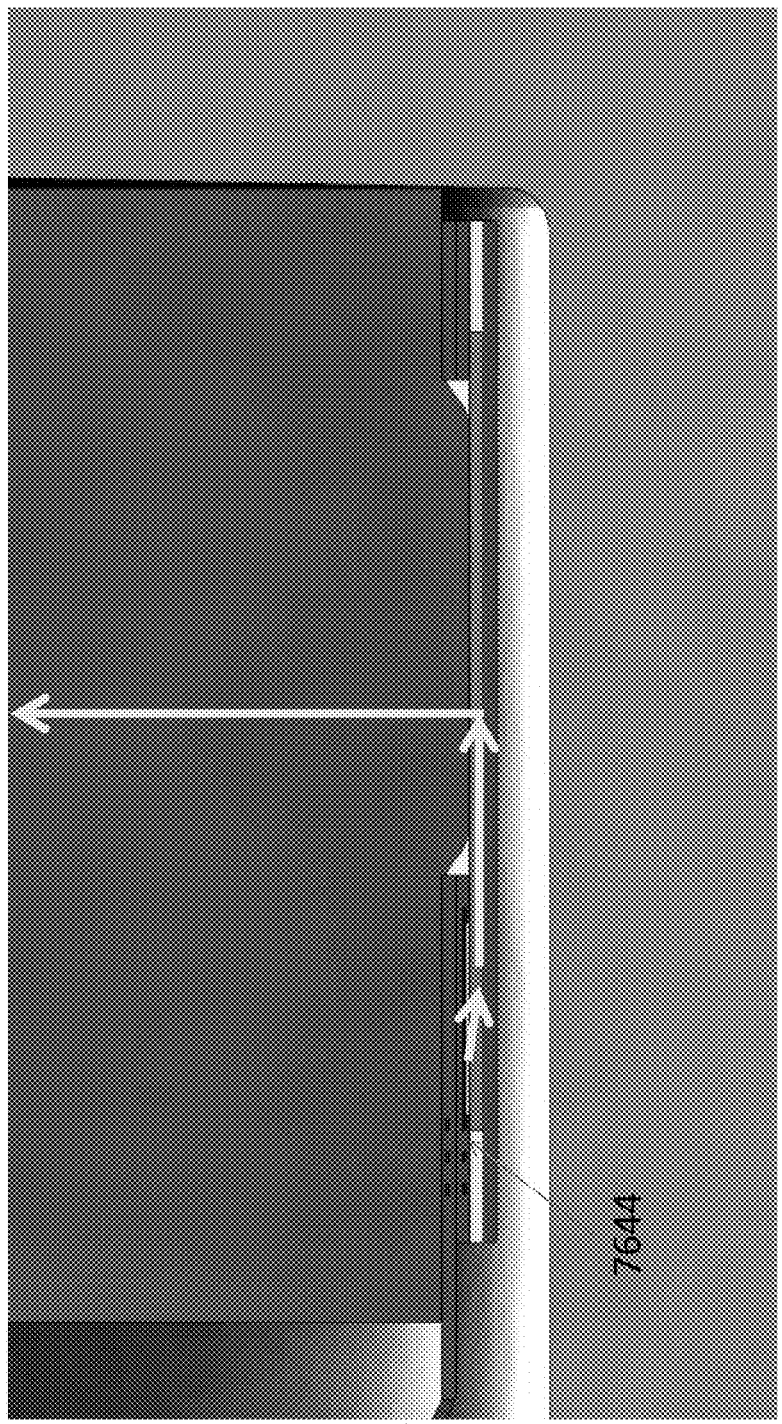
FIG. 78 illustrates a signal path to a transmitter from the lower sensor having an integrated flex connector illustrated in FIGS. 76 and 77A-D according to an embodiment of the present disclosure.
Figure 79:
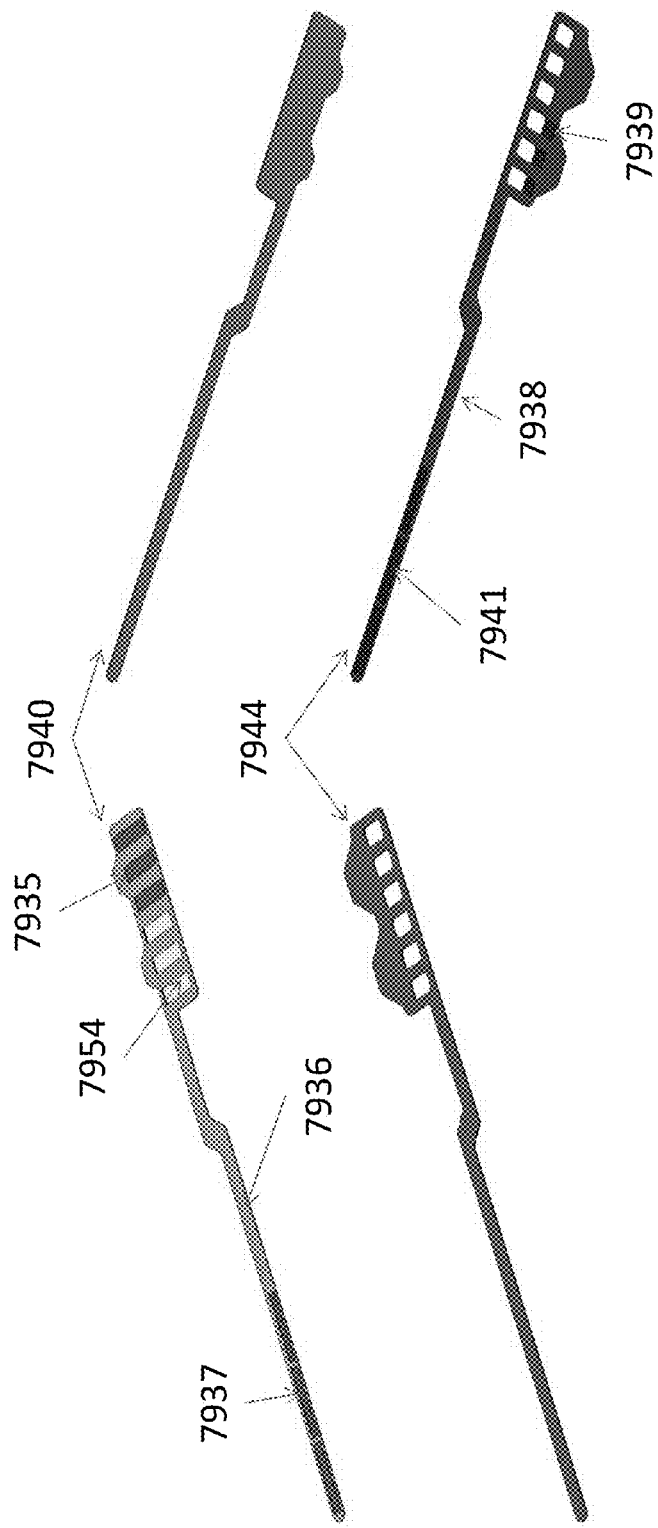
FIG. 79A is an exploded top view of a sensor module having conducting pads integrated into a sensor according to an alternative embodiment of the present disclosure.
FIG. 79B is an exploded bottom view of the sensor module of FIG. 79A according to an alternative embodiment of the present disclosure.
Figure 80:
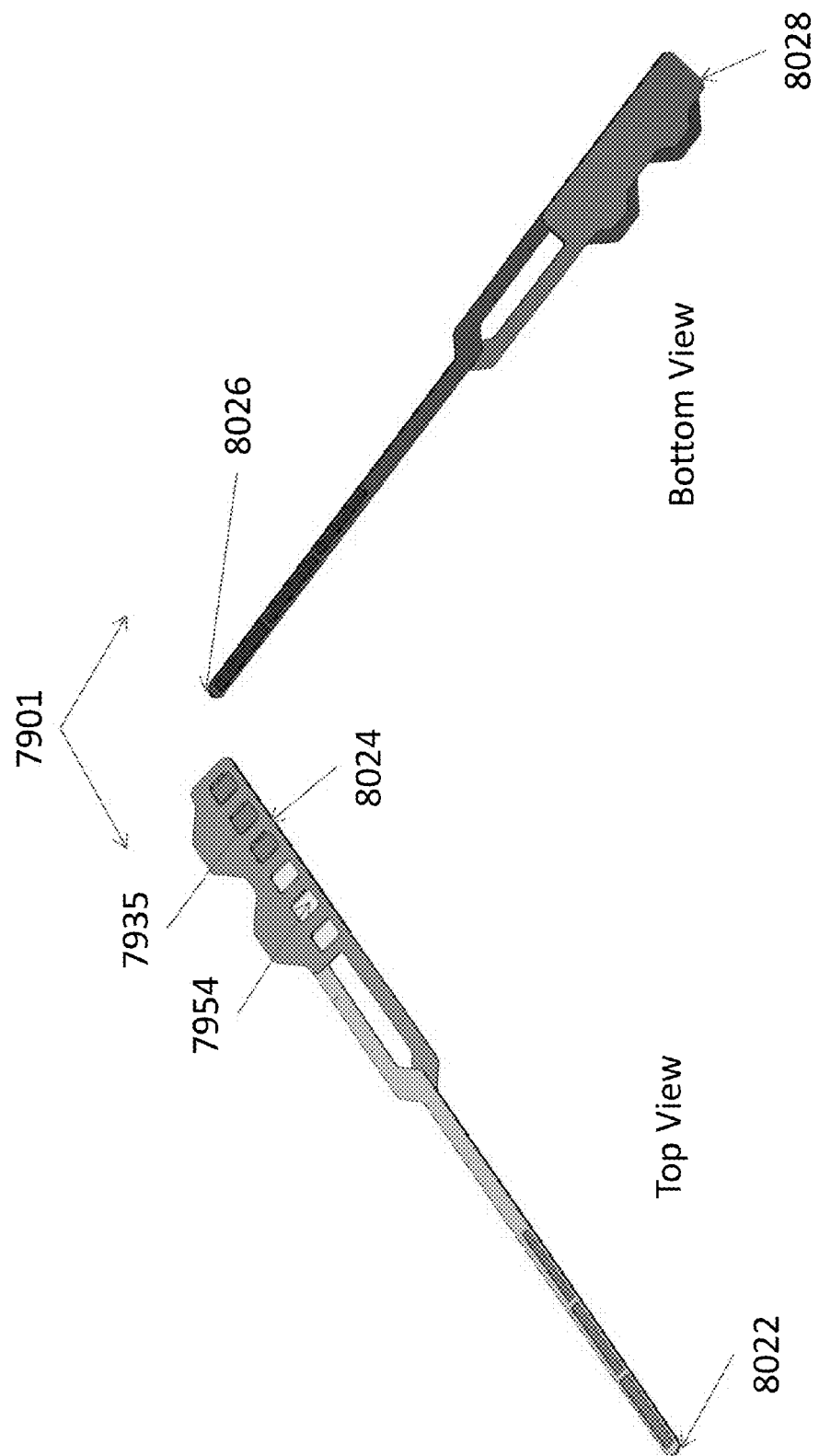
FIG. 80A is a perspective top view illustrating a sensor module with sensor interlacing of the first and second sensors according to an embodiment of the present disclosure.
FIG. 80B is a perspective bottom view of the sensor module of FIG. 80A according to an embodiment of the present disclosure.

FIG. 78 illustrates a signal path to a transmitter from the lower sensor having an integrated flex connector illustrated in FIGS. 76 and 77A-D according to an embodiment of the present disclosure.

A signal path for the lower sensor 7644 is similar to the signal path illustrated in the embodiment of FIG. 74, except that in this embodiment a conducting pad is part of the lower sensor 7644 itself instead of a separate flex connector. As a result of a transmitter assembly being connected to a sensor assembly, at least a portion of a bottom surface of the transmitter assembly compresses a connector, e.g., a z-axis elastomeric connector, against a sensor module. The elastomeric connector compresses the lower sensor contact pads and the conducting pads 7654 (see FIG. 77B-77D). The elastomeric connector extrudes through windows in the sensor module and contacts conducting pads 7654. As a result, a signal path is created between the conducting pads of the lower sensor and corresponding transmitter contacts.

Alternative Embodiment 3—Flex Connector Integrated with Sensor, Sensors Interlaced FIGS. 79A-79B illustrate exploded views of a sensor module having conducting pads integrated into a sensor according to an alternative embodiment of the present disclosure. FIG. 79A is a top exploded view of the sensor module having conducting pads integrated into a sensor according to an alternative embodiment of the present disclosure. FIG. 79B is a bottom exploded view of the sensor module of FIG. 79A according to an alternative embodiment of the present disclosure.

As illustrated in FIG. 79A and FIG. 79B, a sensor module includes a first sensor 7940 and a second sensor 7944. As illustrated in FIG. 79A, first sensor 7940 includes a sensor head having at least one sensor contact pad 7935 and at least one conducting pad 7954 integrated on the first sensor head itself, for example on a portion of the first sensor head such as a portion extending from the first sensor head. In this embodiment, three sensor contact pads 7935 and three conducting pads 7954 are illustrated. First sensor 7940 also includes a leg 7936 extending from the first sensor head having at least one first sensor electrode 7937. In this embodiment three first sensor electrodes 7937 are illustrated. As shown in FIG. 79B, a second sensor 7944 includes at least one second sensor contact pad 7939. In this embodiment, three second sensor contact pads 7939 are illustrated. Second sensor 7944 also includes a leg 7938 extending from the second sensor head having at least one second sensor electrode 7941. In this embodiment, three second sensor electrodes 7941 are illustrated.

FIGS. 80A-80B are perspective views illustrating sensor interlacing of the first and second sensors illustrated in FIGS. 79A-B according to an alternative embodiment of the present disclosure. FIG. 80A is a top perspective view illustrating a sensor module with sensor interlacing of the first and second sensors according to an embodiment of the present disclosure. FIG. 80B is a bottom perspective view of the sensor module of FIG. 80A according to an embodiment of the present disclosure.

Sensor module 7901 is formed by interlacing a first sensor 7940 and a second sensor 7944 (illustrated in FIGS. 79A-B). As illustrated in FIGS. 80A-80B, the first sensor and the second sensor are interlaced such that a distal end 8022 of first sensor 7940 is placed on top of a distal end 8026 of second sensor 7944, but a head 8028 of first sensor 7940 is placed on the bottom or underneath head 8024 of second sensor 7944. Such interlacing of the first and second sensors places the second sensor's contact pads 7939 (shown in FIG. 79B) against the first sensor's conducting pads 7954. Windows on the second sensor head 8024 expose contact pads 7935 and conducting pads 7954 of first sensor 7940.

Figure 81:
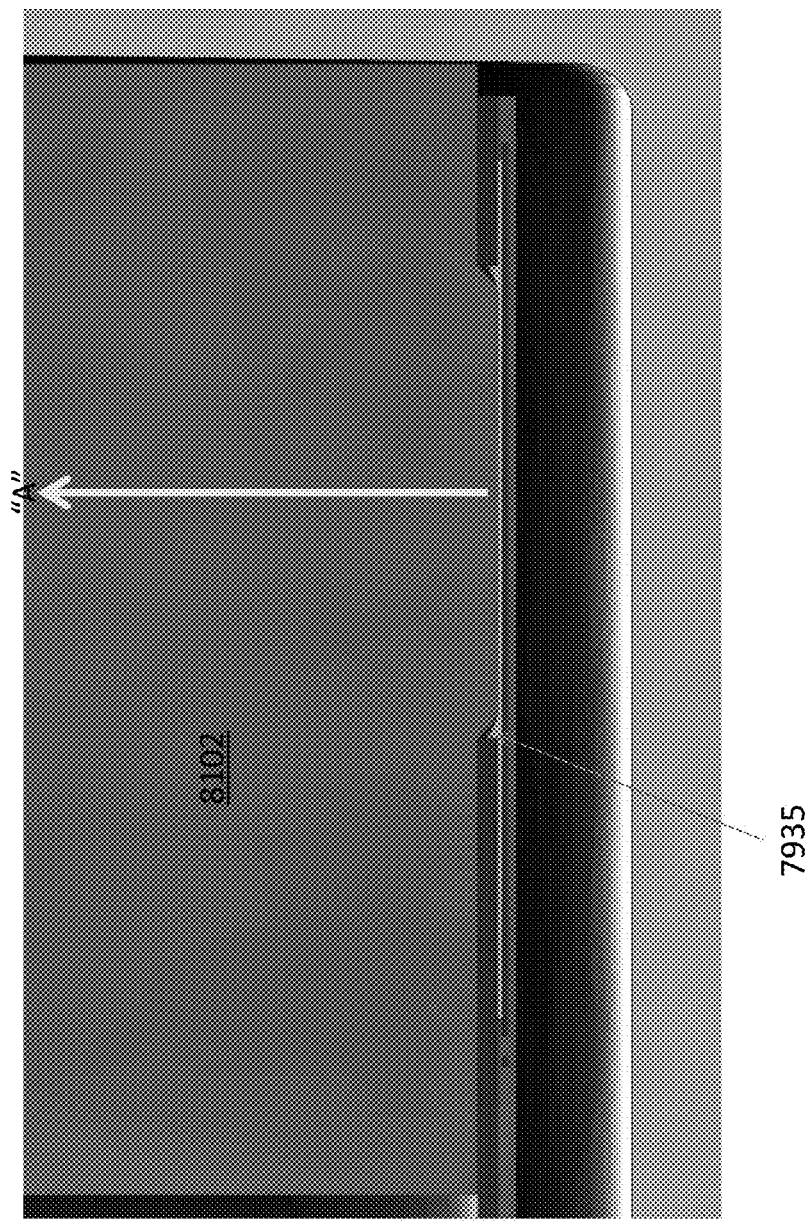
FIG. 81 illustrates a signal path to a transmitter from a first sensor having an integrated flex connector that is interlaced with a second sensor as illustrated in FIGS. 80A-80B according to an embodiment of the present disclosure.

FIG. 81 illustrates a signal path to a transmitter from a first sensor having an integrated flex connector that is interlaced with a second sensor as illustrated in FIGS. 80A-80B according to an embodiment of the present disclosure.

As a result of a transmitter assembly being connected to a sensor assembly, at least a portion of a bottom surface of the transmitter assembly compresses a connector, e.g., a z-axis elastomeric connector, against a sensor module. An elastomeric connector 8102 compresses the first sensor pads 7935. The elastomeric connector extrudes through at least one window in the sensor module and contacts first sensor pads 7935. As a result, a signal path is created from a contact pad 7935 of the first sensor directly through the elastomeric connector 8102 to the transmitter contacts (as indicated by arrow "A").

Figure 82:
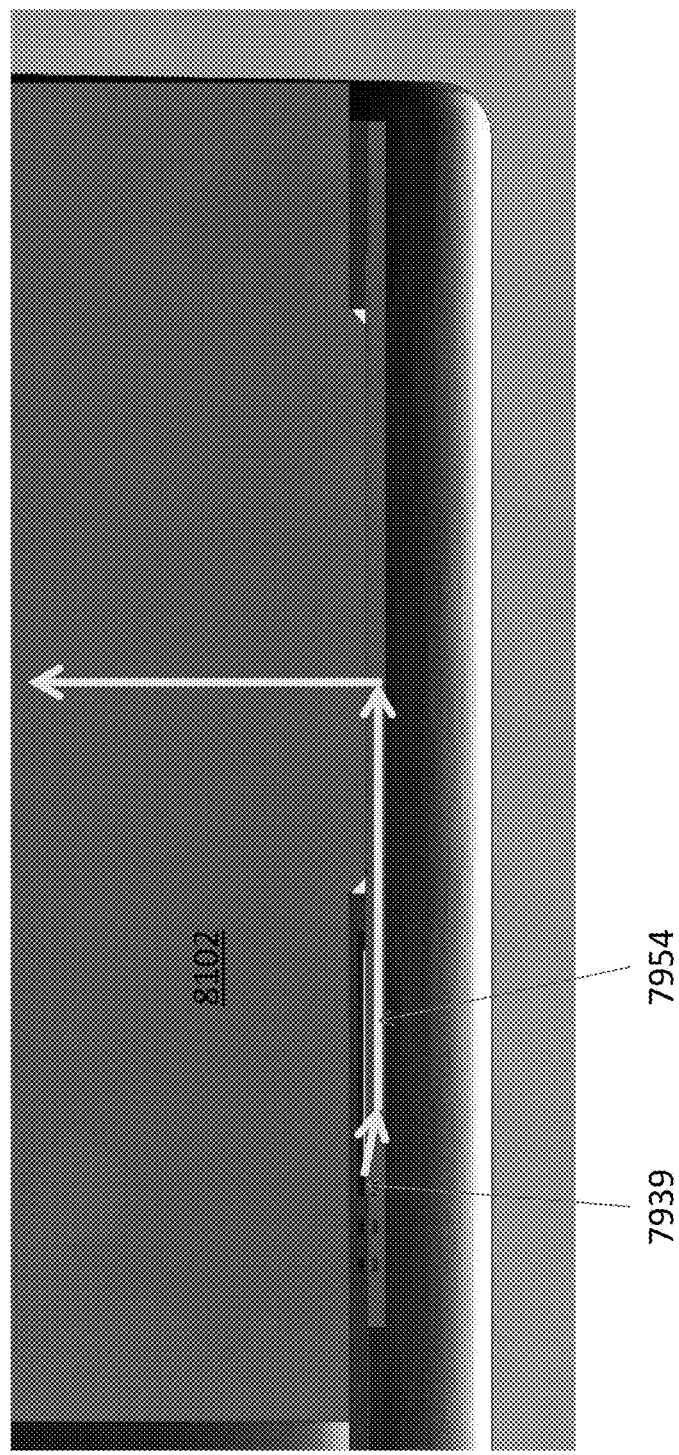
FIG. 82 illustrates a signal path to a transmitter from a second sensor that is interlaced with a first sensor as illustrated in FIGS. 80A-80B according to an embodiment of the present disclosure.

FIG. 82 illustrates a signal path to a transmitter from a second sensor that is interlaced with a first sensor as illustrated in FIGS. 80A-80B according to an embodiment of the present disclosure.

As a result of a transmitter assembly being connected to a sensor assembly, at least a portion of a bottom surface of the transmitter assembly compresses a connector, e.g., a z-axis elastomeric connector, against a sensor module. In this case, a signal from a lower sensor contact pad 7939 travels through a conducting pad 7954 of a first sensor and through an elastomeric connector 8102 to a corresponding transmitter contact.

Combined Sensor and Infusion Set

FIGS. 83A-83E are orthogonal views of a combined sensor and infusion set according to an embodiment of the present disclosure. FIG. 83A is a top orthogonal view, FIG. 83B is a front orthogonal view, FIG. 83C is a side orthogonal view, FIG. 83D is a back orthogonal view, and FIG. 83E is a bottom orthogonal view of a combined sensor and infusion set according to an embodiment of the present disclosure.

Figure 84A:
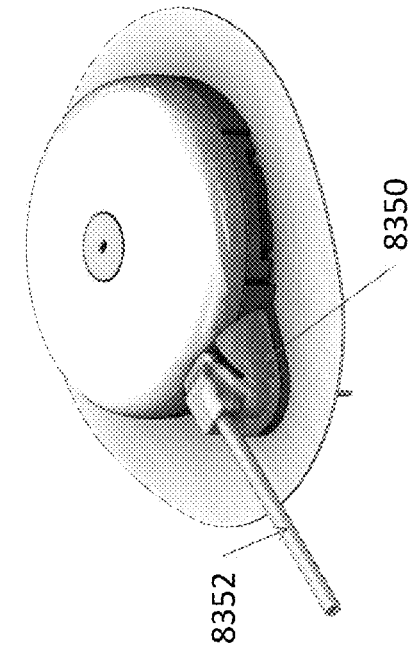
FIG. 84A is an isometric perspective front view of a combined sensor and infusion set according to an embodiment of the present disclosure.
Figure 84B:
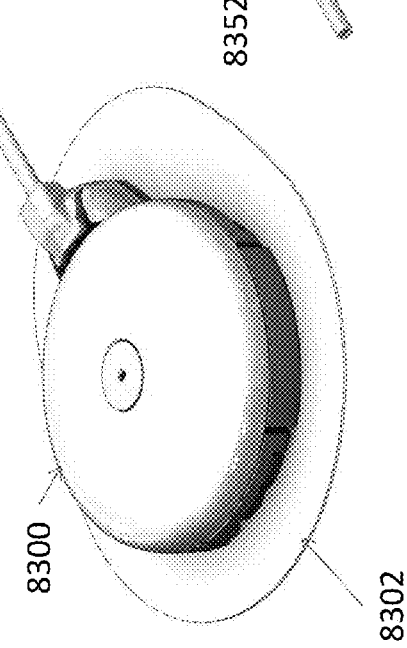
FIG. 84B is an isometric perspective back view of the combined sensor and infusion set of FIG. 84A according to an embodiment of the present disclosure.
Figure 84C:
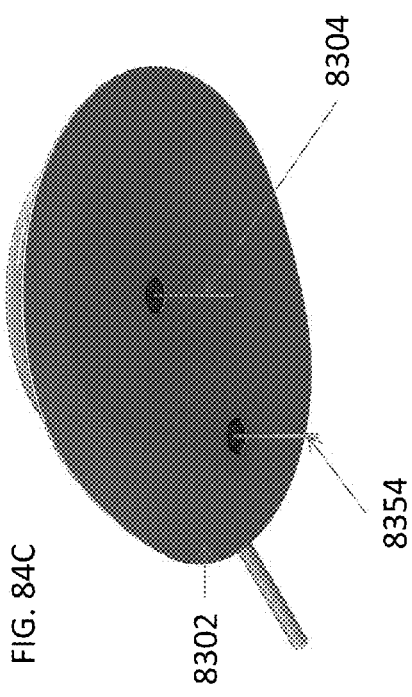
FIG. 84C is an isometric perspective bottom view of the combined sensor and infusion set of FIG. 84A according to an embodiment of the present disclosure.

FIGS. 84A-84C are isometric views of the combined sensor and infusion set of FIGS. 83A-83E according to an embodiment of the present disclosure. FIG. 84A is an isometric perspective front view, FIG. 84B is an isometric perspective back view and FIG. 84C is an isometric perspective bottom view of the combined sensor and infusion set according to an embodiment of the present disclosure.

A sensor transmitter assembly 8300, for example, as described above with respect to at least FIGS. 1A, 1B, 41A-41C and 56A-56B according to various embodiments, is combined with an infusion set 8350. Infusion set 8350 is coupled to an area or portion such as a side of sensor transmitter assembly 8300 as will be described in more detail below, for example, with respect to the embodiments of FIGS. 86A-86E.

As illustrated for example at least in FIGS. 83B, 84A and 84B, and as described above according to one or more embodiments, sensor transmitter assembly 8300 includes a transmitter assembly 8306 placed on top of a sensor assembly 8312. A sensor portion 8304 extends from sensor assembly 8312 from a substantially centered location. The sensor assembly 8312 provides structural support to sensor portion 8304 and facilitates entry of sensor portion 8304 into the body of a patient. As such, in various embodiments, sensor portion 8304 may be positioned subcutaneously/transcutaneously in direct contact with a patient's extracellular fluid. As illustrated for example in FIGS. 83C, 83D and 84C, a cannula 8354 extends from infusion set 8350. Cannula 8354 is also adapted to be introduced into the body of a patient for infusing fluids such as insulin or other medications to a patient. Infusion set 8350 includes an insertion conduit 8352 adapted to be connected to a reservoir or other supply device.

The combined sensor and infusion set can be fastened by a mounting base or patch 8302 that adheres to the patient's skin, as described above for example at least in connection with the embodiments of FIGS. 1A, 1B, 2A, 2B, 57A and 57B.

Referring to FIG. 85, section views of a combined sensor and infusion set are illustrated according to an embodiment of the present disclosure.

A sensor transmitter assembly 8500 is combined with an infusion set 8550. Sensor transmitter assembly 8500 includes components similar to embodiments described above, for example at least in connection with FIGS. 11A-11C, 66A-67.

As illustrated in detail "A", infusion set 8550 includes a housing 8562, a septum 8564, a funnel 8566 and a cannula 8568. Housing 8562 engages with a connection portion 8572 that extends from the sensor assembly as will be described in more detail below. In various embodiments, septum 8564 is compressed between funnel 8566 and the connection portion 8572. When housing 8562 is connected, septum 8564 forms a radial seal around a needle (not shown) contained in housing 8562, creating a sealed fluid path between tubing of housing 8562 and cannula 8568. Funnel 8566 compresses cannula 8568 against connection portion 8572. This mechanically retains cannula 8568 within connection portion 8572 and creates a fluid tight seal between funnel 8566, cannula 8568, and connection portion 8572.

Figure 86B:
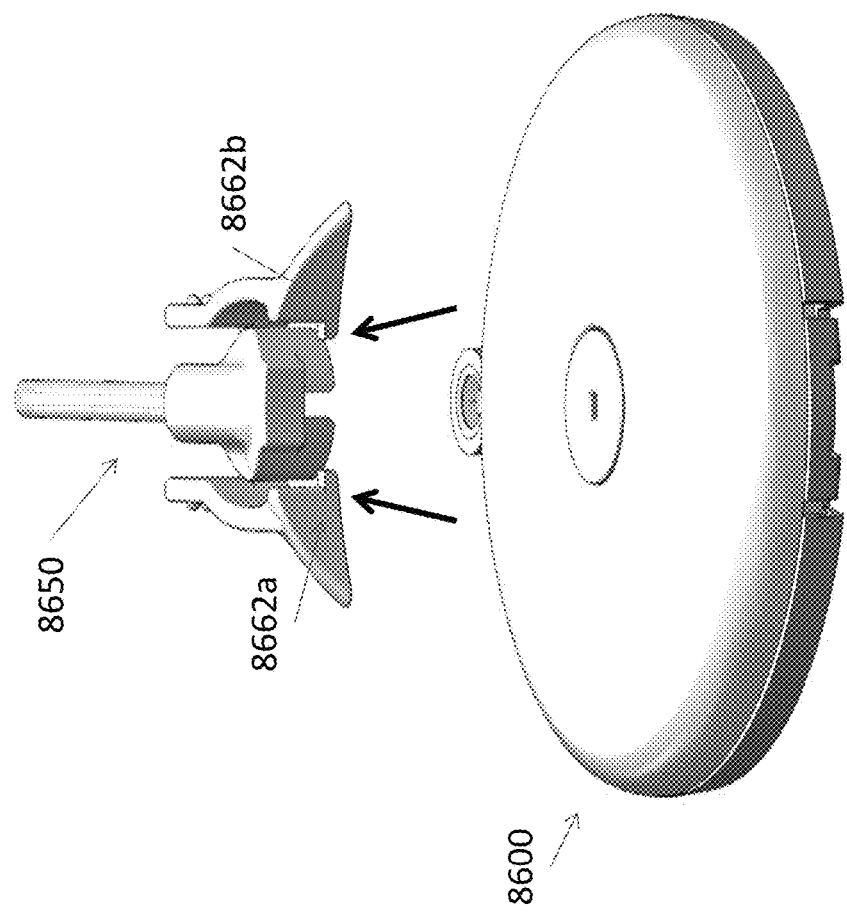
FIG. 86B illustrates a front view of a connection for a sensor and infusion set according to an embodiment of the present disclosure.

FIGS. 86A-86B illustrate a connection for a sensor and infusion set according to an embodiment of the present disclosure.

FIG. 86A illustrates a disconnected sensor and infusion set according to an embodiment. Sensor transmitter assembly 8600 includes a connector portion 8672 that extends from a portion, for example, a base of a sensor assembly 8612. Connection portion 8672 includes a connector cap 8674 adapted to fittingly receive an infusion set 8650. A top down connection is applied as indicated by arrow "A" to connect sensor transmitter assembly 8600 to infusion set 8650.

Figure 86C:
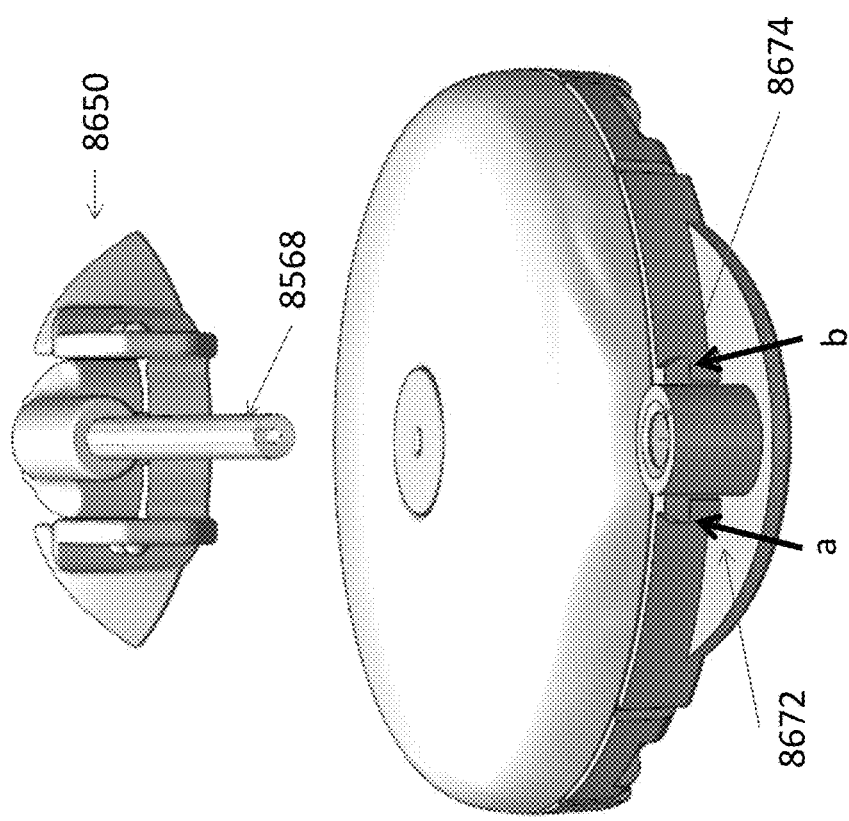
FIG. 86C illustrates a back view of a connection for a sensor and infusion set according to an embodiment of the present disclosure.
Figure 86D:
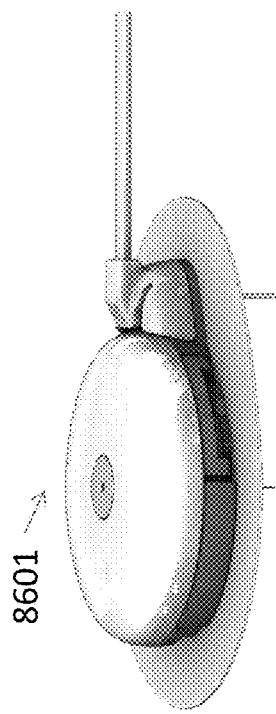
FIG. 86D illustrates a perspective view of a combined sensor infusion set as a result of a top down connection according to an embodiment of the present disclosure.
Figure 86E:
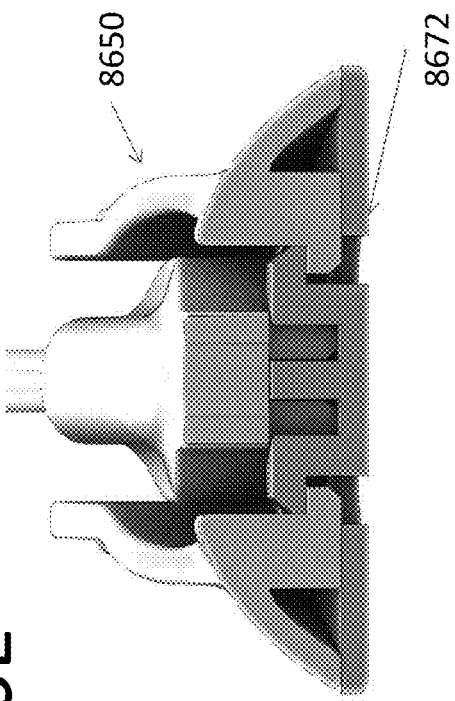
FIG. 86E illustrates a detail of a back surface view of a combined sensor infusion set according to an embodiment of the present disclosure.

FIG. 86B illustrates a perspective front view showing front surfaces 8662a and 8662b of infusion set 8650 that are adapted to fit on or against a surface of sensor transmitter assembly 8600. FIG. 86C illustrates a perspective back view showing a back surface of infusion set 8650. In an embodiment, infusion set 8650 engages, e.g., snaps mechanically with connection portion 8672. For example, infusion set 8650 engages at one or more interfaces such as notches or points "a" and "b" of connection portion 8672, and cannula 8568, which extends out, is adapted to fit and engage with a connector cap 8674 of connection portion 8672. FIG. 86D shows a combined sensor infusion set 8610 as a result of a top down connection, and FIG. 86E shows a detail of a back surface view of infusion set 8650 being connected to connection portion 8672.

Advantageously, the combined sensor infusion set for example as illustrated in FIG. 86D has a small footprint and is smaller in size than prior devices. A combined sensor infusion set according to one or more embodiments can have dimensions as follows: Height=0.32 inches; Width=1.16 inches; Length=1.41 inches; Footprint=1.14 square inches; and Volume=0.32 cubic inches. Table 3 below illustrates reduction in overall size of the combined sensor infusion set according to one or more embodiments of the present disclosure compared to a prior device.

TABLE 3

|  | Previous Device or Duo | New Duo or Device According to one or more Embodiments | % Reduction |
| --- | --- | --- | --- |
| Height (in) | 0.37 | 0.32 | 13.5% |
| Width (in) | 1.40 | 1.16 | 17.1% |
| Length (in) | 2.11 | 1.41 | 33.2% |

TABLE 3-continued

|  | Previous Device or Duo | New Duo or Device According to one or more Embodiments | % Reduction |
| --- | --- | --- | --- |
| Footprint (in$^2$) | 1.91 | 1.14 | 40.3% |
| Volume (in$^3$) | 0.43 | 0.32 | 25.6% |

Disposable Insertion Tool Piercing Member Protection Mechanism

As described above with respect to FIGS. 45A-55 according to one or more embodiments, a disposable insertion tool or device includes various components including a plunger, a striker, a sensor assembly, a needle carrier and a piercing member (e.g. needle), etc. such that a sensor is caused to be inserted at an insertion site on the body of a user where the sensor remains fastened to the user's body via a mounting base. With the sensor assembly adhered to the user's body, the sensor assembly is released from the insertion device in response to the user pulling away the insertion device. The piercing member is retracted such that it is encapsulated well inside the insertion device (see, e.g., FIGS. 53B, 54).

One way to protect the retracted piercing member once the insertion device has been used is to make the plunger long or tall enough so that the piercing member retracts sufficiently far into the insertion device so that it cannot be exposed again even if the user depresses both the plunger and the striker of the insertion device. However, this way would add considerable volume and height to the insertion device, which could be undesirable to the user.

Referring to FIG. 87A, a used insertion device is illustrated according to an embodiment of the present disclosure. Similar to one or more embodiments described above, a used insertion device or tool 8700 includes a needle carrier 8746 in a retracted position. In this regard, a needle carrier spring 8744 expands and retracts needle carrier 8746 such that piercing member 8710 is encapsulated well inside used insertion tool 8700.

FIG. 87B illustrates the used insertion tool of FIG. 87A with a depressed plunger and striker according to an embodiment. In some instances, after insertion tool 8700 has been used, a user may attempt to depress plunger 8702, accidentally or intentionally for example as indicated by downward arrow "A", and striker 8736 as indicated by arrow "B". As a result, a tip 8737 of piercing member 8710 is exposed.

Once the insertion tool or device has been used, that is, released and pulled away from the user's body, a disposable insertion tool piercing member protection mechanism alleviates potential exposure of the tip of the piercing member (e.g., needle). The piercing member remains protected inside the insertion device even if the user attempts to depress the plunger and striker on the used insertion device. According to one or more embodiments, the piercing member (e.g., needle) is prevented from being exposed by preventing the plunger and striker of the insertion device or tool from being fully depressed again once the insertion tool has been used. Advantageously, the user is protected from accidental needle sticks.

Referring to FIG. 88, a cutout section view of an insertion tool having a piercing member protection mechanism is illustrated according to an embodiment of the present disclosure. Insertion tool 8800 includes various components including a needle carrier 8846 (which will be described in more detail below with respect to the embodiment of FIG.

89), a striker 8836 (which will be described in more detail below with respect to the embodiment of FIG. 90), a plunger 8802 (which will be described in more detail below with respect to the embodiment of FIG. 91), and a piercing member 8810 (e.g., a needle). Once insertion tool 8800 has been used, for example, after it has been pulled away after inserting a sensor into the body of a user, plunger 8802 and striker 8836 are prevented from being fully depressed again (for example as indicated by arrows "A" and "B") as will be described in more detail below. As a result, a tip 8837 of piercing member 8810 is protected from exposure without adding excessive volume to insertion tool 8800.

FIG. 89A illustrates a section view of an insertion device having a piercing member protection mechanism including a needle carrier disposed therein according to an embodiment of the present disclosure. FIG. 89B illustrates a perspective view of the needle carrier of FIG. 89A according to an embodiment of the present disclosure. FIG. 89C illustrates a top view of the needle carrier of FIGS. 89A and 89C according to an embodiment of the present disclosure.

As described above according to one or more embodiments and as illustrated in FIG. 89A, a needle carrier 8846 is disposed inside or within an interior volume of an insertion device or tool 8900 along with a needle carrier tension mechanism or spring 8944. As illustrated in the embodiment of FIGS. 89B and 89C, needle carrier 8846 includes at least one cam rail 8954 disposed on or extending along an inner wall or surface of needle carrier 8846. In this embodiment, two cam rails 8954 are illustrated and are disposed on opposite sides along an inner surface of needle carrier 8846. Needle carrier 8846 also includes at least one outer guide rail 8955 disposed on or extending along an outer wall or surface of needle carrier 8846. In this embodiment, two guide rails 8955 are illustrated and are disposed on opposite sides along an outer surface of needle carrier 8846. It should be noted that in this embodiment, needle carrier 8846 has a substantially tube or pipe-like shape with a circular cross-section, however, needle carrier 8846 can be of any appropriate shape or have any appropriate cross-section such as rectangular, oval, square, etc.

FIG. 90A illustrates a section view of an insertion device having a piercing member protection mechanism including a striker disposed therein according to an embodiment of the present disclosure. FIG. 90B illustrates a perspective view of the striker of FIG. 90A according to an embodiment of the present disclosure. FIG. 90C illustrates a top view of the striker of FIGS. 90A and 90B according to an embodiment of the present disclosure.

As described above according to one or more embodiments and as illustrated in FIG. 90A, a striker 8836 is disposed inside or within an interior volume of an insertion device or tool 8900. As illustrated in the embodiment of FIGS. 90B and 90C, striker 8836 includes at least one guide slot 9057 disposed on or extending along an outline of an inner wall. In this embodiment, two guide slots 9057 are illustrated and are disposed on opposite sides along an outline of an inner surface or wall of striker 8836.

FIG. 91A illustrates a section view of an insertion device having a piercing member protection mechanism including a plunger according to an embodiment of the present disclosure. FIG. 91B illustrates a perspective view of the plunger of FIG. 90A according to an embodiment of the present disclosure. FIG. 91C illustrates a section view cutout along line A-A' of the striker of FIG. 91B according to an embodiment of the present disclosure.

As described above according to one or more embodiments and as illustrated in FIG. 91A, insertion tool 8900 includes a plunger 8802. The embodiment of FIG. 91B illustrates an outer surface or shape of plunger 8802. FIG. 91C illustrates a section view of an inside of plunger 8802, which includes a shaft 9159 substantially centered or extending from a top surface of plunger 8802. Shaft 9159 has a cammed surface that includes at least one locking slot 9157 from a first end proximate to the top surface of plunger 8802 and extending along a wall or surface of shaft 9159 into a cam 9158. It should be noted that a similar configuration for a locking slot and a cam is disposed on an opposite side of shaft 9159 (not shown).

FIGS. 92A and 92B illustrate an insertion sequence for an insertion tool having a piercing member protection mechanism according to an embodiment of the present disclosure. In that regard, FIG. 92A illustrates a section view of an insertion tool that has not been used or fired. FIG. 92B illustrates a section view of the insertion tool during insertion. FIG. 92C illustrates a top section view of a needle carrier and a striker of the insertion tool of FIG. 92B during insertion according to an embodiment of the present disclosure.

In FIG. 92A, an insertion tool 9200 is in an unused state, that is, before it has been fired or before it has been used to, for example, insert a sensor into a user's body. As described above according to one or more embodiments, insertion tool 9200 includes various components such as a needle carrier 9246, a striker 9236, a plunger 9202 and a piercing member 9210 (e.g., needle). FIG. 92B illustrates insertion tool 9200 during insertion, for example, being used or fired. In that regard, needle carrier 9246 and striker 9236 have been depressed so that the insertion tool is fired, for example, in response to a user pressing on plunger 9202 so that piercing member 9210 is inserted into the body of the user. As illustrated in FIG. 92C, during insertion, guide rails 9255 of needle carrier 9246 fit inside guide slots 9257 of striker 9236. It should be noted that needle carrier 9246 and striker 9236 can have interfaces such as guide rails 9255 and guide slots 9257 that are sized and/or shaped in any appropriate manner to engage, match or fit each other.

FIG. 93A is a section view illustrating a first half of a retraction of a needle carrier of an insertion tool having a piercing member protection mechanism according to an embodiment of the present disclosure. FIG. 93B illustrates a top section view of a needle carrier and a striker of the insertion tool of FIG. 93A during retraction according to an embodiment of the present disclosure.

As described above according to one or more embodiments, a user can use insertion tool 9200 to insert a sensor into the body of the user. After insertion, the user releases plunger 9202. Releasing plunger 9202 actuates a needle retraction mechanism including a spring 9244. The needle retraction mechanism including spring 9244 retracts needle carrier 9246 back into an interior volume of insertion tool 9200 as indicated by arrow "A". During approximately the first half of the retraction, needle carrier 9246 is guided by guide slots 9257 of striker 9236. As illustrated in FIG. 93B, guide rails 9255 of needle carrier 9246 fit inside guide slots 9257 of striker 9236.

FIGS. 94A-94C-1 illustrate section views of a sequence of rotation of a needle carrier of an insertion tool having a piercing member protection mechanism as the needle carrier continues to retract into the insertion tool according to one or more embodiments.

As described above with respect to the embodiments of FIGS. 93A-93B, a needle carrier is guided by one or more guide slots of a striker during the first half of the retraction of the needle carrier into the insertion tool. FIG. 94A illustrates a section view of a needle carrier 9246 retracted about halfway into a top portion of insertion tool 9200 surrounded or encapsulated by plunger 9202. In this instance, a top of needle carrier 9246 is approximately halfway into plunger 9202 as generally indicated by area G1. As needle carrier 9246 continues to retract, it pulls free from striker 9236 and instead of being guided by the guide slots of striker 9236, needle carrier 9246 becomes guided by a cammed surface 9459 of plunger 9202 as illustrated in detail "A". FIG. 94A-1 illustrates a top view of the needle carrier retracted about halfway into a top portion of the insertion tool that includes the plunger. Cam rails 9254 of needle carrier 9246 contact angled cams 9258 of striker 9202.

FIG. 94B illustrates a section view of a needle carrier 9246 substantially in mid rotation within the insertion tool according to an embodiment of the present disclosure. FIG. 94B-1 is a top section view of the needle carrier substantially in mid rotation. After cam rails 9254 of needle carrier 9246 contact angled cams 9258 of plunger 9202 as described above according to an embodiment, needle carrier 9246 rotates in a certain direction as guided by angled cams 9258 as illustrated in detail "B". In this instance, a top of needle carrier 9246 is such that cam rails 9254 contact angled cams 9258 at an area generally as indicated by "G2". Needle carrier 9246 rotates guided by an angle corresponding to the angle of angled cams 9258, for example, by approximately 60 degrees. It should be noted that angled cams 9258 can be of any appropriate angle for a particular use or design, for example, 50 degrees, 75 degrees, etc., to guide and rotate cam rails 9256 as appropriate. In an example, needle carrier 9246 rotates in a counterclockwise direction as indicated by arrow "C" in FIG. 94B or arrow "D" in FIG. 94B-1.

FIG. 94C is a section view of a needle carrier fully retracted and rotated within the insertion tool according to an embodiment of the present disclosure. FIG. 94C-1 is a top view of the needle carrier fully retracted and rotated. As described above, needle carrier 9246 is rotated by a certain angle, for example approximately 60 degrees, as guided by one or more angled cams of plunger 9202. Needle carrier 9246 fully rotates as indicated by arrow "F" in FIG. 94C (or arrow "H" in FIG. 94C-1), for example, in a counterclockwise direction, and fully retracts as indicated by arrow "E" into insertion tool 9200. In this instance, for example, a top surface of needle carrier 9246 is proximate to an inner portion of a top surface of plunger 9202 as generally indicated as area "G3". As illustrated in FIG. 94C-1, cam rails 9254 of needle carrier 9256 are rotated and fully retracted into corresponding locking slots 9257 of plunger 9202. As described above for example with respect to the embodiment of FIG. 91C, locking slots 9257 are located on a shaft portion of plunger 9202 and extend into the angled cams of plunger 9202. As such, according to one or more embodiments, locking slots 9257 of plunger 9202 engage cam rails 9254 of needle carrier 9246, permanently locking the retracted needle carrier 9246 in the rotated position. Also, spring 9244 of needle carrier 9246 holds the fully retracted needle carrier 9246 against plunger 9202.

FIGS. 95A-95C illustrate section views of a locking or piercing member protection mechanism for an insertion tool according to one or more embodiments of the present disclosure.

As illustrated in FIG. 95A when a needle carrier 9246 is locked in a rotated position as described above according to one or more embodiments, guide rails 9255 of needle carrier 9246 do not line up with guide slots 9257 of striker 9236. As illustrated in detail "A", for example, an end "m" of a guide rail 9255 no longer lines up with striker guide slot 9257. FIG. 95B illustrates a top section view of the insertion tool before insertion according to an embodiment, and FIG. 95C illustrates a top section view of the insertion tool after insertion according to an embodiment of the present disclosure. In FIG. 95B, before insertion tool 9200 is used or fired, for example, before the insertion tool is used by a user to insert a sensor into the user's body, guide rails 9255 of needle carrier 9246 line up with guide slots 9257 of striker 9236. In FIG. 95C, after insertion tool 9200 is used or fired and needle carrier 9246 is retracted and locked in a rotated position as described above, guide rails 9255 of needle carrier 9246 no longer line up with guide slots 9257 of striker 9236.

FIG. 96 illustrates a section view of a used or fired inserter tool having a locking or piercing member protection mechanism with a plunger and striker depressed according to an embodiment of the present disclosure. As described above according to one or more embodiments, after insertion tool 9200 has been used or fired, for example, to insert a sensor into the body of a user, a needle carrier 9246 is fully retracted and rotated into the insertion tool. At this state, as illustrated in the embodiment of FIG. 96, if the user attempts to depress plunger 9202, for example as indicated by arrow "A", and striker 9236, for example as indicated by arrow "B", the guide rails on needle carrier 9246 interfere with at least a portion of a top surface of striker 9236, for example, as indicated at points "p" and "p1". In this regard, needle carrier 9246 acts as a barrier or wedge between plunger 9202 and striker 9236, thus preventing plunger 9202 and striker 9236 from being fully depressed. Advantageously, because plunger 9202 and striker 9236 cannot be fully depressed, needle tip 9237 remains protected within insertion tool 9200 at all times.

While the description above refers to particular embodiments of the present disclosure, it will be understood that many modifications may be made without departing from the spirit thereof. The accompanying claims are intended to cover such modifications as would fall within the true scope and spirit of the present disclosure.

The presently disclosed embodiments are therefore to be considered in all respects as illustrative and not restrictive, the scope of the present disclosure being indicated by the appended claims, rather than the foregoing description, and all changes which come within the meaning and range of equivalency of the claims are therefore intended to be embraced therein.

What is claimed is:

1. An insertion device comprising:
   a plunger coupled with a lock collar, wherein the insertion device houses contents comprising at least one component including:
   a striker comprising at least one self-locking striker snap arm configured to keep the insertion device in a cocked position while not in use such that the striker is kept from firing by a striker spring captured between the plunger and the striker when the insertion device is in the cocked position;
   a sensor assembly comprising a sensor disposed on a bottom surface of the sensor assembly, wherein a mounting base having a first side attaches to the bottom surface of the sensor assembly, and a second side of the mounting base is exposed; and
   a needle carrier adapted to hold a piercing member, the needle carrier captured between the striker and a needle carrier spring wherein at least one self-releasing snap keeps the needle carrier cocked, wherein the plunger prevents the self-releasing snap(s) from repositioning and releasing the needle carrier;

wherein when the insertion device is fired in response to a user depressing at least a portion of the plunger, the striker fires the needle carrier holding the piercing member such that the self-locking striker snap arm(s) are positioned to enter a groove to allow the striker to snap down, wherein after the insertion device is fired, the needle carrier is retracted in response to the user releasing the plunger such that the piercing member is encapsulated within the housing of the insertion device.

2. The insertion device of claim 1, wherein the insertion device is single use and disposable.

3. The insertion device of claim 1, further comprising a lid that completely covers a bottom surface of the lock collar to protect the contents within the insertion device.

4. The insertion device of claim 1, wherein the insertion device is unlocked by the user using two unlocking directional forces including performing a rotation motion while applying a downward force on the plunger to prevent the lock collar from accidentally unlocking.

5. The insertion device of claim 1, wherein the sensor assembly is fastened to a user's skin via the mounting base and the sensor is introduced into a body of the user upon firing of the needle carrier and the piercing member of the insertion device.

6. The insertion device of claim 1 wherein the sensor is introduced into a body of the user upon the user pushing on the plunger using a minimum pushing force for a certain minimum travel or distance.

7. The insertion device of claim 1, wherein the sensor assembly is automatically left behind on an insertion site upon the user pulling away the insertion device away from the insertion site after the insertion device is fired.

8. The insertion device of claim 1, wherein after the insertion device is used to insert the sensor extension into a body of a user, a transmitter assembly is connected to the sensor assembly at one or more areas as a single unit in response to a rotating motion by the user.

* * * * *